United States Patent
Xie et al.

(10) Patent No.: US 9,856,238 B2
(45) Date of Patent: Jan. 2, 2018

(54) 1-HETEROCYCLYL ISOCHROMANYL COMPOUNDS AND ANALOGS FOR TREATING CNS DISORDERS

(71) Applicants: Sunovion Pharmaceuticals Inc., Marlborough, MA (US); PGI Drug Discovery LLC, Tarrytown, NY (US)

(72) Inventors: Linghong Xie, Southborough, MA (US); Philip Glyn Jones, Danvers, MA (US); Kerry L. Spear, Concord, MA (US); Noel Aaron Powell, Westford, MA (US); Taleen G. Hanania, Valhalla, NY (US); Vadim Alexandrov, Hopewell Junction, NY (US)

(73) Assignees: SUNOVION PHARMACEUTICALS INC., Marlborough, MA (US); PGI DRUG DISCOVERY LLC, Tarrytown, NY (US)

( * ) Notice: Subject to any disclaimer, the term of this patent is extended or adjusted under 35 U.S.C. 154(b) by 0 days.

(21) Appl. No.: 15/041,852

(22) Filed: Feb. 11, 2016

(65) Prior Publication Data
US 2017/0001987 A1    Jan. 5, 2017

Related U.S. Application Data

(60) Provisional application No. 62/115,064, filed on Feb. 11, 2015.

(51) Int. Cl.
*C07D 405/04* (2006.01)
*C07D 413/14* (2006.01)
*C07D 405/14* (2006.01)
*C07D 493/04* (2006.01)
*C07D 413/04* (2006.01)

(52) U.S. Cl.
CPC ......... *C07D 405/04* (2013.01); *C07D 405/14* (2013.01); *C07D 413/04* (2013.01); *C07D 413/14* (2013.01); *C07D 493/04* (2013.01)

(58) Field of Classification Search
None
See application file for complete search history.

(56) References Cited

U.S. PATENT DOCUMENTS

| 4,963,568 A | 10/1990 | Schoenleber et al. |
| 5,393,759 A * | 2/1995 | Combourieu ........ C07D 311/76 514/320 |
| 5,621,133 A | 4/1997 | DeNinno et al. |

FOREIGN PATENT DOCUMENTS

| WO | 2009057974 A2 | 5/2009 |
| WO | 2012122340 A1 | 9/2012 |
| WO | 2014106238 A1 | 7/2014 |

OTHER PUBLICATIONS

Ito et al., A medium-term rat liver bioassay for rapid in vivo detection of carcinogenic potential of chemicals. Cancer Science, 2003, 94, 3-8.*
Written opinion in international application No. PCT/US2016/017539 dated Apr. 21, 2016.*
Martial Toffano et al., "Asymmetric Routes Towards Polyfunctionalized Pyrrolidines: Application to the Synthesis of Alkaloid Analogues" Tetrahedron: Asymmetry, 14, pp. 3365-3370 (2003).
International Search Report in International Application No. PCT/US2016/017539 dated Apr. 21, 2016.
CAS Registry No. 1541037-08-4, Pyrrolidine, 2-(3,4-dihydro-1H-2-benzopyran-l-y1)-, listed in AKos Out of Stock Catalog, original date unknown.

* cited by examiner

*Primary Examiner* — Alicia L Otton
*Assistant Examiner* — Po-Chih Chen
(74) *Attorney, Agent, or Firm* — Heslin, Rothenberg, Farley & Mesisi, P.C.

(57) ABSTRACT

Disclosed are compounds of Formula (I):

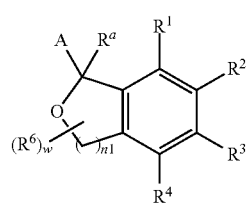

and pharmaceutically acceptable salts thereof, wherein A, $R^a$, $R^1$, $R^2$, $R^3$, $R^4$, $R^6$, w and n1 are defined and described herein; compositions thereof; and methods of use thereof. These compounds are useful for treating a variety of neurological and psychiatric disorders, such as those described herein.

33 Claims, No Drawings

1-HETEROCYCLYL ISOCHROMANYL COMPOUNDS AND ANALOGS FOR TREATING CNS DISORDERS

BACKGROUND

Central nervous system disorders affect a wide range of the population with differing severity. Neurological and psychiatric disorders include major depression, schizophrenia, bipolar disorder, obsessive compulsive disorder (OCD), panic disorder, and posttraumatic stress disorder (PTSD), among others. These disorders affect a person's thoughts, mood, behavior and social interactions and can significantly impair daily functioning. See, e.g., Diagnostic and Statistical Manual of Mental Disorders, 4th Ed., American Psychiatric Association (2000) ("DSM-IV-TR"); Diagnostic and Statistical Manual of Mental Disorders, 5th Ed., American Psychiatric Association (2013) ("DSM-5").

Bipolar disorder is a serious psychiatric disorder that has a prevalence of approximately 2% of the population, and affects both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although patients spend considerable more time in the depressive state. Other related conditions include cyclothymic disorder.

Schizophrenia is a psychopathic disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder.

Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the catatonic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making.

Neurological and psychiatric disorders can exhibit a variety of symptoms, including cognitive impairment, depressive disorders, and anxiety disorders.

Cognitive impairment includes a decline in cognitive functions or cognitive domains, e.g., working memory, attention and vigilance, verbal learning and memory, visual learning and memory, reasoning and problem solving (e.g., executive function, speed of processing and/or social cognition). In particular, cognitive impairment may indicate deficits in attention, disorganized thinking, slow thinking, difficulty in understanding, poor concentration, impairment of problem solving, poor memory, difficulties in expressing thoughts, and/or difficulties in integrating thoughts, feelings and behavior, or difficulties in extinction of irrelevant thoughts.

Depressive disorders include major depressive disorder and dysthymia, and are associated with depressed mood (sadness), poor concentration, insomnia, fatigue, appetite disturbances, excessive guilt and thoughts of suicide.

Anxiety disorders are disorders characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs.

SUMMARY

While medications exist for some aspects of these diseases, there remains a need for effective treatments for various neurological and psychiatric disorders, including mood disorders such as bipolar and related disorders, psychosis and schizophrenia. For example, while mood stabilizers such as lithium and valproate, antidepressants and antipsychotic drugs are used to treat mood disorders, more effective medications are necessary. And current antipsychotics may be successful in treating the positive symptoms of schizophrenia but fare less well for the negative and cognitive symptoms. Additionally, current antidepressants are typically effective only for a proportion of patients suffering from depression.

In some embodiments, the present invention encompasses the insight that compounds of Formula (I):

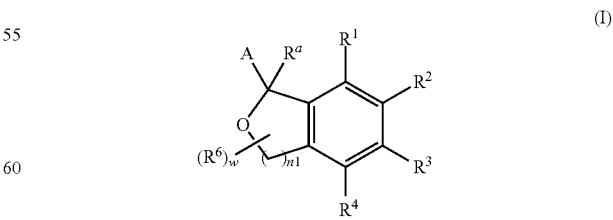

and pharmaceutically acceptable salts thereof, wherein A, $R^a$, $R^1$, $R^2$, $R^3$, $R^4$, $R^6$, w and n1 are defined and described herein, are useful for treating a variety of neurological and psychiatric disorders, such as those described herein.

3

Also provided herein are methods for the treatment of various neurological and psychiatric disorders using the compounds and compositions provided herein.

DETAILED DESCRIPTION OF CERTAIN EMBODIMENTS

1. General Description of Compounds of the Invention

In some embodiments, the present invention provides a compound of Formula (I):

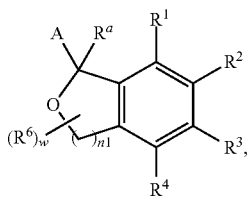

or a pharmaceutically acceptable salt thereof, wherein:

A is

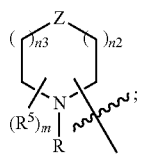

m is 0, 1, or 2;
n1 is 1, 2, or 3;
n2 is 0 or 1;
n3 is 0 or 1;
R is —H or $C_1$-$C_3$ alkyl;
$R^a$ is —H or $C_1$-$C_3$ alkyl;
$R^1$, $R^2$, $R^3$, and $R^4$ are independently —H, halo, —OH, —$NH_2$, $C_1$-$C_3$ alkyl, —$OR^7$, —$NHR^7$, —$N(R^7)R^7$, —CN, phenyl, or 5- or 6-membered heteroaryl, wherein:
  each instance of $R^2$ independently is unsubstituted $C_1$-$C_2$ alkyl or $C_1$-$C_2$ alkyl substituted with 1-3 halo,
  each instance of $C_1$-$C_3$ alkyl independently is unsubstituted or substituted with 1-3 halo,
  and
  the phenyl or heteroaryl is unsubstituted or substituted with 1 or 2 groups independently selected from halo, —OH, —$OCH_3$, —$OCF_3$, —$NH_2$, —$NH(CH_3)$, —$N(CH_3)_2$, —$CH_3$, ethyl, —$CF_3$, and —CN,
optionally wherein
  two adjacent instances of $R^1$, $R^2$, $R^3$, and $R^4$ together form —O—$CH_2$—O—, —O—$CH(CH_3)$—O—, —O—$C(CH_3)_2$—O—, —O—$CH_2$—$CH_2$—O—, or —O—$C(CH_3)_2$—$C(CH_3)_2$—O—;
each instance of $R^5$ independently is halo, —$CH_3$, or ethyl;

4 each instance of $R^6$ independently is halo, —$CH_3$, ethyl or —OH;
w is 0, 1, or 2; and
Z is C or O;
provided that the compound is not

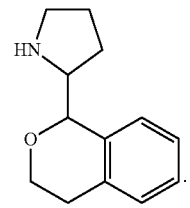

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in M. Loudon, *Organic Chemistry*, 5th Ed., Roberts and Company, Greenwood Village, Colo.: 2009; and M. B. Smith, *March's Advanced Organic Chemistry: Reactions, Mechanisms and Structure*, 7th Ed., John Wiley & Sons, Hoboken: 2013, the entire contents of which are hereby incorporated by reference.

As used herein, the term "halogen" or "halo" means F, Cl, Br, or I.

As used herein, the term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

As used herein, the terms "heteroaryl" and "heteroar-," used alone or as part of a larger moiety, e.g., "heteroaralkyl," or "heteroaralkoxy," refer to groups having 5 to 10 ring atoms, preferably 5, 6, 9 or 10 ring atoms; having 6, 10, or 14 π electrons shared in a cyclic array; and having, in addition to carbon atoms, from one to five ring heteroatoms. Heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. A heteroaryl group may be monocyclic or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to ring carbon atoms, one to four ring heteroatoms. When used in reference to a ring atom of a heterocycle, the term "nitrogen" includes a substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein. A heterocyclyl group may be monocyclic or bicyclic. The term "heterocyclylalkyl" refers to an alkyl group substituted by a heterocyclyl, wherein the alkyl and heterocyclyl portions independently are optionally substituted.

As used herein, the term "unsaturated," as used herein, means that a moiety has one or more units of unsaturation.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein, the term "heteroatom" means one or more of oxygen, sulfur, nitrogen, phosphorus, or silicon (including, any oxidized form of nitrogen, sulfur, phosphorus, boron, or silicon; the quaternized form of any basic nitrogen; or a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein, the term "aryl" used alone or as part of a larger moiety as in "aralkyl," "aralkoxy," or "aryloxyalkyl," refers to carbocyclic aromatic ring systems having a total of six to fourteen ring atoms. The term "aryl" may be used interchangeably with the term "aryl ring." Examples of "aryl" groups include phenyl, naphthyl, anthracyl and the like, which may be optionally substituted.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the phrase "such as" is intended to be open-ended. For example, "A can be a halogen, such as chlorine or bromine" means that A can be, but is not limited to, chlorine or bromine.

3. Description of Exemplary Embodiments

In some embodiments, the present invention provides a compound of formula I:

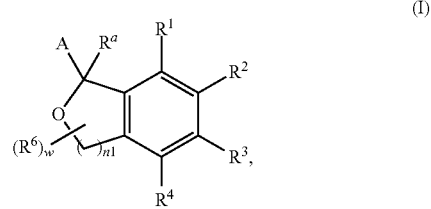

or a pharmaceutically acceptable salt thereof, wherein:
A is

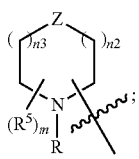

m is 0, 1, or 2;
n1 is 1, 2, or 3;
n2 is 0 or 1;
n3 is 0 or 1;
R is —H or $C_1$-$C_3$ alkyl;
$R^a$ is —H or $C_1$-$C_3$ alkyl;
$R^1$, $R^2$, $R^3$, and $R^4$ are independently —H, halo, —OH, —$NH_2$, $C_1$-$C_3$ alkyl, —$OR^7$, —$NHR^7$, —$N(R^7)R^7$, —CN, phenyl, or 5- or 6-membered heteroaryl, wherein:
  each instance of $R^2$ independently is unsubstituted $C_1$-$C_2$ alkyl or $C_1$-$C_2$ alkyl substituted with 1-3 halo,
  each instance of $C_1$-$C_3$ alkyl independently is unsubstituted or substituted with 1-3 halo,
  and
  the phenyl or heteroaryl is unsubstituted or substituted with 1 or 2 groups independently selected from halo, —OH, —$OCH_3$, —$OCF_3$, —$NH_2$, —$NH(CH_3)$, —$N(CH_3)_2$, —$CH_3$, ethyl, —$CF_3$, and —CN,
optionally wherein
  two adjacent instances of $R^1$, $R^2$, $R^3$, and $R^4$ together form —O—$CH_2$—O—, —O—$CH(CH_3)$—O—, —O—$C(CH_3)_2$—O—, —O—$CH_2$—$CH_2$—O—, or —O—$C(CH_3)_2$—$C(CH_3)_2$—O—;
each instance of $R^5$ independently is halo, —$CH_3$, or ethyl;
each instance of $R^6$ independently is halo, —$CH_3$, ethyl or —OH;
w is 0, 1, or 2; and
Z is C or O;
with the proviso that the compound is not:

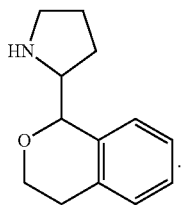

Such a compound (including pharmaceutically acceptable salts) is referred to herein as a "provided compound". Provided compounds are also described in U.S. Application No. 62/115,064, filed Feb. 11, 2015, which is hereby incorporated by reference herein in its entirety.
As defined above, A is

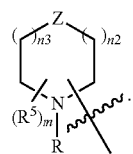

In some embodiments, A is

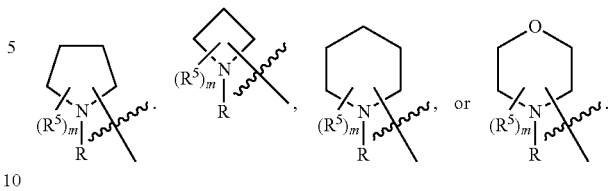

As defined above, m is 0, 1, or 2. In some embodiments, m is 0. In some embodiments, m is 1. In some embodiments, m is 2. In some embodiments, m is 0 or 1. In some embodiments, m is 1 or 2. In some embodiments, m is 0 or 2.

As defined above, n1 is 1, 2, or 3. In some embodiments, n1 is 1. In some embodiments, n1 is 2. In some embodiments, n1 is 3. In some embodiments, n1 is 1 or 2. In some embodiments, n1 is 1 or 3. In some embodiments, n1 is 2 or 3.

As defined above, n2 is 0 or 1. In some embodiments, n2 is 0. In some embodiments, n2 is 1.

As defined above, n3 is 0 or 1. In some embodiments, n3 is 0. In some embodiments, n3 is 1.

As defined above, R is —H or $C_1$-$C_3$ alkyl. In some embodiments, R is —H. In some embodiments, R is $C_1$-$C_3$ alkyl. In some embodiments, R is —H or —$CH_3$.

As defined above, $R^a$ is —H or $C_1$-$C_3$ alkyl. In some embodiments, $R^a$ is —H. In some embodiments, $R^a$ is $C_1$-$C_3$ alkyl. In some embodiments, $R^a$ is —H or —$CH_3$.

As defined above, $R^1$, $R^2$, $R^3$, and $R^4$ are independently —H, halo, —OH, —$NH_2$, $C_1$-$C_3$ alkyl, —$OR^7$, —$NHR^7$, —$N(R^7)R^7$, —CN, phenyl, or 5- or 6-membered heteroaryl, wherein:
  each instance of $R^7$ independently is unsubstituted $C_1$-$C_2$ alkyl or $C_1$-$C_2$ alkyl substituted with 1-3 halo,
  each instance of $C_1$-$C_3$ alkyl independently is unsubstituted or substituted with 1-3 halo, and
  the phenyl or heteroaryl is unsubstituted or substituted with 1 or 2 groups independently selected from halo, —OH, —$OCH_3$, —$OCF_3$, —$NH_2$, —$NH(CH_3)$, —$N(CH_3)_2$, —$CH_3$, ethyl, —$CF_3$, and —CN,
optionally wherein two adjacent instances of $R^1$, $R^2$, $R^3$, and $R^4$ together form —O—$CH_2$—O—, —O—$CH(CH_3)$—O—, —O—$C(CH_3)_2$—O—, —O—$CH_2$—$CH_2$—O—, or —O—$C(CH_3)_2$—$C(CH_3)_2$—O—

In some embodiments, at least two of $R^1$, $R^2$, $R^3$, and $R^4$ are —H. In some embodiments, at least three of $R^1$, $R^2$, $R^3$, and $R^4$ are —H. In some embodiments, the 5- or 6-membered heteroaryl of $R^1$, $R^2$, $R^3$, and $R^4$ has at least 1 nitrogen ring atom and is unsubstituted or substituted with 1 group selected from halo, —OH, —$OCH_3$, —$OCF_3$, —$NH_2$, —$NH(CH_3)$, —$N(CH_3)_2$, —$CH_3$, ethyl, —$CF_3$, and —CN. In some embodiments, the 5- or 6-membered heteroaryl of $R^1$, $R^2$, $R^3$, and $R^4$ is unsubstituted pyridyl, pyrimidinyl, pyrrolyl, pyrazolyl, isoxazolyl, imidazolyl, or oxazolyl. In some embodiments, the 5- or 6-membered heteroaryl of $R^1$, $R^2$, $R^3$, and $R^4$ is unsubstituted pyridyl or isoxazolyl. In some embodiments, two adjacent instances of $R^1$, $R^2$, $R^3$, and $R^4$ together form —O—$CH_2$—O—, —O—$CH(CH_3)$—O—, or —O—$C(CH_3)_2$—O—. In some embodiments, two adjacent instances of $R^1$, $R^2$, $R^3$, and $R^4$ together form —O—$CH_2$—O—. In some embodiments, $R^1$, $R^2$, $R^3$, and $R^4$ are independently —H, halo, $C_1$-$C_3$ alkyl, —$OR^7$ or —CN. In some embodiments, $R^1$, $R^2$, $R^3$, and $R^4$ are independently —H, —F, —$CH_3$, —$OCH_3$, or —CN.

As defined above, each instance of $R^5$ independently is halo, —$CH_3$, or ethyl. In some embodiments, each instance of $R^5$ independently is halo. In some embodiments, each instance of $R^5$ independently is —$CH_3$. In some embodiments, each instance of $R^5$ independently is ethyl. In some embodiments, each instance of $R^5$ independently is halo or —$CH_3$. In some embodiments, each instance of $R^5$ independently is halo or ethyl. In some embodiments, each instance of $R^5$ independently is —$CH_3$ or ethyl. In some embodiments, each instance of $R^5$ independently is —F or —$CH_3$.

As defined above, each instance of $R^6$ independently is halo, —$CH_3$, ethyl or —OH. In some embodiments, each instance of $R^6$ independently is halo. In some embodiments, each instance of $R^6$ independently is —$CH_3$. In some embodiments, each instance of $R^6$ independently is ethyl. In some embodiments, each instance of $R^6$ independently is —OH. In some embodiments, each instance of $R^6$ independently is halo or —$CH_3$. In some embodiments, each instance of $R^6$ independently is halo or ethyl. In some embodiments, each instance of $R^6$ independently is —$CH_3$ or ethyl. In some embodiments, each instance of $R^6$ independently is —F or —$CH_3$.

As defined above, w is 0, 1, or 2. In some embodiments, w is 0. In some embodiments, w is 1. In some embodiments, w is 2. In some embodiments, w is 0 or 1. In some embodiments, w is 1 or 2. In some embodiments, w is 0 or 2.

As defined above, Z is C or O. In some embodiments, Z is C. In some embodiments, Z is O.

In some embodiments, a provided compound is a compound of formula (I-A) or (I-B):

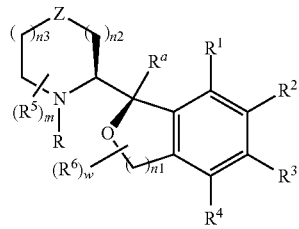

(I-A)

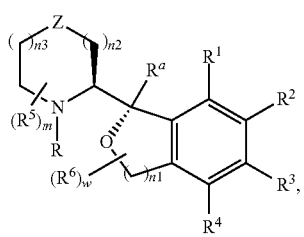

(I-B)

or a pharmaceutically acceptable salt thereof, wherein each of m, n1, n2, n3, R, $R^a$, $R^1$, $R^2$, $R^3$, $R^4$, $R^5$, $R^6$, w, and Z is as described in embodiments for formula I, supra, or described in embodiments herein, both singly and in combination.

In some embodiments, a provided compound is a compound of formula (I-A1) or (I-B1):

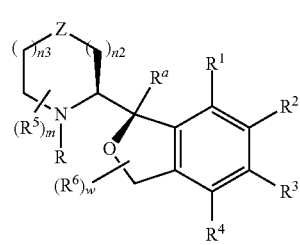

(I-A1)

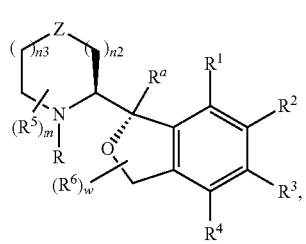

(I-B1)

or a pharmaceutically acceptable salt thereof, wherein each of m, n2, n3, R, $R^a$, $R^1$, $R^2$, $R^3$, $R^4$, $R^5$, $R^6$, w, and Z is as described in embodiments for formula I, supra, or described in embodiments herein, both singly and in combination.

In some embodiments, a provided compound is a compound of formula (I-A2) or (I-B2):

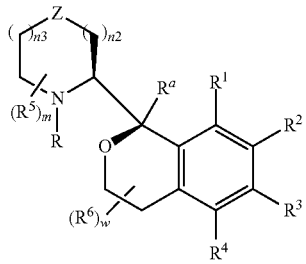

(I-A2)

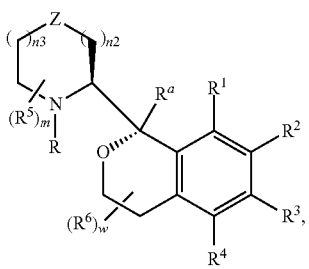

(I-B2)

or a pharmaceutically acceptable salt thereof, wherein each of m, n2, n3, R, $R^a$, $R^1$, $R^2$, $R^3$, $R^4$, $R^5$, $R^6$, w, and Z is as described in embodiments for formula I, supra, or described in embodiments herein, both singly and in combination.

In some embodiments, a provided compound is a compound of formula (I-A3) or (I-B3):

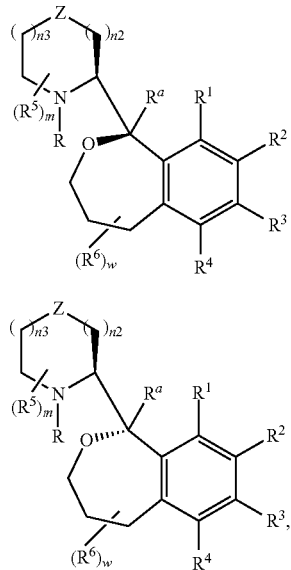

(I-A3)

(I-B3)

or a pharmaceutically acceptable salt thereof, wherein each of m, $n^2$, $n^3$, R, $R^a$, $R^1$, $R^2$, $R^3$, $R^4$, $R^5$, $R^6$, w, and Z is as described in embodiments for formula I, supra, or described in embodiments herein, both singly and in combination.

In some embodiments, a provided compound is a compound of formula (I-A), or a pharmaceutically acceptable salt thereof, wherein each of m, $n^1$, $n^2$, $n^3$, R, $R^a$, $R^1$, $R^2$, $R^3$, $R^4$, $R^5$, $R^6$, w, and Z is as described in embodiments for formula I, supra, or described in embodiments herein, both singly and in combination. In some such embodiments, Z is C. In some such embodiments, Z is C, n2 is 0 and n3 is 0. In some such embodiments, Z is C, and one of n2 and n3 is 0 and the other is 1. In some such embodiments, Z is C, n2 is 1 and n3 is 1. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —CH$_3$. In some such embodiments, $R^a$ is —H, R is —H, and each instance of $R^5$ is —F or —CH$_3$. In some such embodiments, each instance of $R^6$ is —F or —CH$_3$. In some such embodiments, $R^a$ is —H; R is —H; each instance of $R^5$ is —F or —CH$_3$; and each instance of $R^6$ is —F or —CH$_3$. In some such embodiments, each instance of $R^6$ is —CH$_3$. In some such embodiments, $R^a$ is —H; R is —H; each instance of $R^5$ is —F or —CH$_3$; and each instance of $R^6$ is —CH$_3$. In some such embodiments, m is 0. In some such embodiments, $R^a$ is —H; R is —H; each instance of $R^5$ is —F or —CH$_3$; each instance of $R^6$ is —F or —CH$_3$; and m is 0. In some such embodiments, w is 0. In some such embodiments, $R^a$ is —H; R is —H; each instance of $R^5$ is —F or —CH$_3$; each instance of $R^6$ is —F or —CH$_3$; m is 0; and w is 0. In some such embodiments, $R^1$, $R^2$, $R^3$, and $R^4$ are independently —H, halo, $C_1$-$C_3$ alkyl, —OR$^7$ or —CN. In some such embodiments, w is 0. In some such embodiments, $R^a$ is —H; R is —H; each instance of $R^5$ is —F or —CH$_3$; each instance of $R^6$ is —F or —CH$_3$; m is 0; w is 0; and $R^1$, $R^2$, $R^3$, and $R^4$ are independently —H, halo, $C_1$-$C_3$ alkyl, —OR$^7$ or —CN. In some such embodiments, two adjacent instances of $R^1$, $R^2$, $R^3$, and $R^4$ together form —O—CH$_2$—O—, —O—CH(CH$_3$)—O—, or —O—C(CH$_3$)$_2$—O—. In some such embodiments, $R^a$ is —H; R is —H; each instance of $R^5$ is —F or —CH$_3$; each instance of $R^6$ is —F or —CH$_3$; m is 0; w is 0; and two adjacent instances of $R^1$, $R^2$, $R^3$, and $R^4$ together form —O—CH$_2$—O—, —O—CH(CH$_3$)—O—, or —O—C(CH$_3$)$_2$—O—.

In some embodiments, a provided compound is a compound of formula (I-A1), (I-A2), or (I-A3), or a pharmaceutically acceptable salt thereof, wherein each of m, n2, n3, R, $R^a$, $R^1$, $R^2$, $R^3$, $R^4$, $R^5$, $R^6$, w, and Z is as described in embodiments for formula I, supra, or described in embodiments herein, both singly and in combination. In some such embodiments, Z is C. In some such embodiments, Z is C, n2 is 0 and n3 is 0. In some such embodiments, Z is C, and one of n2 and n3 is 0 and the other is 1. In some such embodiments, Z is C, n2 is 1 and n3 is 1. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —CH$_3$. In some such embodiments, $R^a$ is —H, R is —H, and each instance of $R^5$ is —F or —CH$_3$. In some such embodiments, each instance of $R^6$ is —F or —CH$_3$. In some such embodiments, $R^a$ is —H; R is —H; each instance of $R^5$ is —F or —CH$_3$; and each instance of $R^6$ is —F or —CH$_3$. In some such embodiments, each instance of $R^6$ is —CH$_3$. In some such embodiments, $R^a$ is —H; R is —H; each instance of $R^5$ is —F or —CH$_3$; and each instance of $R^6$ is —CH$_3$. In some such embodiments, m is 0. In some such embodiments, $R^a$ is —H; R is —H; each instance of $R^5$ is —F or —CH$_3$; each instance of $R^6$ is —F or —CH$_3$; and m is 0. In some such embodiments, w is 0. In some such embodiments, $R^a$ is —H; R is —H; each instance of $R^5$ is —F or —CH$_3$; each instance of $R^6$ is —F or —CH$_3$; m is 0; w is 0; and $R^1$, $R^2$, $R^3$, and $R^4$ are independently —H, halo, $C_1$-$C_3$ alkyl, —OR$^7$ or —CN. In some such embodiments, two adjacent instances of $R^1$, $R^2$, $R^3$, and $R^4$ together form —O—CH$_2$—O—, —O—CH(CH$_3$)—O—, or —O—C(CH$_3$)$_2$—O—. In some such embodiments, $R^a$ is —H; R is —H; each instance of $R^5$ is —F or —CH$_3$; each instance of $R^6$ is —F or —CH$_3$; m is 0; w is 0; and two adjacent instances of $R^1$, $R^2$, $R^3$, and $R^4$ together form —O—CH$_2$—O—, —O—CH(CH$_3$)—O—, or —O—C(CH$_3$)$_2$—O—.

In some embodiments, a provided compound is a compound of formula (I-B), or a pharmaceutically acceptable salt thereof, wherein each of m, n1, n2, n3, R, $R^a$, $R^1$, $R^2$, $R^3$, $R^4$, $R^5$, $R^6$, w, and Z is as described in embodiments for formula I, supra, or described in embodiments herein, both singly and in combination. In some such embodiments, Z is C. In some such embodiments, Z is C, n2 is 0 and n3 is 0. In some such embodiments, Z is C, and one of n2 and n3 is 0 and the other is 1. In some such embodiments, Z is C, n2 is 1 and n3 is 1. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —CH$_3$. In some such embodiments, $R^a$ is —H, R is —H, and each instance of $R^5$ is —F or —CH$_3$. In some such embodiments, each instance of $R^6$ is —F or —CH$_3$. In some such embodiments, $R^a$ is —H; R is —H; each instance of $R^5$ is —F or —CH$_3$; and each instance of $R^6$ is —F or —CH$_3$. In some such embodiments, each instance of $R^6$ is —CH$_3$. In some such embodiments, $R^a$ is —H; R is —H; each instance of $R^5$ is —F or —CH$_3$; and each instance of $R^6$ is —CH$_3$. In some such embodiments, m is 0. In some such embodiments, $R^a$ is —H; R is —H; each instance of $R^5$ is —F or —CH$_3$; each instance of $R^6$ is —F or —CH$_3$; and m is 0. In some such embodiments, w is 0. In some such embodiments, $R^a$ is —H; R is —H; each instance of $R^5$ is —F or —CH$_3$; each instance of $R^6$ is —F or —CH$_3$; m is 0; and w is 0. In some such embodiments, $R^1$, $R^2$, $R^3$, and $R^4$ are independently —H, halo, $C_1$-$C_3$ alkyl, —OR$^7$ or —CN. In some such embodiments, w is 0. In some such embodiments, $R^a$ is —H; R is —H; each instance of $R^5$ is —F or —CH$_3$; each instance of $R^6$ is —F or —CH$_3$; m is 0; w is 0; and $R^1$, $R^2$, $R^3$, and $R^4$ are independently —H, halo, $C_1$-$C_3$ alkyl, —OR$^7$ or —CN. In some such embodiments, two adjacent instances of $R^1$, $R^2$, $R^3$, and $R^4$ together form —O—CH$_2$—O—, —O—CH(CH$_3$)—O—, or —O—C(CH$_3$)$_2$—O—. In some such embodiments, $R^a$ is —H; R is —H; each instance of $R^5$ is —F or —CH$_3$; each instance of $R^6$ is —F or —CH$_3$; m is 0; w is 0; and two adjacent instances of $R^1$, $R^2$, $R^3$, and $R^4$ together form —O—CH$_2$—O—, —O—CH(CH$_3$)—O—, or —O—C(CH$_3$)$_2$—O—.

In some embodiments, a provided compound is a compound of formula (I-B1), (I-B2), or (I-B3), or a pharmaceutically acceptable salt thereof, wherein each of m, n2, n3, R, $R^a$, $R^1$, $R^2$, $R^3$, $R^4$, $R^5$, $R^6$, w, and Z is as described in embodiments for formula I, supra, or described in embodiments herein, both singly and in combination. In some such embodiments, Z is C. In some such embodiments, Z is C, n2 is 0 and n3 is 0. In some such embodiments, Z is C, and one of n2 and n3 is 0 and the other is 1. In some such embodiments, Z is C, n2 is 1 and n3 is 1. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —CH$_3$. In some such embodiments, $R^a$ is —H, R is —H, and each instance of $R^5$ is —F or —CH$_3$. In some such embodiments, each instance of $R^6$ is —F or —CH$_3$. In some such embodiments, $R^a$ is —H; R is —H; each instance of $R^5$ is —F or —CH$_3$; and each instance of $R^6$ is —F or —CH$_3$. In some such embodiments, each instance of $R^6$ is —CH$_3$. In some such embodiments, $R^a$ is —H; R is —H; each instance of $R^5$ is —F or —CH$_3$; and each instance of $R^6$ is —CH$_3$. In some such embodiments, m is 0. In some such embodiments, $R^a$ is —H; R is —H; each instance of $R^5$ is —F or —CH$_3$; each instance of $R^6$ is —F or —CH$_3$; and m is 0. In some such embodiments, w is 0. In some such embodiments, $R^a$ is —H; R is —H; each instance of $R^5$ is —F or —CH$_3$; each instance of $R^6$ is —F or —CH$_3$; m is 0; and w is 0. In some such embodiments, $R^1$, $R^2$, $R^3$, and $R^4$ are independently —H, halo, $C_1$-$C_3$ alkyl, —OR$^7$ or —CN. In some such embodiments, w is 0. In some such embodiments, $R^a$ is —H; R is —H; each instance of $R^5$ is —F or —CH$_3$; each instance of $R^6$ is —F or —CH$_3$; m is 0; w is 0; and $R^1$, $R^2$, $R^3$, and $R^4$ are independently —H, halo, $C_1$-$C_3$ alkyl, —OR$^7$ or —CN. In some such embodiments, two adjacent instances of $R^1$, $R^2$, $R^3$, and $R^4$ together form —O—CH$_2$—O—, —O—CH(CH$_3$)—O—, or —O—C(CH$_3$)$_2$—O—. In some such embodiments, $R^a$ is —H; R is —H; each instance of $R^5$ is —F or —CH$_3$; each instance of $R^6$ is —F or —CH$_3$; m is 0; w is 0; and two adjacent instances of $R^1$, $R^2$, $R^3$, and $R^4$ together form —O—CH$_2$—O—, —O—CH(CH$_3$)—O—, or —O—C(CH$_3$)$_2$—O—.

In some embodiments, a provided compound is a compound of formula (Ia), (Ib), (Ic), or (Id):

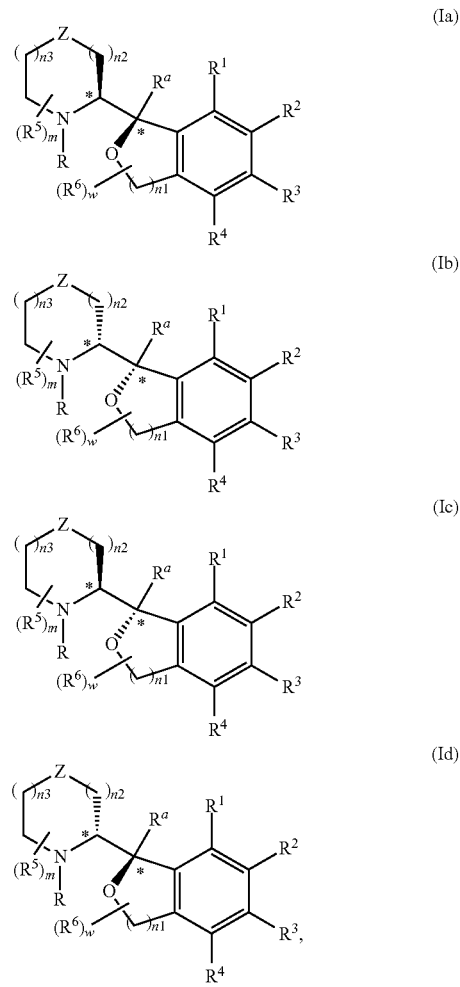

or a pharmaceutically acceptable salt thereof, wherein each of m, n1, n2, n3, R, $R^a$, $R^1$, $R^2$, $R^3$, $R^4$, $R^5$, $R^6$, w, and Z is as described in embodiments for formula I, supra, or described in embodiments herein, both singly and in combination, and where the depictions of stereochemistry at the stereocenters marked with an asterisk (*) are absolute.

In some embodiments, a provided compound is a compound of formula (Ia), or a pharmaceutically acceptable salt thereof, wherein each of m, n1, n2, n3, R, $R^a$, $R^1$, $R^2$, $R^3$, $R^4$, $R^5$, $R^6$, w, and Z is as described in embodiments for formula I, supra, or described in embodiments herein, both singly and in combination. In some such embodiments, Z is C. In some such embodiments, Z is C, n2 is 0 and n3 is 0. In some such embodiments, Z is C, and one of n2 and n3 is 0 and the other is 1. In some such embodiments, Z is C, n2 is 1 and n3 is 1. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —CH$_3$. In some such embodiments, $R^a$ is —H, R is —H, and each instance of $R^5$ is —F or —CH$_3$. In some such embodiments, each instance of $R^6$ is —F or —CH$_3$. In some such embodiments, $R^a$ is —H; R is —H; each instance of $R^5$ is —F or —CH$_3$; and each instance of $R^6$ is —F or —CH$_3$. In some such embodiments, each instance of $R^6$ is —CH$_3$. In some such embodiments, $R^a$ is —H; R is —H; each instance of $R^5$ is —F or —CH$_3$; and each instance of $R^6$ is —CH$_3$. In some such embodiments, m is 0. In some such embodiments, $R^a$ is —H; R is —H; each instance of $R^5$ is —F or —CH$_3$; each instance of $R^6$ is —F or —CH$_3$; and m is 0. In some such embodiments, w is 0. In some such embodiments, $R^a$ is —H; R is —H; each instance of $R^5$ is —F or —CH$_3$; each instance of $R^6$ is —F or —CH$_3$; m is 0; and w is 0. In some such embodiments, $R^1$, $R^2$, $R^3$, and $R^4$ are independently —H, halo, $C_1$-$C_3$ alkyl, —OR$^7$ or —CN. In some such embodiments, w is 0. In some such embodiments, $R^a$ is —H; R is —H; each instance of $R^5$ is —F or —CH$_3$; each instance of $R^6$ is —F or —CH$_3$; m is 0; w is 0; and $R^1$, $R^2$, $R^3$, and $R^4$ are independently —H, halo, $C_1$-$C_3$ alkyl, —OR$^7$ or —CN. In some such embodiments, two adjacent instances of $R^1$, $R^2$, $R^3$, and $R^4$ together form —O—CH$_2$—O—, —O—CH(CH$_3$)—O—, or —O—C(CH$_3$)$_2$—O—. In some such embodiments, $R^a$ is —H; R is —H; each instance of $R^5$ is —F or —CH$_3$; each instance of $R^6$ is —F or —CH$_3$; m is 0; w is 0; and two adjacent instances of $R^1$, $R^2$, $R^3$, and $R^4$ together form —O—CH$_2$—O—, —O—CH(CH$_3$)—O—, or —O—C(CH$_3$)$_2$—O—.

In some embodiments, a provided compound is a compound of formula (Ib), or a pharmaceutically acceptable salt thereof, wherein each of m, n1, n2, n3, R, $R^a$, $R^1$, $R^2$, $R^3$, $R^4$, $R^5$, $R^6$, w, and Z is as described in embodiments for formula I, supra, or described in embodiments herein, both singly and in combination. In some such embodiments, Z is C. In some such embodiments, Z is C, n2 is 0 and n3 is 0. In some such embodiments, Z is C, and one of n2 and n3 is 0 and the other is 1. In some such embodiments, Z is C, n2 is 1 and n3 is 1. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —CH$_3$. In some such embodiments, $R^a$ is —H, R is —H, and each instance of $R^5$ is —F or —CH$_3$. In some such embodiments, each instance of $R^6$ is —F or —CH$_3$. In some such embodiments, $R^a$ is —H; R is —H; each instance of $R^5$ is —F or —CH$_3$; and each instance of $R^6$ is —F or —CH$_3$. In some such embodiments, each instance of $R^6$ is —CH$_3$. In some such embodiments, $R^a$ is —H; R is —H; each instance of $R^5$ is —F or —CH$_3$; and each instance of $R^6$ is —CH$_3$. In some such embodiments, m is 0. In some such embodiments, $R^a$ is —H; R is —H; each instance of $R^5$ is —F or —CH$_3$; each instance of $R^6$ is —F or —CH$_3$; and m is 0. In some such embodiments, w is 0. In some such embodiments, $R^a$ is —H; R is —H; each instance of $R^5$ is —F or —CH$_3$; each instance of $R^6$ is —F or —CH$_3$; m is 0; and w is 0. In some such embodiments, $R^1$, $R^2$, $R^3$, and $R^4$ are independently —H, halo, $C_1$-$C_3$ alkyl, —OR$^7$ or —CN. In some such embodiments, w is 0. In some such embodiments, $R^a$ is —H; R is —H; each instance of $R^5$ is —F or —CH$_3$; each instance of $R^6$ is —F or —CH$_3$; m is 0; w is 0; and $R^1$, $R^2$, $R^3$, and $R^4$ are independently —H, halo, $C_1$-$C_3$ alkyl, —OR$^7$ or —CN. In some such embodiments, two adjacent instances of $R^1$, $R^2$, $R^3$, and $R^4$ together form —O—CH$_2$—O—, —O—CH(CH$_3$)—O—, or —O—C(CH$_3$)$_2$—O—. In some such embodiments, $R^a$ is —H; R is —H; each instance of $R^5$ is —F or —CH$_3$; each instance of $R^6$ is —F or —CH$_3$; m is 0; w is 0; and two adjacent instances of $R^1$, $R^2$, $R^3$, and $R^4$ together form —O—CH$_2$—O—, —O—CH(CH$_3$)—O—, or —O—C(CH$_3$)$_2$—O—.

In some embodiments, a provided compound is a compound of formula (Ic), or a pharmaceutically acceptable salt thereof, wherein each of m, n1, n2, n3, R, $R^a$, $R^1$, $R^2$, $R^3$, $R^4$, $R^5$, $R^6$, w, and Z is as described in embodiments for formula I, supra, or described in embodiments herein, both singly and in combination. In some such embodiments, Z is C. In some such embodiments, Z is C, n2 is 0 and n3 is 0. In some such embodiments, Z is C, and one of n2 and n3 is 0 and the other is 1. In some such embodiments, Z is C, n2 is 1 and n3 is 1. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —CH$_3$. In some such embodiments, $R^a$ is —H, R is —H, and each instance of $R^5$ is —F or —CH$_3$. In some such embodiments, each instance of $R^6$ is —F or —CH$_3$. In some such embodiments, $R^a$ is —H; R is —H; each instance of $R^5$ is —F or —CH$_3$; and each instance of $R^6$ is —F or —CH$_3$. In some such embodiments, each instance of $R^6$ is —CH$_3$. In some such embodiments, $R^a$ is —H; R is —H; each instance of $R^5$ is —F or —CH$_3$; and each instance of $R^6$ is —CH$_3$. In some such embodiments, m is 0. In some such embodiments, $R^a$ is —H; R is —H; each instance of $R^5$ is —F or —CH$_3$; each instance of $R^6$ is —F or —CH$_3$; and m is 0. In some such embodiments, w is 0. In some such embodiments, $R^a$ is —H; R is —H; each instance of $R^5$ is —F or —CH$_3$; each instance of $R^6$ is —F or —CH$_3$; m is 0; and w is 0. In some such embodiments, $R^1$, $R^2$, $R^3$, and $R^4$ are independently —H, halo, $C_1$-$C_3$ alkyl, —OR$^7$ or —CN. In some such embodiments, w is 0. In some such embodiments, $R^a$ is —H; R is —H; each instance of $R^5$ is —F or —CH$_3$; each instance of $R^6$ is —F or —CH$_3$; m is 0; w is 0; and $R^1$, $R^2$, $R^3$, and $R^4$ are independently —H, halo, $C_1$-$C_3$ alkyl, —OR$^7$ or —CN. In some such embodiments, two adjacent instances of Fe, $R^2$, $R^3$, and $R^4$ together form —O—CH$_2$—O—, —O—CH(CH$_3$)—O—, or —O—C(CH$_3$)$_2$—O—. In some such embodiments, $R^a$ is —H; R is —H; each instance of $R^5$ is —F or —CH$_3$; each instance of $R^6$ is —F or —CH$_3$; m is 0; w is 0; and two adjacent instances of $R^1$, $R^2$, $R^3$, and $R^4$ together form —O—CH$_2$—O—, —O—CH(CH$_3$)—O—, or —O—C(CH$_3$)$_2$—O—.

In some embodiments, a provided compound is a compound of formula (Id), or a pharmaceutically acceptable salt thereof, wherein each of m, n1, n2, n3, R, $R^a$, $R^1$, $R^2$, $R^3$, $R^4$, $R^5$, $R^6$, w, and Z is as described in embodiments for formula I, supra, or described in embodiments herein, both singly and in combination. In some such embodiments, Z is C. In some such embodiments, Z is C, n2 is 0 and n3 is 0. In some such embodiments, Z is C, and one of n2 and n3 is 0 and the other is 1. In some such embodiments, Z is C, n2 is 1 and n3 is 1. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —CH$_3$. In some such embodiments, $R^a$ is —H, R is —H, and each instance of $R^5$ is —F or —CH$_3$. In some such embodiments, each instance of $R^6$ is —F or —CH$_3$. In some such embodiments, $R^a$ is —H; R is —H; each instance of $R^5$ is —F or —CH$_3$; and each instance of $R^6$ is —F or —CH$_3$. In some such embodiments, each instance of $R^6$ is —$CH_3$. In some such embodiments, $R^a$ is —H; R is —H; each instance of $R^5$ is —F or —$CH_3$; and each instance of $R^6$ is —$CH_3$. In some such embodiments, m is 0. In some such embodiments, $R^a$ is —H; R is —H; each instance of $R^5$ is —F or —$CH_3$; each instance of $R^6$ is —F or —$CH_3$; and m is 0. In some such embodiments, w is 0. In some such embodiments, $R^a$ is —H; R is —H; each instance of $R^5$ is —F or —$CH_3$; each instance of $R^6$ is —F or —$CH_3$; m is 0; and w is 0. In some such embodiments, $R^1$, $R^2$, $R^3$, and $R^4$ are independently —H, halo, $C_1$-$C_3$ alkyl, —$OR^7$ or —CN. In some such embodiments, w is 0. In some such embodiments, $R^a$ is —H; R is —H; each instance of $R^5$ is —F or —$CH_3$; each instance of $R^6$ is —F or —$CH_3$; m is 0; w is 0; and $R^1$, $R^2$, $R^3$, and $R^4$ are independently —H, halo, $C_1$-$C_3$ alkyl, —$OR^7$ or —CN. In some such embodiments, two adjacent instances of Fe, $R^2$, $R^3$, and $R^4$ together form —O—$CH_2$—O—, —O—CH($CH_3$)—O—, or —O—C($CH_3$)$_2$—O—. In some such embodiments, $R^a$ is —H; R is —H; each instance of $R^5$ is —F or —$CH_3$; each instance of $R^6$ is —F or —$CH_3$; m is 0; w is 0; and two adjacent instances of $R^1$, $R^2$, $R^3$, and $R^4$ together form —O—$CH_2$—O—, —O—CH($CH_3$)—O—, or —O—C($CH_3$)$_2$—O—.

In some embodiments, a provided compound is a compound of formula (I-C):

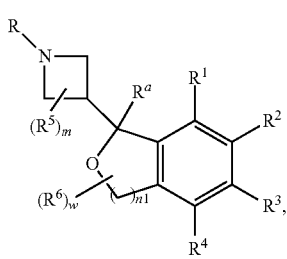

(I-C)

or a pharmaceutically acceptable salt thereof, wherein each of m, n1, R, $R^a$, $R^1$, $R^2$, $R^3$, $R^4$, $R^5$, $R^6$, and w is as described in embodiments for formula I, supra, or described in embodiments herein, both singly and in combination.

In some embodiments, a provided compound is a compound of formula (I-C), or a pharmaceutically acceptable salt thereof, wherein each of m, n1, R, $R^a$, $R^1$, $R^2$, $R^3$, $R^4$, $R^5$, $R^6$, and w is as described in embodiments for formula I, supra, or described in embodiments herein, both singly and in combination. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —$CH_3$. In some such embodiments, $R^a$ is —H, R is —H, and each instance of $R^5$ is —F or —$CH_3$. In some such embodiments, each instance of $R^6$ is —F or —$CH_3$. In some such embodiments, $R^a$ is —H; R is —H; each instance of $R^5$ is —F or —$CH_3$; and each instance of $R^6$ is —F or —$CH_3$. In some such embodiments, each instance of $R^6$ is —$CH_3$. In some such embodiments, $R^a$ is —H; R is —H; each instance of $R^5$ is —F or —$CH_3$; and each instance of $R^6$ is —$CH_3$. In some such embodiments, m is 0. In some such embodiments, $R^a$ is —H; R is —H; each instance of $R^5$ is —F or —$CH_3$; each instance of $R^6$ is —F or —$CH_3$; and m is 0. In some such embodiments, w is 0. In some such embodiments, $R^a$ is —H; R is —H; each instance of $R^5$ is —F or —$CH_3$; each instance of $R^6$ is —F or —$CH_3$; m is 0; and w is 0. In some such embodiments, $R^1$, $R^2$, $R^3$, and $R^4$ are independently —H, halo, $C_1$-$C_3$ alkyl, —$OR^7$ or —CN. In some such embodiments, w is 0. In some such embodiments, $R^a$ is —H; R is —H; each instance of $R^5$ is —F or —$CH_3$; each instance of $R^6$ is —F or —$CH_3$; m is 0; w is 0; and $R^1$, $R^2$, $R^3$, and $R^4$ are independently —H, halo, $C_1$-$C_3$ alkyl, —$OR^7$ or —CN. In some such embodiments, two adjacent instances of $R^1$, $R^2$, $R^3$, and $R^4$ together form —O—$CH_2$—O—, —O—CH($CH_3$)—O—, or —O—C($CH_3$)$_2$—O—. In some such embodiments, $R^a$ is —H; R is —H; each instance of $R^5$ is —F or —$CH_3$; each instance of $R^6$ is —F or —$CH_3$; m is 0; w is 0; and two adjacent instances of $R^1$, $R^2$, $R^3$, and $R^4$ together form —O—$CH_2$—O—, —O—CH($CH_3$)—O—, or —O—C($CH_3$)$_2$—O—.

In some embodiments, a provided compound is a compound of formula II:

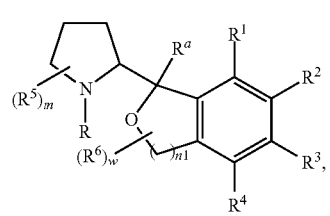

(II)

or a pharmaceutically acceptable salt thereof, wherein each of m, n1, R, $R^a$, $R^1$, $R^2$, $R^3$, $R^4$, $R^5$, $R^6$, and w is as described in embodiments for formula I, supra, or described in embodiments herein, both singly and in combination. In some such embodiments, at least two of $R^1$, $R^2$, $R^3$, and $R^4$ are —H. In some such embodiments, at least three of $R^1$, $R^2$, $R^3$, and $R^4$ are —H. In some such embodiments, $R^a$ is —H. In some such embodiments, R is —H. In some such embodiments, $R^a$ is —H and R is —H. In some such embodiments, each instance of $R^5$ is —F or —$CH_3$. In some such embodiments, $R^a$ is —H, R is —H, and each instance of $R^5$ is —F or —$CH_3$. In some such embodiments, each instance of $R^6$ is —F or —$CH_3$. In some such embodiments, $R^a$ is —H; R is —H; each instance of $R^5$ is —F or —$CH_3$; and each instance of $R^6$ is —F or —$CH_3$. In some such embodiments, each instance of $R^6$ is —$CH_3$. In some such embodiments, $R^a$ is —H; R is —H; each instance of $R^5$ is —F or —$CH_3$; and each instance of $R^6$ is —$CH_3$. In some such embodiments, m is 0. In some such embodiments, $R^a$ is —H; R is —H; each instance of $R^5$ is —F or —$CH_3$; each instance of $R^6$ is —F or —$CH_3$; and m is 0. In some such embodiments, w is 0. In some such embodiments, $R^a$ is —H; R is —H; each instance of $R^5$ is —F or —$CH_3$; each instance of $R^6$ is —F or —$CH_3$; m is 0; and w is 0. In some such embodiments, $R^1$, $R^2$, $R^3$, and $R^4$ are independently —H, halo, $C_1$-$C_3$ alkyl, —$OR^7$ or —CN. In some such embodiments, w is 0. In some such embodiments, $R^a$ is —H; R is —H; each instance of $R^5$ is —F or —$CH_3$; each instance of $R^6$ is —F or —$CH_3$; m is 0; w is 0; and $R^1$, $R^2$, $R^3$, and $R^4$ are independently —H, halo, $C_1$-$C_3$ alkyl, —$OR^7$ or —CN. In some such embodiments, two adjacent instances of $R^1$, $R^2$, $R^3$, and $R^4$ together form —O—$CH_2$—O—, —O—CH($CH_3$)—O—, or —O—C($CH_3$)$_2$—O—. In some such embodiments, $R^a$ is —H; R is —H; each instance of $R^5$ is —F or —$CH_3$; each instance of $R^6$ is —F or —$CH_3$; m is 0; w is 0; and two adjacent instances of $R^1$, $R^2$, $R^3$, and $R^4$ together form —O—$CH_2$—O—, —O—CH($CH_3$)—O—, or —O—C($CH_3$)$_2$—O—.

In some embodiments, a provided compound is a compound of formula (IIa), (IIb), (IIc), or (IId):

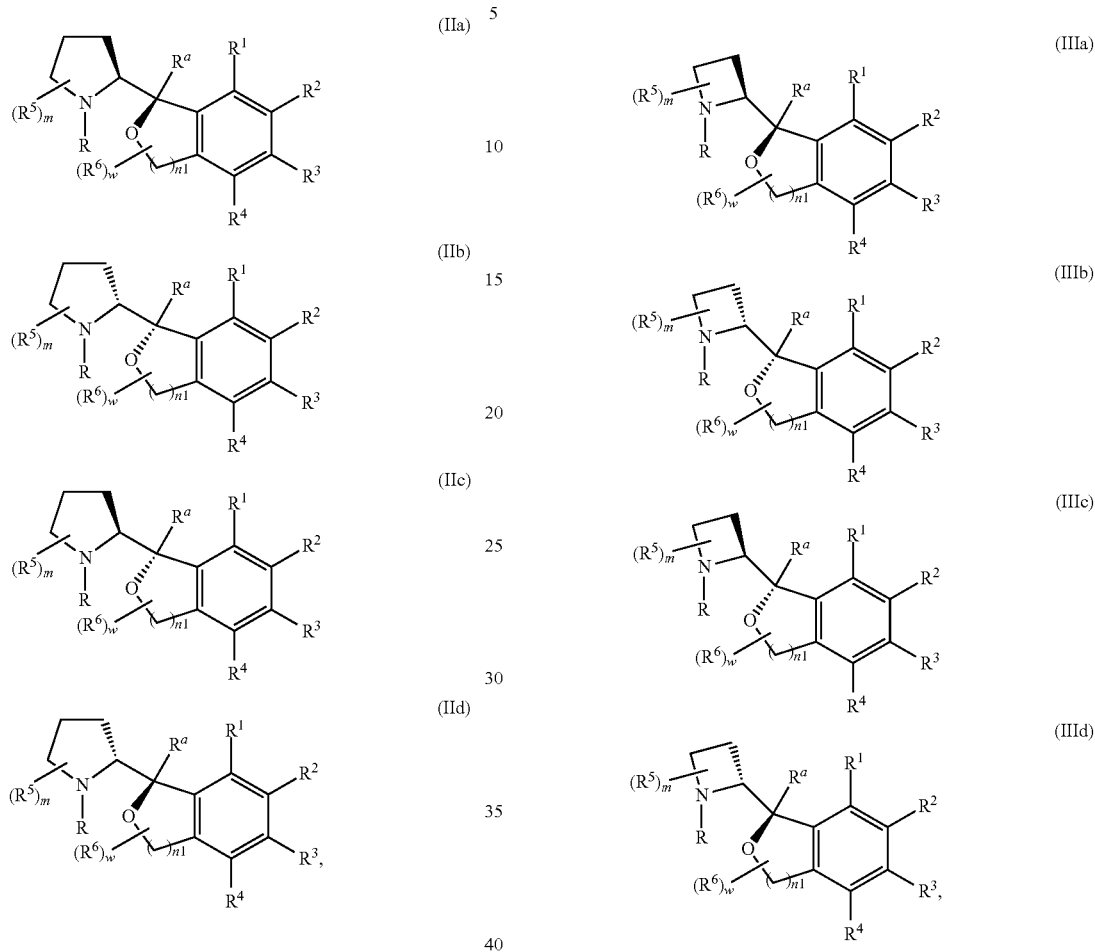

or a pharmaceutically acceptable salt thereof, with the proviso as described in embodiments for formula I, wherein each of m, n1, R, $R^a$, $R^1$, $R^2$, $R^3$, $R^4$, $R^5$, $R^6$, and w is as described in embodiments for formula I, supra, or described in embodiments herein, both singly and in combination.

In some embodiments, the present invention provides a compound of formula I, or a pharmaceutically acceptable salt thereof, wherein the compound of formula I is a compound of formula III:

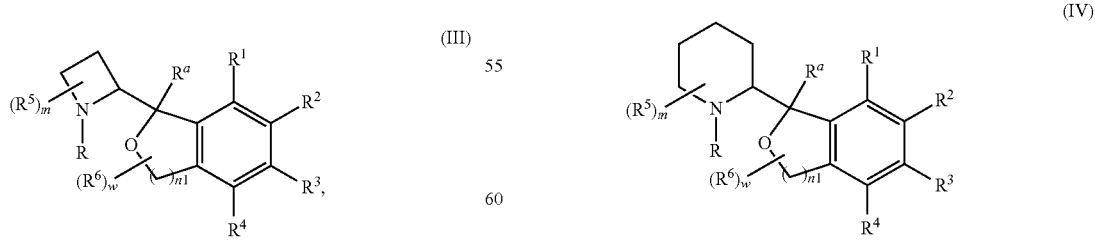

wherein each of m, n1, R, $R^a$, $R^1$, $R^2$, $R^3$, $R^4$, $R^5$, $R^6$, and w is as described in embodiments for formula I, supra, or described in embodiments herein, both singly and in combination.

In some embodiments, the present invention provides a compound of formula I selected from formulas (IIIa), (IIIb), (IIIc), and (IIId):

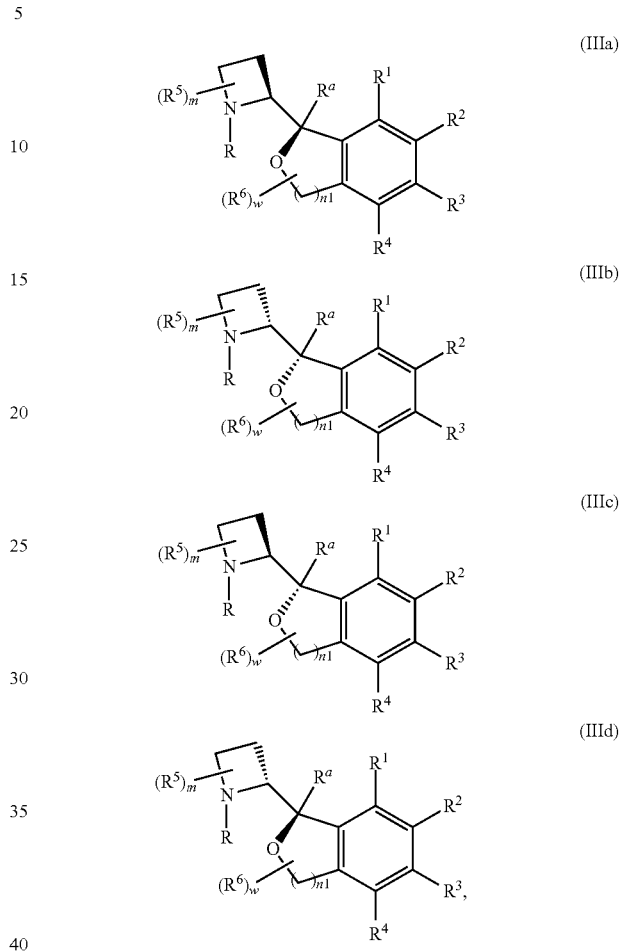

or a pharmaceutically acceptable salt thereof, wherein each of m, n1, R, $R^a$, $R^1$, $R^2$, $R^3$, $R^4$, $R^5$, $R^6$, and w is as described in embodiments for formula I, supra, or described in embodiments herein, both singly and in combination.

In some embodiments, the present invention provides a compound of formula I, or a pharmaceutically acceptable salt thereof, wherein the compound of formula I is a compound of formula IV:

(IV)

wherein each of m, n1, R, $R^a$, $R^1$, $R^2$, $R^3$, $R^4$, $R^5$, $R^6$, and w is as described in embodiments for formula I, supra, or described in embodiments herein, both singly and in combination.

In some embodiments, the present invention provides a compound of formula I selected from formulas (IVa), (IVb), (IVc), and (IVd):

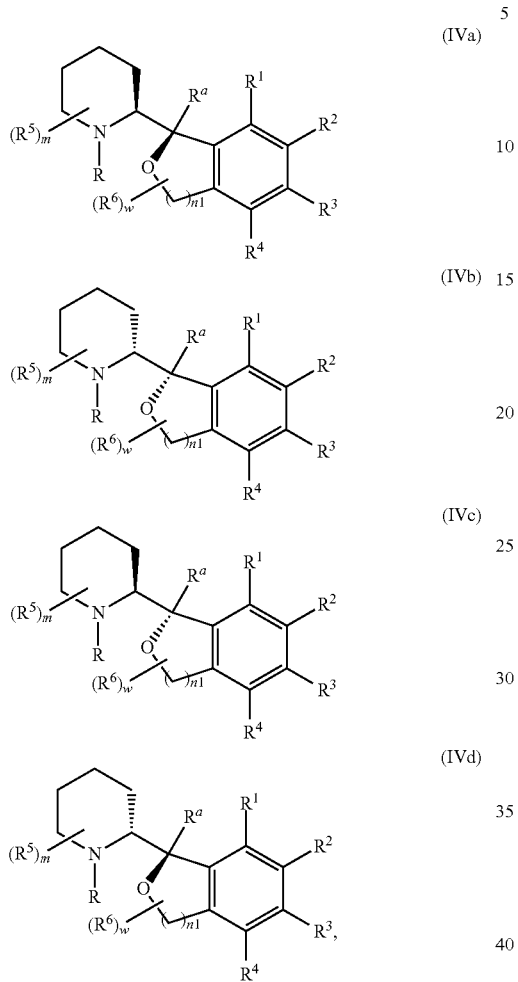

or a pharmaceutically acceptable salt thereof, wherein each of m, n1, R, $R^a$, $R^1$, $R^2$, $R^3$, $R^4$, $R^5$, $R^6$, and w is as described in embodiments for formula I, supra, or described in embodiments herein, both singly and in combination.

In some embodiments, the present invention provides a compound of formula I, or a pharmaceutically acceptable salt thereof, wherein the compound of formula I is a compound of formula V:

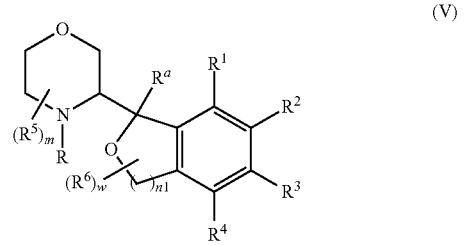

wherein each of m, n1, R, $R^a$, $R^1$, $R^2$, $R^3$, $R^4$, $R^5$, $R^6$, and w is as described in embodiments for formula I, supra, or described in embodiments herein, both singly and in combination.

In some embodiments, the present invention provides a compound of formula I selected from formulas (Va), (Vb), (Vc), and (Vd):

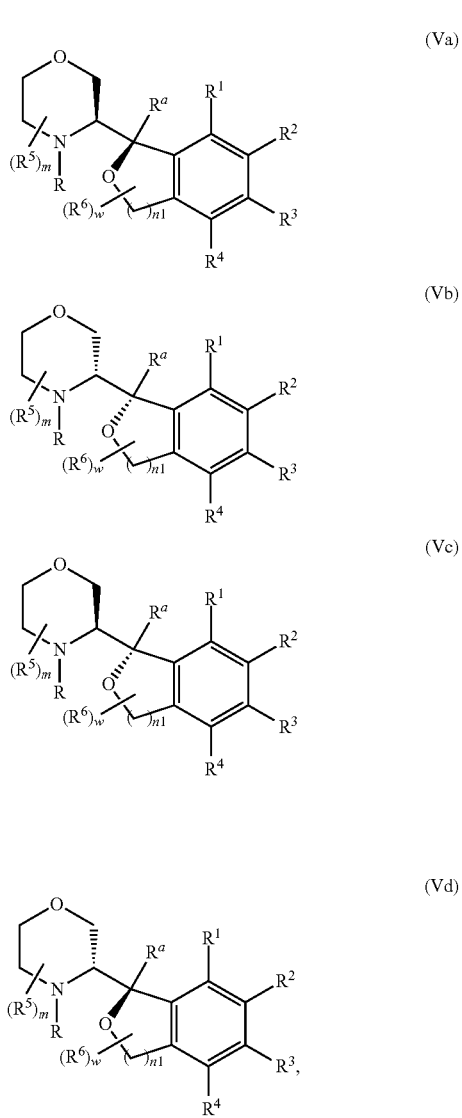

or a pharmaceutically acceptable salt thereof, wherein each of m, n1, R, $R^a$, $R^1$, $R^2$, $R^3$, $R^4$, $R^5$, $R^6$, and w is as described in embodiments for formula I, supra, or described in embodiments herein, both singly and in combination.

Exemplary compounds of formula I are set forth in Table 1, below.

TABLE 1

I-1

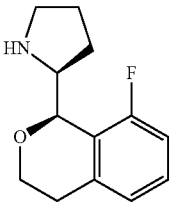 [SMILES: Fc1cccc2c1[C@H]([C@@H]1CCCN1)OCC2]

TABLE 1-continued
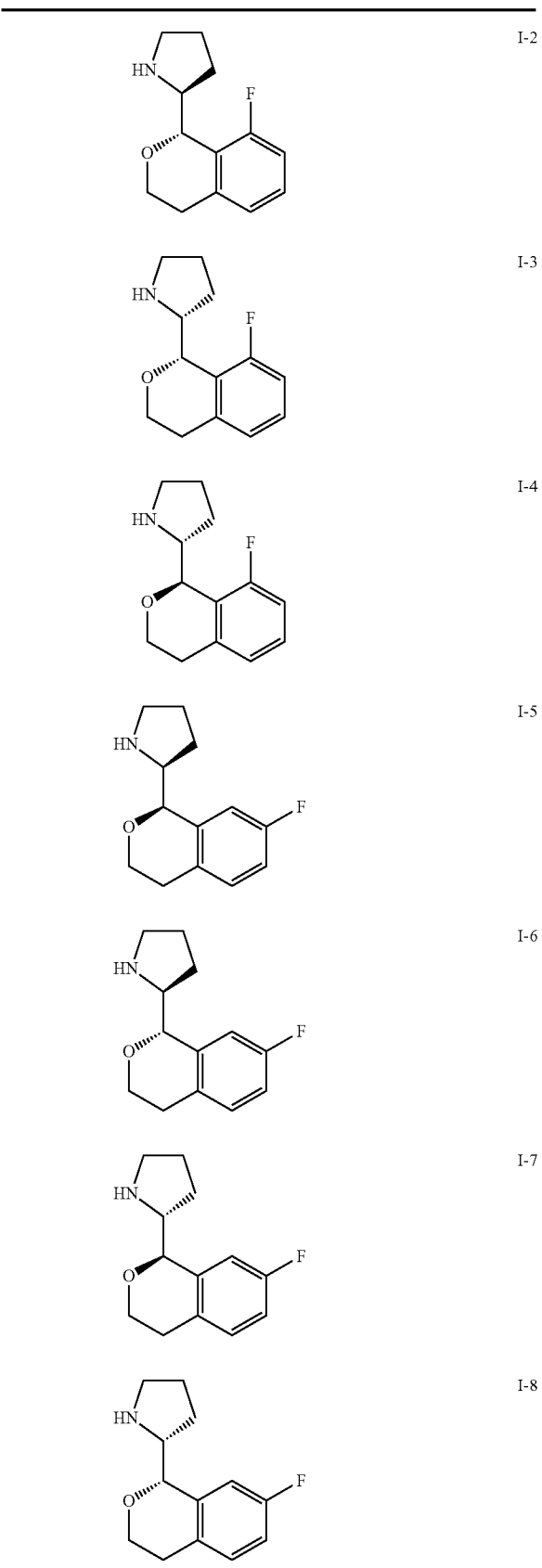
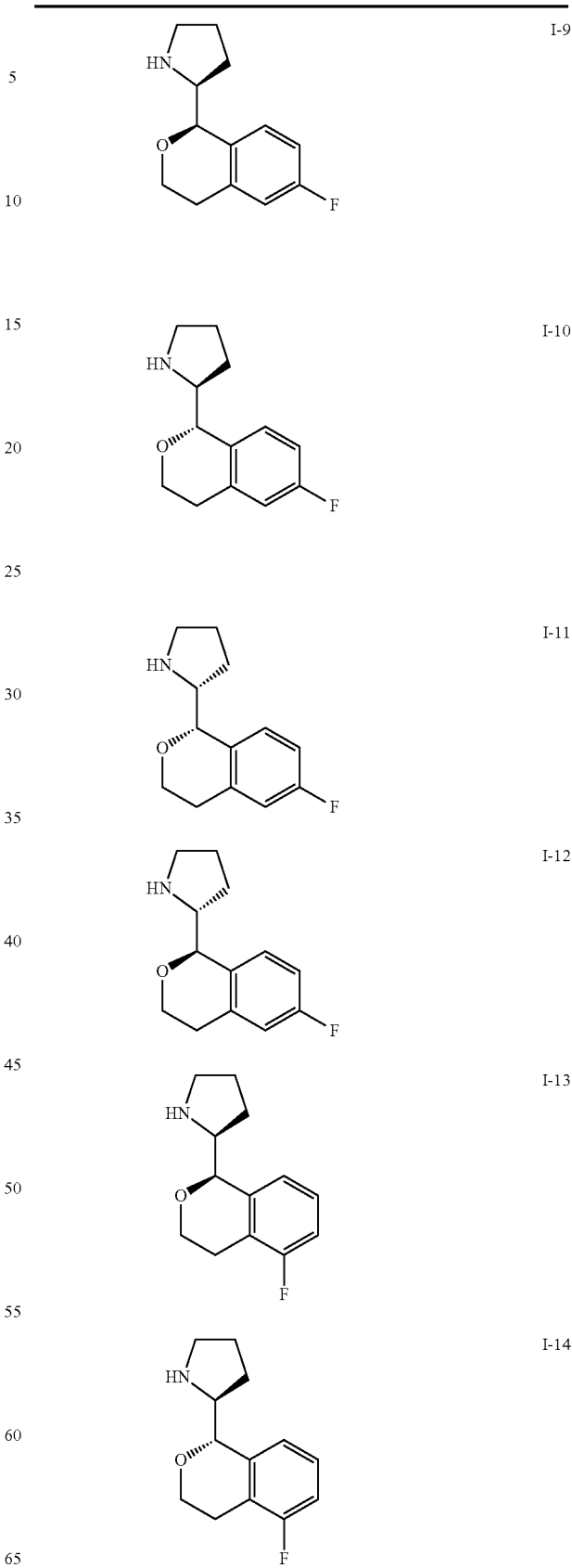

TABLE 1-continued
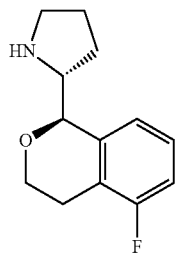 I-15
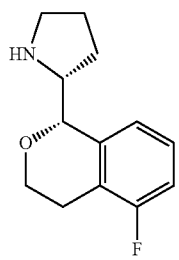 I-16
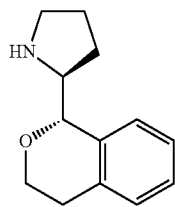 [SMILES: c1ccc2c(c1)CCO[C@@H]2[C@@H]1CCCN1] I-17
 I-18
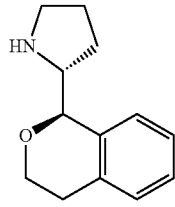 I-19
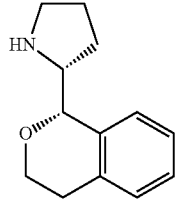 I-20
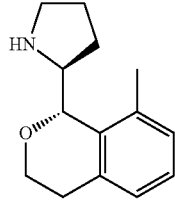 I-21
TABLE 1-continued
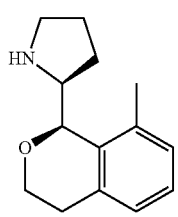 [SMILES: Cc1cccc2c1[C@H]([C@@H]1CCCN1)OCC2] I-22
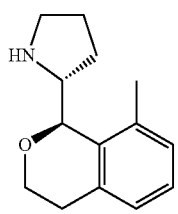 I-23
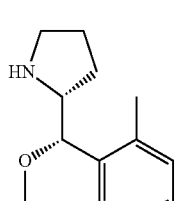 I-24
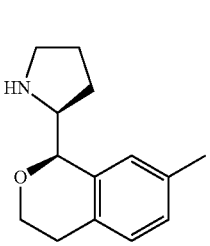 [SMILES: Cc1ccc2c(c1)[C@H]([C@@H]1CCCN1)OCC2] I-25
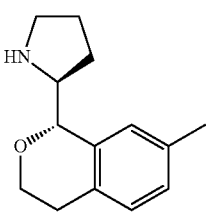 [SMILES: Cc1ccc2c(c1)[C@@H]([C@@H]1CCCN1)OCC2] I-26
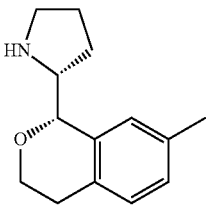 I-27
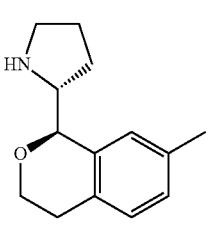 [SMILES: Cc1ccc2c(c1)[C@H]([C@H]1CCCN1)OCC2] I-28

| | |
|---|---|
| 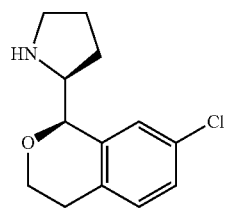 [SMILES: Clc1ccc2c(c1)[C@H]([C@@H]1CCCN1)OCC2] | I-29 |
| 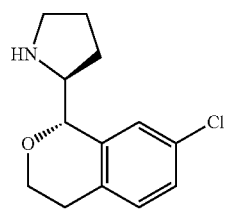 [SMILES: Clc1ccc2c(c1)[C@@H]([C@@H]1CCCN1)OCC2] | I-30 |
| 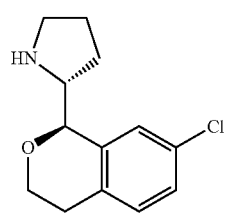 [SMILES: Clc1ccc2c(c1)[C@H]([C@H]1CCCN1)OCC2] | I-31 |
| 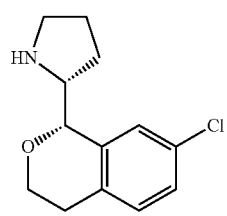 [SMILES: Clc1ccc2c(c1)[C@@H]([C@H]1CCCN1)OCC2] | I-32 |
| 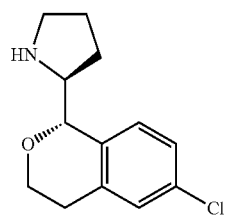 [SMILES: Clc1ccc2c(c1)CCO[C@@H]2[C@@H]1CCCN1] | I-33 |
| 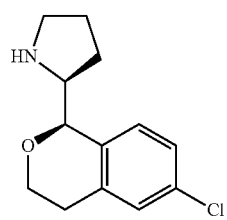 [SMILES: Clc1ccc2c(c1)CCO[C@H]2[C@@H]1CCCN1] | I-34 |
| 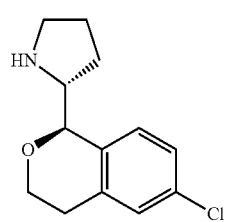 | I-35 |
| 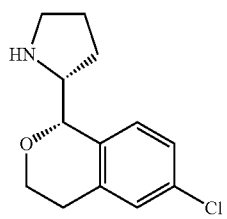 [SMILES: Clc1ccc2c(c1)CCO[C@@H]2[C@H]1CCCN1] | I-36 |
| 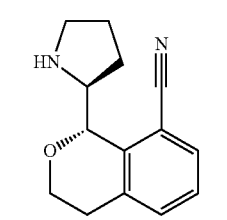 | I-37 |
| 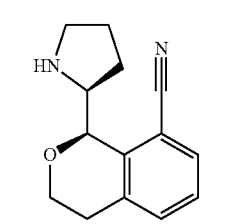 [SMILES: N#Cc1cccc2c1[C@H]([C@@H]1CCCN1)OCC2] | I-38 |
| 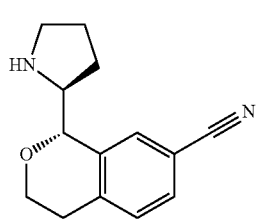 [SMILES: N#Cc1ccc2c(c1)[C@@H]([C@@H]1CCCN1)OCC2] | I-39 |
| 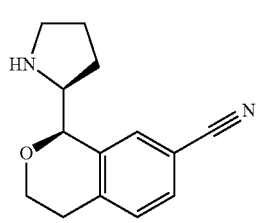 [SMILES: N#Cc1ccc2c(c1)[C@H]([C@@H]1CCCN1)OCC2] | I-40 |
| 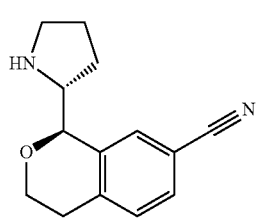 [SMILES: N#Cc1ccc2c(c1)[C@H]([C@H]1CCCN1)OCC2] | I-41 |
| 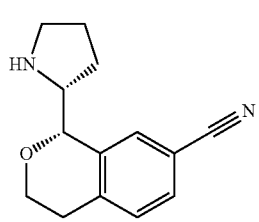 [SMILES: N#Cc1ccc2c(c1)[C@@H]([C@H]1CCCN1)OCC2] | I-42 |

TABLE 1-continued
I-43
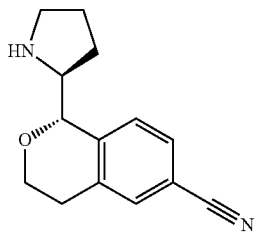 [SMILES: N#Cc1ccc2c(c1)CCO[C@@H]2[C@@H]1CCCN1]
I-44
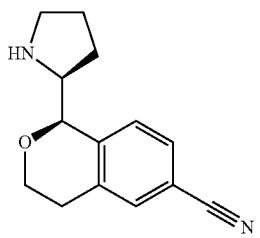 [SMILES: N#Cc1ccc2c(c1)CCO[C@H]2[C@@H]1CCCN1]
I-45
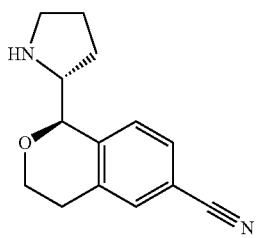 [SMILES: N#Cc1ccc2c(c1)CCO[C@H]2[C@H]1CCCN1]
I-46
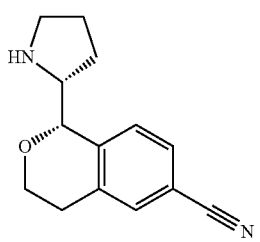 [SMILES: N#Cc1ccc2c(c1)CCO[C@@H]2[C@H]1CCCN1]
I-47
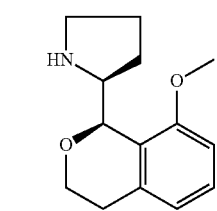 [SMILES: COc1cccc2c1[C@H]([C@@H]1CCCN1)OCC2]
I-48
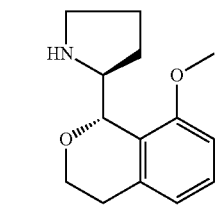 [SMILES: COc1cccc2c1[C@@H]([C@@H]1CCCN1)OCC2]
I-49
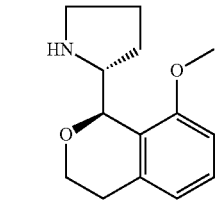 [SMILES: COc1cccc2c1[C@H]([C@H]1CCCN1)OCC2]
I-50
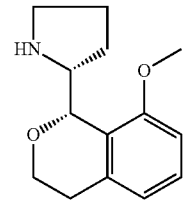 [SMILES: COc1cccc2c1[C@@H]([C@H]1CCCN1)OCC2]
I-51
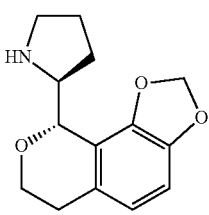
I-52
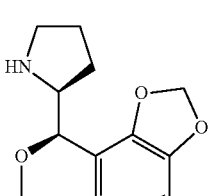
I-53
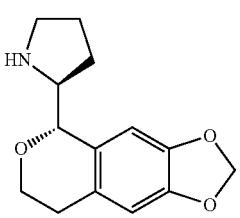 [SMILES: c1c2c(cc3c1OCO3)[C@@H]([C@@H]1CCCN1)OCC2]
I-54
I-55
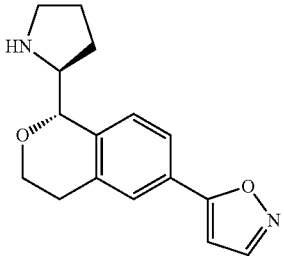 [SMILES: c1cc(-c2ccc3c(c2)CCO[C@@H]3[C@@H]2CCCN2)on1]
I-56
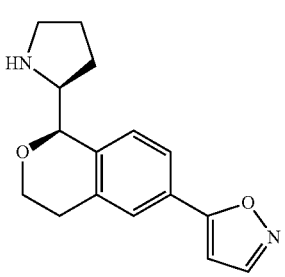 [SMILES: c1cc(-c2ccc3c(c2)CCO[C@H]3[C@@H]2CCCN2)on1]

TABLE 1-continued
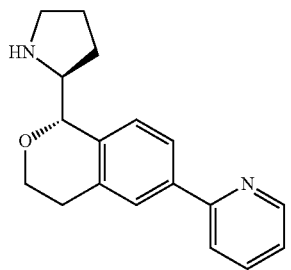 [SMILES: c1ccc(-c2ccc3c(c2)CCO[C@@H]3[C@@H]2CCCN2)nc1] I-57
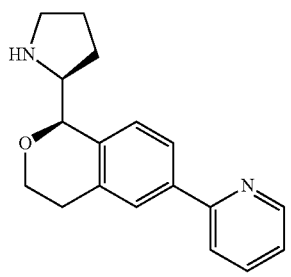 I-58
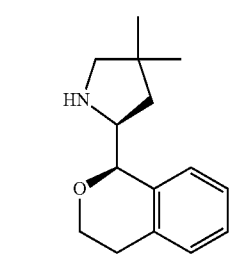 [SMILES: CC1(C)CN[C@H]([C@@H]2OCCc3ccccc32)C1] I-59
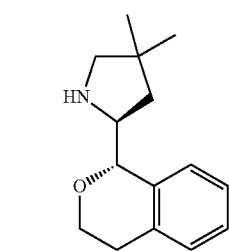 I-60
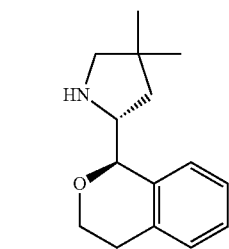 [SMILES: CC1(C)CN[C@@H]([C@@H]2OCCc3ccccc32)C1] I-61
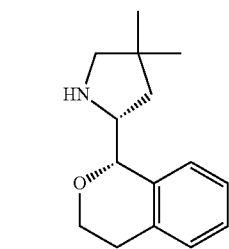 I-62
TABLE 1-continued
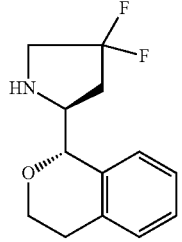 I-63
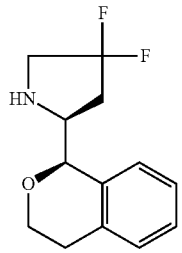 [SMILES: FC1(F)CN[C@H]([C@@H]2OCCc3ccccc32)C1] I-64
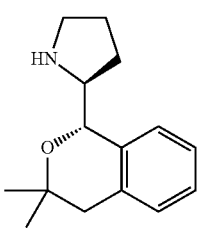 [SMILES: CC1(C)Cc2ccccc2[C@@H]([C@@H]2CCCN2)O1] I-65
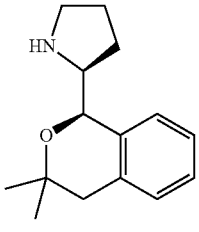 [SMILES: CC1(C)Cc2ccccc2[C@H]([C@@H]2CCCN2)O1] I-66
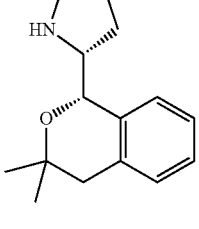 I-67
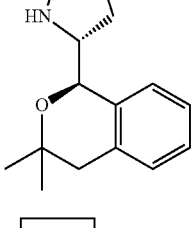 I-68
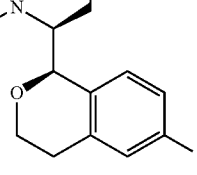 I-69

TABLE 1-continued
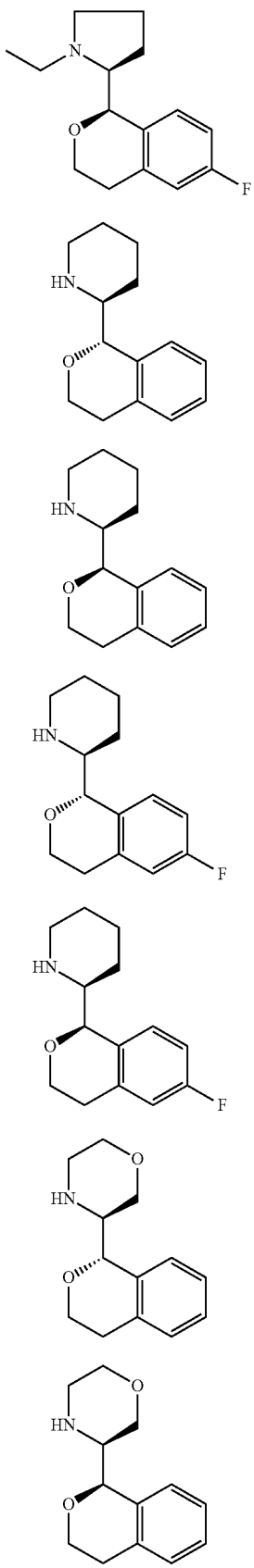
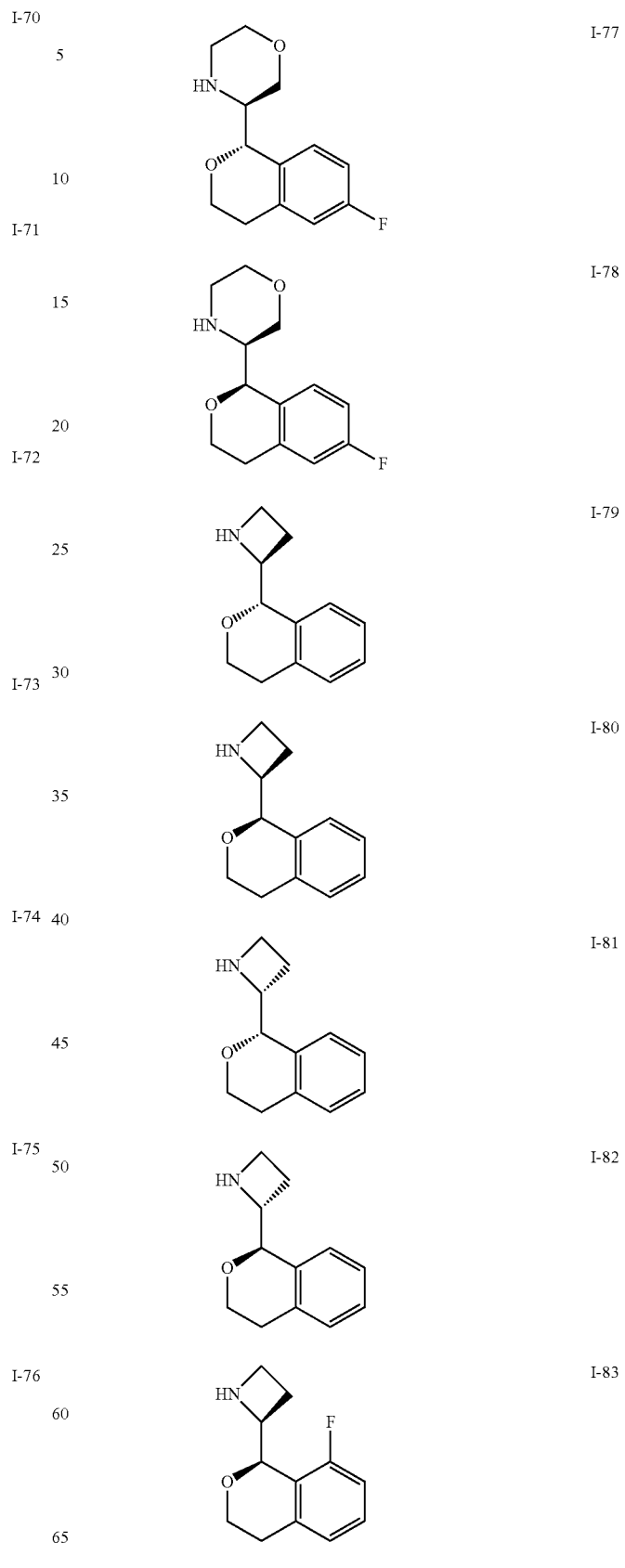

TABLE 1-continued

| | |
|---|---|
| I-84 | I-91 |
| I-85 | I-92 |
| I-86 | I-93 |
| I-87 | I-94 |
| I-88 | I-95 |
| I-89 | I-96 |
| I-90 | |

TABLE 1-continued
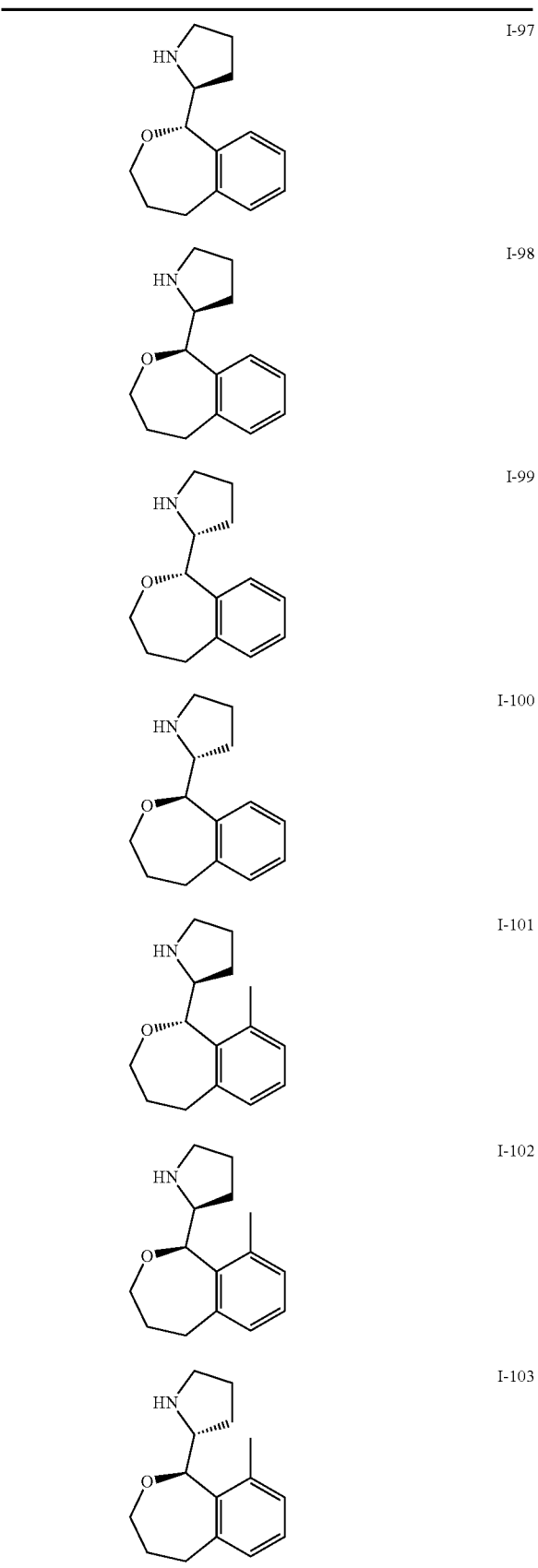
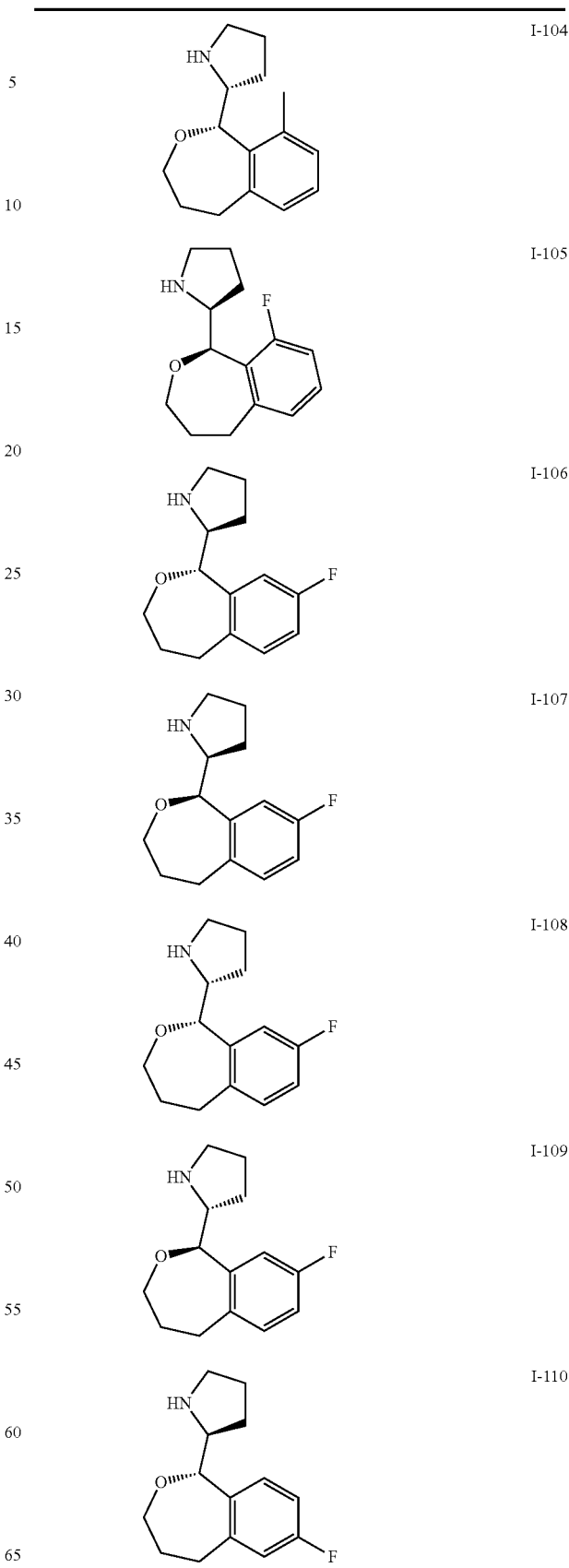

TABLE 1-continued
 I-111
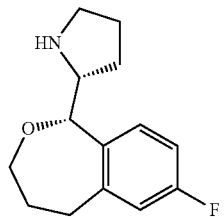 [SMILES: Fc1ccc2c(c1)CCCO[C@@H]2[C@H]1CCCN1] I-112
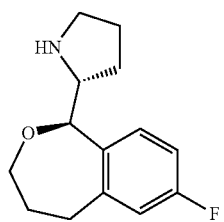 [SMILES: Fc1ccc2c(c1)CCCO[C@H]2[C@H]1CCCN1] I-113
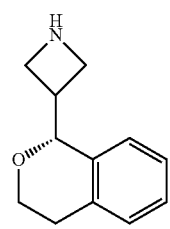 [SMILES: c1ccc2c(c1)CCO[C@@H]2C1CNC1] I-114
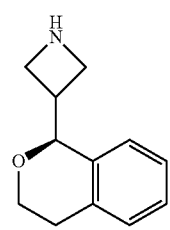 [SMILES: c1ccc2c(c1)CCO[C@H]2C1CNC1] I-115
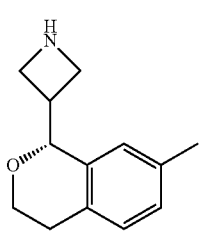 I-116
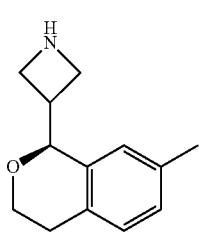 I-117
TABLE 1-continued
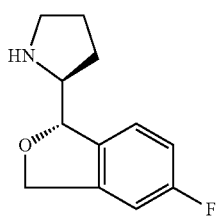 [SMILES: Fc1ccc2c(c1)CO[C@@H]2[C@@H]1CCCN1] I-118
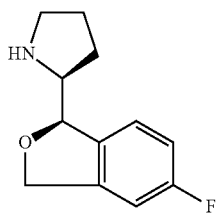 [SMILES: Fc1ccc2c(c1)CO[C@H]2[C@@H]1CCCN1] I-119
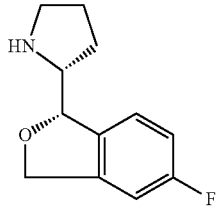 [SMILES: Fc1ccc2c(c1)CO[C@@H]2[C@H]1CCCN1] I-120
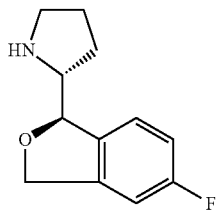 [SMILES: Fc1ccc2c(c1)CO[C@H]2[C@H]1CCCN1] I-121
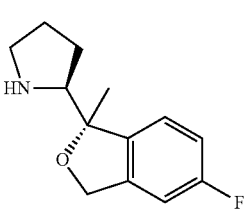 [SMILES: C[C@@]1([C@@H]2CCCN2)OCc2cc(F)ccc21] I-122
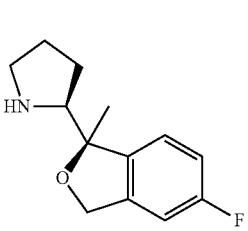 [SMILES: C[C@]1([C@@H]2CCCN2)OCc2cc(F)ccc21] I-123
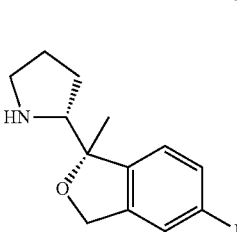 I-124

TABLE 1-continued
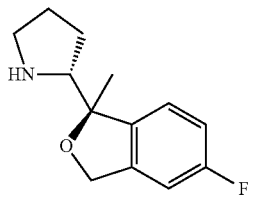 [SMILES: C[C@]1([C@H]2CCCN2)OCc2cc(F)ccc21] I-125
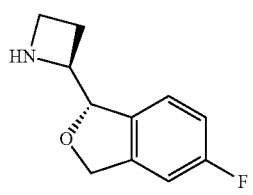 [SMILES: Fc1ccc2c(c1)CO[C@@H]2[C@@H]1CCN1] I-126
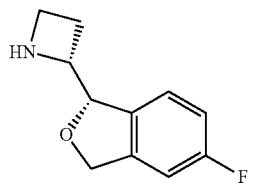 [SMILES: Fc1ccc2c(c1)CO[C@@H]2[C@H]1CCN1] I-127
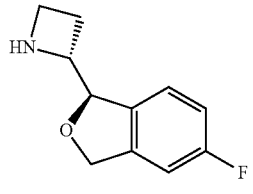 [SMILES: Fc1ccc2c(c1)CO[C@H]2[C@H]1CCN1] I-128
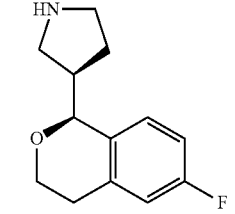 [SMILES: Fc1ccc2c(c1)CCO[C@H]2[C@@H]1CCNC1] I-129
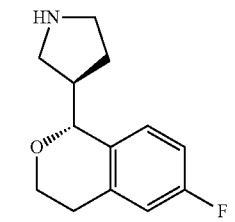 [SMILES: Fc1ccc2c(c1)CCO[C@@H]2[C@@H]1CCNC1] I-130
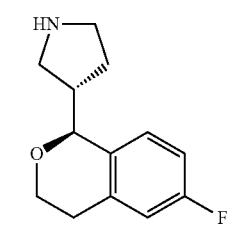 [SMILES: Fc1ccc2c(c1)CCO[C@H]2[C@H]1CCNC1] I-131
TABLE 1-continued
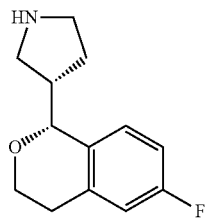 [SMILES: Fc1ccc2c(c1)CCO[C@@H]2[C@H]1CCNC1] I-132
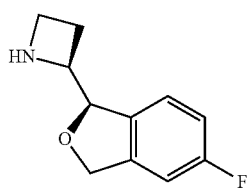 [SMILES: Fc1ccc2c(c1)CO[C@H]2[C@@H]1CCN1] I-133
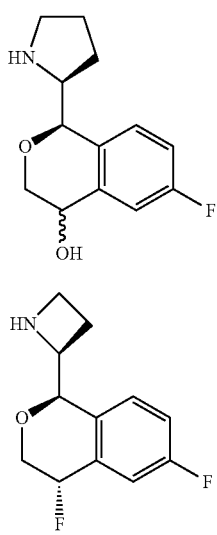 I-134
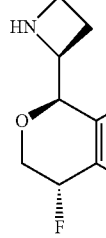 I-135
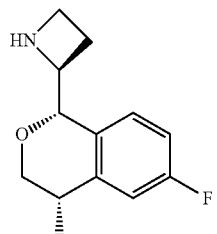 I-136
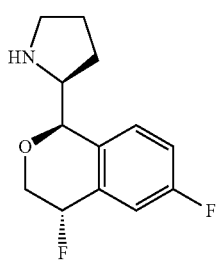 [SMILES: Fc1ccc2c(c1)[C@H](F)CO[C@H]2[C@@H]1CCCN1] I-137

TABLE 1-continued

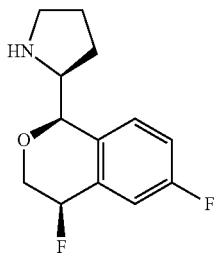 [SMILES: Fc1ccc2c(c1)[C@@H](F)CO[C@H]2[C@@H]1CCCN1]
I-138

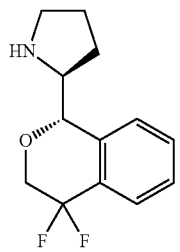 [SMILES: FC1(F)CO[C@H]([C@@H]2CCCN2)c2ccccc21]
I-139

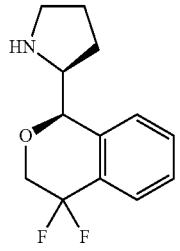 [SMILES: FC1(F)CO[C@@H]([C@@H]2CCCN2)c2ccccc21]
I-140

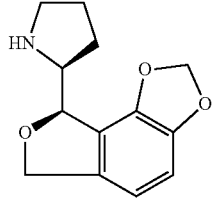 [SMILES: c1cc2c(c3c1CO[C@H]3[C@@H]1CCCN1)OCO2]
I-141

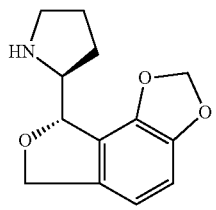 [SMILES: c1cc2c(c3c1CO[C@@H]3[C@@H]1CCCN1)OCO2]
I-142

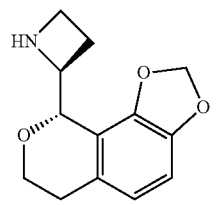 [SMILES: c1cc2c(c3c1CCO[C@@H]3[C@@H]1CCN1)OCO2]
I-143

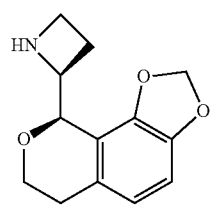 [SMILES: c1cc2c(c3c1CCO[C@H]3[C@@H]1CCN1)OCO2]
I-144

TABLE 1-continued

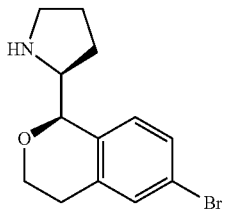
I-145

In some embodiments, the present invention provides a compound selected from those depicted in Table 1, above, or a pharmaceutically acceptable salt thereof.

Schemes below provide exemplary synthetic methods for the preparation of the compounds provided herein. One skilled in the art will understand that suitable adjustments to reagents, protecting groups, reaction conditions, and reaction sequences may be employed to prepare the compounds provided herein.

The compounds of formula (I) may be prepared following Schemes A-D, using suitable starting materials known in the art and/or available from a commercial source. The starting materials of Schemes A-D may be prepared from commercially available compounds using procedures and conditions known in the art.

Scheme A

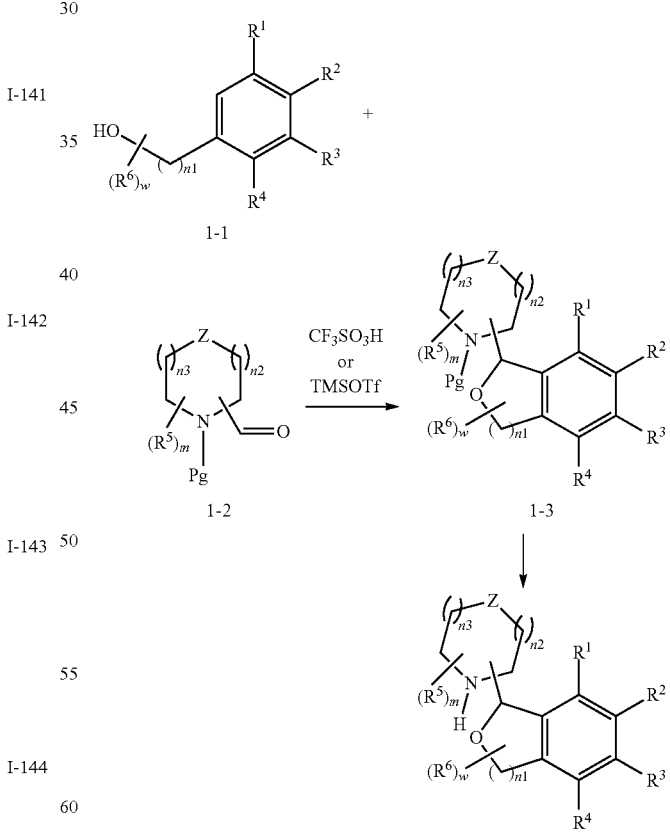

As shown in Scheme A, a suitable hydroxyalkyl substituted benzene (1-1) is reacted with a suitable N-protected aminoaldehyde (1-2) in the presence of an acid or a Lewis acid such as trifluoromethanesulfonic acid or trimethylsilyl trifluoromethanesulfonate to afford a cyclized product (1-3), which can be deprotected to afford a compound of formula (I). Chiral HPLC may be used to separate the enantiomers of a compound of formula (I).

Scheme B

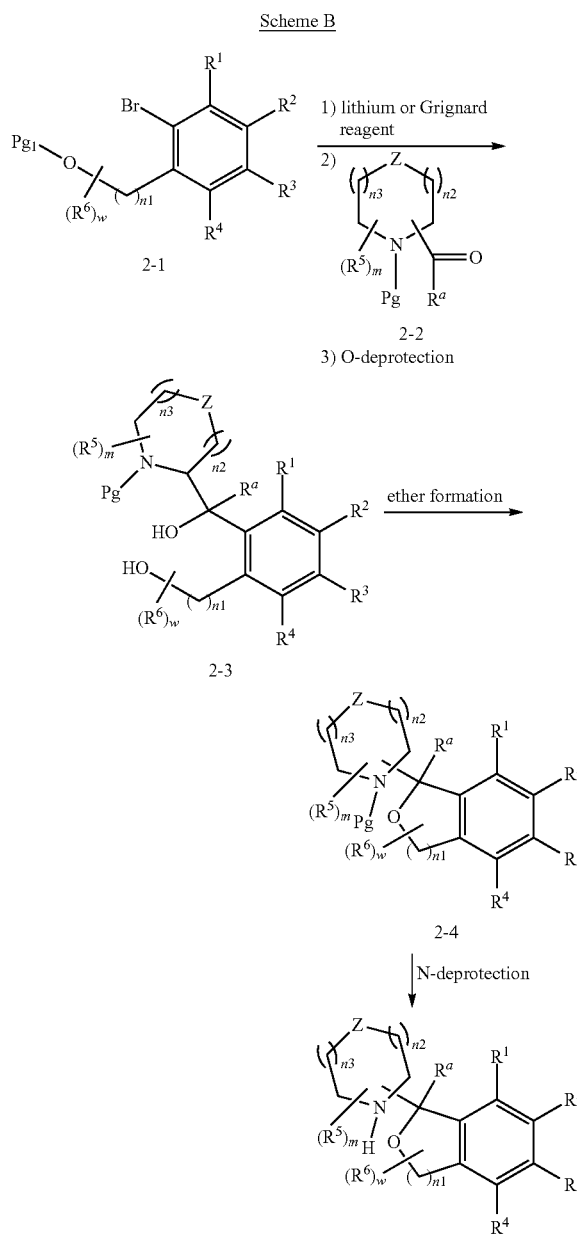

Scheme C

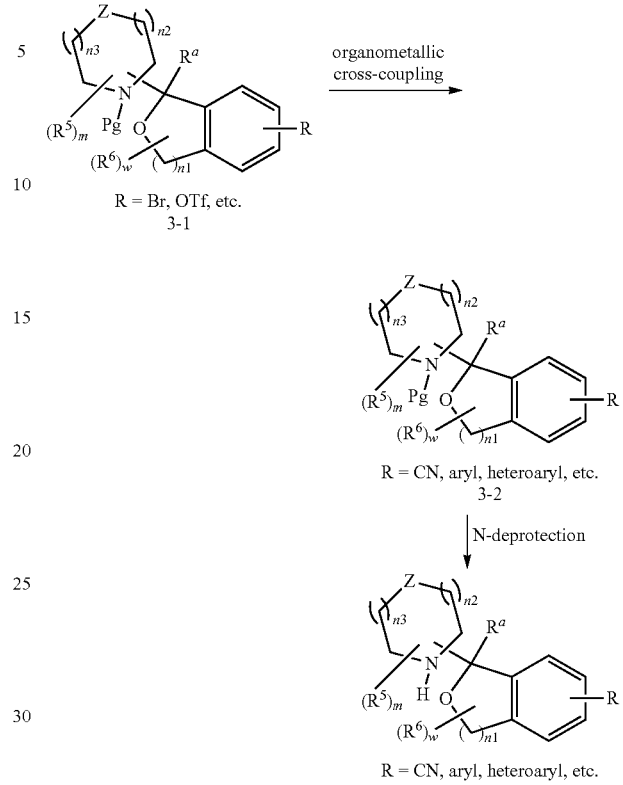

As shown in Scheme C, a suitable bromo- or OTf-substituted N-protected cyclized product (3-1) is converted to the corresponding CN, aryl or heteroaryl substituted product (3-2) under various organometallic cross-coupling conditions known in the art. The cyclized product (3-2) can be N-deprotected to afford a compound of formula (I). Chiral HPLC may be used to separate the enantiomers of a compound of formula (I).

Scheme D

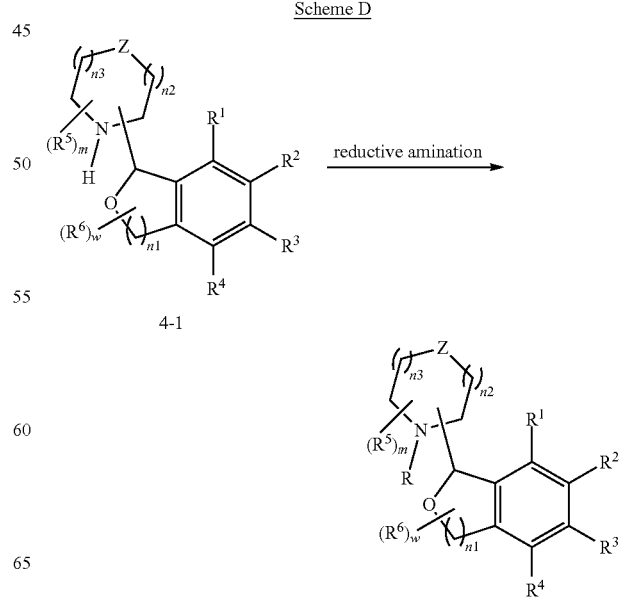

As shown in Scheme B, a suitable 0-protected 1-hydroxy-alkyl-2-bromo-benzene (2-1) is treated with a lithium or Grignard reagent. The anion formed is reacted with a suitable N-protected aminoketone (2-2), followed by 0-deprotection with a suitable deprotecting reagent to afford a diol (2-3). Cyclization of the diol (2-3) to a cyclized product (2-4) is achieved under various conditions (for example, MsCl/Et$_3$N followed by t-BuOK treatment; TMSOTf treatment, etc.). The cyclized product (2-4) can be N-deprotected to afford a compound of formula (I). Chiral HPLC may be used to separate the enantiomers of a compound of formula (I).

As shown in Scheme D, a suitable N-unsubstituted product (4-1) is alkylated under any reductive amination condition known in the art to afford the corresponding compound of formula (I).

4. Uses, Formulation and Administration and Pharmaceutically Acceptable Compositions According to another embodiment, the invention provides a composition comprising a compound of this invention, or a pharmaceutically acceptable salt, ester, or salt of ester thereof, and a pharmaceutically acceptable carrier, adjuvant, or vehicle. In some embodiments, the amount of compound in compositions of this invention is such that is effective to treat, prevent, and/or manage various neurological and/or psychiatric disorders and/or symptoms in a patient. In some embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient may be combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon a variety of factors, including the host treated and the particular mode of administration. Preferably, provided compositions should be formulated so that a dosage of between 0.01-100 mg/kg body weight/day of a compound of the present invention can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

5. Uses of Compounds and Pharmaceutically Acceptable Compositions

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating a neurological or psychiatric disorder.

In some embodiments, the compounds and compositions, according to the method of the present invention, may be administered using any amount and any route of administration effective for treating a neurological and/or psychiatric disorder in a patient.

In some embodiments, the neurological or psychiatric disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both positive, negative, and cognitive symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Down syndrome, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, Parkinsonism-ALS dementia complex and basal ganglia calcification), medication-induced Parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias {including drug e.g. L-DOPA induced dyskinesia tremor (such as rest tremor, postural tremor, intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)}; urinary incontinence; neuronal damage including ocular damage, retinopathy or macular degeneration of the eye, tinnitus, hearing impairment and loss, and brain edema; emesis; and sleep disorders including insomnia and narcolepsy.

In some embodiments, the neurological or psychiatric disorder is Alzheimer's Disease, Parkinson's Disease, depression, cognitive impairment, stroke, schizophrenia, Down Syndrome, or Fetal Alcohol Syndrome. In some embodiments, the neurological or psychiatric disorder is Alzheimer's Disease. In some embodiments, the neurological or psychiatric disorder is Parkinson's Disease. In some embodiments, the neurological or psychiatric disorder is depression. In some embodiments, the neurological or psychiatric disorder is cognitive impairment. In some embodiments, the cognitive impairment is cognitive dysfunction associated with depression, for example, major depressive disorder. In some embodiments, the neurological or psychiatric disorder is stroke. In some embodiments, the neurological or psychiatric disorder is schizophrenia. In some embodiments, the neurological or psychiatric disorder is Down Syndrome. In some embodiments, the neurological or psychiatric disorder is Fetal Alcohol Syndrome.

In some embodiments, the neurological or psychiatric disorder involves a deficit in cognition (cognitive domains as defined by the DSM-5 are: complex attention, executive function, learning and memory, language, perceptual-motor, social cognition). In some embodiments, the neurological or psychiatric disorder is associated with a deficit in dopamine signaling. In some embodiments, the neurological or psychiatric disorder is associated with basal ganglia dysfunction. In some embodiments, the neurological or psychiatric disorder is associated with dysregulated locomotor activity. In some embodiments, the neurological or psychiatric disorder is associated with impairment of prefrontal cortex functioning.

In some embodiments, the present invention provides a method of treating one or more symptoms of a neurological and/or psychiatric disorder provided herein. Such disorders include mood disorders, including bipolar I disorder, bipolar II disorder, bipolar depression, mania, cyclothymic disorder, substance/medication-induced bipolar and related disorders, bipolar and related disorder due to another medical condition, other specified bipolar and related disorder, and unspecified bipolar and related disorders; psychotic disorders, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), schizoaffective disorder, aggression, delirium, Parkinson's psychosis, excitative psychosis, Tourette's syndrome, and organic or NOS psychosis; depressive disorders, including disruptive mood dysregulation disorder, major depressive disorder (MDD) (including major depressive episode), dysthymia, persistent depressive disorder (dysthymia), treatment resistant depression, premenstrual dysphoric disorder, substance/medication-induced depressive disorder, depressive disorder due to another medical condition, other specified depressive disorder, and unspecified depressive disorder; anxiety disorders, including separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders; and other disorders including substance abuse or dependency (e.g., nicotine, alcohol, cocaine), addiction, eating disorders, behavior disorder, seizure, vertigo, epilepsy, agitation, aggression, neurodegenerative disease, Alzheimer's disease, Parkinson's disease, dyskinesias, Huntington's disease, dementia, premenstrual dysphoria; and attention deficit disorder (ADD) and neurodevelopmental disorders, including attention deficit hyperactivity disorder (ADHD)), autism, autism spectrum disorder, obsessive-compulsive disorder, pain (e.g., neuropathic pain, sensitization accompanying neuropathic pain, and inflammatory pain), fibromyalgia, migraine, cognitive impairment, movement disorder, restless leg syndrome (RLS), multiple sclerosis, Parkinson's disease, Huntington's disease, dyskinesias multiple sclerosis, sleep disorder, sleep apnea, narcolepsy, excessive daytime sleepiness, jet lag, drowsy side effect of medications, insomnia, sexual dysfunction, hypertension, emesis, Lesche-Nyhane disease, Wilson's disease, and Huntington's chorea. In some embodiments, the neurological and/or psychiatric disorders include agitation and aggression. In some embodiments, the agitation and aggression are associated with Alzheimer's Disease, Parkinson's Disease, and/or autism. In some embodiments, the neurological and/or psychiatric disorders are obsessive-compulsive disorder and related disorders (e.g., body dysmorphic disorder, hoarding disorder, trichotillomania, excoriation disorder). In some embodiments, the neurological and/or psychiatric disorders are disruptive, impulse-control, and conduct disorders including oppositional defiant disorder, intermittent explosive disorder, conduct disorder, antisocial personality disorder, pyromania, kleptomania, other specified disruptive, impulse-control, and conduct disorder, unspecified disruptive, impulse-control, and conduct disorder.

In some embodiments, the present invention provides a method of treating one or more symptoms including depression (e.g., major depressive disorder or dysthymia); bipolar disorder, seasonal affective disorder; cognitive deficit; sleep related disorder (e.g., sleep apnea, insomnia, narcolepsy, cataplexy) including those sleep disorders which are produced by psychiatric conditions; chronic fatigue syndrome; anxieties (e.g., general anxiety disorder, social anxiety disorder, panic disorder); obsessive compulsive disorder; postmenopausal vasomotor symptoms (e.g., hot flashes, night sweats); neurodegenerative disease (e.g., Parkinson's disease, Alzheimer's disease and amyotrophic lateral sclerosis); manic disorder; dysthymic disorder; and obesity.

In some embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In some embodiments, a provided compound does not increase the risk of suicidal thinking and/or behavior in children, adolescents and/or young adults with a depressive disorder, e.g., with MDD. In some embodiments, the present invention provides a method of treating one or more symptoms of a depressive disorder (e.g., MDD) in children, adolescents and/or young adults without increasing the risk of suicidal thinking and/or behavior.

In some embodiments, the present invention provides a method of treating one or more symptoms including senile dementia, Alzheimer's type dementia, cognition, memory loss, amnesia/amnestic syndrome, disturbances of consciousness, coma, lowering of attention, speech disorder, Lennox syndrome, and hyperkinetic syndrome.

In some embodiments, the present invention provides a method of treating one or more symptoms of neuropathic pain, including post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

In some embodiments, the present invention provides a method of treating one or more symptoms including obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In some embodiments, the present invention provides a method of suppressing rapid eye movement (REM) during both sleep and daytime equivalent.

In some embodiments, the present invention provides a method of suppressing or eliminating pathological or excessive REM during the night or daytime equivalent.

In some embodiments, the present invention provides a method of treating one or more symptoms including cataplexy (sudden involuntary transient bouts of muscle weakness or paralysis while awake); nighttime sleep disturbance/sleep fragmentation associated with narcolepsy or other conditions; sleep paralysis associated with narcolepsy or other conditions; hypnagogic and hypnapompic hallucinations associated with narcolepsy or other conditions; and excessive daytime sleepiness associated with narcolepsy, sleep apnea or shift work disorder and other medical conditions such as cancer, chronic fatigue syndrome and fibromyalgia.

In some embodiments, the present invention provides a method of treating a neurological and/or psychiatric disorder described herein, comprising administering a compound of the invention in conjunction with one or more pharmaceutical agents. Suitable pharmaceutical agents that may be used in combination with the compounds of the present invention include anti-Parkinson's drugs, anti-Alzheimer's drugs, anti-depressants, anti-psychotics, mood stabilizers, anti-ischemics, CNS depressants, anticholinergics, and nootropics. In some embodiments, suitable pharmaceutical agents are anxiolytics.

Suitable anti-Parkinson's drugs include dopamine replacement therapy (e.g. L-DOPA, carbidopa, COMT inhibitors such as entacapone), dopamine agonists (e.g. D1 agonists, D2 agonists, mixed D1/D2 agonists; bromocriptine, pergolide, cabergoline, ropinirole, pramipexole, or apomorphine in combination with domperidone), histamine H2 antagonists, and monoamine oxidase inhibitors such as selegiline and tranylcypromine.

In some embodiments, compounds of the invention can be used in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MAO A/B inhibitors, antioxidants, Ata adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexole are commonly used in a non-salt form.

Suitable anti-Alzheimer's drugs include beta-secretase inhibitors, gamma-secretase inhibitors, HMG-CoA reductase inhibitors, NSAID's including ibuprofen, vitamin E, and anti-amyloid antibodies. In some embodiments, an anti-Alzheimer's drug is memantine.

Suitable anti-depressants and anti-anxiety agents include norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), serotonin, norepinephrine and dopamine reuptake inhibitors, corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists.

Specific suitable anti-depressant and anti-anxiety agents include amitriptyline, clomipramine, doxepin, imipramine and trimipramine; amoxapine, desipramine, citalopram, escitalopram, maprotiline, nortriptyline and protriptyline; fluoxetine, fluvoxamine, paroxetine and sertraline; isocarboxazid, phenelzine, tranylcypromine and selegiline; moclobemide: venlafaxine; desvenlafaxine; duloxetine; aprepitant; bupropion, mirtazapine, vilazodone, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof. In some embodiments, suitable anti-depressants and anti-anxiety agents are tianeptine, or pharmaceutically acceptable salts thereof.

Suitable anti-psychotic and mood stabilizer agents include D2 antagonists, 5HT2A antagonists, atypical antipsychotics, lithium, and anticonvulsants.

Specific suitable anti-psychotic and mood stabilizer agents include chlorpromazine, fluphenazine, haloperidol, amisulpride, chlorpromazine, perphenazine, thioridazine, trifluoperazine, aripiprazole, asenapine, clozapine, olanzapine, paliperidone, quetiapine, risperidone, ziprasidone, lurasidone, flupentixol, levomepromazine, pericyazine, perphenazine, pimozide, prochlorperazine, zuclopenthixol, olanzapine and fluoxetine, lithium, carbamazepine, lamotrigine, valproic acid and pharmaceutically acceptable salts thereof.

In some embodiments, compounds of the invention may be used in combination with other therapies. Suitable therapies include psychotherapy, cognitive behavioral therapy, electroconvulsive therapy, transcranial magnetic stimulation, vagus nerve stimulation, and deep-brain stimulation.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In some embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In some embodiments, a combination of 2 or more therapeutic agents may be administered together with the compounds of the invention. In some embodiments, a combination of 3 or more therapeutic agents may be administered with the compounds of the invention.

Other examples of agents the compounds of this invention may also be combined with include: vitamins and nutritional supplements, antiemetics (e.g. 5-HT3 receptor antagonists, dopamine antagonists, NK1 receptor antagonists, histamine receptor antagonists, cannabinoids, benzodiazepines, or anticholinergics), agents for treating Multiple Sclerosis (MS) such as beta interferon (e.g., Avonex® and Rebif®), Copaxone®, and mitoxantrone; treatments for asthma such as albuterol and Singulair®; anti-inflammatory agents such as corticosteroids, TNF blockers, IL-1 RA, azathioprine, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In some embodiments, a compound of the present invention, or a pharmaceutically acceptable salt thereof, is administered in combination with an antisense agent, a monoclonal or polyclonal antibody, or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, or a pharmaceutically acceptable salt thereof, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions may be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present invention provides a medicament comprising at least one compound of formula I, or a pharmaceutically acceptable salt thereof, and a pharmaceutically acceptable carrier, adjuvant, or vehicle.

In some embodiments, the present invention provides the use of a compound of formula I, or a pharmaceutically acceptable salt thereof, in the manufacture of a medicament for the treatment of a neurological and/or psychiatric disorder.

EXAMPLES

As depicted in the Examples below, in some embodiments, compounds are prepared according to the following procedures. It will be appreciated that, although the general methods depict the synthesis of certain compounds of the present invention, the following methods, and other methods known to one of ordinary skill in the art, can be applied to all compounds and subclasses and species of each of these compounds, as described herein.

In the examples below, unless otherwise indicated, all temperatures are set forth in degrees Celsius and all parts and percentages are by weight. Reagents were purchased from commercial suppliers, such as Sigma-Aldrich Chemical Company, and were used without further purification unless otherwise indicated. Reagents were prepared following standard literature procedures known to those skilled in the art. All solvents requiring purification or drying were treated using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates (Merck Art 5719) and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous KMnO$_4$ solution activated with heat. Flash column chromatography (See, e.g., Still et al., J. Org. Chem., 43: 2923 (1978)) was performed using silica gel 60 (Merck Art 9385) or various MPLC systems.

The compound structures in the examples below were confirmed by one or more of the following methods: proton magnetic resonance spectroscopy, mass spectroscopy, and melting point. Proton magnetic resonance ($^1$H NMR) spectra were determined using an NMR spectrometer operating at 400 MHz field strength. Chemical shifts are reported in the form of delta (δ) values given in parts per million (ppm) relative to an internal standard, such as tetramethylsilane (TMS). Alternatively, $^1$H NMR spectra were referenced to signals from residual protons in deuterated solvents as follows: CDCl$_3$=7.25 ppm; DMSO-d$_6$=2.49 ppm; C$_6$D$_6$=7.16 ppm; CD$_3$OD=3.30 ppm. Peak multiplicities are designated as follows: s, singlet; d, doublet; dd, doublet of doublets; t, triplet; dt, doublet of triplets; q, quartet; quint, quintet; sept, septet; br, broadened; and m, multiplet. Coupling constants are given in Hertz (Hz). Mass spectra (MS) data were obtained using a mass spectrometer with APCI or ESI ionization.

As used herein, and unless otherwise specified, "Me" means methyl, "Et" means ethyl, "Ac" means acetyl, "BINAP" means 2,2'-bis(diphenylphosphino)-1,1'-binaphthyl, "Dens-Martin reagent" means 1,1,1-tris(acetyloxy)-1,1-dihydro-1,2-benziodoxol-3-(1H)-one, "DCM" means dichloromethane, "DIEA" means diisopropylethylamine, "DMF" means dimethylformamide, "EDCI" means N-(3-dimethylaminopropyl)-N'-ethylcarbodiimide hydrochloride, "EtOAc" means ethyl acetate, "EtOH" means ethanol, "HATU" means O-(7-azabenzotriazol-1-yl)-N, N, N', N'-tetramethyluronium hexafluorophosphate, "HOBt" means hydroxybenzotriazole, "m-CPBA" means 3-chloro-perbenzoic acid, "MeCN" means acetonitrile, "MeOH" means methanol, "PE" means petroleum ether, "RT" or "rt" means room temperature, "t-BuOH" means Cert-butanol, "t-BuONa" means sodium Cert-butoxide, "TBDMSCI" means Cert-butyldimethylsilyl chloride, "TEA" means triethylamine, "THF" means tetrahydrofuran, "TMSI" means iodotrimethylsilane, "Xantphos" means 4,5-bis(diphenylphosphino)-9,9-dimethylxanthene, "h" or "hr" means hour(s), "min" means minute(s), "cat." means catalytic, "aq" means aqueous, and "TFA" means trifluoroacetic acid.

Example 1. Preparation of Compounds

Example 1.1. Procedure A. Certain Provided Compounds were Made Following a Procedure Exemplified by Example 1.1.1

Example 1.1.1. (S)-2-((S)-isochroman-1-yl)pyrrolidine (I-17) and (S)-2-((R)-isochroman-1-yl)pyrrolidine (I-18)

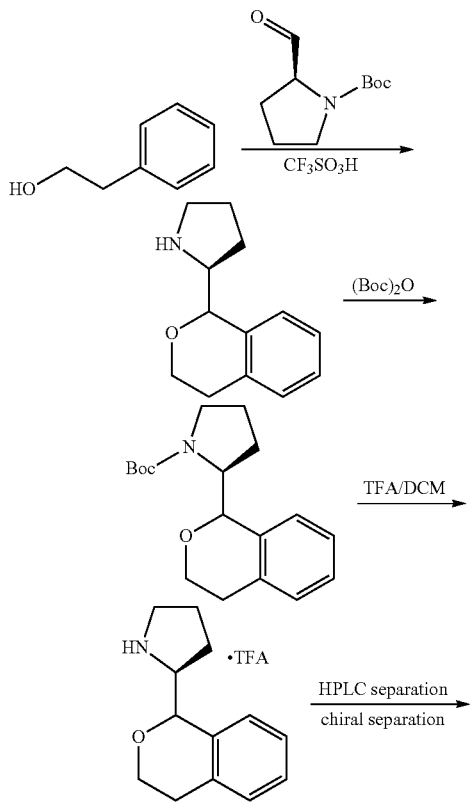

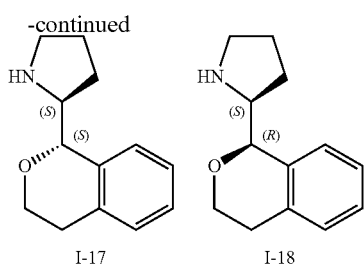

(a). (2S)-2-(isochroman-1-yl)pyrrolidine

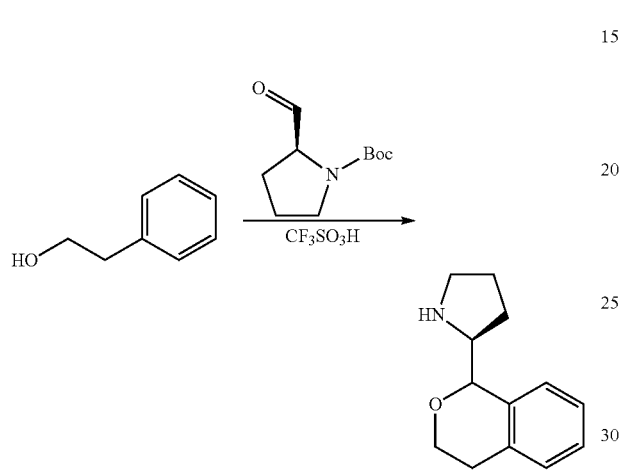

To a mixture of 2-phenylethanol (2 g, 16.38 mmol) and (S)-tert-butyl 2-formylpyrrolidine-1-carboxylate (6.52 g, 32.76 mmol) was added trifluoromethanesulphonic acid (3 mL) at 0° C. slowly. After the reaction was stirred at room temperature for 2 h, ice-water (50 mL) was added. The mixture was extracted with dichloromethane/MeOH (10:1, 50 mL×3). The organic layers were combined, dried and concentrated to give the crude product (2.65 g) as brown oil. ESI: m/z=204[M+H]$^+$.

(b). (2S)-tert-butyl 2-(isochroman-1-yl) pyrrolidine-1-carboxylase

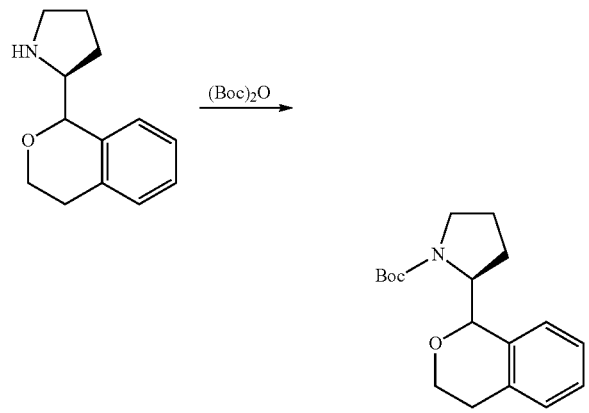

To crude (2S)-2-(isochroman-1-yl) pyrrolidine (2.65 g, 13 mmol) obtained above was added water (50 mL), sodium hydroxide (1 g, 26 mmol), and then di-tert-butyl dicarbonate (5.69 g, 26 mmol). The mixture was stirred at room temperature for 1 h. The mixture was extracted with EtOAc (30 mL×3), and the organic layers were combined, dried and concentrated. The crude was purified by reverse gel column chromatography (eluted with water/CH$_3$CN=100:65, 0.01% NH$_4$OH) to give the desired compound (3.65 g as a colorless oil).

(c). TFA Salt of (2S)-2-(isochroman-1-yl) pyrrolidine

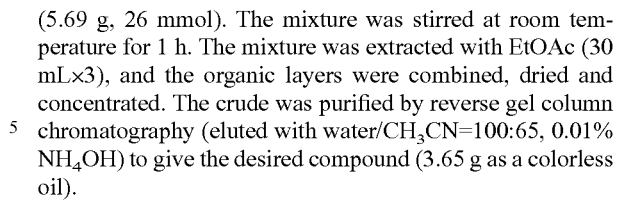

To a solution of TFA (5 mL) in methylene chloride (20 mL) was added (2S)-tert-butyl 2-(isochroman-1-yl) pyrrolidine-1-carboxylate (3.65 g, 12 mmol). The mixture was stirred at room temperature for 3 h and the solvent was removed to yield the crude product 2.3 g, as colorless oil. MS (ESI): m/z=204[M+H]$^+$.

(d). (S)-2-((S)-isochroman-1-yl) pyrrolidine and (S)-2-((R)-isochroman-1-yl) pyrrolidine

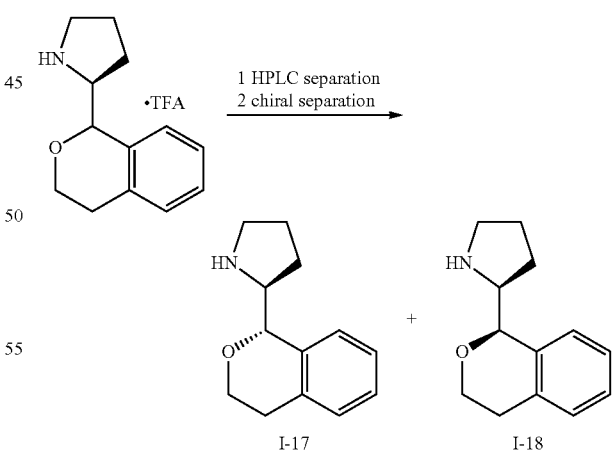

The mixture from previous step (1.95 g, 9.6 mmol) was purified and separated by prep. HPLC in 0.01% aqueous TFA to give the two diastereoisomers, which were separately further purified by chiral HPLC using Column: AY-H (250*4.6 mm 5 μm) and Mobile Phase: n-Hexane (0.1% DEA):EtOH (0.1% DEA)=90:10 to give (S)-2-((S)-isochroman-1-yl)pyrrolidine (86 mg yellow oil, R.T.: 7.042 min, ee %: 98%) and (S)-2-((R)-6-fluoroisochroman-1-yl) pyrrolidine (360 mg yellow oil, R.T.: 7.408 min, ee %: 100%).

¹HNMR of (S)-2-((S)-isochroman-1-yl)pyrrolidine (I-17) (400 MHz, CDCl₃) δ 7.26~7.11 (m, 4H), 4.78 (d, J=3.2 Hz, 1H), 4.24~4.20 (m, 1H), 3.79~3.76 (td, J₁=10.8, J₂=3.5 Hz, 1H), 3.59~3.57 (td, J₁=7.5, J₂=3.9 Hz, 1H), 3.11~2.98 (m, 2H), 2.79~2.76 (m, 1H), 2.69~2.65 (m, 1H), 2.28 (s, 1H), 1.96~1.73 (m, 4H).

¹HNMR of (S)-2-((R)-isochroman-1-yl)pyrrolidine (I-18) (400 MHz, CDCl₃) δ 7.19~7.12 (m, 4H), 5.00 (d, J=2.5 Hz, 1H), 4.23~4.18 (m, 1H), 3.78~3.72 (td, J₁=11.3, J₁=3.0 Hz, 1H), 3.59~3.57 (td, J₁=7.9, J₁=3.5 Hz, 1H), 3.22~2.99 (m, 2H), 2.86~2.81 (m, 1H), 2.63~2.61 (m, 1H), 2.27 (s, 1H), 1.71~1.66 (m, 2H), 1.50~1.44 (m, 2H).

Example 1.1.2. (R)-2-((S)-5-fluoroisochroman-1-yl) pyrrolidine (I-16) and (R)-2-((R)-5-fluoroisochroman-1-yl)pyrrolidine (I-15)

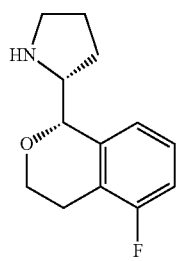

I-16

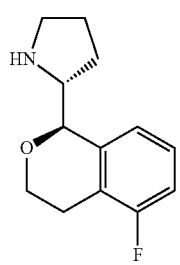

I-15

(R)-2-((S)-5-fluoroisochroman-1-yl)pyrrolidine (I-16) and (R)-2-((R)-5-fluoroisochroman-1-yl)pyrrolidine (I-15) were prepared using a procedure analogous to that described in Example 1.1.1, but using 2-(2-fluoro-phenyl)-ethanol in place of 2-phenylethanol and (R)-tert-butyl 2-formylpyrrolidine-1-carboxylate in place of (S)-tert-butyl 2-formylpyrrolidine-1-carboxylate.

(R)-2-((S)-5-fluoroisochroman-1-yl)pyrrolidine (I-16): MS (ESI): m/z 222 (M+H)⁺. ¹H NMR (400 MHz, CDCl₃) δ 7.21-7.10 (m, 1H), 6.97 (d, J=7.8 Hz, 1H), 6.89 (t, J=8.7 Hz, 1H), 4.94 (s, 1H), 4.23 (ddd, J=11.3, 5.8, 1.9 Hz, 1H), 3.69 (td, J=11.1, 3.7 Hz, 1H), 3.57 (td, J=7.9, 3.5 Hz, 1H), 3.19-3.06 (m, 1H), 2.91-2.68 (m, 3H), 1.76-1.62 (m, 2H), 1.53-1.37 (m, 2H).

(R)-2-((R)-5-fluoroisochroman-1-yl)pyrrolidine (I-15): MS (ESI): m/z 222 (M+H)⁺. ¹H NMR (400 MHz, CDCl₃) δ 7.21-7.10 (m, 1H), 7.05 (d, J=7.8 Hz, 1H), 6.89 (t, J=8.7 Hz, 1H), 4.72 (d, J=3.2 Hz, 1H), 4.24 (ddd, J=11.3, 5.8, 2.9 Hz, 1H), 3.73 (ddd, J=11.2, 10.3, 4.0 Hz, 1H), 3.58 (td, J=7.5, 3.8 Hz, 1H), 3.03 (ddd, J=10.3, 6.9, 5.4 Hz, 1H), 2.87 (ddd, J=16.1, 10.1, 5.8 Hz, 1H), 2.76 (dt, J=10.4, 7.5 Hz, 2H), 1.90 (dd, J=11.6, 4.2 Hz, 2H), 1.84-1.71 (m, 2H).

Example 1.1.3. (S)-2-((S)-isochroman-1-yl)azetidine (I-79) and (S)-2-((R)-iso-chroman-1-yl)azetidine (I-80)

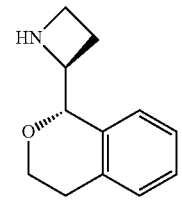

I-79

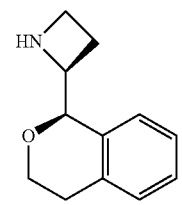

I-80

(S)-2-((S)-isochroman-1-yl)azetidine (I-79) and (S)-2-((R)-iso-chroman-1-yl)azetidine (I-80) were prepared using a procedure analogous to that described in Example 1.1.1, but using (S)-tert-butyl 2-formylazetidine-1-carboxylate in place of (S)-tert-butyl 2-formylpyrrolidine-1-carboxylate.

(S)-2-((S)-isochroman-1-yl)azetidine (I-79): MS (ESI): m/z 190 [M+H]⁺, ¹HNMR (400 MHz, CDCL3): δ 7.10-7.21 (m, 4H), 4.73-4.74 (d, 1=6.0 Hz, 1H), 4.18-4.26 (m, 2H), 3.78-3.85 (dt, J₁=3.6 Hz, J₂=10.0 Hz, 1H), 3.59-3.65 (q, 1=7.6 Hz, 1H), 3.42-3.47 (m, 1H), 3.00-3.06 (m, 1H), 2.55-2.74 (m, 2H), 2.35-2.43 (m, 1H), 2.11 (br, 1H).

(S)-2-((R)-iso-chroman-1-yl)azetidine (I-80): MS (ESI): m/z 190 [M+H]⁺, ¹HNMR (400 MHz, MeOD): δ 7.20-7.271 (m, 3H), 7.10-7.12 (m, 1H), 5.10-5.14 (m, 2H), 4.39-4.44 (m, 1H), 3.85-4.05 (m, 3H), 3.14-3.23 (m, 1H), 2.72-2.76 (m, 1H), 2.21-39 (m, 2H).

Example 1.1.4. (S)-2-((S)-5-fluoroisochroman-1-yl) azetidine (I-94) and (S)-2-((R)-5-fluoroisochroman-1-yl)azetidine (I-93)

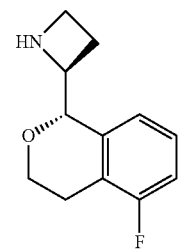

I-94

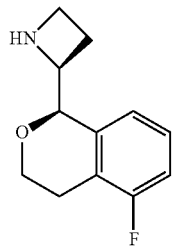

I-93

(S)-2-((S)-5-fluoroisochroman-1-yl)azetidine (I-94) and (S)-2-((R)-5-fluoroisochroman-1-yl)azetidine (I-93) were prepared using a procedure analogous to that described in Example 1.1.1, but using 2-(2-fluorophenyl)ethanol in place of 2-phenylethanol and (S)-tert-butyl 2-formylazetidine-1-carboxylate in place of (S)-tert-butyl 2-formylpyrrolidine-1-carboxylate.

(S)-2-((S)-5-fluoroisochroman-1-yl)azetidine (I-94): MS (ESI): m/z 208 [M+H]$^+$, $^1$HNMR (HCl salt, 400 MHz, MeOD): δ 7.27-7.33 (m, 1H), 7.04-7.08 (m, 2H), 5.13-5.18 (dt, J$_1$=3.6 Hz, J$_2$=8.4 Hz, 1H), 5.02 (s, 1H), 4.39-4.44 (m, 1H), 4.04-4.11 (q, 1=8.8 Hz, 1H), 3.81-3.91 (m, 2H), 2.94-3.08 (m, 2H), 2.79-2.93 (m, 1H), 2.51-2.66 (m, 1H).

(S)-2-((R)-5-fluoroisochroman-1-yl)azetidine (I-93): MS (ESI): m/z 208 [M+H]$^+$, $^1$HNMR (HCl salt, 400 MHz, MeOD): δ 7.24-7.29 (m, 1H), 7.02-7.06 (t, 1=8.8 Hz, 1H), 6.94-6.96 (d, 1=7.6 Hz, 1H), 5.13-5.16 (m, 2H), 4.44-4.49 (m, 1H), 3.83-4.04 (m, 3H), 2.95-3.03 (m, 1H), 2.83-2.88 (m, 1H), 2.10-2.36 (m, 2H).

Example 1.1.5. (S)-2-((S)-6-fluoroisochroman-1-yl)azetidine (I-89) and (S)-2-((R)-6-fluoroisochroman-1-yl)azetidine (I-90)

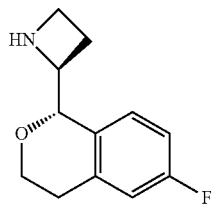

I-89

I-90

(S)-2-((S)-6-fluoroisochroman-1-yl)azetidine (I-89) and (S)-2-((R)-6-fluoroisochroman-1-yl)azetidine (I-90) were prepared using a procedure analogous to that described in Example 1.1.1, but using 2-(3-fluorophenyl) ethanol in place of 2-phenylethanol and (S)-tert-butyl 2-formylazetidine-1-carboxylate in place of (S)-tert-butyl 2-formylpyrrolidine-1-carboxylate.

(S)-2-((S)-6-fluoroisochroman-1-yl)azetidine (I-89): MS (ESI) m/z 208 (M+H)$^+$ $^1$H NMR (HCl salt, 400 MHz, MeOD) δ 7.13 (m, 1H), 6.90 (m, 2H), 4.69 (d, J=6.0 Hz, 1H), 4.28 (m, 1H), 4.19 (m, 1H), 3.77 (m, 1H), 3.58 (m, 1H), 3.37 (m, 1H), 3.05 (m, 1H), 2.72 (m, 2H), 2.38 (m, 1H).

(S)-2-((R)-6-fluoroisochroman-1-yl)azetidine (I-90): MS (ESI) m/z 208 (M+H)$^+$ $^1$H NMR (HCl salt, 400 MHz, MeOD) δ 7.17-7.14 (m, 1H), 7.01-6.99 (m, 2H), 5.10-5.12 (m, 2H), 4.39-4.44 (m, 1H), 3.98-4.03 (m, 1H), 3.92-3.85 (m, 2H), 3.18 (m, 1H), 2.78-2.79 (m, 1H), 2.30-2.34 (m, 2H).

Example 1.1.6. (S)-2-((S)-7-fluoroisochroman-1-yl)azetidine (I-85) and (S)-2-((R)-7-fluoroisochroman-1-yl)azetidine (I-86)

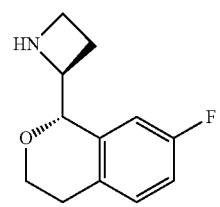

I-85

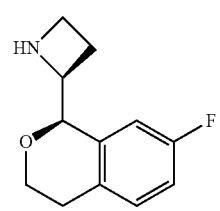

I-86

(S)-2-((S)-7-fluoroisochroman-1-yl)azetidine (I-85) and (S)-2-((R)-7-fluoroisochroman-1-yl)azetidine (I-86) were prepared using a procedure analogous to that described in Example 1.1.1, but using 2-(4-fluorophenyl)ethanol in place of 2-phenylethanol and (S)-tert-butyl 2-formylazetidine-1-carboxylate in place of (S)-tert-butyl 2-formylpyrrolidine-1-carboxylate.

(S)-2-((S)-7-fluoroisochroman-1-yl)azetidine (I-85): MS (ESI) m/z 208 (M+H)$^+$, $^1$H NMR (400 MHz, MeOD) δ 7.26 (m, 1H), 7.03 (m, 2H), 5.11 (m, 1H), 4.98 (m, 1H), 4.36 (m, 1H), 4.08 (m, 1H), 3.87 (m, 2H), 3.16 (m, 1H), 2.98 (m, 1H), 2.73 (m, 1H), 2.61 (m, 1H).

(S)-2-((R)-7-fluoroisochroman-1-yl)azetidine (I-86): MS (ESI) m/z 208 (M+H)$^+$, $^1$H NMR (HCl salt, 400 MHz, MeOD) δ 7.15 (m, 1H), 6.93 (m, 2H), 4.73 (d, J=5.2 Hz, 1H), 4.30 (m, 1H), 4.23 (m, 1H), 3.74 (m, 1H), 3.59 (m, 1H), 3.39 (m, 1H), 2.98 (m, 1H), 2.69 (m, 1H), 2.31 (m, 1H), 2.15 (m, 1H).

Example 1.1.7. (R)-2-((S)-7-fluoroisochroman-1-yl)azetidine (I-88) and (R)-2-((R)-7-fluoroisochroman-1-yl)azetidine (I-87)

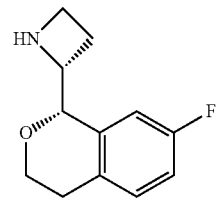

I-88

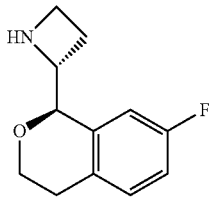

I-87

(R)-2-((S)-7-fluoroisochroman-1-yl)azetidine (I-88) and (R)-2-((R)-7-fluoroisochroman-1-yl)azetidine (I-87) were prepared using a procedure analogous to that described in Example 1.1.1, but using 2-(4-fluorophenyl)ethanol in place of 2-phenylethanol and (R)-tert-butyl 2-formylazetidine-1-carboxylate in place of (S)-tert-butyl 2-formylpyrrolidine-1-carboxylate.

(R)-2-((S)-7-fluoroisochroman-1-yl)azetidine (I-88): MS (ESI) m/z: 208 (M+H)$^{+1}$. $^1$H NMR (HCl salt, 400 MHz, MeOD) δ 7.20~'7.16 (q, J=6.4 Hz, 1H), 6.96~'6.91 (m, 2H), 4.77 (d, J=4.8 Hz, 1H), 4.40~'4.34 (m, 1H), 4.28~'4.24 (m, 1H), 3.80~3.73 (m, 1H), 3.65~'3.59 (q, I=8.4 Hz, 1H), 3.48~'3.42 (m, 1H), 3.04~'2.96 (m, 1H), 2.71~'2.67 (m, 1H), 2.35~'2.21 (m, 1H), 2.19~2.12 (m, 1H).

(R)-2-((R)-7-fluoroisochroman-1-yl)azetidine (I-87): MS (ESI) m/z: 208 (M+H)$^{+1}$. $^1$H NMR (HCl salt, 400 MHz, MeOD) δ 7.18~'7.15 (q, J=5.6 Hz, 1H), 6.95~'6.87 (m, 2H), 4.69 (d, J=5.6 Hz, 1H), 4.32'''4.21 (m, 2H), 3.80~'3.74 (m, 1H), 3.61~'3.55 (q, J=8.4 Hz, 1H), 3.40~'3.32 (m, 1H), 3.06~2.98 (m, 1H), 2.72~2.63 (m, 2H), 2.43~2.35 (m, 1H).

Example 1.1.8. (R)-2-((S)-isochroman-1-yl)azetidine (I-81) and (R)-2-((R)-isochroman-1-yl)azetidine (I-82)

I-81

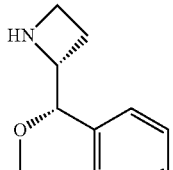

I-82

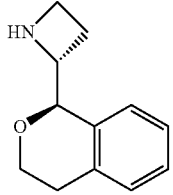

(R)-2-((S)-isochroman-1-yl)azetidine (I-81) and (R)-2-((R)-isochroman-1-yl)azetidine (I-82) were prepared using a procedure analogous to that described in Example 1.1.1, but using (R)-tert-butyl 2-formylazetidine-1-carboxylate in place of (S)-tert-butyl 2-formylpyrrolidine-1-carboxylate.

(R)-2-((S)-isochroman-1-yl)azetidine (I-81): MS (ESI) m/z: 190 (M+H)$^{+1}$. $^1$H NMR 400 MHz, CDCl$_3$) δ 7.25~7.09 (m, 4H), 4.79~4.78 (d, J=5.6 Hz, 1H), 4.35-4.18 (m, 2H), 3.78 (td, J$_1$=10.9, J$_2$=3.2 Hz, 1H), 3.62 (q, J=8.1 Hz, 1H), 3.44~3.39 (m, 1H), 3.07~3.0 (m, 1H), 2.69~2.65 (m, 1H), 2.59 (s, 1H), 2.43~2.31 (m, 1H), 2.18~2.14 (m, 1H).

(R)-2-((R)-isochroman-1-yl)azetidine (I-82): MS (ESI) m/z: 190 (M+H)$^{+1}$. $^1$H NMR (400 MHz, CDCl$_3$) δ 7.25~7.06 (m, 4H), 4.75~4.739 (d, J=6.3 Hz, 1H), 4.26~4.21 (m, 2H), 3.87~3.78 (m, 1H), 3.63 (dd, J$_1$=15.5, J$_2$=8.0 Hz, 1H), 3.50~3.42 (m, 1H), 3.08~3.01 (m, 1H), 2.74~2.69 (m, 1H), 2.66-2.55 (m, 1H), 2.42~2.36 (m, 2H).

Example 1.1.9. (R)-2-((S)-5-fluoroisochroman-1-yl)azetidine (I-96) and (R)-2-((R)-5-fluoroisochroman-1-yl)azetidine (I-95)

I-96

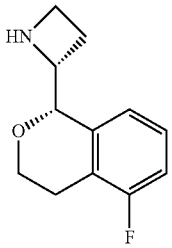

I-95

(R)-2-((S)-5-fluoroisochroman-1-yl)azetidine (I-96) and (R)-2-((R)-5-fluoroisochroman-1-yl)azetidine (I-95) were prepared using a procedure analogous to that described in Example 1.1.1, but using 2-(2-fluorophenyl)ethanol in place of 2-phenylethanol and (R)-tert-butyl 2-formylazetidine-1-carboxylate in place of (S)-tert-butyl 2-formylpyrrolidine-1-carboxylate.

(R)-2-((S)-5-fluoroisochroman-1-yl)azetidine (I-96): MS (ESI) m/z: 208 (M+H)$^{+1}$. $^1$H NMR (HCl salt, 400 MHz, MeOD) δ 7.30~7.24 (m, 1H), 7.04 (t, J=8.8 Hz, 1H), 6.97 (d, J=7.8 Hz, 1H), 5.16 (d, J=13.4 Hz, 2H), 4.53-4.42 (m, 1H), 4.07-3.97 (m, 1H), 3.92~3.84 (m, 2H), 2.99~2.95 (m, 1H), 2.88~2.83 (m, 1H), 2.42-2.19 (m, 2H).

(R)-2-((R)-5-fluoroisochroman-1-yl)azetidine (I-95): MS (ESI) m/z: 208 (M+H)$^{+1}$. $^1$H NMR (HCl salt, 400 MHz, MeOD) δ 7.33~7.27 (m, 1H), 7.08~7.03 (m, 1H), 5.15 (s, 1H), 5.02 (s, 1H), 4.43~4.38 (m, 1H), 4.09~4.06 (m, 1H), 3.91~3.84 (m, 2H), 3.03~2.96 (m, 1H), 2.83~2.79 (m, 1H), 2.64~2.62 (m, 1H).

Example 1.1.10. (R)-2-((S)-6-fluoroisochroman-1-yl)azetidine (I-91) and (R)-2-((R)-6-fluoroisochroman-1-yl)azetidine (I-92)

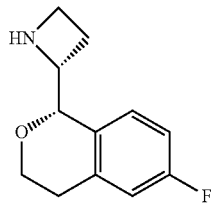

I-91

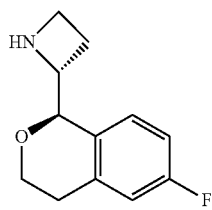

I-92

(R)-2-((S)-6-fluoroisochroman-1-yl)azetidine (I-91) and (R)-2-((R)-6-fluoroisochroman-1-yl)azetidine (I-92) were prepared using a procedure analogous to that described in Example 1.1.1, but using 2-(3-fluorophenyl)ethanol in place of 2-phenylethanol and (R)-tert-butyl 2-formylazetidine-1-carboxylate in place of (5)-tert-butyl 2-formylpyrrolidine-1-carboxylate.

(R)-2-((S)-6-fluoroisochroman-1-yl)azetidine (I-91): MS (ESI) m/z: 208 (M+H)$^{+1}$. $^1$H NMR (HCl salt, 400 MHz, MeOD) δ 7.25 (dd, J=8.5, 5.7 Hz, 1H), 7.02 (dd, J=13.0, 5.7 Hz, 2H), 5.11 (td, J=8.6, 3.7 Hz, 1H), 4.99 (s, 1H), 4.35 (ddd, J=11.3, 6.0, 1.7 Hz, 1H), 4.17-3.99 (m, 1H), 3.97-3.75 (m, 2H), 3.22 (ddd, J=17.1, 11.4, 6.0 Hz, 1H), 3.08-2.88 (m, 1H), 2.74 (d, J=16.7 Hz, 1H), 2.68-2.50 (m, 1H).

(R)-2-((R)-6-fluoroisochroman-1-yl)azetidine (I-92): MS (ESI) m/z: 208 (M+H)$^{+1}$. $^1$H NMR (HCl salt, 400 MHz, MeOD) δ 7.15 (dd, J=8.3, 5.5 Hz, 1H), 6.98 (dd, J=15.4, 6.3 Hz, 2H), 5.12 (p, J=3.2 Hz, 2H), 4.41 (dd, J=11.3, 5.9 Hz, 1H), 4.02 (td, J=9.8, 8.0 Hz, 1H), 3.96-3.78 (m, 2H), 3.28-3.09 (m, 1H), 2.76 (d, J=16.6 Hz, 1H), 2.44-2.18 (m, 2H).

Example 1.1.11. (S)-2-((S)-7-chloroisochroman-1-yl)pyrrolidine (I-30) and (S)-2-((R)-7-chloroisochroman-1-yl)pyrrolidine (I-29)

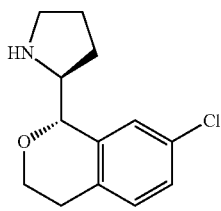

I-30

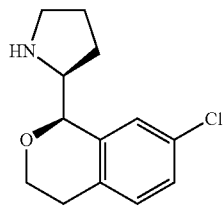

I-29

(S)-2-((S)-7-chloroisochroman-1-yl)pyrrolidine (I-30) and (S)-2-((R)-7-chloroisochroman-1-yl)pyrrolidine (I-29) were prepared using a procedure analogous to that described in Example 1.1.1, but using 2-(4-chlorophenyl)ethanol in place of 2-phenylethanol.

(S)-2-((S)-7-chloroisochroman-1-yl)pyrrolidine (I-30): MS (ESI) m/z: 238 (M+H)$^{+1}$. $^1$H NMR (HCl salt, 400 MHz, MeOD) δ 7.32-7.33 (m, 1H), 7.13-7.21 (m, 2H), 4.79 (s, 1H), 4.20-4.25 (m, 1H), 3.70-3.77 (m, 1H), 3.61-3.66 (m, 1H), 2.98-3.08 (m, 2H), 2.64-2.77 (m, 2H), 1.95-2.01 (m, 2H), 1.81-1.88 (m, 2H).

(S)-2-((R)-7-chloroisochroman-1-yl)pyrrolidine (I-29): MS (ESI) m/z: 238 (M+H)$^{+1}$. $^1$H NMR (HCl salt, 400 MHz, MeOD) δ 7.23 (s, 1H), 7.14-7.21 (m, 2H), 4.93 (s, 1H), 4.20-4.24 (m, 1H), 3.67-3.74 (m, 1H), 3.59-3.64 (m, 1H), 3.08-3.14 (m, 1H), 2.95-3.04 (m, 1H), 2.78-2.84 (m, 1H), 2.63-2.67 (1=16.4 Hz, d, 1H), 1.70-1.78 (m, 2H), 1.45-1.51 (m, 2H).

Example 1.1.12. (S)-2-((S)-7-methylisochroman-1-yl)pyrrolidine (I-26) and (S)-2-((R)-7-methylisochroman-1-yl)pyrrolidine (I-25)

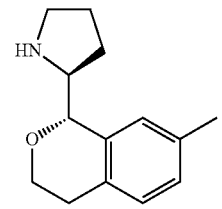

I-26

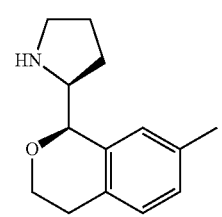

I-25

(S)-2-((S)-7-methylisochroman-1-yl)pyrrolidine (I-26) and (S)-2-((R)-7-methylisochroman-1-yl)pyrrolidine (I-25) were prepared using a procedure analogous to that described in Example 1.1.1, but using 2-(p-tolyl)ethanol in place of 2-phenylethanol.

(S)-2-((S)-7-methylisochroman-1-yl)pyrrolidine (I-26): MS (ESI) m/z: 218 (M+H)$^{+1}$.

(S)-2-((R)-7-methylisochroman-1-yl)pyrrolidine (I-25): MS (ESI) m/z: 218 (M+H)$^{+1}$.

Example 1.1.13. (R)-2-((S)-7-methylisochroman-1-yl)pyrrolidine (I-27) and (R)-2-((R)-7-methylisochroman-1-yl)pyrrolidine (I-28)

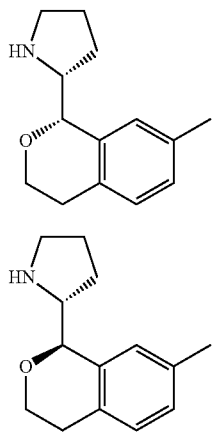

(R)-2-((S)-7-methylisochroman-1-yl)pyrrolidine (I-27) and (R)-2-((R)-7-methylisochroman-1-yl)pyrrolidine (I-28) were prepared using a procedure analogous to that described in Example 1.1.1, but using 2-(p-tolyl)ethanol in place of 2-phenylethanol and (R)-tert-butyl 2-formylpyrrolidine-1-carboxylate in place of (S)-tert-butyl 2-formylpyrrolidine-1-carboxylate.

(R)-2-((S)-7-methylisochroman-1-yl)pyrrolidine (I-27): MS (ESI) m/z: 218 (M+H)$^{+1}$.

(R)-2-((R)-7-methylisochroman-1-yl)pyrrolidine (I-28): MS (ESI) m/z: 218 (M+H)$^{+1}$.

Example 1.1.14. (R)-2-((S)-7-chloroisochroman-1-yl)pyrrolidine (I-32) and (R)-2-((R)-7-chloroisochroman-1-yl)pyrrolidine (I-31)

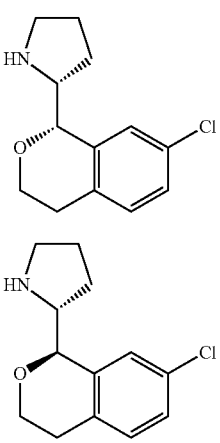

(R)-2-((S)-7-chloroisochroman-1-yl)pyrrolidine (I-32) and (R)-2-((R)-7-chloroisochroman-1-yl)pyrrolidine (I-31) were prepared using a procedure analogous to that described in Example 1.1.1, but using 2-(4-chlorophenyl)ethanol in place of 2-phenylethanol and (R)-tert-butyl 2-formylpyrrolidine-1-carboxylate in place of (S)-tert-butyl 2-formylpyrrolidine-1-carboxylate.

(R)-2-((S)-7-chloroisochroman-1-yl)pyrrolidine (I-32): MS (ESI) m/z: 238 (M+H)$^{+1}$.

(R)-2-((R)-7-chloroisochroman-1-yl)pyrrolidine (I-31): MS (ESI) m/z: 238 (M+H)$^{+1}$.

Example 1.1.15. (S)-2-((S)-6-chloroisochroman-1-yl)pyrrolidine (I-33) and (S)-2-((R)-6-chloroisochroman-1-yl)pyrrolidine (I-34)

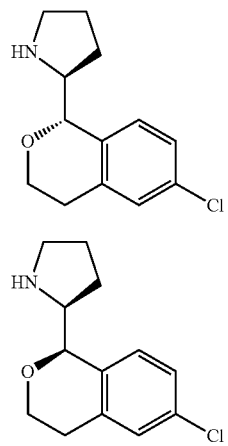

(S)-2-((S)-6-chloroisochroman-1-yl)pyrrolidine (I-33) and (S)-2-((R)-6-chloroisochroman-1-yl)pyrrolidine (I-34) were prepared using a procedure analogous to that described in Example 1.1.1, but using 2-(3-chlorophenyl)ethanol in place of 2-phenylethanol.

(S)-2-((S)-6-chloroisochroman-1-yl)pyrrolidine (I-33): (ESI) m/z: 238[M+H]$^{+}$. $^{1}$H NMR (400 MHz, CDCl$_{3}$): δ 7.21-7.15 (m, 2H), 7.12 (s, 1H), 4.74 (d, J=3.6 Hz, 1H), 4.24-4.19 (m, 1H), 3.77-3.71 (m, 1H), 3.63-3.58 (m, 1H), 3.08-3.00 (m, 2H), 2.82-2.76 (m, 2H), 2.66 (m, 1H), 1.94-1.77 (m, 4H).

(S)-2-((R)-6-chloroisochroman-1-yl)pyrrolidine (I-34): (ESI) m/z: 238[M+H]$^{+}$. $^{1}$H NMR (400 MHz, MeOD): δ 7.28-7.21 (m, 3H), 5.19 (s, 1H), 4.38-4.29 (m, 2H), 3.83-3.76 (td, J$^{1}$=2.8 Hz, J$^{2}$=12.0 Hz, 1H), 3.38-3.32 (m, 2H), 3.14-3.06 (m, 1H), 2.73-2.69 (m, 1H), 2.09-1.93 (m, 2H), 1.80-1.74 (m, 2H).

Example 1.1.16. (R)-2-((S)-6-chloroisochroman-1-yl)pyrrolidine (I-36) and ((R)-2-((R)-6-chloroisochroman-1-yl)pyrrolidine (I-35)

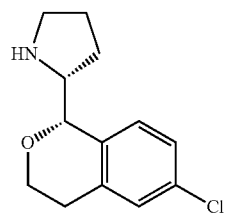

-continued

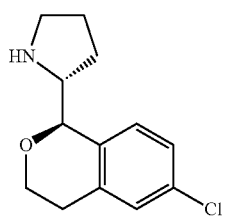

I-35

(R)-2-((S)-6-chloroisochroman-1-yl)pyrrolidine (I-36) and (R)-2-((R)-6-chloroisochroman-1-yl)pyrrolidine (I-35) were prepared using a procedure analogous to that described in Example 1.1.1, but using 2-(3-chlorophenyl)ethanol in place of 2-phenylethanol and (R)-tert-butyl 2-formylpyrrolidine-1-carboxylate in place of (S)-tert-butyl 2-formylpyrrolidine-1-carboxylate.

(R)-2-((S)-6-chloroisochroman-1-yl)pyrrolidine (I-36): MS (ESH: m/z 238 [M+H]$^+$; $^1$H NMR (300 MHz, DMSO-d$_6$) δ9.65 (s, 1H), 8.70 (s, 1H), 7.40-7.20 (m, 3H), 5.12 (s, 1H), 4.40-4.10 (m, 2H), 3.71 (td, J=11.5, 2.9 Hz, 1H), 3.27-3.06 (m, 2H), 3.06-2.92 (m, 1H), 2.69 (d, J=16.7 Hz, 1H), 1.97-1.45 (m, 4H).

(R)-2-((R)-6-chloroisochroman-1-yl)pyrrolidine (I-35): MS (ESI): m/z 238 [M+H]$^+$; $^1$H NMR (300 MHz, DMSO-d$_6$) δ9.55 (s, 1H), 8.28 (s, 1H), 7.37-7.24 (m, 3H), 4.94 (d, J=4.1 Hz, 1H), 4.21-4.06 (m, 2H), 3.73 (td, J=10.9, 3.6 Hz, 1H), 3.15-3.00 (m, 3H), 2.70 (d, J=16.7 Hz, 1H), 2.09-1.79 (m, 4H).

Example 1.1.17. (S)-2-((S)-isochroman-1-yl)piperidine (I-71) and (S)-2-((R)-isochroman-1-yl)piperidine (I-72)

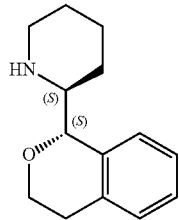

I-71

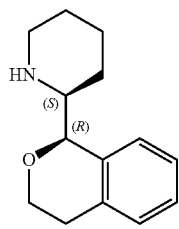

I-72

(S)-2-((S)-isochroman-1-yl)piperidine (I-71) and (S)-2-((R)-isochroman-1-yl)piperidine (I-72) were prepared using a procedure analogous to that described in Example 1.1.1, but using (5)-tert-butyl 2-formylpiperidine-1-carboxylate in place of (5)-tert-butyl 2-formylpyrrolidine-1-carboxylate.

(S)-2-((S)-isochroman-1-yl)piperidine (I-71): MS (ESI): m/z 218 [M+H]+. $^1$HNMR (400 MHz, MeOD): δ 7.30-7.32 (m, 3H), 7.25 (m, 1H), 4.88 (s, 1H), 4.28-4.30 (m, 1H), 3.71-3.79 (m, 2H), 3.23-3.26 (m, 1H), 3.07-3.13 (m, 1H), 2.90-2.96 (m, 1H), 2.69-2.73 (d, J=16, 1H), 2.05-2.07 (m, 3H), 1.99-2.01 (m, 1H), 1.69-1.91 (m, 2H).

(S)-2-((R)-isochroman-1-yl)piperidine (I-72): MS (ESI): m/z 218 [M+H]+. $^1$HNMR (400 MHz, MeOD): δ 7.18-7.29 (m, 4H), 5.10 (s, 1H), 4.28-4.32 (m, 1H), 3.74-3.80 (m, 2H), 3.41-3.45 (m, 1H), 3.02-3.19 (m, 2H), 2.66-2.70 (d, J=16, 1 H), 1.81-2.03 (m, 2H), 2.05-2.07 (m, 3H), 1.99-2.01 (m, 1H).

Example 1.1.18. (S)-2-((S)-6-fluoroisochroman-1-yl)piperidine (I-73) and (S)-2-((R)-6-fluoroisochroman-1-yl)piperidine (I-74)

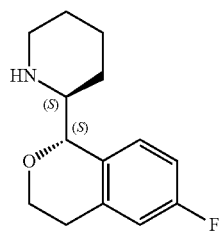

I-73

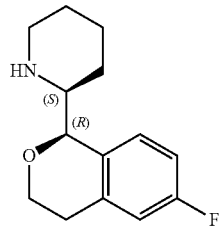

I-74

(S)-2-((S)-6-fluoroisochroman-1-yl)piperidine (I-73) and (S)-2-((R)-6-fluoroisochroman-1-yl)piperidine (I-74) were prepared using a procedure analogous to that described in Example 1.1.1, but using 2-(3-fluorophenyl)ethanol in place of 2-phenylethanol and (S)-tert-butyl 2-formylpiperidine-1-carboxylate in place of (S)-tert-butyl 2-formylpyrrolidine-1-carboxylate.

(S)-2-((S)-6-fluoroisochroman-1-yl)piperidine (I-73): MS (ESI): m/z 236 [M+H]$^+$, $^1$HNMR (400 MHz, MeOD): δ 7.34-7.37 (m, 1H), 6.99-7.09 (m, 2H), 4.87 (s, 1H), 4.27-4.32 (m, 1H), 3.71-3.80 (m, 2H), 3.24-3.28 (m, 1H), 3.05-3.13 (m, 1H), 2.92-2.97 (m, 1H), 2.70-2.74 (d, J=16, 1 H), 1.89-2.08 (m, 4H), 1.66-1.72 (m, 2H).

(S)-2-((R)-6-fluoroisochroman-1-yl)piperidine (I-74): MS (ESI): m/z 236 [M+H]$^+$, $^1$HNMR (400 MHz, MeOD): δ 7.21-7.24 (m, 1H), 6.98-7.05 (m, 2H), 5.07 (s, 1H), 4.28-4.32 (m, 1H), 3.73-3.79 (m, 2H), 3.41-3.45 (m, 1H), 3.02-3.18 (m, 2H), 2.67-2.71 (d, J=16, 1 H), 1.82-1.91 (m, 2H), 1.49-1.72 (m, 3H), 1.36-1.40 (m, 1H).

Example 1.1.19. (S)-2-((S)-7,8-dihydro-5H-[1,3]dioxolo[4,5-g]isochromen-5-yl)pyrrolidine (I-53) and (S)-2-((R)-7,8-dihydro-5H-[1,3]dioxolo[4,5-g]isochromen-5-yl)pyrrolidine (I-54)

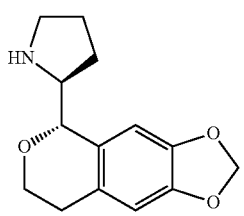

I-53

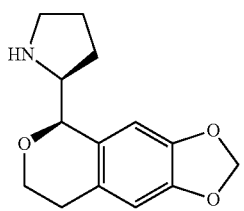

I-54

(S)-2-((S)-7,8-dihydro-5H-[1,3]dioxolo[4,5-g]isochromen-5-yl)pyrrolidine (I-53) and (S)-2-((R)-7,8-dihydro-5H-[1,3]dioxolo[4,5-g]isochromen-5-yl)pyrrolidine (I-54) were prepared using a procedure analogous to that described in Example 1.1.1, but using 2-(benzo[d][1,3]dioxol-5-yl)ethanol in place of 2-phenylethanol.

(S)-2-((S)-7,8-dihydro-5H-[1,3]dioxolo[4,5-g]isochromen-5-yl)pyrrolidine (I-53): MS (ESI): m/z 248 (M+H)$^+$. $^1$H NMR (HCl salt, 400 MHz, MeOD) δ 6.81 (t, J=40.4 Hz, 2H), 5.95 (d, J=0.5 Hz, 2H), 4.94 (s, 1H), 4.25 (ddd, J=11.2, 5.8, 1.7 Hz, 1H), 4.22-4.03 (m, 1H), 3.77 (td, J=11.3, 3.2 Hz, 1H), 3.31-3.17 (m, 2H), 3.16-3.02 (m, 1H), 2.59 (d, J=16.3 Hz, 1H), 2.33-2.19 (m, 2H), 2.20-1.98 (m, 2H).

(S)-2-((R)-7,8-dihydro-5H-[1,3]dioxolo[4,5-g]isochromen-5-yl)pyrrolidine (I-54): MS (ESI): m/z 248 (M+H)$^+$. $^1$H NMR (HCl salt, 400 MHz, MeOD) δ 6.70 (d, J=9.1 Hz, 2H), 5.94 (d, J=1.7 Hz, 2H), 5.11 (s, 1H), 4.36-4.12 (m, 2H), 3.84-3.61 (m, 1H), 3.35 (d, J=8.3 Hz, 2H), 3.10-2.90 (m, 1H), 2.59 (d, J=16.2 Hz, 1H), 2.15-1.86 (m, 2H), 1.78 (td, J=8.4, 3.8 Hz, 2H).

Example 1.1.20. (S)-2-((R)-6-bromoisochroman-1-yl)pyrrolidine (I-145)

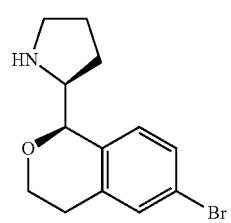

I-145

(S)-2-((R)-6-bromoisochroman-1-yl)pyrrolidine (I-145) were prepared using a procedure analogous to that described in Example 1.1.1, but using 2-(3-bromophenyl)ethanol in place of 2-phenylethanol.

(S)-2-((R)-6-bromoisochroman-1-yl)pyrrolidine (I-145): MS (ESI): m/z 282 (M+H)$^+$. $^1$H NMR (400 MHz, CDCl3) δ 7.29-7.03 (m, 2H), 7.04 (d, J=8.4 Hz, 1H), 4.86 (d, J=2.4 Hz, 1H), 4.18-4.13 (m, 1H), 3.71-3.64 (m, 1H), 3.53-3.48 (m, 1H), 3.12-2.96 (m, 2H), 2.83-2.76 (m, 1H), 2.58 (d, J=16.4 Hz, 1H), 2.17 (br, 1H), 1.70-1.63 (m, 2H), 1.45-1.39 (m, 2H).

Example 1.2. Procedure B. Certain Provided Compounds were Made Following a Procedure Exemplified by Example 1.2.1

Example 1.2.1. (S)-2-((S)-6-fluoroisochroman-1-yl)pyrrolidine (I-10) and (S)-2-((R)-6-fluoroisochroman-1-yl)pyrrolidine (I-9)

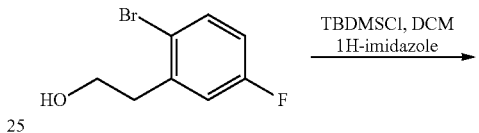

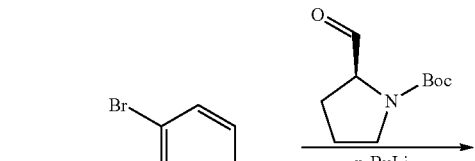

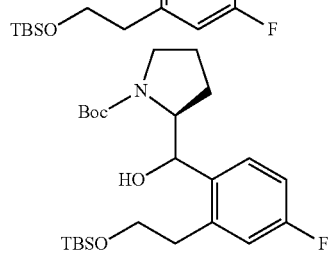

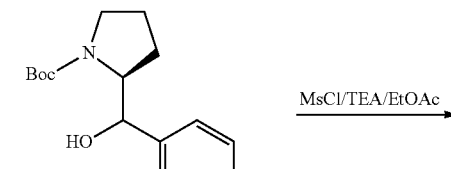

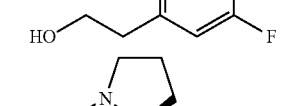

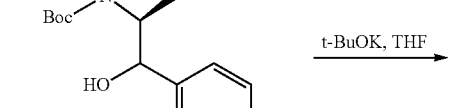

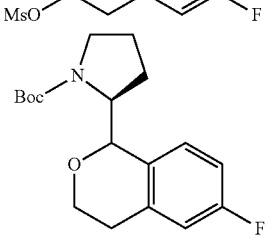

-continued

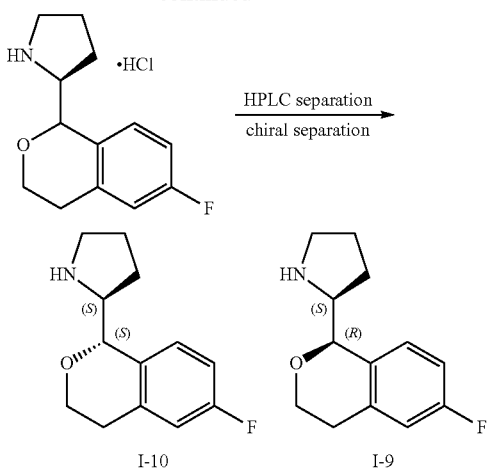

(a). (2-bromo-5-fluorophenethoxy)(tert-butyl)dimethylsilane

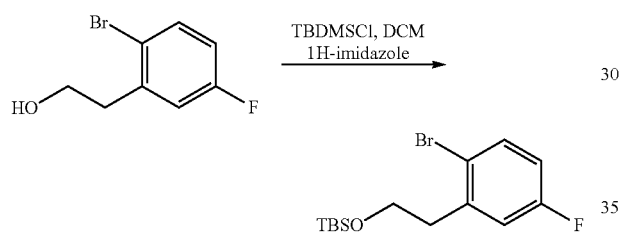

To a solution of 2-(2-bromo-5-fluorophenyl)ethanol (23.2 g, 105.91 mmol) in DCM (300 mL) was added 1H-imidazole (14.4 g, 211.8 mmol) and tert-butylchlorodimethylsilane (20.8 g, 137.7 mmol). After the mixture was stirred at room temperature overnight, it was quenched with H$_2$O (300 mL) at 0° C. The resulting mixture was extracted with DCM (2×100 mL). The combined organic layers were washed with brine (400 mL), dried over sodium sulfate, filtered, and concentrated. The crude product was purified by silica gel chromatography (eluted with petroleum ether: ethyl acetate=40:1) to give (2-bromo-5-fluorophenethoxy) (tert-butyl)dimethylsilane. MS (ESI): m/z 333 [M+H]$^+$, 32.3 g colorless oil.

(b). (2S)-tert-butyl 2-((2-(2-(tert-butyldimethylsilyloxy)ethyl)-4-fluorophenyl)(hydroxy)-methyl)pyrrolidine-1-carboxylate

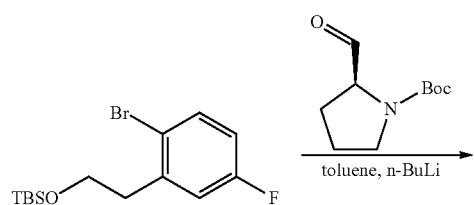

-continued

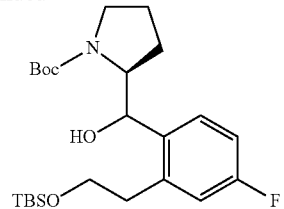

To a mixture of (2-bromo-5-fluorophenethoxy)(tert-butyl) dimethylsilane (5.0 g, 15.0 mmol) in toluene (60 mL) was added n-butyllithium (2.4 M, 12.5 mL, 30.0 mmol) at −78° C. After stirred at −78° C. for 1 h, (S)-tert-butyl 2-formylpyrrolidine-1-carboxylate (4.48 g, 22.5 mmol) in toluene (10 mL) was added at −78° C. The mixture was stirred at −78° C. for 2 h. Upon completion, sat. NH$_4$Cl solution (100 mL) and EtOAc (50 mL) was added. The organic layer was separated, washed with brine, dried, filtered, and concentrated. The crude product was purified by silica gel (eluted from PE:EtOAc=100:1 to PE:EtOAc=20:1) to yield the desired compound: 2.5 g colorless oil. (ESI) m/z: 454 (M+H)$^+$.

(c). (2S)-tert-butyl 2-((4-fluoro-2-(2-hydroxyethyl) phenyl)(hydroxy)methyl) pyrrolidine-1-carboxylate

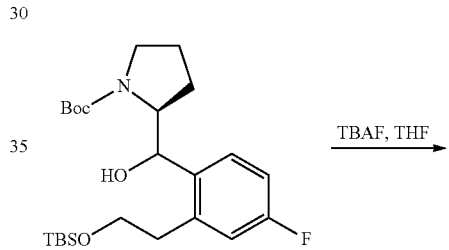

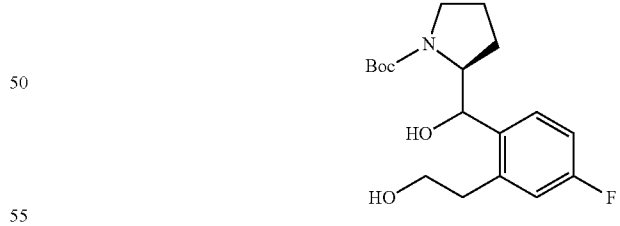

To a solution of (2S)-tert-butyl 2-((2-(2-((tert-butyldimethylsilyl)oxy)ethyl)-4-fluorophenyl)(hydroxy)methyl)pyrrolidine-1-carboxylate (2.5 g, 5.07 mmol) in THF (50 mL) was added TBAF (2.64 g, 10.14 mmol) at room temperature. The mixture was stirred at room temperature for 3 h. The mixture was evaporated in vacuo. The residue was dissolved in EtOAc (100 mL) and washed with water (80 mL×2). The organic layer was dried, filtered and concentrated in vacuo to give the crude product. The crude was purified by reverse flash column (mobile phase: MeCN and 0.1% aqueous ammonia) to afford the desired product: 1.2 g yellow oil.

(d). (2S)-tert-butyl 2-((4-fluoro-2-(2-(methylsulfonyloxy)ethyl)phenyl) (hydroxy)methyl)-pyrrolidine-1-carboxylase

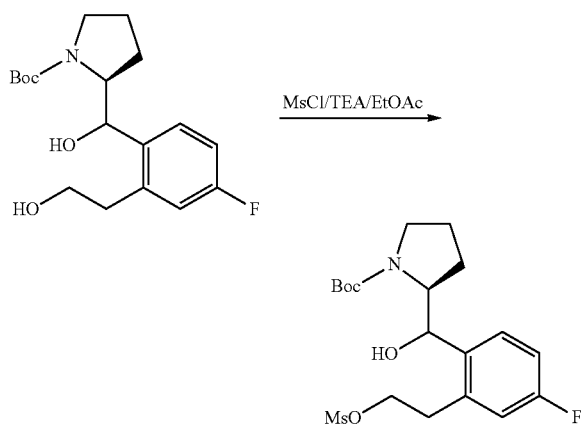

To a solution of (2S)-tert-butyl 2-((4-fluoro-2-(2-hydroxyethyl)phenyl)(hydroxy) methyl)pyrrolidine-1-carboxylate (1.0 g, 2.95 mmol) in ethyl acetate (50 mL) was added methanesulfonyl chloride (372 mg, 3.2 mmol) and triethylamine (894 mg, 8.85 mmol) at 0° C. The mixture was stirred at room temperature for 2 h. Upon completion, aq NaHCO$_3$ (10 mL) was added to the mixture. The organic layer was separated, washed with water (3×150 mL), dried over Na$_2$SO$_4$, filtered and concentrated to give the product: 1.2 g light yellow oil.

(e). (2S)-tert-butyl 2-(6-fluoroisochroman-1-yl)pyrrolidine-1-carboxylate

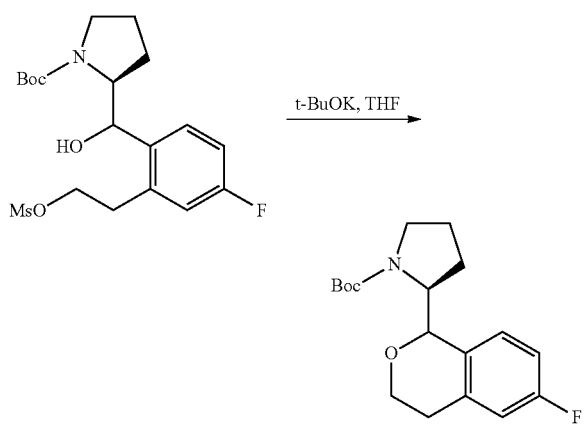

To a solution of (2S)-tert-butyl 2-((4-fluoro-2-(2-((methylsulfonyl)oxy)ethyl)phenyl) (hydroxy)methyl)pyrrolidine-1-carboxylate (1.2 g, 2.44 mmol) in tetrahydrofuran (80 mL) was added potassium t-butoxide (0.55 g, 4.9 mmol) at 0° C. The mixture was stirred at room temperature for 2 h. Upon completion, the mixture was concentrated, diluted with EtOAc (60 mL), washed with water (3×40 mL). The organic layer was dried over Na$_2$SO$_4$, filtered and concentrated to give the crude product as a yellow oil (600 mg).

(f). (2S)-2-(6-fluoroisochroman-1-yl)pyrrolidine

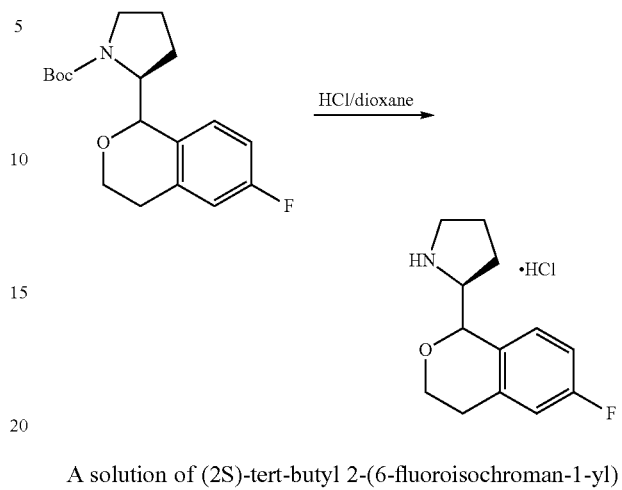

A solution of (2S)-tert-butyl 2-(6-fluoroisochroman-1-yl) pyrrolidine-1-carboxylate (600 mg, 1.87 mmol) in 4 N HCl/dioxane (10 mL) was stirred at room temperature for 3 h. The mixture was evaporated in vacuo to give the crude product: 390 mg off-white solid. (ESI) m/z: 222[M+H]$^+$.

(g). (S)-2-((S)-6-fluoroisochroman-1-yl)pyrrolidine (I-10) and (S)-2-((R)-6-fluoroisochroman-1-yl)pyrrolidine (I-9)

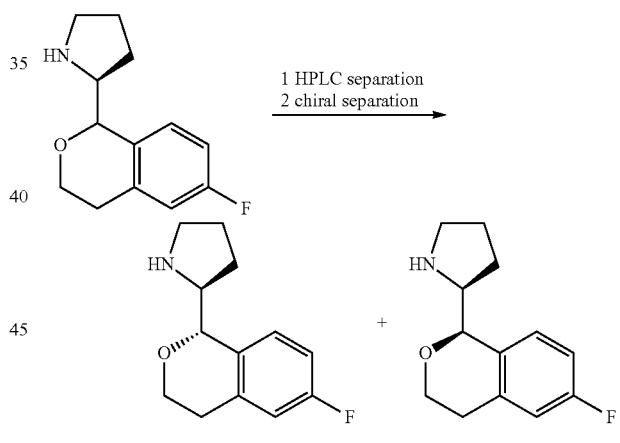

(2S)-2-(6-fluoroisochroman-1-yl)pyrrolidine from previous step (2 batches) (780 mg, 3.52 mmol) was separated by preparative HPLC to give the two diastereoisomers, which were separately further purified by chiral column chromatography: Column AY-H (250*4.6 mm 5 μm) and Mobile Phase: n-Hexane (0.1% DEA):EtOH (0.1% DEA)=80:20 to give (S)-2-((S)-6-fluoroisochroman-1-yl)pyrrolidine (160 mg yellow oil, (ESI) m/z: 222[M+H]$^+$) and (S)-2-((R)-6-fluoroisochroman-1-yl) pyrrolidine (180 mg yellow oil, (ESI) m/z: 222[M+H]$^+$).

$^1$HNMR of (S)-2-((S)-6-fluoroisochroman-1-yl)pyrrolidine (I-10) (400 MHz, CDCl$_3$): δ 7.23-7.19 (m, 1H), 6.90-6.85 (m, 1H), 6.81-6.79 (m, 1H), 4.71 (d, J=2.4 Hz, 1H), 4.21-4.16 (m, 1H), 3.76-3.69 (m, 1H), 3.57-3.52 (m, 1H), 3.06-2.98 (m, 2H), 2.79-2.73 (m, 1H), 2.65 (d, J=16.4 Hz, 1H), 2.45 (brs, 1H), 1.90-1.73 (m, 4H).

¹HNMR of (S)-2-((R)-6-fluoroisochroman-1-yl)pyrrolidine (I-9) (400 MHz, CDCl₃): δ 7.17-7.14 (m, 1H), 6.92-6.82 (m, 2H), 4.93 (s, 1H), 4.22-4.17 (m, 1H), 3.76-3.69 (m, 1H), 3.58-3.53 (m, 1H), 3.17-3.00 (m, 2H), 2.87-2.80 (m, 1H), 2.64-2.60 (m, 1H), 2.20 (brs, 1H), 1.74-1.66 (m, 2H), 1.49-1.43 (m, 2H).

Example 1.2.2. (2S)-2-((S)-7-fluoroisochroman-1-yl)pyrrolidine (I-6) and (2S)-2-((R)-7-fluoroisochroman-1-yl)pyrrolidine (I-5)

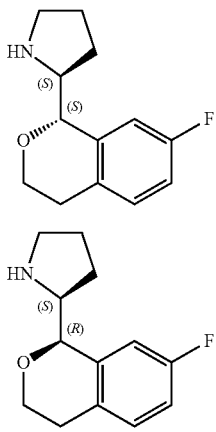

Compound I-6

Compound I-5

(2S)-2-((S)-7-fluoroisochroman-1-yl)pyrrolidine (I-6) and (2S)-2-((R)-7-fluoroisochroman-1-yl)pyrrolidine (I-5) were prepared using a procedure analogous to that described in Example 1.2.1, but using 2-(2-bromo-4-fluorophenyl)ethanol in place of 2-(2-bromo-5-fluorophenyl)ethanol.

(2S)-2-((S)-7-fluoroisochroman-1-yl)pyrrolidine (I-6): MS (ESI): m/z 222 [M+H]⁺, ¹H NMR (400 MHz, CDCl3): δ 7.06-7.09 (m, 1H), 6.85-6.92 (m, 2H), 4.92 (s, 1H), 4.18-4.22 (m, 1H), 3.67-3.74 (m, 1H), 3.51-3.56 (m, 1H), 3.10-3.16 (m, 1H), 2.94-3.03 (m, 1H), 2.81-2.87 (m, 1H), 2.51-2.62 (m, 2H), 1.67-1.74 (m, 2H), 1.44-1.50 (m, 2H).

(2S)-2-((R)-7-fluoroisochroman-1-yl)pyrrolidine (I-5): MS (ESI): m/z 222 [M+H]⁺, ¹H NMR (400 MHz, CDCl3): δ 7.06-7.09 (m, 1H), 6.93-6.86 (m, 2H), 4.93 (s, 1H), 4.23-4.18 (m, 1H), 3.74-3.68 (m, 1H), 3.56-3.51 (m, 1H), 3.17-3.11 (m, 1H), 3.03-2.94 (m, 1H), 2.88-2.81 (m, 1H), 2.61 (d, 1H), 2.52 (s, br. 1H), 1.74-1.67 (m, 2H), 1.51-1.45 (m, 2H).

Example 1.2.3. ((S)-2-((S)-5-fluoroisochroman-1-yl)pyrrolidine (I-14) and (S)-2-((R)-5-fluoroisochroman-1-yl)pyrrolidine (I-13)

I-14

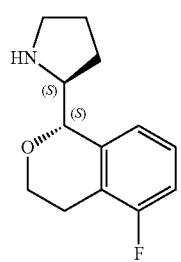

I-13

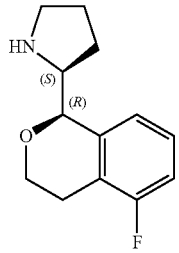

((S)-2-((S)-5-fluoroisochroman-1-yl)pyrrolidine (I-14) and (S)-2-((R)-5-fluoroisochroman-1-yl)pyrrolidine (I-13) were prepared using a procedure analogous to that described in Example 1.2.1, but using 2-(2-bromo-6-fluorophenyl)ethanol in place of 2-(2-bromo-5-fluorophenyl)ethanol.

((S)-2-((S)-5-fluoroisochroman-1-yl)pyrrolidine (I-14): MS (ESI) m/z 222.1 (M+H)⁺¹. ¹H NMR (400 MHz, MeOD): δ 7.28~7.22 (m, 1H), 7.12 (d, J=8.0 Hz, 1H), 6.99~6.95 (q, J=4.4 Hz, 1H), 4.82 (d, J=2.4 Hz, 1H), 4.30~4.25 (m, 1H), 3.79~3.72 (m, 2H), 3.07~3.01 (m, 1H), 2.95~2.75 (m, 3H), 2.06~2.00 (m, 2H) 1.96~1.79 (m, 2H).

(S)-2-((R)-5-fluoroisochroman-1-yl)pyrrolidine (I-13): MS (ESI) m/z 222.1 (M+H)⁺¹. ¹H NMR (400 MHz, MeOD): δ 7.25~7.19 (m, 1H), 7.03 (d, J=8.0 Hz, 1H), 6.97~6.92 (q, J=4.4 Hz, 1H), 4.96 (d, J=0.8 Hz, 1H), 4.28~4.23 (m, 1H), 3.73~3.63 (m, 2H), 3.14~3.09 (m, 1H), 2.88~2.73 (m, 3H), 1.76~1.69 (m, 2H) 1.51~1.41 (m, 2H).

Example 1.2.4. (R)-2-((S)-isochroman-1-yl)pyrrolidine (I-20) and (R)-2-((R)-isochroman-1-yl)pyrrolidine (I-19)

I-20

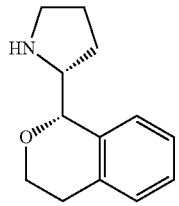

I-19

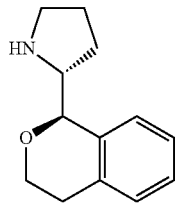

(R)-2-((S)-isochroman-1-yl)pyrrolidine (I-20) and (R)-2-((R)-isochroman-1-yl)pyrrolidine (I-19) were prepared using a procedure analogous to that described in Example 1.2.1, but using 2-(2-bromophenyl)ethanol in place of 2-(2-bromo-5-fluorophenyl)ethanol and (R)-tert-butyl 2-formylpyrrolidine-1-carboxylate in place of (S)-tert-butyl 2-formylpyrrolidine-1-carboxylate.

(R)-2-((S)-isochroman-1-yl)pyrrolidine (I-20): m/z=204 [M+1]⁺. ¹H NMR (400 MHz, CDCl3) δ 7.24-7.05 (m, 4H), 4.98 (d, J=1.7 Hz, 1H), 4.21~4.16 (m, 1H), 3.76~3.69 (td, J=11.3, 3.0 Hz, 1H), 3.60~3.57 (td, J=7.9, 3.5 Hz, 1H), 3.14~3.04 (m, 2H), 2.85~2.81 (m, 1H), 2.73 (s, 1H), 2.62~2.58 (d, J=16.1 Hz, 1H), 1.75-1.61 (m, 2H), 1.53-1.38 (m, 2H).

(R)-2-((R)-isochroman-1-yl)pyrrolidine (I-19): m/z=204 [M+1]⁺. ¹H NMR (HCl salt, 400 MHz, MeOD) δ 7.36-7.18 (m, 4H), 5.04 (d, J=2.4 Hz, 1H), 4.34-4.22 (m, 2H), 3.83 (td, J=11.3, 3.3 Hz, 1H), 3.32-3.14 (m, 3H), 2.71 (d, J=16.4 Hz, 1H), 2.34-2.03 (m, 4H).

Example 1.2.5. (R)-2-((S)-7-fluoroisochroman-1-yl)pyrrolidine (I-8) and (R)-2-((R)-7-fluoroisochroman-1-yl)pyrrolidine (I-7)

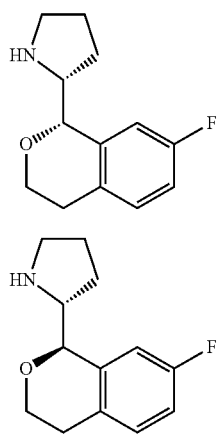

I-8

I-7

(R)-2-((S)-7-fluoroisochroman-1-yl)pyrrolidine (I-8) and (R)-2-((R)-7-fluoroisochroman-1-yl)pyrrolidine (I-7) were prepared using a procedure analogous to that described in Example 1.2.1, but using 2-(2-bromo-4-fluorophenyl) ethanol in place of 2-(2-bromo-5-fluorophenyl)ethanol and (R)-tert-butyl 2-formylpyrrolidine-1-carboxylate in place of (S)-tert-butyl 2-formylpyrrolidine-1-carboxylate.

(R)-2-((S)-7-fluoroisochroman-1-yl)pyrrolidine (I-8): m/z=222 [M+1]⁺. ¹HNMR (400 MHz, CDCl₃): δ 7.07-7.11 (m, 1H), 6.87-6.93 (m, 2H), 4.93 (s, 1H), 4.19-4.23 (m, 1H), 3.69-3.75 (m, 1H), 3.51-3.55 (m, 1H), 3.11-3.17 (m, 1H), 2.99-3.00 (m, 1H), 2.81-2.88 (m, 1H), 2.60-2.63 (J=15.6 Hz, d, 1H), 1.68-1.73 (m, 2H), 1.45-1.49 (m, 2H).

(R)-2-((R)-7-fluoroisochroman-1-yl)pyrrolidine (I-7): m/z=222[M+1⁺. ¹HNMR (HCl salt, 400 MHz, MeOD): δ 7.14-7.18 (m, 1H), 7.03-7.06 (m, 1H), 6.91-6.96 (m, 1H), 4.77 (s, 1H), 4.20-4.24 (m, 1H), 3.70-3.76 (m, 1H), 3.58-3.62 (m, 1H), 2.99-3.03 (m, 2H), 2.63-2.75 (m, 2H), 1.94-2.00 (m, 2H), 1.80-1.87 (m, 2H).

Example 1.2.6. (R)-2-((S)-6-fluoroisochroman-1-yl)pyrrolidine (I-11) and (R)-2-((R)-6-fluoroisochroman-1-yl)pyrrolidine (I-12)

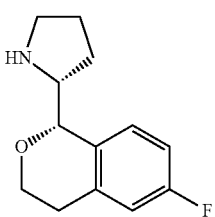

I-11

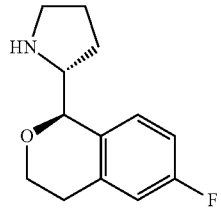

I-12

(R)-2-((S)-6-fluoroisochroman-1-yl)pyrrolidine (I-11) and (R)-2-((R)-6-fluoroisochroman-1-yl)pyrrolidine (I-12) were prepared using a procedure analogous to that described in Example 1.2.1, but using (R)-tert-butyl 2-formylpyrrolidine-1-carboxylate in place of (S)-tert-butyl 2-formylpyrrolidine-1-carboxylate.

(R)-2-((S)-6-fluoroisochroman-1-yl)pyrrolidine (I-11): ESI: m/z=222 (M+H⁺). ¹HNMR (400 MHz, CDCl₃): δ 7.21 (dd, J¹=5.6 Hz, J²=8.4 Hz, 1H), 6.88 (td, J¹=2.8 Hz, J²=8.4 Hz, 1H), 6.79 (dd, J¹=2.4 Hz, J²=9.2 Hz, 1H), 4.69 (d, J=3.2 Hz, 1H), 4.19 (m, 1H), 3.73 (m, 1H), 3.56 (m, 1H), 3.03 (m, 2H), 2.77 (m, 1H), 2.63 (m, 1H), 2.48 (brs, 1H), 1.87-1.68 (m, 4H).

(R)-2-((R)-6-fluoroisochroman-1-yl)pyrrolidine (I-12): ESI: m/z=222 (M+H⁺). ¹HNMR of freebase (400 MHz, CDCl₃): δ 7.11 (dd, J¹=5.6 Hz, J²=8.8 Hz, 1H), 6.85 (td, J¹=2.8 Hz, J²=8.8 Hz, 1H), 6.77 (dd, J¹=2.4 Hz, J²=9.2 Hz, 1H), 4.87 (s, 1H), 4.15 (m, 1H), 3.69 (td, J¹=2.8 Hz, J²=11.2 Hz, 1H), 3.53 (m, 1H), 3.10-2.95 (m, 2H), 2.81-2.74 (m, 1H), 2.58-2.53 (m, 2H), 1.67-1.60 (m, 2H), 1.45-1.38 (m, 2H).

Example 1.2.7. (S)-2-((S)-4,4-difluoroisochroman-1-yl)pyrrolidine (I-139) and (S)-2-((R)-4,4-difluoroisochroman-1-yl)pyrrolidine (I-140)

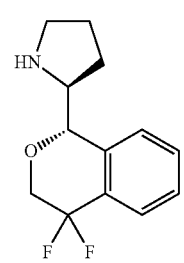

I-139

I-140

(S)-2-((S)-4,4-difluoroisochroman-1-yl)pyrrolidine (I-139) and (S)-2-((R)-4,4-difluoro-isochroman-1-yl)pyrrolidine (I-140) were prepared using a procedure analogous to that described in Example 1.2.1, but using 2-(2-bromophenyl)-2,2-difluoroethanol in place of 2-(2-bromo-5-fluorophenyl)ethanol.

(S)-2-((S)-4,4-difluoroisochroman-1-yl)pyrrolidine (I-139): MS (ESI): m/z=240[M+H]+; 1H NMR (HCl salt, 400 MHz, MeOD) 7.80~7.78 (m, 1H), 7.65~7.54 (m, 2H), 7.50~7.48 (m, 1H), 5.16 (brs, 1H), 4.47~4.39 (m, 1H), 4.38~4.34 (m, 1H), 4.17~4.07 (m, 1H), 3.27~3.22 (m, 2H), 2.39~2.23 (m, 2H), 2.18~2.08 (m, 2H).

(S)-2-((R)-4,4-difluoro-isochroman-1-yl)pyrrolidine (I-140): MS (ESI): m/z=240[M+H]+; 1H NMR (HCl salt, 400 MHz, MeOD) 7.76~7.75 (m, 1H), 7.60~7.50 (m, 2H), 7.41~7.39 (m, 1H), 5.34 (brs, 1H), 4.54~4.50 (m, 1H), 4.45~4.39 (m, 1H), 4.10~4.00 (m, 1H), 3.41~3.30 (m, 2H), 2.07~1.95 (m, 2H), 1.82~1.60 (m, 2H).

Example 1.3. Procedure C. Certain Provided Compounds were Made Following a Procedure Exemplified by Example 1.3.1

Example 1.3.1. (S)-2-((S)-8-fluoroisochroman-1-yl)pyrrolidine (I-2) and (S)-2-((R)-8-fluoroisochroman-1-yl)pyrrolidine (I-1)

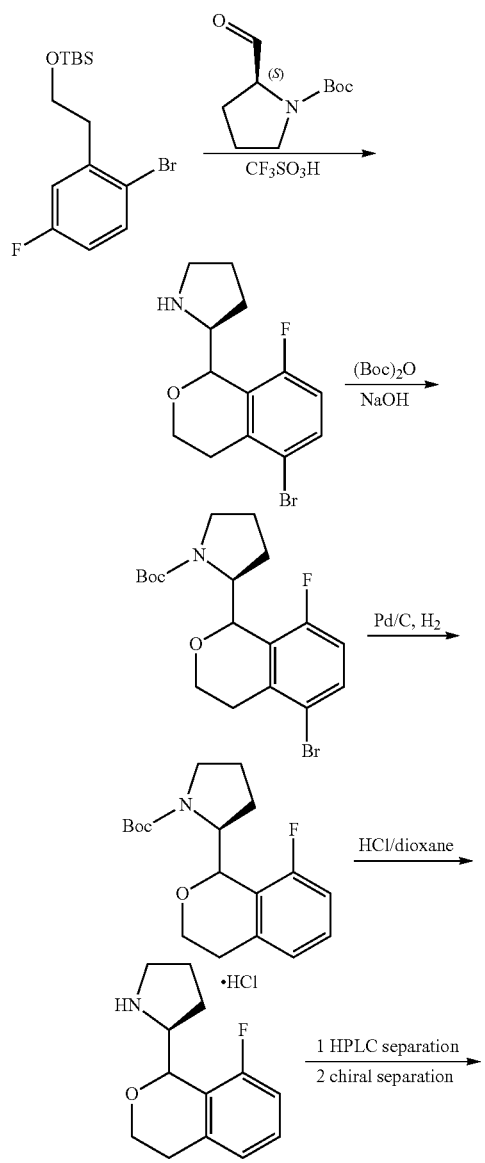

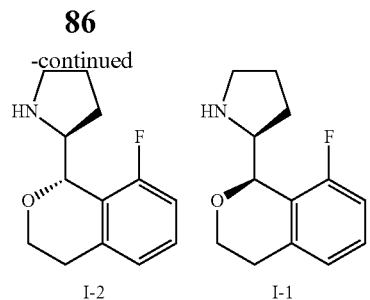

(a). (2S)-tert-butyl 2-(5-bromo-8-fluoroisochroman-1-yl) pyrrolidine-1-carboxylate

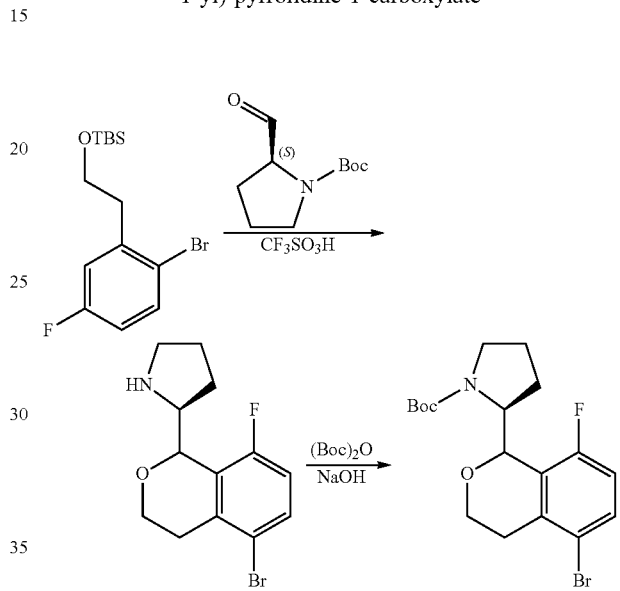

(2S)-tert-butyl 2-(5-bromo-8-fluoroisochroman-1-yl) pyrrolidine-1-carboxylate was prepared using a procedure analogous to that described in Example 1.1.1 (step a and step b), but using 2-(2-bromo-5-fluorophenyl)ethanol in place of 2-phenylethanol.

(b). (2S)-tert-butyl 2-(8-fluoroisochroman-1-yl) pyrrolidine-1-carboxylate

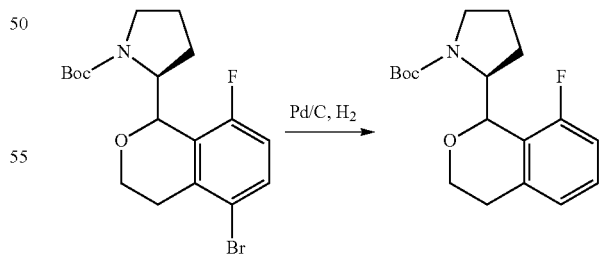

A mixture of (2S)-tert-butyl-2-(5-bromo-8-fluoroisochroman-1-yl)pyrrolidine-1-carboxylate (2.0 g, 5.0 mmol) and 10% dry Pd/C (320 mg) in methanol (40 mL) was stirred at room temperature under hydrogen for 2 h. The reaction mixture was filtered and the filtrate was concentrated in vacuo to give the crude, which was purified by preparative HPLC to give the desired product, 1.3 g, as a light yellow oil.

(c). (S)-2-((S)-8-fluoroisochroman-1-yl)pyrrolidine (I-2) and (S)-2-((R)-8-fluoroisochroman-1-yl)pyrrolidine (I-1)

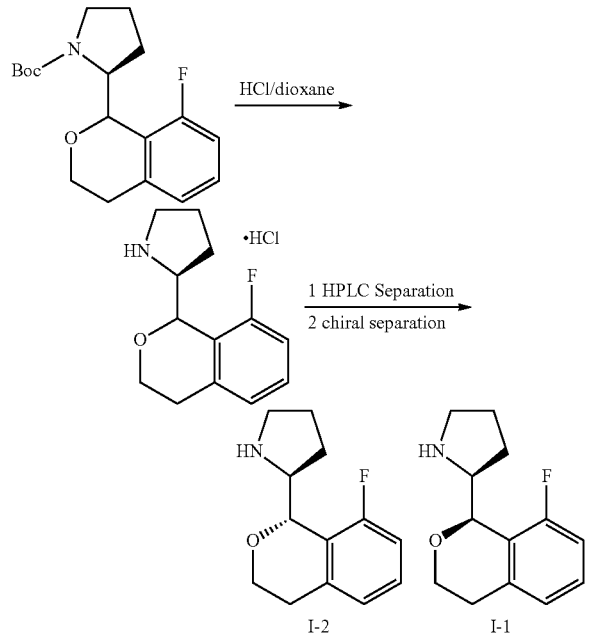

(S)-2-((S)-8-fluoroisochroman-1-yl)pyrrolidine (I-2) and (S)-2-((R)-8-fluoroisochroman-1-yl)-pyrrolidine (I-1) were prepared using a procedure similar to that described in Example 1.1.1 (step c and step d).

(S)-2-((S)-8-fluoroisochroman-1-yl)pyrrolidine (I-2): (ESI) m/z: 222[M+H]+. $^1$HNMR (400 MHz, CDCl$_3$): δ 7.19-7.14 (q, J=5.6 Hz, 1H), 6.93-6.87 (m, 2H), 5.42 (brs, 1H), 5.03 (d, J=4.0 Hz, 1H), 4.27-4.20 (m, 1H), 3.87-3.82 (m, 1H), 3.71-3.65 (td, J$^1$=3.6 Hz, J$^2$=10.4 Hz, 1H), 3.15-3.01 (m, 2H), 2.89-2.83 (m, 1H), 2.70-2.64 (m, 1H), 2.05-1.75 (m, 4H).

(S)-2-((R)-8-fluoroisochroman-1-yl)pyrrolidine (I-1): (ESI) m/z: 222[M+H]+. $^1$HNMR (HCl salt, 400 MHz, MeOD): δ 7.35-7.30 (q, J=7.6 Hz, 1H), 7.10 (d, J=7.6 Hz, 1H), 7.04 (t, J=9.6 Hz, 1H), 5.37 (s, 1H), 4.45-4.41 (td, J$^1$=2.4 Hz, J$^2$=8.0 Hz, 1H), 4.33 (q, J=5.6 Hz, 1H), 3.78-3.72 (td, J$^1$=2.0 Hz, J$^2$=11.6 Hz, 1H), 3.37 (m, 2H), 3.14 (m, 1H), 2.77 (d, J=16.4 Hz, 1H), 2.11-1.93 (m, 2H), 1.83-1.71 (m, 2H).

Example 1.3.2. (R)-2-((S)-8-fluoroisochroman-1-yl)pyrrolidine (I-3) and (R)-2-((R)-8-fluoroisochroman-1-yl)pyrrolidine (I-4)

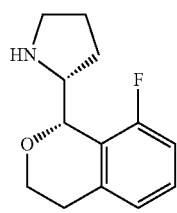

I-3

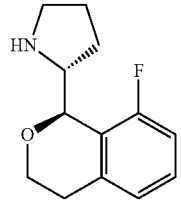

I-4

(R)-2-((S)-8-fluoroisochroman-1-yl)pyrrolidine (I-3) and (R)-2-((R)-8-fluoroisochroman-1-yl)pyrrolidine (I-4) were prepared using a procedure analogous to that described in Example 1.3.1, but using (R)-tert-butyl 2-formylpyrrolidine-1-carboxylate in place of (S)-tert-butyl 2-formylpyrrolidine-1-carboxylate.

(R)-2-((S)-8-fluoroisochroman-1-yl)pyrrolidine (I-3): ESI: m/z=222 (M+H+). $^1$HNMR (400 MHz, CDCl$_3$): δ 7.18 (m, 1H), 6.93 (m, 2H), 5.19 (s, 1H), 4.20 (m, 1H), 3.84 (m, 1H), 3.67 (td, J$^1$=2.8 Hz, J$^2$=11.6 Hz, 1H), 3.14-2.97 (m, 2H), 2.87 (m, 1H), 2.64 (s, 1H), 2.60 (brs, 1H), 1.74-1.65 (m, 2H), 1.49-1.37 (m, 2H).

(R)-2-((R)-8-fluoroisochroman-1-yl)pyrrolidine (I-4): ESI: m/z=222 (M+H+). $^1$HNMR (400 MHz, CDCl$_3$): δ 7.18 (m, 1H), 6.93 (m, 2H), 4.99 (d, J=3.2 Hz, 1H), 4.26 (m, 1H), 3.72 (m, 2H), 3.08 (m, 2H), 2.80 (m, 2H), 2.16 (brs, 1H), 1.93-1.72 (m, 4H).

Example 1.3.3. (S)-2-((S)-8-fluoroisochroman-1-yl)azetidine (I-84) and (S)-2-((R)-8-fluoroisochroman-1-yl)azetidine (I-83)

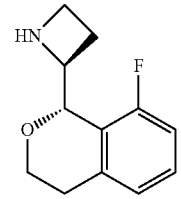

I-84

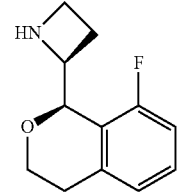

I-83

(S)-2-((S)-8-fluoroisochroman-1-yl)azetidine (I-84) and (S)-2-((R)-8-fluoroisochroman-1-yl)azetidine (I-83) were prepared using a procedure analogous to that described in Example 1.3.1, but using (S)-tert-butyl 2-formylazetidine-1-carboxylate in place of (S)-tert-butyl 2-formylpyrrolidine-1-carboxylate.

(S)-2-((S)-8-fluoroisochroman-1-yl)azetidine (I-84): MS (ESI): m/z 208 [M+H]+, $^1$HNMR (HCl salt, 400 MHz, MeOD): δ 7.24-7.18 (m, 1H), 6.99 (d, J=7.6, 1 H), 6.93 (t, 1H), 5.08 (s, 2H), 4.23-4.18 (m, 1H), 3.99-3.92 (d, J=9.6 Hz, 1H), 3.74-3.67 (m, 2H), 3.14-3.05 (m, 1H), 2.89-2.84 (m, 1H), 2.66 (d, J=11.6, 1 H), 2.43 (m, 1H).

(S)-2-((R)-8-fluoroisochroman-1-yl)azetidine (I-83): MS (ESI): m/z 208 [M+H]+, $^1$HNMR (HCl salt, 400 MHz, MeOD): δ 7.35-7.29 (m, 1H), 7.09 (d, J=7.6, 1 H), 6.98 (t, 1H), 5.29 (s, 1H), 5.19 (t, 1H), 4.44-4.39 (m, 1H), 4.04 (d, J=9.6 Hz, 1H), 3.93-3.78 (m, 2H), 3.18 (m, 1H), 2.82 (d, J=16, 1 H), 2.38 (m, 2H).

Example 1.3.4. (S)-2-((S)-8-methylisochroman-1-yl)pyrrolidine (I-21) and (S)-2-((R)-8-methylisochroman-1-yl)pyrrolidine (I-22)

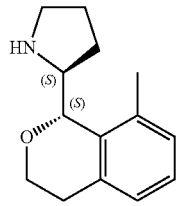
I-21

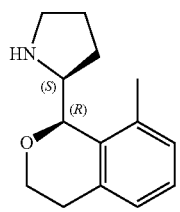
I-22

(S)-2-((S)-8-methylisochroman-1-yl)pyrrolidine (I-21) and (S)-2-((R)-8-methylisochroman-1-yl)pyrrolidine (I-22) were prepared using a procedure analogous to that described in Example 1.3.1, but using 2-(2-bromo-5-methylphenyl)ethanol in place of 2-(2-bromo-5-fluorophenyl)ethanol.

(S)-2-((S)-8-methylisochroman-1-yl)pyrrolidine (I-21): ESI: m/z=218 (M+H⁺). ¹HNMR (HCl salt, 400 MHz, MeOD): δ 7.14-7.22 (m, 2H), 7.08-7.09 (1=7.2 Hz, d, 1H), 5.31 (s, 1H), 4.24-4.29 (m, 1H), 4.01-4.05 (m, 1H), 3.60-3.66 (m, 1H), 3.36-3.38 (m, 1H), 3.20-3.24 (m, 2H), 2.66-2.70 (1=16 Hz, d, 1H), 2.38 (s, 3H), 2.03-2.24 (m, 4H).

(S)-2-((R)-8-methylisochroman-1-yl)pyrrolidine (I-22): ESI: m/z=218 (M+H⁺). ¹HNMR (HCl salt, 400 MHz, MeOD): δ 7.16-7.19 (J=14.8 Hz, t, 1H), 7.05-7.11 (m, 2H), 5.44 (s, 1H), 4.21-4.27 (m, 2H), 3.60-2.67 (m, 1H), 3.35-3.38 (m, 2H), 3.04-3.13 (m, 1H), 2.65-2.69 (J=16 Hz, d, 1H), 2.35 (s, 3H), 1.90-2.06 (m, 2H), 1.76-1.83 (m, 1H), 1.56-1.59 (m, 1H).

Example 1.3.5. (R)-2-((S)-8-methylisochroman-1-yl)pyrrolidine (I-24) and (R)-2-((R)-8-methylisochroman-1-yl)pyrrolidine (I-23)

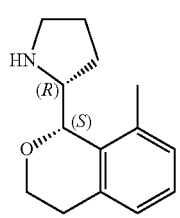
I-24

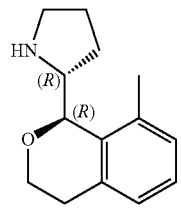
I-23

(R)-2-((S)-8-methylisochroman-1-yl)pyrrolidine (I-24) and (R)-2-((R)-8-methylisochroman-1-yl)pyrrolidine (I-23) were prepared using a procedure analogous to that described in Example 1.3.1, but using 2-(2-bromo-5-methylphenyl)ethanol in place of 2-(2-bromo-5-fluorophenyl)ethanol and (R)-tert-butyl 2-formylpyrrolidine-1-carboxylate in place of (S)-tert-butyl 2-formylpyrrolidine-1-carboxylate.

(R)-2-((S)-8-methylisochroman-1-yl)pyrrolidine (I-24): ESI: m/z=218 (M+H⁺). ¹H NMR (HCl salt, 400 MHz, MeOD): δ 7.05-7.19 (m, 3H), 5.44 (s, 1H), 4.21-4.27 (m, 2H), 3.60-3.66 (m, 1H), 3.35-3.39 (m, 2H), 3.04-3.13 (m, 1H), 2.65-2.69 (J=16.4 Hz, d, 1H), 2.35 (s, 3H), 1.90-2.06 (m, 2H), 1.76-1.83 (m, 1H), 1.53-1.59 (m, 1H).

(R)-2-((R)-8-methylisochroman-1-yl)pyrrolidine (I-23): ESI: m/z=218 (M+H⁺). ¹H NMR (HCl salt, 400 MHz, MeOD): δ 7.19-7.23 (1=14.8 Hz, t, 1H), 7.14-7.16 (J=7.2 Hz, d, 1H), 7.08-7.09 (J=7.6 Hz, d, 1H), 5.31 (s, 1H), 4.24-4.28 (m, 1H), 4.00-4.04 (m, 1H), 3.60-3.66 (m, 1H), 3.35-3.39 (m, 1H), 3.17-3.26 (m, 2H), 2.66-2.70 (J=16 Hz, d, 1H), 2.36 (s, 3H), 2.03-2.25 (m, 4H).

Example 1.3.6. ((S)-2-((S)-7,9-dihydro-6H-[1,3]dioxolo[4,5-h]isochromen-9-yl)pyrrolidine (I-51) and (S)-2-((R)-7,9-dihydro-6H-[1,3]dioxolo[4,5-h]isochromen-9-yl)pyrrolidine (I-52)

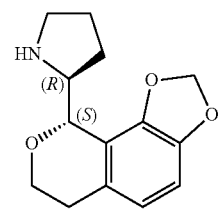
I-51

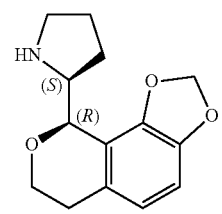
I-52

(S)-2-((S)-7,9-dihydro-6H-[1,3]dioxolo[4,5-h]isochromen-9-yl)pyrrolidine (I-51) and (S)-2-((R)-7,9-dihydro-6H-[1,3]dioxolo[4,5-h]isochromen-9-yl)pyrrolidine (I-52) were prepared using a procedure analogous to that described in Example 1.3.1, but using 2-(6-bromobenzo[d][1,3]dioxol-5-yl)ethanol in place of 2-(2-bromo-5-fluorophenyl)ethanol.

(S)-2-((S)-7,9-dihydro-6H-[1,3]dioxolo[4,5-h]isochromen-9-yl)pyrrolidine (I-51): ESI: M/Z=248[M+H]⁺. ¹H NMR (400 MHz, CDCl3) δ 6.68 (d, J=7.9 Hz, 1H), 6.60 (d, J=7.9 Hz, 1H), 5.99 (d, J=1.5 Hz, 1H), 5.88 (d, J=1.5 Hz, 1H), 4.86 (d, J=2.2 Hz, 1H), 4.21~4.17 (m, 2.7 Hz, 1H), 3.85 (td, J₁=7.6, J₂=2.9 Hz, 1H), 3.68 (td, J₁=10.9, J₂=3.1 Hz, 1H), 3.08~3.02 (m, 1H), 3.00-2.89 (m, 1H), 2.79~2.74 (m, 1H), 2.61~2.56 (m, 1H), 2.17 (s, 1H), 1.91~1.75 (m, 4H).

(S)-2-((R)-7,9-dihydro-6H-[1,3]dioxolo[4,5-h]isochromen-9-yl)pyrrolidine (I-52): ESI: M/Z=248[M+H]⁺. ¹H NMR (400 MHz, MeOD) δ 6.70 (d, J=8.0 Hz, 1H), 6.63 (d, J=8.0 Hz, 1H), 5.94 (d, J=1.1 Hz, 1H), 5.86 (d, J=1.1 Hz, 1H), 5.03 (s, 1H), 4.18~4.14 (m, 1H), 3.96 (td, J₁=7.9, J₂=3.0 Hz, 1H), 3.64 (td, J₁=11.5, J₂=2.7 Hz, 1H), 3.17-3.05 (m, 1H), 3.00-2.85 (m, 1H), 2.81~2.75 (m, 1H), 2.59~2.55 (m, 1H), 1.75~1.70 (m, 2H), 1.56~1.48 (m, 2H).

Example 1.3.7. (S)-2-((R)-8-methoxyisochroman-1-yl)pyrrolidine (I-47) and (S)-2-((S)-8-methoxyisochroman-1-yl)pyrrolidine (I-48)

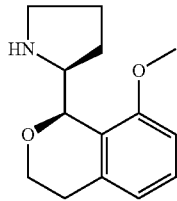

I-47

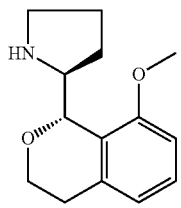

I-48

(S)-2-((R)-8-methoxyisochroman-1-yl)pyrrolidine (I-47) and (S)-2-((S)-8-methoxyisochroman-1-yl)pyrrolidine (I-48) were prepared using a procedure analogous to that described in Example 1.3.1, but using 2-(2-bromo-5-methoxyphenyl)ethanol in place of 2-(2-bromo-5-fluorophenyl)ethanol.

(S)-2-((R)-8-methoxyisochroman-1-yl)pyrrolidine (I-47): MS (ESI): m/z 234.1 (M+H)⁺. ¹H NMR (400 MHz, CDCl3): δ 10.42 (s, 1H), 8.23 (s, 1H), 7.19 (t, J=8.0 Hz, 1H), 6.76~6.70 (q, J=7.6 Hz, 2H), 5.41 (s, 1H), 4.81 (s, 1H), 4.26~4.22 (q, J=5.2 Hz, 1H), 3.98~3.82 (m, 1H), 3.70 (s, 3H), 3.50~3.44 (m, 2H), 3.05~2.96 (m, 1H), 2.58 (d, J=16.0 Hz, 1H), 2.07~1.88 (m, 2H), 1.75~1.61 (m, 1H).

(S)-2-((S)-8-methoxyisochroman-1-yl)pyrrolidine (I-48): MS (ESI): m/z 234.1 (M+H)⁺. ¹H NMR (400 MHz, CDCl₃): δ 9.46 (s, 1H), 7.87 (s, 1H), 7.15 (t, J=8.0 Hz, 1H), 6.74~6.71 (m, 2H), 5.02 (s, 1H), 4.46~4.41 (m, 1H), 4.23~4.18 (m, 1H), 3.87 (s, 3H), 3.75~3.67 (m, 1H), 3.61~3.55 (m, 1H), 3.11~3.042 (m, 1H), 2.78~2.72 (m, 1H), 2.51 (d, J=16.0 Hz, 1H), 2.24~2.16 (m, 1H), 2.04~1.86 (m, 2H), 1.84~1.78 (m, 1H).

Example 1.3.8. (R)-2-((R)-8-methoxyisochroman-1-yl)pyrrolidine (I-49) and (R)-2-((S)-8-methoxyisochroman-1-yl)pyrrolidine (I-50)

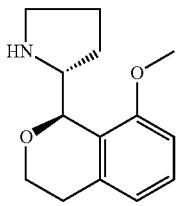

I-49

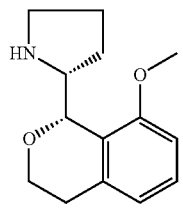

I-50

(R)-2-((R)-8-methoxyisochroman-1-yl)pyrrolidine (I-49) and (R)-2-((S)-8-methoxyisochroman-1-yl)pyrrolidine (I-50) were prepared using a procedure analogous to that described in Example 1.3.1, but using 2-(2-bromo-5-methoxyphenyl)ethanol in place of 2-(2-bromo-5-fluorophenyl)ethanol and (R)-tert-butyl 2-formylpyrrolidine-1-carboxylate in place of (S)-tert-butyl 2-formylpyrrolidine-1-carboxylate.

(R)-2-((R)-8-methoxyisochroman-1-yl)pyrrolidine (I-49): MS (ESI): m/z 234.1 (M+H)⁺. ¹H NMR (HCl salt, 400 MHz, MeOD): δ 7.19 (t, J=7.6 Hz, 1H), 6.84 (d, J=8.0 Hz, 1H), 6.77 (d, J=7.6 Hz, 1H), 5.04 (s, 1H), 4.19~4.14 (m, 1H), 3.86~3.82 (m, 4H), 3.63~3.56 (m, 1H), 3.09~2.98 (m, 2H), 2.74~2.60 (m, 2H), 1.99~1.81 (m, 4H).

(R)-2-((S)-8-methoxyisochroman-1-yl)pyrrolidine (I-50): MS (ESI): m/z 234.1 (M+H)⁺. ¹H NMR (400 MHz, MeOD): δ 7.18 (t, J=7.6 Hz, 1H), 6.83 (d, J=7.6 Hz, 1H), 6.76 (d, J=7.6 Hz, 1H), 5.18 (s, 1H), 4.16~4.12 (m, 1H), 4.03~4.01 (m, 1H), 3.99 (s, 3H), 3.82~3.54 (m, 1H), 3.16~3.10 (m, 1H), 3.02~2.93 (m, 1H), 2.60 (d, J=16.0 Hz, 1H), 1.78~1.70 (m, 2H), 1.69~1.53 (m, 1H), 1.52~1.48 (m, 1H).

Example 1.3.9. (S)-2-((S)-7,9-dihydro-6H-[1,3]dioxolo[4,5-h]isochromen-9-yl)azetidine (I-143) and (S)-2-((R)-7,9-dihydro-6H-[1,3]dioxolo[4,5-h]isochromen-9-yl)azetidine (I-144)

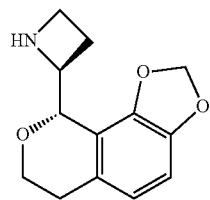

I-143

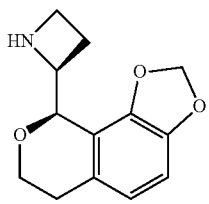

(S)-2-((S)-7,9-dihydro-6H-[1,3]dioxolo[4,5-h]iso-chromen-9-yl)azetidine (I-143) and (S)-2-((R)-7,9-dihydro-6H-[1,3]dioxolo[4,5-h]isochromen-9-yl)azetidine (I-144) were prepared using a procedure analogous to that described in Example 1.3.1, but using 2-(6-bromobenzo[d][1,3]dioxol-5-yl)ethanol in place of 2-(2-bromo-5-fluorophenyl)ethanol and (S)-tert-butyl 2-formylazetidine-1-carboxylate in place of (S)-tert-butyl 2-formylpyrrolidine-1-carboxylate.

(S)-2-((S)-7,9-dihydro-6H-[1,3]dioxolo[4,5-h]iso-chromen-9-yl)azetidine (I-143): MS (ESI): m/z 234.1 (M+H)+. 1H NMR (400 MHz, CDCl3) 6.69~6.59 (m, 2H), 5.95 (s, 1H), 5.88 (s, 1H), 4.75~4.74 (m, 1H), 4.61~4.56 (m, 1H), 4.29~4.24 (m, 1H), 3.76~3.72 (m, 1H), 3.58~3.54 (m, 1H), 3.46~3.41 (m, 1H), 3.01~2.93 (m, 1H), 2.70~2.62 (m, 2H), 2.32~2.02 (m, 1H).

(S)-2-((R)-7,9-dihydro-6H-[1,3]dioxolo[4,5-h]iso-chromen-9-yl)azetidine (I-144): MS (ESI): m/z 234.1 (M+H)+. 1H NMR (400 MHz, MeOD) 6.78~6.71 (m, 2H), 5.98 (s, 1H), 5.93 (s, 1H), 5.28~5.23 (m, 1H), 5.14~5.13 (m, 1H), 4.39~4.36 (m, 1H), 4.02~3.98 (m, 1H), 3.92~3.80 (m, 2H), 3.08~3.01 (m, 1H), 2.71~2.66 (m, 1H), 2.18~2.08 (m, 2H).

Example 1.4. Procedure D. Certain Provided Compounds were Made Following a Procedure Exemplified by Example 1.4.1

Example 1.4.1. (S)-2-((S)-8-fluoro-1,3,4,5-tetrahyd-robenzo[c]oxepin-1-yl)pyrrolidine (I-106) and (S)-2-((R)-8-fluoro-1,3,4,5-tetrahydrobenzo[c]oxepin-1-yl)pyrrolidine (I-107)

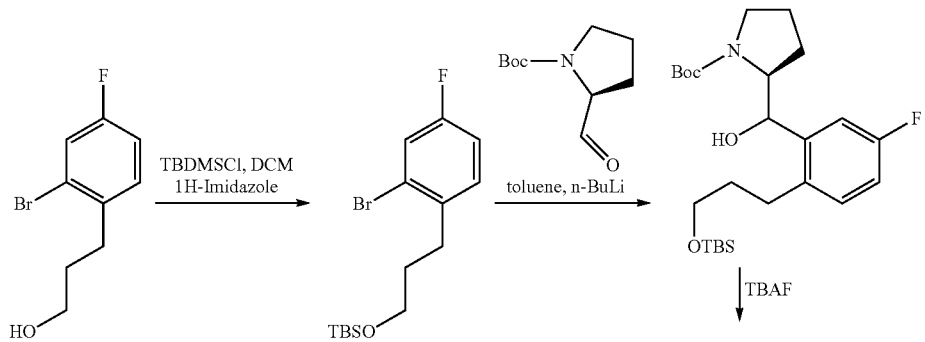

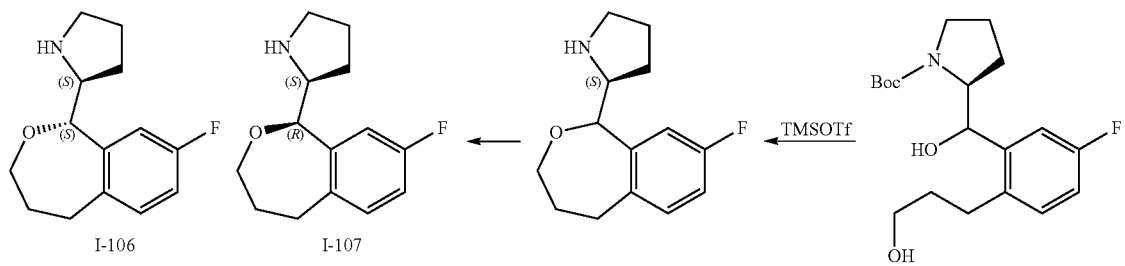

(a). (3-(2-bromo-4-fluorophenyl)propoxy)(tert-butyl)dimethylsilane

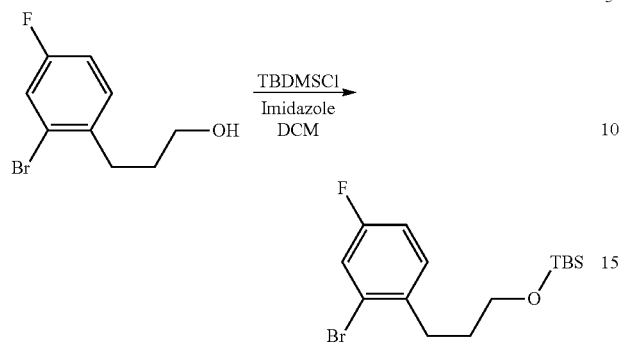

To a solution of 3-(2-bromo-4-fluorophenyl)propanol (14.2 g, 60.9 mmol) in DCM (150 mL) was added imidazole (8.29 g, 121.8 mmol) and TBDMSCI (11.9 g, 79.2 mmol). The mixture was stirred at room temperature for 2 h and water (300 mL) was added. The mixture was extracted with DCM (3×150 mL) and the organic layers were combined, washed, dried, filtered, and concentrated in vacuo to give the crude product, which was purified by column chromatography (PE) to give 3-(2-bromo-4-fluorophenylpropoxy)(tert-butyl)dimethylsilane (19.6 g) as a colorless oil. MS (ESI): m/z 329 (M+H)$^+$.

(b) (2S)-tert-butyl 2-((2-(3-(tert-butyldimethylsilyloxy)propyl)-5-fluorophenyl) (hydroxy)-methyl)pyrrolidine-1-carboxylate

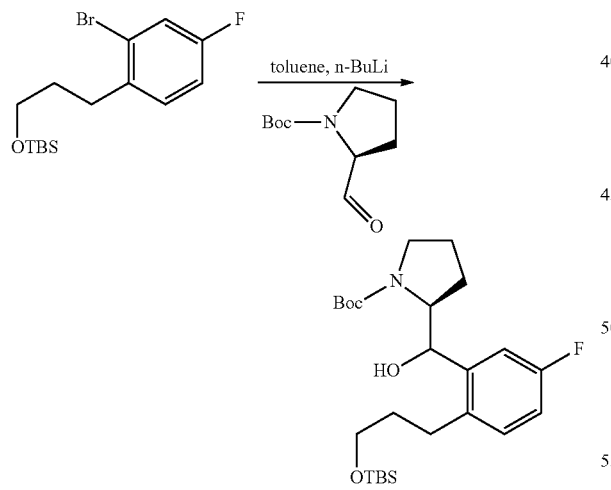

To a solution of (3-(2-bromo-4-fluorophenyl)propoxy)(tert-butyl)dimethylsilane (6.95 g, 20 mmol) in toluene (60 mL) at −78° C. was added n-BuLi (16 mL, 40 mmol). After the mixture was stirred at this temperature for 2 h, (S)-tert-butyl 2-formylpyrrolidine-1-carboxylate (5.98 g, 30 mmol) was added. The mixture was stirred at this temperature for an additional 3 h, and quenched with ammonium chloride (aq. sat. 20 mL). The mixture was extracted with ethyl acetate (20 mL×2), and the organic phase was washed with saturated aqueous brine (2×20 mL). The combined organic layers were dried over anhydrous sodium sulfate, filtered and concentrated in vacuo. The crude was purified by silica gel chromatography (petro ether:ethyl acetate=10:1) to give the desired product (3.2 g) as orange oil.

(c). (2S)-tert-butyl 2-((5-fluoro-2-(3-hydroxypropyl)phenyl)(hydroxy)-methyl)pyrrolidine-1-carboxylate

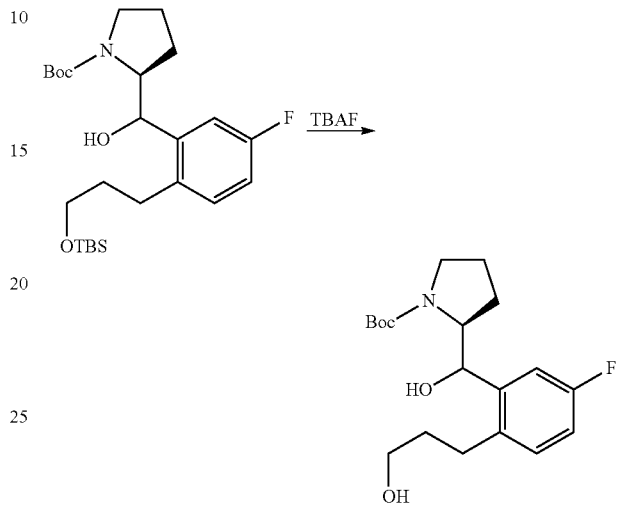

To a solution of (2S)-tert-butyl 2-((2-(3-((tert-butyldimethylsilyl)oxy)propyl)-5-fluorophenyl)(hydroxy)methyl)pyrrolidine-1-carboxylate (3.2 g, 6.84 mmol) in THF (30 mL) was added TBAF (3.58 g, 13.68 mmol). After the mixture was stirred at room temperature for 3 h, the solvent was evaporated in vacuo to give an oil. EtOAc (150 mL) was added to the reaction vessel and the resulting biphasic mixture was transferred to a reparatory funnel. The layers were separated and the organic phase was washed with water (3×100 mL). The organic layer was dried over anhydrous Na$_2$SO$_4$, filtered and concentrated in vacuo to give the crude product, which was used in the next step without further purification. MS (ESI) m/z 354 (M+H)$^+$

(d). (2S)-2-(8-fluoro-1,3,4,5-tetrahydrobenzo[c]oxepin-1-yl)pyrrolidine

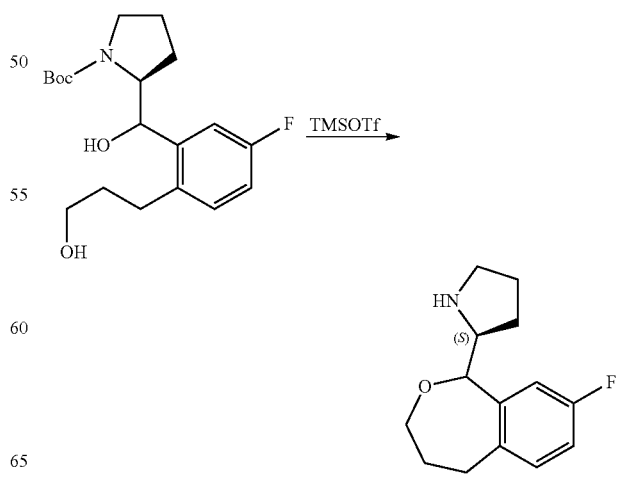

To a solution of (2S)-tert-butyl 2-((5-fluoro-2-(3-hydroxypropyl)phenyl)(hydroxy) methyl)pyrrolidine-1-carboxylate (2 g, 5.66 mmol) in DCM (10 mL) was added trimethylsilyl trifluoromethanesulfonate (3.77 g, 16.98 mmol). After the mixture was stirred at room temperature for 3 h, solvent was evaporated in vacuo to give the crude product. To the crude product, water (50 mL) was added. The mixture was washed with PE (50 mL×3). NaOH (aq. 40%) was added to the mixture until basic (pH>9). The mixture was then extracted with DCM (100 mL×3). The combined organic layers were dried over anhydrous Na₂SO₄, filtered and concentrated in vacuo to give the crude product as a mixture of diastereoisomers. MS (ESI) m/z 236 (M+H)⁺.

(e). (S)-2-((S)-8-fluoro-1,3,4,5-tetrahydrobenzo[c]oxepin-1-yl)pyrrolidine (I-106) and (S)-2-((R)-8-fluoro-1,3,4,5-tetrahydrobenzo[c]oxepin-1-yl) pyrrolidine (I-107)

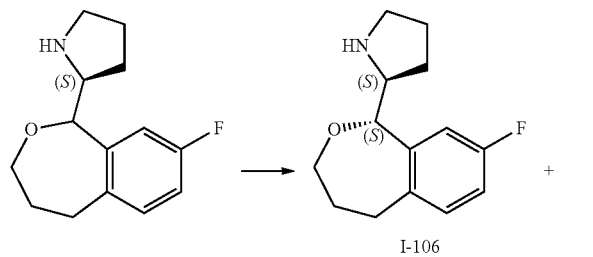

I-106

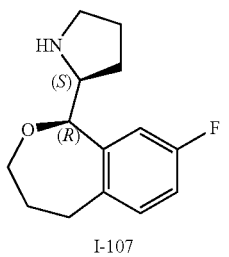

I-107

(S)-2-(8-fluoro-1,3,4,5-tetrahydrobenzo[c]oxepin-1-yl) pyrrolidine from previous step (800 mg) was purified by Prep-HPLC to give (S)-2-((S)-8-fluoro-1,3,4,5-tetrahydrobenzo[c]oxepin-1-yl)pyrrolidine (I-106, 200 mg) and (S)-2-((R)-8-fluoro-1,3,4,5-tetrahydrobenzo[c]oxepin-1-yl) pyrrolidine (I-107, 250 mg).

(S)-2-((S)-8-fluoro-1,3,4,5-tetrahydrobenzo[c]oxepin-1-yl)pyrrolidine (I-106): MS (ESI) m/z 236 (M+H)⁺. ¹H NMR (HCl salt, 400 MHz, MeOD) δ 7.26~7.23 (m, 1H), 7.02~6.95 (m, 2H), 5.06 (m, 1H), 4.28~4.20 (m, 2H), 3.93~3.86 (m, 1H), 3.44~3.31 (m, 2H), 3.17~3.10 (m, 1H), 2.97~2.91 (m, 1H), 2.24~2.05 (m, 4H), 1.98~1.92 (m, 2H).

(S)-2-((R)-8-fluoro-1,3,4,5-tetrahydrobenzo[c]oxepin-1-yl) pyrrolidine (I-107): MS (ESI) m/z 236 (M+H)⁺. ¹H NMR (HCl salt, 400 MHz, MeOD) δ 7.28~7.25 (m, 1H), 7.05~6.78 (m, 2H), 4.85 (d, J=8.8 Hz, 1H), 4.28~4.15 (m, 2H), 4.06~3.99 (m, 1H), 3.45~3.39 (m, 2H), 3.1~3.04 (m, 1H), 2.31~2.11 (m, 3H), 1.86~1.81 (m, 3H)

Example 1.4.2. (S)-2-((S)-1,3,4,5-tetrahydrobenzo[c]oxepin-1-yl)pyrrolidine (I-97) and (S)-2-((R)-1,3,4,5-tetrahydrobenzo[c]oxepin-1-yl)pyrrolidine (I-98)

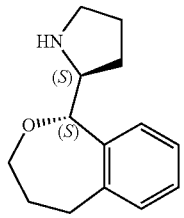

I-97

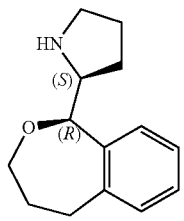

I-98

(S)-2-((S)-1,3,4,5-tetrahydrobenzo[c]oxepin-1-yl)pyrrolidine (I-97) and (S)-2-((R)-1,3,4,5-tetrahydrobenzo[c]oxepin-1-yl)pyrrolidine (I-98) were prepared using a procedure analogous to that described in Example 1.4.1, but using 3-(2-bromophenyl)propan-1-ol in place of 3-(2-bromo-4-fluorophenyl)propan-1-ol.

(S)-2-((S)-1,3,4,5-tetrahydrobenzo[c]oxepin-1-yl)pyrrolidine (I-97): MS (ESI): m/z 218 [M+H]⁺, ¹HNMR (HCl salt, 400 MHz, MeOD): δ 7.35-7.11 (m, 4H), 4.83 (d, J=8.6 Hz, 1H), 4.31-4.13 (m, 2H), 4.02-3.95 (m, 1H), 3.47-3.34 (m, 2H), 3.17-3.06 (m, 2H), 2.37-2.21 (m, 1H), 2.19-2.06 (m, 2H), 1.96-1.74 (m, 3H).

(S)-2-((R)-1,3,4,5-tetrahydrobenzo[c]oxepin-1-yl)pyrrolidine (I-98): MS (ESI): m/z 218 [M+H]⁺, ¹HNMR (HCl salt, 400 MHz, MeOD): δ 7.36-7.12 (m, 4H), 5.08 (d, J=3.4 Hz, 1H), 4.37-4.18 (m, 2H), 4.02-3.81 (m, 1H), 3.54-3.38 (m, 2H), 3.22-3.16 (m, 1H), 3.10-2.92 (m, 1H), 2.32-1.87 (m, 6H).

Example 1.4.3. (R)-2-((S)-1,3,4,5-tetrahydrobenzo[c]oxepin-1-yl)pyrrolidine (I-99) and (R)-2-((R)-1,3,4,5-tetrahydrobenzo[c]oxepin-1-yl)pyrrolidine (I-100)

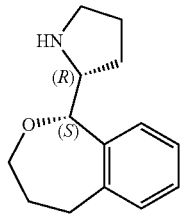

I-99

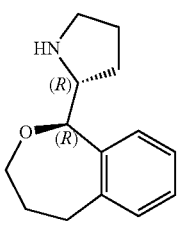

I-100

(R)-2-((S)-1,3,4,5-tetrahydrobenzo[c]oxepin-1-yl)pyrrolidine (I-99) and (R)-2-((R)-1,3,4,5-tetrahydrobenzo[c]oxepin-1-yl)pyrrolidine (I-100) were prepared using a procedure analogous to that described in Example 1.4.1, but using 3-(2-bromophenyl)propan-1-ol in place of 3-(2-bromo-4-fluorophenyl)propan-1-ol and (R)-tert-butyl 2-formylpyrrolidine-1-carboxylate in place of (S)-tert-butyl 2-formylpyrrolidine-1-carboxylate.

(R)-2-((S)-1,3,4,5-tetrahydrobenzo[c]oxepin-1-yl)pyrrolidine (I-99): MS (ESI): m/z 218 [M+H]$^+$, $^1$HNMR (HCl salt, 400 MHz, MeOD): δ 7.30-7.16 (m, 4H), 5.07 (d, J=3.5 Hz, 1H), 4.25 (tt, J=8.5, 3.2 Hz, 2H), 3.90 (ddd, J=12.2, 10.5, 4.4 Hz, 1H), 3.47-3.33 (m, 2H), 3.15 (ddd, J=14.4, 8.7, 3.4 Hz, 1H), 2.97 (ddd, J=14.5, 8.5, 3.2 Hz, 1H), 2.28-2.04 (m, 4H), 2.02-1.82 (m, 2H).

(R)-2-((R)-1,3,4,5-tetrahydrobenzo[c]oxepin-1-yl)pyrrolidine (I-100): MS (ESI): m/z 218 [M+H]$^+$, $^1$HNMR (HCl salt, 400 MHz, MeOD): δ 7.37-7.12 (m, 4H), 4.85 (t, J=6.4 Hz, 1H), 4.34-4.12 (m, 2H), 3.99 (ddd, J=12.2, 10.7, 4.2 Hz, 1H), 3.40 (ddd, J=24.0, 12.0, 7.5 Hz, 2H), 3.21-2.95 (m, 2H), 2.27 (dtd, J=12.6, 7.8, 4.8 Hz, 1H), 2.20-2.05 (m, 2H), 1.96-1.72 (m, 3H).

Example 1.4.4. (R)-2-((S)-8-fluoro-1,3,4,5-tetrahydrobenzo[c]oxepin-1-yl)pyrrolidine (I-108) and (R)-2-((R)-8-fluoro-1,3,4,5-tetrahydrobenzo[c]oxepin-1-yl)pyrrolidine (I-109)

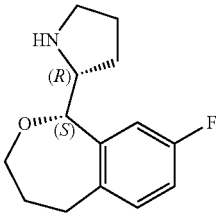

I-108

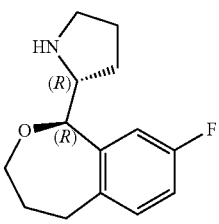

I-109

(R)-2-((S)-8-fluoro-1,3,4,5-tetrahydrobenzo[c]oxepin-1-yl)pyrrolidine (I-108) and (R)-2-((R)-8-fluoro-1,3,4,5-tetrahydrobenzo[c]oxepin-1-yl)pyrrolidine (I-109) were prepared using a procedure analogous to that described in Example 1.4.1, but using (R)-tert-butyl 2-formylpyrrolidine-1-carboxylate in place of (S)-tert-butyl 2-formylpyrrolidine-1-carboxylate.

(R)-2-((S)-8-fluoro-1,3,4,5-tetrahydrobenzo[c]oxepin-1-yl)pyrrolidine (I-108): MS (ESI): m/z 236 [M+H]$^+$, $^1$HNMR (HCl salt, 400 MHz, MeOD): δ 7.08~7.04 (m, 1H), 6.92~6.89 (m, 1H), 6.80~6.75 (m, 1H), 4.36 (m, 1H), 4.09 (m, 1H), 3.81 (m, 1H), 3.51 (m, 1H), 2.94 (m, 2H), 2.80 (m, 2H), 1.88 (m, 1H), 1.73 (m, 2H), 1.64 (m, 2H), 1.40 (m, 1H).

(R)-2-((R)-8-fluoro-1,3,4,5-tetrahydrobenzo[c]oxepin-1-yl)pyrrolidine (I-109): MS (ESI): m/z 236 [M+H]$^+$, $^1$HNMR (HCl salt, 400 MHz, MeOD): δ 7.27~7.23 (m, 1H), 7.01~6.98 (m, 2H), 5.06 (d, J=3.6 Hz, 1H), 4.24 (m, 2H), 3.92 (m, 1H), 3.40 (m, 2H), 3.14 (m, 1H), 2.97 (m, 1H), 2.11 (m, 4H), 1.93 (m, 2H).

Example 1.4.5. (S)-2-((S)-7-fluoro-1,3,4,5-tetrahydrobenzo[c]oxepin-1-yl)pyrrolidine (I-110) and (S)-2-((R)-7-fluoro-1,3,4,5-tetrahydrobenzo[c]oxepin-1-yl)pyrrolidine (I-111)

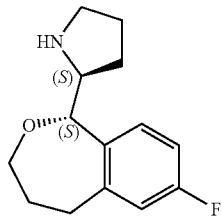

I-110

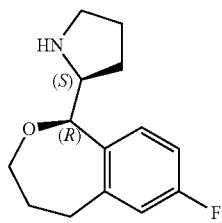

I-111

(S)-2-((S)-7-fluoro-1,3,4,5-tetrahydrobenzo[c]oxepin-1-yl)pyrrolidine (I-110) and (S)-2-((R)-7-fluoro-1,3,4,5-tetrahydrobenzo[c]oxepin-1-yl)pyrrolidine (I-111) were prepared using a procedure analogous to that described in Example 1.4.1, but using 3-(2-bromo-5-fluorophenyl)propan-1-ol in place of 3-(2-bromo-4-fluorophenyl)propan-1-ol.

(S)-2-((S)-7-fluoro-1,3,4,5-tetrahydrobenzo[c]oxepin-1-yl)pyrrolidine (I-110): MS (ESI): m/z 236 [M+H]$^+$, $^1$HNMR (400 MHz, CDCl$_3$): δ 7.24 (dd, J$^1$=5.2 Hz, J$^2$=8.0 Hz, 1H), 6.91-6.83 (m, 2H), 5.53 (brs, 1H), 4.55 (d, J=8.0 Hz, 1H), 4.25-4.20 (m, 1H), 3.94-3.87 (td, J$^1$=3.2 Hz, J$^2$=12.0 Hz, 1H), 3.85-3.79 (q, J=8.0 Hz, 1H), 3.27-3.21 (m, 1H), 3.12-3.01 (m, 2H), 2.97-2.91 (m, 1H), 2.06-1.72 (m, 5H), 1.66-1.54 (m, 1H).

(S)-2-((R)-7-fluoro-1,3,4,5-tetrahydrobenzo[c]oxepin-1-yl)pyrrolidine (I-111): MS (ESI): m/z 236 [M+H]$^+$, $^1$HNMR (400 MHz, CDCl$_3$): δ 7.25-7.22 (dd, J$^1$=6.0 Hz, J$^2$=8.0 Hz, 1H), 6.90-6.84 (m, 2H), 4.52 (d, J=6.4 Hz, 1H), 4.24-4.19 (m, 1H), 3.85-3.79 (td, J$^1$=3.6 Hz, J$^2$=11.2 Hz, 1H), 3.61-3.55 (m, 1H), 3.10-2.86 (m, 4H), 2.21 (brs, 1H), 2.06-1.75 (m, 6H).

Example 1.4.6. (R)-2-((S)-7-fluoro-1,3,4,5-tetrahydrobenzo[c]oxepin-1-yl)pyrrolidine (I-112) and (R)-2-((R)-7-fluoro-1,3,4,5-tetrahydrobenzo[c]oxepin-1-yl)pyrrolidine (I-113)

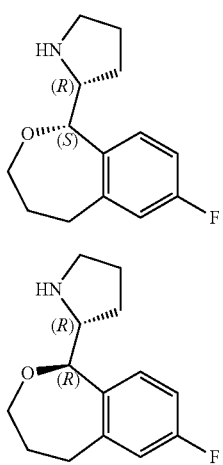

I-112

I-113

(R)-2-((S)-7-fluoro-1,3,4,5-tetrahydrobenzo[c]oxepin-1-yl)pyrrolidine (I-112) and (R)-2-((R)-7-fluoro-1,3,4,5-tetrahydrobenzo[c]oxepin-1-yl)pyrrolidine (I-113) were prepared using a procedure analogous to that described in Example 1.4.1, but using 3-(2-bromo-5-fluorophenyl)propan-1-ol in place of 3-(2-bromo-4-fluorophenyl)propan-1-ol and (R)-tert-butyl 2-formylpyrrolidine-1-carboxylate in place of (S)-tert-butyl 2-formylpyrrolidine-1-carboxylate.

(R)-2-((S)-7-fluoro-1,3,4,5-tetrahydrobenzo[c]oxepin-1-yl)pyrrolidine (I-112): MS (ESI): m/z 236 [M+H]$^+$, $^1$HNMR (HCl salt, 400 MHz, MeOD): δ 7.24-7.21 (dd, J$^1$=5.6 Hz, J$^2$=8.4 Hz, 1H), 7.04-6.95 (m, 2H), 5.03 (d, J=3.2 Hz, 1H), 4.29-4.20 (m, 2H), 3.93-3.86 (m, 1H), 3.44-3.33 (m, 2H), 3.16-3.10 (m, 1H), 3.01-2.95 (m, 1H), 2.27-2.06 (m, 4H), 1.97-1.85 (m, 2H).

(R)-2-((R)-7-fluoro-1,3,4,5-tetrahydrobenzo[c]oxepin-1-yl)pyrrolidine (I-113): MS (ESI): m/z 236 [M+H]$^+$, $^1$HNMR (400 MHz, CDCl$_3$): δ 7.24 (dd, J$^1$=5.6 Hz, J$^2$=8.0 Hz, 1H), 6.91-6.83 (m, 2H), 5.57 (brs, 1H), 4.55 (d, J=8.0 Hz, 1H), 4.25-4.20 (m, 1H), 3.94-3.79 (m, 2H), 3.27-3.21 (m, 1H), 3.12-3.01 (m, 2H), 2.97-2.91 (m, 1H), 2.06-1.72 (m, 5H), 1.66-1.54 (m, 1H).

Example 1.4.7. (S)-2-((R)-9-fluoro-1,3,4,5-tetrahydrobenzo[c]oxepin-1-yl)pyrrolidine (I-105)

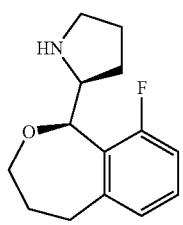

I-105

(S)-2-((R)-9-fluoro-1,3,4,5-tetrahydrobenzo[c]oxepin-1-yl)pyrrolidine (I-105) was prepared using a procedure analogous to that described in Example 1.4.1, but using 3-(2-bromo-3-fluorophenyl)propan-1-ol in place of 3-(2-bromo-4-fluorophenyl)propan-1-ol. ESI: m/z=236 (M+H)$^+$. $^1$H NMR (HCl salt, 400 MHz, MeOD): δ 7.33~7.28 (m, 1H), 7.06~7.01 (m, 2H), 5.37 (s, 1H), 4.20~4.15 (m, 1H), 4.09~4.06 (m, 1H), 3.68~3.60 (m, 1H), 3.46~3.35 (m, 3H), 2.69~2.66 (m, 1H), 2.26~2.15 (m, 3H), 2.01~1.96 (m, 1H), 1.89~1.84 (m, 2H).

Example 1.4.8. ((S)-2-((S)-9-methyl-1,3,4,5-tetrahydrobenzo[c]oxepin-1-yl)pyrrolidine (I-101) and (S)-2-((R)-9-methyl-1,3,4,5-tetrahydrobenzo[c]oxepin-1-yl)pyrrolidine (I-102)

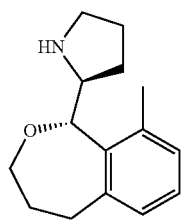

I-101

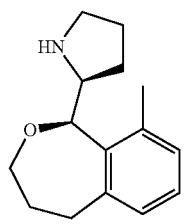

I-102

(S)-2-((S)-9-methyl-1,3,4,5-tetrahydrobenzo[c]oxepin-1-yl)pyrrolidine (I-101) and (S)-2-((R)-9-methyl-1,3,4,5-tetrahydrobenzo[c]oxepin-1-yl)pyrrolidine (I-102) were prepared using a procedure analogous to that described in Example 1.4.1, but using 3-(2-bromo-3-methylphenyl)propan-1-ol in place of 3-(2-bromo-4-fluorophenyl)propan-1-ol.

(S)-2-((S)-9-methyl-1,3,4,5-tetrahydrobenzo[c]oxepin-1-yl)pyrrolidine (I-101): (ESI) m/z: 232[M+H]$^+$. $^1$HNMR (400 MHz, CDCl$_3$): δ 7.11-7.07 (t, J=7.6 Hz, 1H), 7.04-7.02 (d, J=7.2 Hz, 1H), 6.97-6.95 (d, J=7.6 Hz, 1H), 5.06-5.04 (d, J=6.0 Hz, 1H), 4.02-3.96 (m, 1H), 3.61-3.46 (m, 3H), 3.17-3.11 (m, 1H), 2.90-2.83 (m, 1H), 2.56-2.51 (m, 1H), 2.34 (s, 3H), 2.10-2.05 (m, 1H), 2.04 (brs, 1H), 1.84-1.57 (m, 5H).

(S)-2-((R)-9-methyl-1,3,4,5-tetrahydrobenzo[c]oxepin-1-yl)pyrrolidine (I-102): (ESI) m/z: 232[M+H]$^+$. $^1$HNMR (400 MHz, MeOD): δ 7.18-7.15 (t, J=7.6 Hz, 1H), 7.12-7.10 (d, J=6.8 Hz, 1H), 7.04-7.02 (d, J=7.2 Hz, 1H), 5.39-5.38 (d, J=3.2 Hz, 1H), 4.14-4.08 (m, 1H), 3.99-3.94 (m, 1H), 3.61-3.35 (m, 4H), 2.58-2.53 (m, 1H), 2.37 (s, 3H), 2.35-2.10 (m, 3H), 2.04-1.92 (m, 1H), 1.83-1.72 (m, 2H).

103

Example 1.4.9. (R)-2-((S)-9-methyl-1,3,4,5-tetrahydrobenzo[c]oxepin-1-yl)pyrrolidine (I-104) and (R)-2-((R)-9-methyl-1,3,4,5-tetrahydrobenzo[c]oxepin-1-yl)pyrrolidine (I-103)

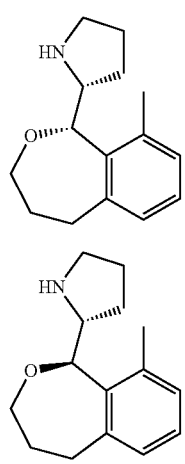

I-104

I-103

(R)-2-((S)-9-methyl-1,3,4,5-tetrahydrobenzo[c]oxepin-1-yl)pyrrolidine (I-104) and (R)-2-((R)-9-methyl-1,3,4,5-tetrahydrobenzo[c]oxepin-1-yl)pyrrolidine (I-103) were prepared using a procedure analogous to that described in Example 1.4.1, but using 3-(2-bromo-3-methylphenyl)propan-1-ol in place of 3-(2-bromo-4-fluorophenyl)propan-1-ol and (R)-tert-butyl 2-formylpyrrolidine-1-carboxylate in place of (S)-tert-butyl 2-formylpyrrolidine-1-carboxylate.

(R)-2-((S)-9-methyl-1,3,4,5-tetrahydrobenzo[c]oxepin-1-yl)pyrrolidine (I-104): (ESI) m/z: 232[M+H]$^+$. $^1$HNMR (400 MHz, MeOD): δ 7.18-7.15 (t, J=7.6 Hz, 1H), 7.12-7.10 (d, J=6.8 Hz, 1H), 7.04-7.02 (d, J=7.2 Hz, 1H), 5.39-5.38 (d, J=3.2 Hz, 1H), 4.14-4.08 (m, 1H), 3.99-3.94 (m, 1H), 3.61-3.35 (m, 4H), 2.58-2.53 (m, 1H), 2.37 (s, 3H), 2.35-2.10 (m, 3H), 2.04-1.92 (m, 1H), 1.83-1.72 (m, 2H).

(R)-2-((R)-9-methyl-1,3,4,5-tetrahydrobenzo[c]oxepin-1-yl)pyrrolidine (I-103): (ESI) m/z: 232 [M+H]$^+$. $^1$HNMR (400 MHz, CDCl$_3$): δ 7.11-7.07 (t, J=7.6 Hz, 1H), 7.04-7.02 (d, J=7.2 Hz, 1H), 6.97-6.95 (d, J=7.6 Hz, 1H), 5.06-5.04 (d, J=6.0 Hz, 1H), 4.02-3.96 (m, 1H), 3.61-3.46 (m, 3H), 3.17-3.11 (m, 1H), 2.90-2.83 (m, 1H), 2.56-2.51 (m, 1H), 2.34 (s, 3H), 2.17 (brs, 1H), 2.10-2.05 (m, 1H), 1.84-1.57 (m, 5H).

Example 1.5. Procedure E. Certain Provided Compounds were Made Following a Procedure Exemplified by Example 1.5.1

Example 1.5.1. (S)-2-((S)-3,3-dimethylisochroman-1-yl)pyrrolidine (I-65) and (S)-2-((R)-3,3-dimethylisochroman-1-yl)pyrrolidine (I-66)

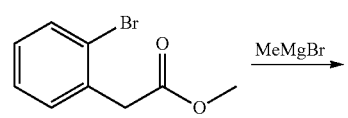

104

-continued

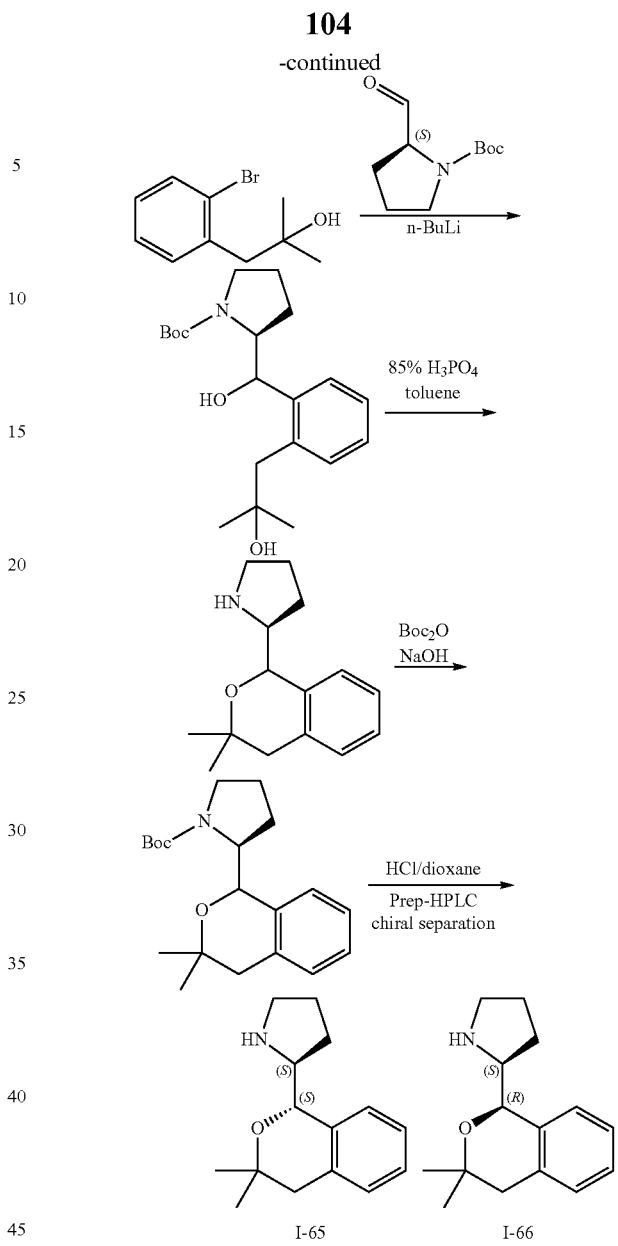

(a). 1-(2-bromophenyl)-2-methylpropan-2-ol

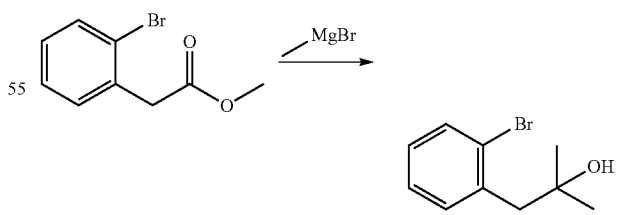

To a solution of methyl 2-(2-bromophenyl)acetate (5 g, 21.83 mmol) in THF (100 mL) at −78° C. was added dropwise methylmagnesium bromide (21.83 mL, 3M in Et$_2$O). The mixture was stirred at this temperature for 16 h, then gradually warmed to room temperature. The mixture was then cooled to 0° C., and saturated aqueous ammonium chloride (2 mL) was added. After 10 minutes, the mixture was extracted with EtOAc (3×120 mL). The organic layers were combined, dried, filtered and concentrated. The crude material was purified by silica gel chromatography (PE:EtOAc=20:1) to yield 1-(2-bromophenyl)-2-methylpropan-2-ol (4.5 g) as a colorless oil.

(b). (2S)-tert-butyl 2-(hydroxy(2-(2-hydroxy-2-methylpropyl)phenyl)methyl)pyrrolidine-1-carboxylate

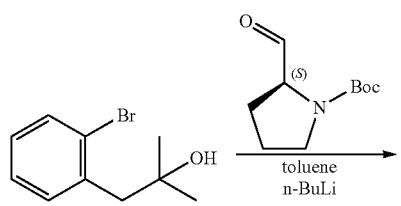

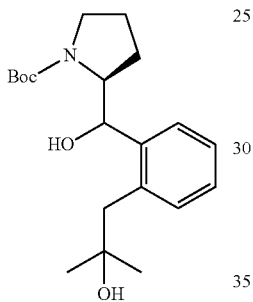

To a solution of 1-(2-bromophenyl)-2-methylpropan-2-ol (4.5 g, 15.71 mmol) in toluene (80 mL) was added butyllithium (2.21 g, 34.56 mmol) at −78° C. After stirring at −78° C. for 1 h, (S)-tert-butyl 2-formylpyrrolidine-1-carboxylate (4.07 g, 20.42 mmol) in toluene (20 mL) was added. The mixture was stirred at −78° C. for an additional 3 h. The mixture was poured into iced water and extracted with EtOAc (3×100 mL). The organic layers were combined, dried over Na₂SO₄, filtered and concentrated. The residue was then purified by column chromatography to give the crude product (0.99 g). ESI: m/z=350 (M+H⁺).

(c). (2S)-2-(3,3-dimethylisochroman-1-yl)pyrrolidine

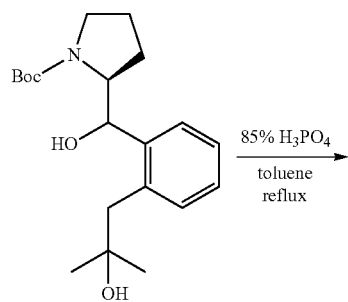

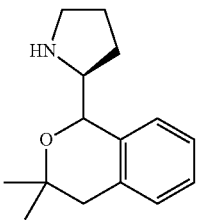

To a solution of (2S)-tert-butyl 2-(hydroxy(2-(2-hydroxy-2-methylpropyl)phenyl) methyl)pyrrolidine-1-carboxylate (4 g, 5.95 mmol) in toluene (100 mL) was added 85% phosphoric acid (10 mL). The reaction mixture was heated at 110° C. for 16 h. Toluene was removed by distillation and to the resulting residue was added water (100 mL), and washed with ethyl acetate (2×80 mL). The aqueous layer was used for next step without further purification. ESI: m/z=232 (M+H⁺).

(d). (2S)-tert-butyl 2-(3,3-dimethylisochroman-1-yl)pyrrolidine-1-carboxylase

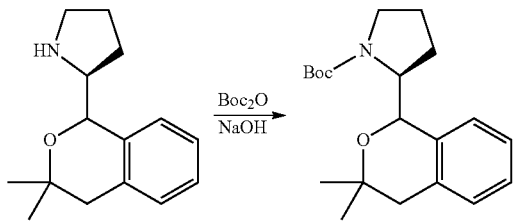

To a solution of (2S)-2-(3,3-dimethylisochroman-1-yl)pyrrolidine in water from previous step was added NaOH (0.31 g, 7.86 mmol) and di-tert-butyl dicarbonate (1.72 g, 7.86 mmol) at 0° C. The mixture was stirred at room temperature for 2 h and then was extracted with EtOAc (3×100 mL). The organic layers were combined, washed with brine (2×60 mL), dried over Na₂SO₄, filtered and concentrated to give the residue, which was purified by prep-HPLC to give (2S)-tert-butyl 2-(3,3-dimethylisochroman-1-yl)pyrrolidine-1-carboxylate 780 mg as a yellow oil. ESI: m/z=332 (M+H⁺).

(e). (S)-2-((S)-3,3-dimethylisochroman-1-yl)pyrrolidine (I-65) and (S)-2-((R)-3,3-dimethyl-isochroman-1-yl)pyrrolidine (I-66)

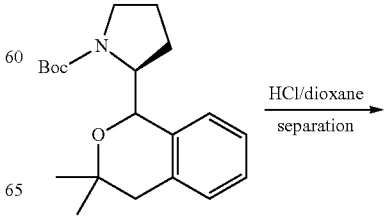

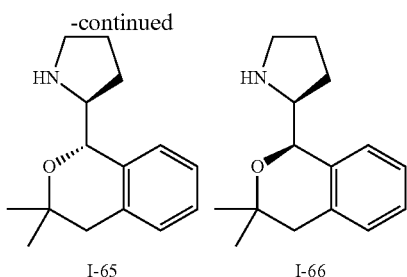

I-65    I-66

To a solution of (2S)-tert-butyl 2-(3,3-dimethylisochroman-1-yl)pyrrolidine-1-carboxylate (780 mg, 2.35 mmol) in ethyl acetate (20 mL) was added HCl/dioxane (1.44 g, 40 mmol). The reaction mixture was stirred at room temperature for 4 h. Upon completion, the mixture was concentrated and the residue separated by PREP-HPLC to give two diastereoisomers, which were each purified again by chiral HPLC: AS-H (250*4.6 mm 5 μm) and mobile phase: MeOH (0.1% DEA) to give (S)-2-((S)-3,3-dimethylisochroman-1-yl) pyrrolidine (I-65) (120 mg) and (S)-2-((R)-3,3-dimethylisochroman1-yl) pyrrolidine (I-66) (80 mg).

(S)-2-((S)-3,3-dimethylisochroman-1-yl) pyrrolidine (I-65): ESI: m/z=232 (M+H$^+$). $^1$HNMR (HCl salt, 400 MHz, MeOD): δ 7.28-7.37 (m, 3H), 7.19-7.21 (m, 1H), 5.03 (s, 1H), 4.23-4.28 (m, 1H), 3.30-3.33 (m, 2H), 3.06-3.10 (1=15.6 Hz, d, 1H), 2.64-2.68 (J=16 Hz, d, 1H), 2.26-2.32 (m, 2H), 2.02-2.18 (m, 2H), 1.43 (s, 3H), 1.20 (s, 3H).

(S)-2-((R)-3,3-dimethylisochroman)-yl) pyrrolidine (I-66): ESI: m/z=232 (M+H$^+$). $^1$HNMR (400 MHz, MeOD): δ 7.17-7.28 (m, 4H), 5.23 (s, 1H), 4.31-4.35 (m, 1H), 3.32-3.37 (m, 2H), 2.89-2.94 (1=16.4 Hz, d, 1H), 2.65-2.69 (1=16 Hz, d, 1H), 2.03-2.08 (m, 1H), 1.93-1.98 (m, 1H), 1.70-1.76 (m, 2H), 1.44 (s, 3H), 1.21 (s, 3H).

Example 1.5.2. ((R)-2-((S)-3,3-dimethylisochroman-1-yl)pyrrolidine (I-67) and (R)-2-((R)-3,3-dimethylisochroman-1-yl)pyrrolidine (I-68)

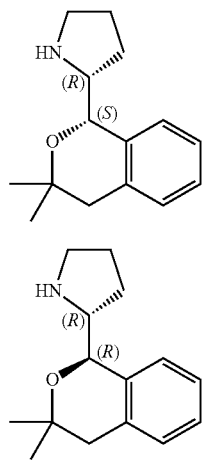

(R)-2-((S)-3,3-dimethylisochroman-1-yl)pyrrolidine (I-67) and (R)-2-((R)-3,3-dimethyl-isochroman-1-yl)pyrrolidine (I-68) were prepared using a procedure analogous to that described in Example 1.5.1, but using (R)-tert-butyl 2-formylpyrrolidine-1-carboxylate in place of (S)-tert-butyl 2-formylpyrrolidine-1-carboxylate.

(R)-2-((S)-3,3-dimethylisochroman-1-yl)pyrrolidine (I-67): ESI: m/z=232 (M+H$^+$). $^1$HNMR (HCl salt, 400 MHz, MeOD): δ 7.14-7.25 (m, 4H), 5.15 (s, 1H), 4.01-4.06 (m, 1H), 3.24-3.32 (m, 1H), 3.10-3.16 (m, 1H), 2.87-2.91 (J=15.6 Hz, d, 1H), 2.62-2.66 (J=15.6 Hz, d, 1H), 1.83-1.95 (m, 2H), 1.56-1.67 (m, 2H), 1.41 (s, 3H), 1.19 (s, 3H).

(R)-2-((R)-3,3-dimethyl-isochroman-1-yl)pyrrolidine (I-68): ESI: m/z=232 (M+H$^+$). $^1$HNMR (400 MHz, MeOD): δ 7.28-7.36 (m, 3H), 7.19-7.21 (m, 1H), 5.03 (s, 1H), 4.23-4.27 (m, 1H), 3.23-3.32 (m, 2H), 3.05-3.09 (J=16 Hz, d, 1H), 2.64-2.68 (J=16 Hz, d, 1H), 2.26-2.32 (m, 2H), 2.04-2.17 (m, 2H), 1.44 (s, 3H), 1.20 (s, 3H).

Example 1.6. General Procedure F. Certain Provided Compounds were Made Following a Procedure Exemplified by Example 1.6.1

Example 1.6.1. (R)-2-((S)-isochroman-1-yl)-4,4-dimethylpyrrolidine (I-62) and (R)-2-((R)-isochroman-1-yl)-4,4-dimethylpyrrolidine (I-61)

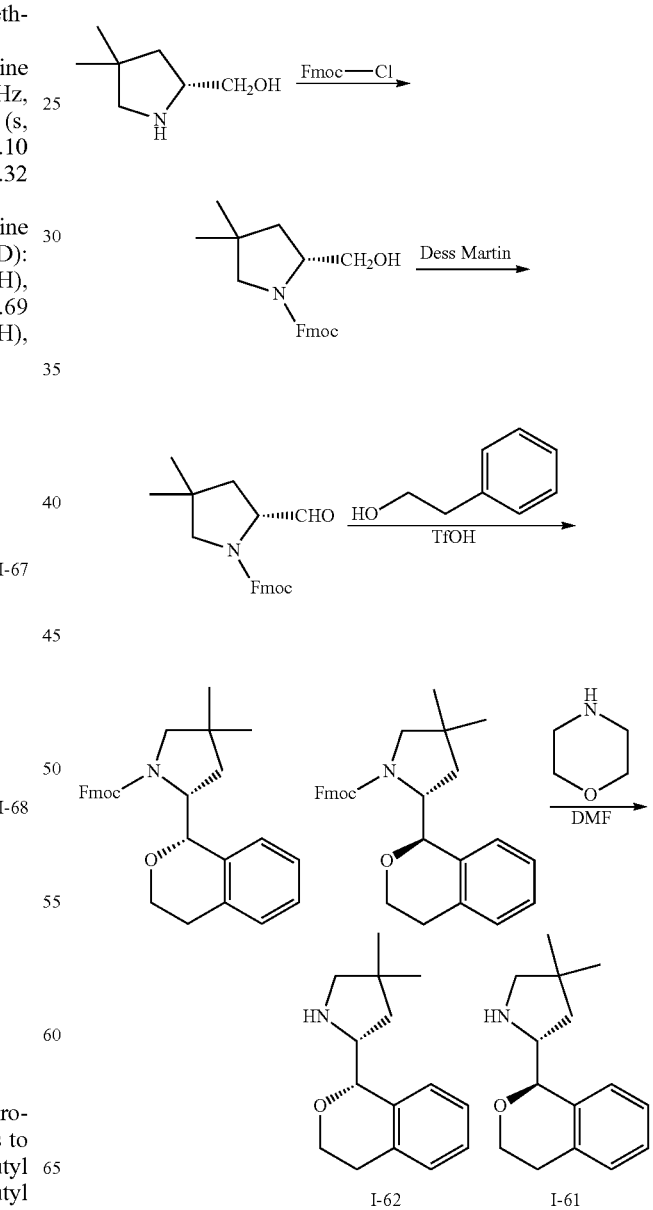

(a). (R)-(9H-fluoren-9-yl)methyl 2-(hydroxymethyl)-4,4-dimethyl-pyrrolidine-1-carboxylate

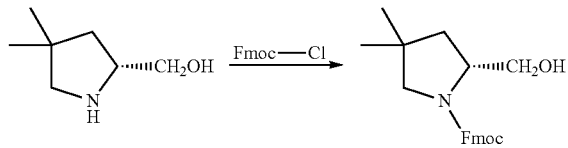

To a solution of (R)-(4,4-dimethylpyrrolidin-2-yl)methanol (3.2 g, 24.77 mmole) in THF (100 mL) and water (30 mL) was added $Na_2CO_3$ (7.87 g, 74.30 mmole) as solid. The suspension was cooled to 0° C. and Fmoc-Cl (9.61 g, 37.15 mmole) was added dropwise. After the addition, the cold bath was removed and the reaction mixture was stirred at room temperature for 2 h. Water (200 mL) was added. The resulting solid was filtered off through a pad of Celite. The filtrate was separated and extracted with ethyl acetate (200 mL×2). The combined organic layers were washed with dilute brine (50 mL×2), dried over sodium sulfate, filtered and concentrated to give a crude product which was purified through column chromatography (EtOAc/PE=1:10) to give the product (7.1 g) as a colorless oil. LC/MS (ESI+): m/z=352.3 (M+H).

(b). (R)-(9H-fluoren-9-yl)methyl 2-formyl-4,4-dimethylpyrrolidine-1-carboxylate

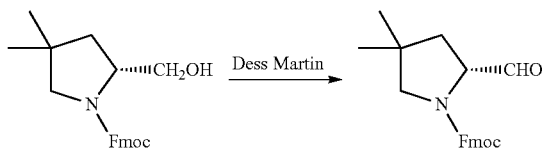

To a solution of (R)-(9H-fluoren-9-yl)methyl 2-(hydroxymethyl)-4,4-dimethylpyrrolidine-1-carboxylate (7.1 g, 20.20 mmole) in DCM (80 mL) was added Dess-Martin reagent (25.71 g, 60.61 mmole) slowly at 0° C. The mixture was stirred at room temperature overnight and the reaction was then quenched with $NaHCO_3$ (sat. aq. 100 mL). The resulting mixture was then extracted with DCM (200 mL×2). The combined organic layers were washed with brine (50 mL×2), dried over $Na_2SO_4$, filtered and concentrated to give the crude product, which was purified by column chromatography (EtOAc/PE=1:10) to give the product (3.25 g) as a colorless oil. LC/MS (ESI+): m/z=351.2 (M+H).

(c). (R)-(9H-fluoren-9-yl)methyl 2-((S)-isochroman-1-yl)-4,4-dimethylpyrrolidine-1-carboxylate and (R)-(9H-fluoren-9-yl)methyl 2-((R)-isochroman-1-yl)-4,4-dimethyl-pyrrolidine-1-carboxylate

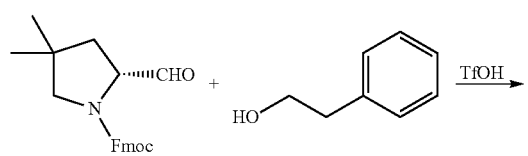

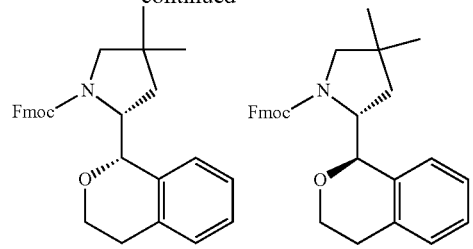

To a solution of (R)-(9H-fluoren-9-yl)methyl 2-formyl-4,4-dimethylpyrrolidine-1-carboxylate (3.25 g, 9.30 mmole) in DCM (16 mL) was added 2-phenylethanol (1.136 g, 9.30 mmole) and TfOH (2 mL) at 0° C. The mixture was stirred at room temperature for 1 h. Solid $Na_2CO_3$ was added to adjust the pH to 7-8, and EtOAc (300 mL) was added. The mixture was washed with water (100 mL×2), sat.NaCl (100 mL×2), dried and concentrated to give the crude product, which was purified by Prep-HPLC to give (R)-(9H-fluoren-9-yl)methyl 2-((S)-isochroman-1-yl)-4,4-dimethylpyrrolidine-1-carboxylate (1.02 g) and (R)-(9H-fluoren-9-yl)methyl 2-((R)-isochroman-1-yl)-4,4-dimethylpyrrolidine-1-carboxylate (I-11) (805 mg). LC-MS: 454.1 (M+H).

(d). (R)-2-((S)-isochroman-1-yl)-4,4-dimethylpyrrolidine

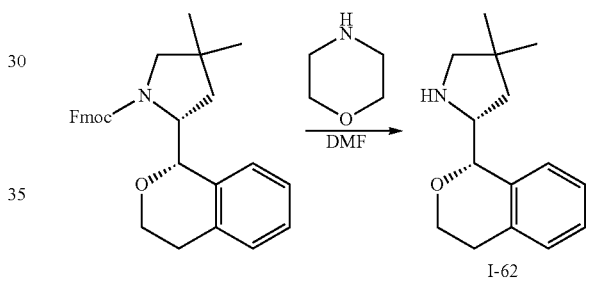

To a solution of (R)-(9H-fluoren-9-yl)methyl 2-((S)-isochroman-1-yl)-4,4-dimethyl-pyrrolidine-1-carboxylate (1.02 g) in DMF (8 mL) was added morpholine (8 mL). The mixture was stirred at room temperature for 2 h. The resulting solid was filtered off. To the filtrate was added EtOAc (200 mL) and the mixture was then washed with water (30 mL×3), sat. NaCl (30 mL×3), dried, and concentrated to give a residue, which was purified by prep-HPLC to give the product (300 mg). LC-MS: 232.2 (M+H). $^1$H NMR ($CDCl_3$, 400 MHz): 7.28-7.10 (m, 4H), 4.96 (d, J=3.2 Hz, 1H), 4.25-4.20 (m, 1H), 3.80-3.72 (m, 2H), 3.10-3.02 (m, 1H), 2.80 (d, J=10.8 Hz, 1H), 2.70-2.61 (m, 2H), 1.40-1.26 (m, 1H), 1.24-1.19 (m, 1H), 1.03 (s, 3H), 1.01 (s, 3H).

(e). (R)-2-((R)-isochroman-1-yl)-4,4-dimethylpyrrolidine

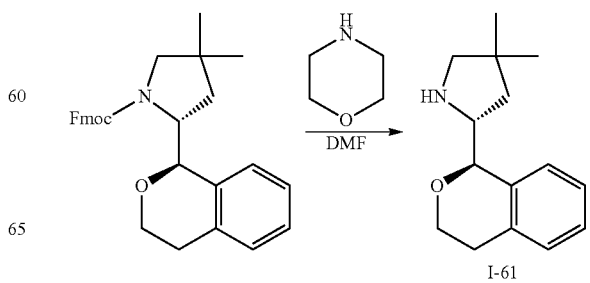

To a solution of (R)-(9H-fluoren-9-yl)methyl 2-((R)-isochroman-1-yl)-4,4-dimethylpyrrolidine-1-carboxylate (805 mg) in DMF (8 mL) was added morpholine (8 mL). The mixture was stirred at room temperature for 2 h. The resulting solid was filtered off and to the filtrate was added EtOAc (200 mL). The mixture was washed with water (30 mL×3), sat. NaCl (30 mL×3), dried and concentrated to give a residue, which was purified by prep-HPLC to give the product (242 mg). LC-MS: 232.2 (M+H). $^1$H NMR (CDCl3, 400 MHz): 7.28-7.10 (m, 4H), 4.71 (d, J=4.0 Hz, 1H), 4.25-4.20 (m, 1H), 3.80-3.72 (m, 2H), 3.07-2.98 (m, 1H), 2.80 (d, J=10.8 Hz, 1H), 2.70-2.61 (m, 2H), 1.79-1.74 (m, 1H), 1.68-1.63 (m, 1H), 1.10 (s, 3H), 1.08 (s, 3H).

Example 1.6.2. (S)-2-((S)-isochroman-1-yl)-4,4-dimethylpyrrolidine (I-60) and (S)-2-((R)-isochroman-1-yl)-4,4-dimethylpyrrolidine (I-59)

I-60

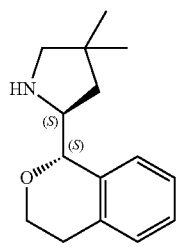

I-59

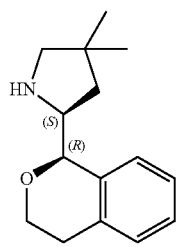

(S)-2-((S)-isochroman-1-yl)-4,4-dimethylpyrrolidine (I-60) and (S)-2-((R)-isochroman-1-yl)-4,4-dimethylpyrrolidine (I-59) were prepared using a procedure analogous to that described in Example 1.6.1, but using (S)-(4,4-dimethylpyrrolidin-2-yl)methanol in place of (R)-(4,4-dimethylpyrrolidin-2-yl)methanol.

(S)-2-((S)-isochroman-1-yl)-4,4-dimethylpyrrolidine (I-60): LC-MS: 232.2 (M+H). $^1$HNMR (HCl salt, DMSO-d6, 400 MHz): 9.62 (s, 1H), 8.45 (s, 1H), 7.33-7.18 (m, 4H), 4.90 (s, 1H), 4.32-4.28 (m, 1H), 4.27-4.18 (m, 1H), 3.78-3.73 (m, 1H), 3.17-3.04 (m, 1H), 2.83-2.66 (m, 2H), 2.58-2.53 (m, 1H), 2.12-1.93 (m, 1H), 1.89-1.78 (m, 1H), 1.17 (s, 3H), 1.12 (s, 3H).

(S)-2-((R)-isochroman-1-yl)-4,4-dimethylpyrrolidine (I-59): LC-MS: 232.2 (M+H). $^1$HNMR (HCl salt, DMSO-d6, 400 MHz): 9.62 (s, 1H), 8.45 (s, 1H), 7.33-7.18 (m, 4H), 4.90 (s, 1H), 4.32-4.28 (m, 1H), 4.27-4.18 (m, 1H), 3.78-3.73 (m, 1H), 3.17-3.04 (m, 1H), 2.83-2.66 (m, 2H), 2.58-2.53 (m, 1H), 2.12-1.93 (m, 1H), 1.89-1.78 (m, 1H), 1.17 (s, 3H), 1.12 (s, 3H).

Example 1.7. Procedure G. Certain Provided Compounds were Made Following a Procedure Exemplified by Example 1.7.1

Example 1.7.1. (R)-3-(isochroman-1-yl)azetidine (I-114) and (S)-3-(isochroman-1-yl)azetidine (I-115)

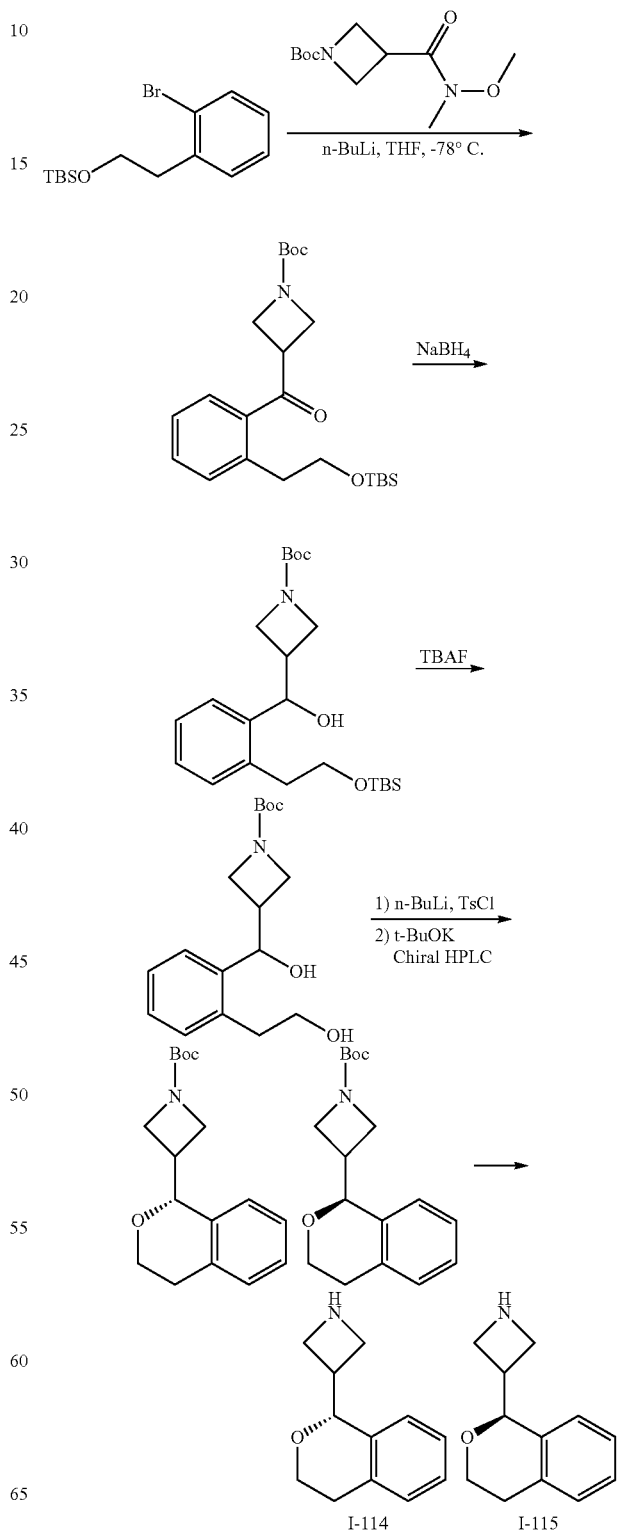

(a). tert-butyl 3-(2-(2-(tert-butyldimethylsilyloxy)ethyl)benzoyl)azetidine-1-carboxylate

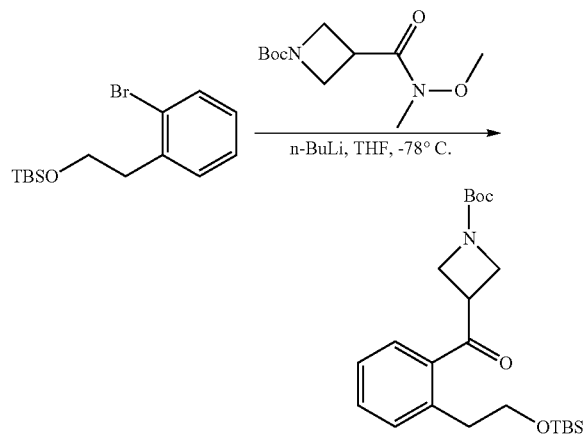

To a stirred solution of (2-bromophenethoxy)(tert-butyl)dimethylsilane (15.77 g, 50 mmol) in dry THF (200 mL) was added dropwise n-Butyl lithium (25 mL, 60 mmol, 2.4 M solution in hexane) at −78° C. under nitrogen, and the reaction mixture was stirred at this temperature for 1 h. To the reaction mixture, a solution of tert-butyl 3-(methoxy(methyl) carbamoyl)azetidine-1-carboxylate (12.2 g, 50 mmol) in dry THF (50 mL) was added dropwise. The reaction mixture was stirred at −78° C. for 1 h and then quenched by addition of a saturated aqueous NH4Cl solution (50 mL). The aqueous phase was extracted with ethyl acetate and the combined organic phase were washed with brine, dried over anhydrous sodium sulfate, filtered and concentrated in vacuo to give a residue, which was purified by column chromatography (petroleum ether/ethyl acetate: 5/1) to afford butyldimethylsilyl)oxy)ethyl)benzoyl)azetidine-1-carboxylate (13.3 g) as colorless oil.

(b). tert-butyl 3-((2-(2-((tert-butyldimethylsilyl)oxy)ethyl)phenyl)(hydroxy)methyl)-azetidine-1-carboxylate

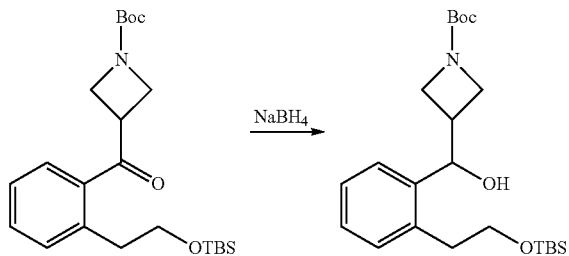 [SMILES: CC(C)(C)OC(=O)N1CC(C(=O)c2ccccc2CCO[Si](C)(C)C(C)(C)C)C1 ; "NaBH4" ; CC(C)(C)OC(=O)N1CC(C(O)c2ccccc2CCO[Si](C)(C)C(C)(C)C)C1]

To a solution of tert-butyl 3-(2-(2-((tert-butyldimethylsilyl)oxy)ethyl)benzoyl)azetidine-1-carboxylate (13.22 g, 31.5 mmol) in methanol (157 mL) was added sodium borohydride (1.79 g, 47.25 mmol) slowly at 0° C. Then mixture was stirred at room temperature for 1 h. The solvent was removed and the residue was added water (100 mL) and ethyl acetate (100 mL). The resulting biphasic mixture was transferred to a reparatory funnel. The layers were separated and the organic phase was washed with brine (50 mL), dried over anhydrous sodium sulfate, filtered, concentrated to give a residue, which was purified by column chromatography (ethyl acetate/petroleum ether=1:5) to give the product (13 g) as a colorless oil.

(c). (tert-butyl 3-(hydroxy(2-(2-hydroxyethyl)phenyl)methyl)azetidine-1-carboxylate

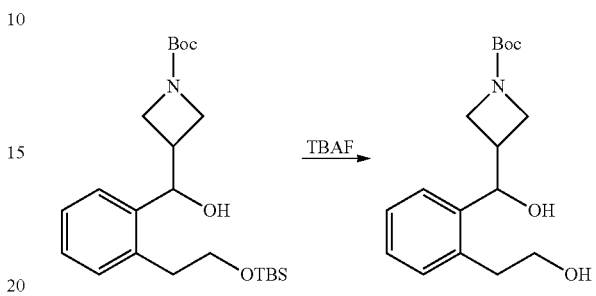

To a solution of tert-butyl 3-((2-(2-((tert-butyldimethylsilyl)oxy)ethyl)phenyl) (hydroxy)methyl)azetidine-1-carboxylate (6.5 g, 15.42 mmol) in tetrahydrofuran (75 mL) was added tetrabutylammonium fluoride (4.03 g, 15.42 mmol) at 0° C. The mixture was stirred at room temperature overnight and solvent removed. The residue was diluted with EtOAc (500 mL), washed with brine (4×50 mL), dried over sodium sulfate and concentrated. The crude product was purified by silica gel chromatography (ethyl acetate/petroleum ether=1:5) to give the product as a colorless oil (4.7 g).

(d). (R)-tert-butyl 3-(isochroman-1-yl)azetidine-1-carboxylate and (S)-tert-butyl 3-(isochroman-1-yl)azetidine-1-carboxylate

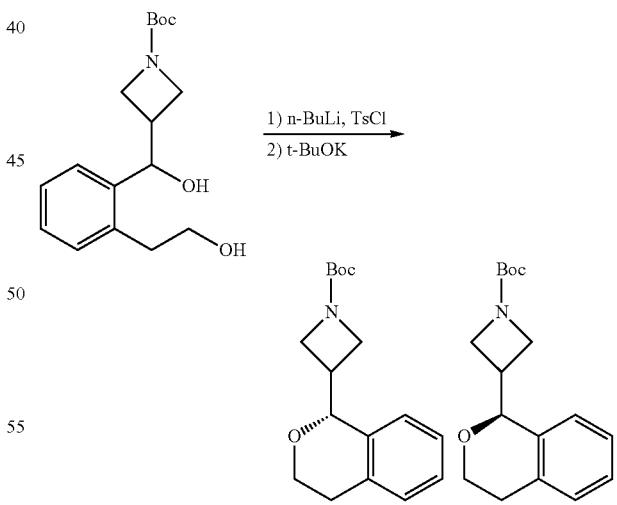

To a solution of tert-butyl 3-(hydroxy(2-(2-hydroxyethyl)phenyl)methyl)azetidine-1-carboxylate (4.5 g, 14.64 mmol) in toluene (100 mL) was added n-butyllithium (6.89 mL, 16.54 mmol) at 0° C. After 30 min, 4-methyl-benzenesulfonyl chloride (3.15 g, 16.54 mmol) was added to the mixture. The mixture was stirred at this temperature for another 1 h and n-butyllithium (9.15 mL, 21.96 mmol) was added. The reaction mixture was stirred at 40° C. for 16 h and then poured into iced-water, and extracted with EtOAc (3×100 mL). The combined organic layers were washed with brine (2×100 mL), dried over Na₂SO₄, filtered and concentrated to give a residue, which was purified by pre-HPLC to give the racemic mixture of tert-butyl 3-(isochroman-1-yl)azetidine-1-carboxylate as yellow of (1.5 g). The racemate was then separated by chiral HPLC, column: OZ-H (250*4.6 mm 5 μm) and mobile phase: MeOH (0.1% DEA) to give (R)-tert-butyl-3-(isochroman-1-yl)azetidine-1-carboxylate and (S)-tert-butyl-3-(isochroman-1-yl)azetidine-1-carboxylate as colorless oil.

(e). (R)-3-(isochroman-1-yl)azetidine (I-114)

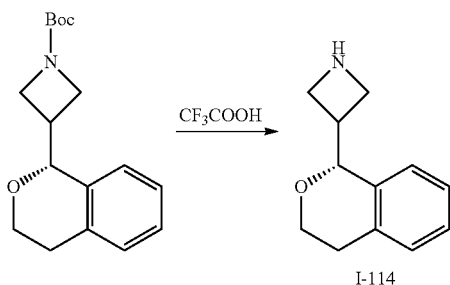 [SMILES: CC(C)(C)OC(=O)N1CC([C@H]2OCCc3ccccc32)C1 ; "CF3COOH" ; c1ccc2c(c1)CCO[C@@H]2C1CNC1]

To a solution of (R)-tert-butyl 3-(isochroman-1-yl)azetidine-1-carboxylate (0.4 g, 1.38 mmol) in DCM (10 mL) was added 2,2,2-trifluoroacetic acid (2 mL) dropwise. The mixture was stirred at room temperature for 2 h and solvent was removed. The residue was dissolved in water (15 mL), followed by addition of aqueous NH₄OH. The resulting mixture was extracted with DCM (20 mL×5). The organic phase was combined, dried over Na₂SO₄, filtered, and concentrated to give (R)-3-(isochroman-1-yl)azetidine (I-114) (0.25 g) as a yellow oil. MS (ESI): m/z 190 [M+H]⁺, ¹H NMR (HCl salt, 400 MHz, MeOD) δ 7.26-7.17 (m, 3H), 7.13-7.06 (m, 1H), 4.94 (s, 1H), 4.38 (m, 1H), 4.34-4.22 (m, 2H), 3.98-3.82 (m, 2H), 3.77 (dd, J=10.4, 6.3 Hz, 1H), 3.69-3.55 (m, 1H), 3.17 (m, 1H), 2.79-2.67 (m, 1H).

(f). (S)-3-(isochroman-1-yl)azetidine (I-115)

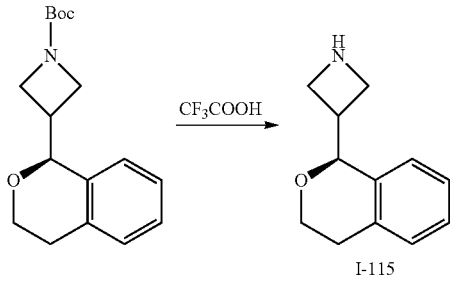 [SMILES: CC(C)(C)OC(=O)N1CC([C@@H]2OCCc3ccccc32)C1 ; "CF3COOH" ; c1ccc2c(c1)CCO[C@H]2C1CNC1]

To a solution of (S)-tert-butyl 3-(isochroman-1-yl)azetidine-1-carboxylate (0.45 g, 1.56 mmol) in DCM (10 mL) was added 2,2,2-trifluoroacetic acid (2 mL) dropwise. The mixture was stirred at room temperature for 2 h, and solvent was removed. The residue was dissolved in water (15 mL), followed by addition of aqueous NH₄OH. The resulting mixture was extracted with DCM (20 mL×5). The organic phase was combined, dried over Na₂SO₄, and concentrated to give (S)-3-(isochroman-1-yl)azetidine (0.27 gas a yellow oil. MS (ESI): m/z 190 [M+H]⁺, ¹H NMR (HCl salt, 400 MHz, MeOD) δ 7.15-7.04 (m, 3H), 7.00-6.92 (m, 1H), 4.82 (s, 1H), 4.26 (m, 1H), 4.16 (p, J=10.2 Hz, 2H), 3.76 (m, 2H), 3.65 (dd, J=10.3, 6.4 Hz, 1H), 3.55-3.44 (m, 1H), 3.05 (m, 1H), 2.61 (d, J=16.5 Hz, 1H).

Example 1.7.2. ((R)-3-(7-methylisochroman-1-yl)azetidine (I-116) and (S)-3-(7-methylisochroman-1-yl)azetidine (I-117)

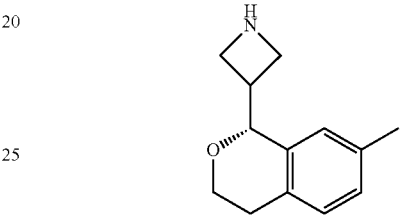

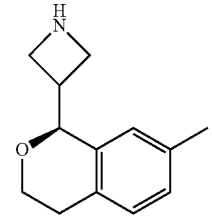

(R)-3-(7-methylisochroman-1-yl)azetidine (I-116) and (S)-3-(7-methylisochroman-1-yl)azetidine (I-117) were prepared using a procedure analogous to that described in Example 1.7.1, but using (2-bromo-4-methylphenethoxy)(tert-butyl)dimethylsilane in place of (2-bromophenethoxy)(tert-butyl)dimethylsilane.

(R)-3-(7-methylisochroman-1-yl)azetidine (I-116): MS m/z 204 [M+H]⁺, ¹H NMR (HCl salt, 400 MHz, MeOD) δ 7.06 (M, 2H), 6.91 (s, 1H), 4.90 (s, 1H), 4.36 (M, 1H), 4.33-4.20 (m, 2H), 3.98-3.89 (m, 1H), 3.88-3.72 (m, 2H), 3.67-3.54 (m, 1H), 3.19-3.04 (m, 1H), 2.67 (d, J=15.5 Hz, 1H), 2.30 (s, 3H).

(S)-3-(7-methylisochroman-1-yl)azetidine (I-117): MS m/z 204 [M+H]⁺, ¹H NMR (HCl salt, 400 MHz, MeOD) δ 7.05 (m, 2H), 6.91 (s, 1H), 4.89 (s, 1H), 4.36 (m 1H), 4.27 (dd, J=15.6, 7.1 Hz, 2H), 3.93 (t, J=9.6 Hz, 1H), 3.89-3.72 (m, 2H), 3.66-3.54 (m, 1H), 3.20-3.05 (m, 1H), 2.67 (d, J=15.3 Hz, 1H), 2.30 (s, 3H).

117

Example 1.8. Procedure H. Certain Provided Compounds were Made Following a Procedure Exemplified by Example 1.8.1

Example 1.8.1. (S)-1-((S)-pyrrolidin-2-yl)isochroman-6-carbonitrile (I-43) and (R)-1-((S)-pyrrolidin-2-yl)isochroman-6-carbonitrile (I-44)

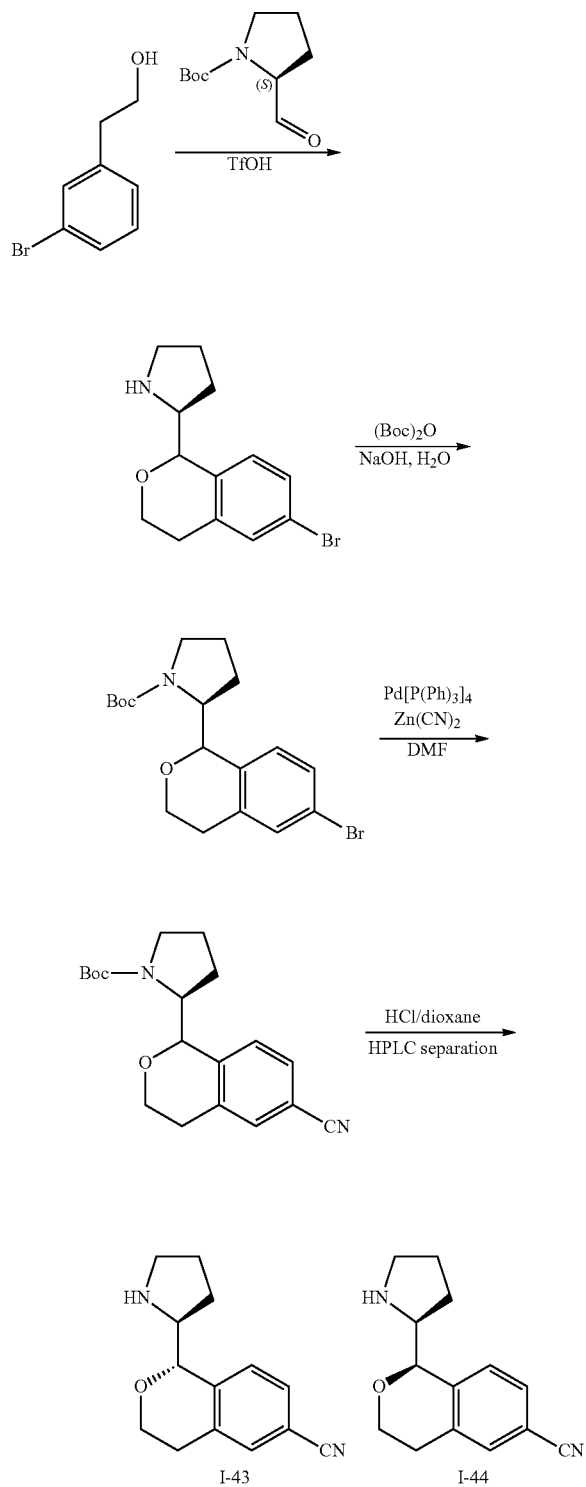

118

(a). (2S)-tert-butyl 2-(6-bromoisochroman-1-yl)pyrrolidine-1-carboxylate

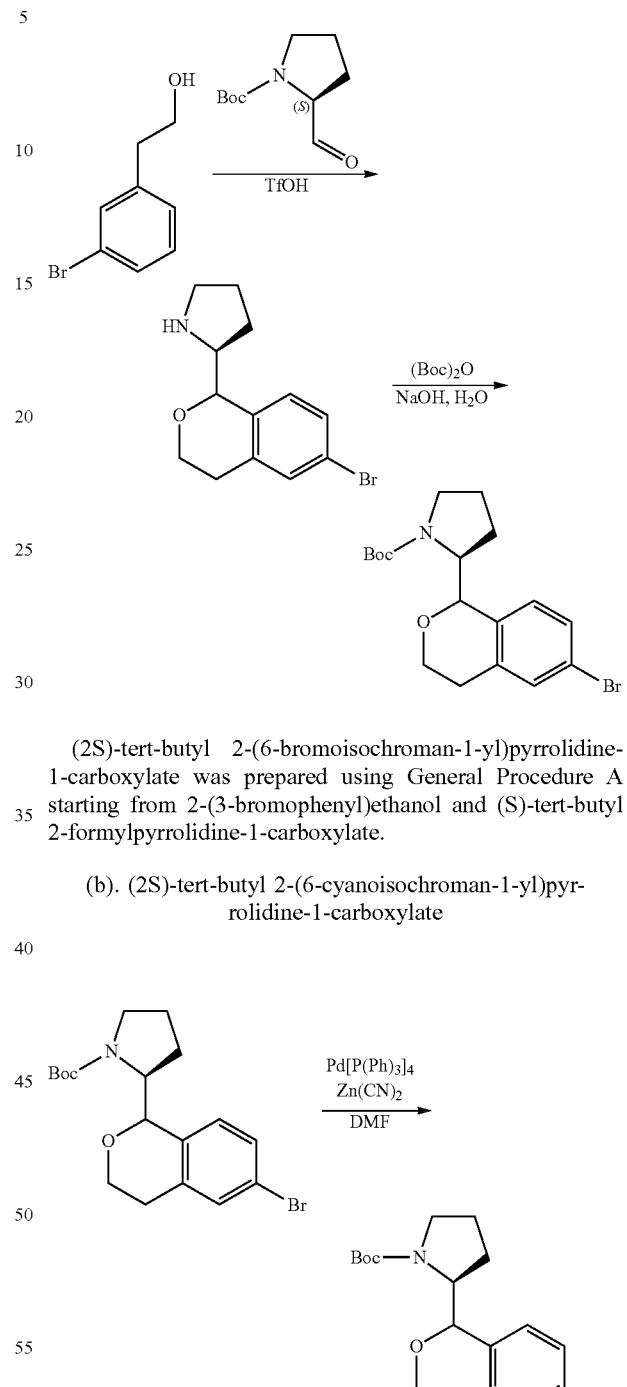

(2S)-tert-butyl 2-(6-bromoisochroman-1-yl)pyrrolidine-1-carboxylate was prepared using General Procedure A starting from 2-(3-bromophenyl)ethanol and (S)-tert-butyl 2-formylpyrrolidine-1-carboxylate.

(b). (2S)-tert-butyl 2-(6-cyanoisochroman-1-yl)pyrrolidine-1-carboxylate

A mixture of (2S)-tert-butyl 2-(6-bromoisochroman-1-yl)pyrrolidine-1-carboxylate (3.93 g, 10.31 mmol), dicyanozinc (2.42 g, 20.63 mmol), tetrakis(triphenylphosphine)palladium (1.19 g, 1.03 mmol) in DMF (20 mL) was stirred at 120° C. in microwave reactor for 3 h under nitrogen atmosphere. Upon completion, the mixture was filtered and the filtrate was purified by flash chromatography to afford the product (2.2 g) as a light yellow oil.

(c). (S)-1-((S)-pyrrolidin-2-yl)isochroman-6-carbonitrile (I-43) and (R)-1-((S)-pyrrolidin-2-yl)isochroman-6-carbonitrile (I-44)

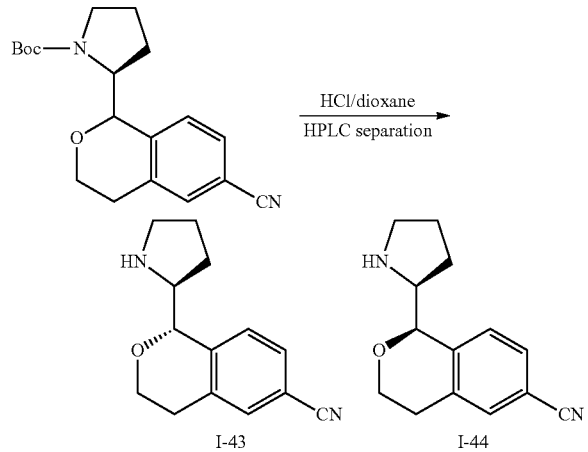

(2S)-tert-butyl 2-(6-cyanoisochroman-1-yl)pyrrolidine-1-carboxylate (2.1 g, 6.39 mmol) was stirred in HCl/dioxane (3 M) (20 mL) at room temperature for about 2 h. To the mixture was added NH₄OH (aq.) till pH 8~9 and the mixture was concentrated in vacuo. The crude product was purified by Prep-HPLC to give the two diastereoisomers, which then were each separately purified by chiral separation using column: AY-H (250*4.6 mm 5 μm); Mobile Phase: n-Hexane (0.1% DEA): EtOH (0.1% DEA)=80:20, followed by another chiral separation using column: OJ-H 4.6*250 mm 5 μm, Mobile Phase: MeOH (0.1% DEA), to afford I-43 and I-44. MS (ESI) m/z 229.1 (M+H)⁺.

(S)-1-((S)-pyrrolidin-2-yl)isochroman-6-carbonitrile (I-43): MS (ESI) m/z 229.1 (M+H)⁺. $^1$H NMR (400 MHz, CDCl₃): δ 7.49~7.40 (m, 3H), 4.79 (s, 1H), 4.27~4.22 (m, 1H), 3.78~3.72 (m, 1H), 3.60~3.55 (m, 1H), 3.11~3.06 (m, 2H), 2.80~2.67 (m, 2H), 1.95~1.75 (m, 5H).

(R)-1-((S)-pyrrolidin-2-yl)isochroman-6-carbonitrile (I-44): MS (ESI) m/z: 229.1 (M+H)⁺¹. $^1$H NMR (HCl salt, 400 MHz, MeOD): δ 7.62 (d, J=7.2 Hz, 2H), 7.42 (d, J=8.4 Hz, 1H), 5.27 (s, 1H), 4.42~4.33 (m, 2H), 3.86~3.79 (m, 1H), 3.38~3.33 (m, 2H), 3.19~3.11 (m, 1H), 2.79 (d, J=16.8 Hz, 1H), 2.11~1.93 (m, 2H), 1.79~1.72 (m, 2H).

Example 1.8.2. (S)-1-((R)-pyrrolidin-2-yl)isochroman-6-carbonitrile (I-46) and (R)-1-((R)-pyrrolidin-2-yl)isochroman-6-carbonitrile (I-45)

I-46

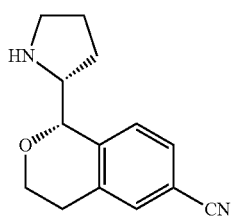

I-45

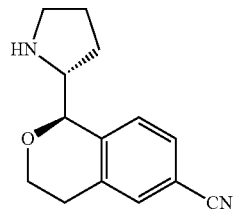

(S)-1-((R)-pyrrolidin-2-yl)isochroman-6-carbonitrile (I-46) and (R)-1-((R)-pyrrolidin-2-yl)isochroman-6-carbonitrile (I-45) were prepared using a procedure analogous to that described in Example 1.8.1, but using (R)-tert-butyl 2-formylpyrrolidine-1-carboxylate in place of (S)-tert-butyl 2-formylpyrrolidine-1-carboxylate.

(S)-1-((R)-pyrrolidin-2-yl)isochroman-6-carbonitrile (I-46): ESI: m/z=229 (M+H⁺). $^1$HNMR (HCl salt, 400 MHz, MeOD): δ 7.62-7.63 (1=6.8 Hz, d, 1H), 7.43-7.45 (J=8.4 Hz, d, 1H), 5.28 (s, 1H), 4.33-4.43 (m, 2H), 3.79-3.86 (m, 1H), 3.34-3.39 (m, 2H), 3.11-3.19 (m, 1H), 2.64-2.77 (m, 2H), 2.77-2.81 (1=16 Hz, d, 1H), 1.94-2.10 (m, 2H), 1.65-1.79 (m, 2H).

(R)-1-((R)-pyrrolidin-2-yl)isochroman-6-carbonitrile (I-45): ESI: m/z=229 (M+H⁺). $^1$HNMR (HCl salt, 400 MHz, MeOD): δ 7.65-7.67 (1=13.2 Hz, d, 1H), 7.53-7.55 (m, 1H), 5.10 (s, 1H), 4.28-4.35 (m, 2H), 3.83-3.89 (m, 1H), 3.20-3.30 (m, 3H), 2.77-2.82 (1=17.2 Hz, d, 1H), 2.07-2.35 (m, 4H).

Example 1.8.3. (S)-1-((S)-pyrrolidin-2-yl)isochroman-7-carbonitrile (I-39) and (R)-1-((S)-pyrrolidin-2-yl)isochroman-7-carbonitrile (I-40)

I-39

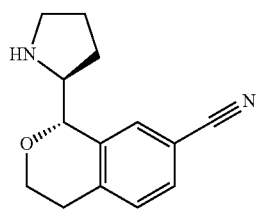

I-40

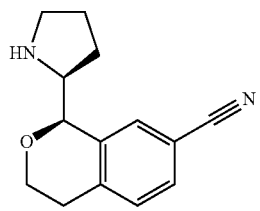

(S)-1-((S)-pyrrolidin-2-yl)isochroman-7-carbonitrile (I-39) and (R)-1-((S)-pyrrolidin-2-yl)isochroman-7-carbonitrile (I-40) were prepared using a procedure analogous to that described in Example 1.8.1, but using 2-(4-bromophenyl)ethanol in place of 2-(3-bromophenyl) ethanol.

(S)-1-((S)-pyrrolidin-2-yl)isochroman-7-carbonitrile (I-39): MS (ESI) m/z 229 (M+H)⁺. $^1$H NMR (HCl salt, 400 MHz, MeOD) δ 7.78 (s, 1H), 7.66 (dd, J=7.9, 0.9 Hz, 1H), 7.44 (d, J=8.0 Hz, 1H), 5.08 (s, 1H), 4.45-4.24 (m, 2H), 3.87 (td, J=11.4, 3.3 Hz, 1H), 3.32-3.19 (m, 3H), 2.82 (d, J=17.2 Hz, 1H), 2.41-2.23 (m, 2H), 2.22-1.97 (m, 2H).

(R)-1-((S)-pyrrolidin-2-yl)isochroman-7-carbonitrile (I-40): MS (ESI): m/z 229 (M+H)+. 1H NMR (HCl salt, 400 MHz, MeOD) δ 7.72 (d, J=23.5 Hz, 1H), 7.62 (d, J=8.0 Hz, 1H), 7.43 (d, J=8.0 Hz, 1H), 5.25 (s, 1H), 4.43 (td, J=8.3, 2.7 Hz, 1H), 4.35 (dd, J=11.4, 6.0 Hz, 1H), 3.83 (td, J=11.7, 2.9 Hz, 1H), 3.38 (ddd, J=11.9, 10.4, 7.6 Hz, 2H), 3.18 (ddd, J=17.8, 11.9, 6.2 Hz, 1H), 2.82 (d, J=17.0 Hz, 1H), 2.14-1.90 (m, 2H), 1.87-1.66 (m, 2H).

Example 1.8.4. (S)-1-((R)-pyrrolidin-2-yl)isochroman-7-carbonitrile (I-42) and (R)-1-((R)-pyrrolidin-2-yl)isochroman-7-carbonitrile (I-41)

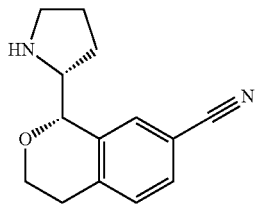

I-42

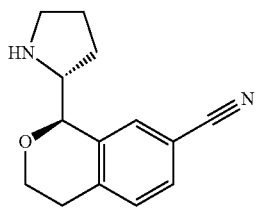

I-41

(S)-1-((R)-pyrrolidin-2-yl)isochroman-7-carbonitrile (I-42) and (R)-1-((R)-pyrrolidin-2-yl)isochroman-7-carbonitrile (I-41) were prepared using a procedure analogous to that described in Example 1.8.1, but using 2-(4-bromophenyl)ethanol in place of 2-(3-bromophenyl) ethanol and (R)-tert-butyl 2-formylpyrrolidine-1-carboxylate in place of (S)-tert-butyl 2-formylpyrrolidine-1-carboxylate.

(S)-1-((R)-pyrrolidin-2-yl)isochroman-7-carbonitrile (I-42): MS (ESI) m/z: 229.1 (M+H)+1. 1H NMR (HCl salt, 400 MHz, MeOD): δ 7.70 (s, 1H), 7.62 (d, J=8.0 Hz, 1H), 7.42 (d, J=8.0 Hz, 1H), 5.25 (s, 1H), 4.46~4.42 (m, 1H), 4.37~4.11 (m, 1H), 3.87~3.80 (m, 1H), 3.42~3.32 (m, 2H), 3.22~3.14 (m, 1H), 2.81 (d, J=16.4 Hz, 1H), 2.10~1.82 (m, 2H), 1.80~1.71 (m, 2H).

(R)-1-((R)-pyrrolidin-2-yl)isochroman-7-carbonitrile (I-41): MS (ESI) m/z: 229.1 (M+H)+1 1H NMR (HCl salt, 400 MHz, MeOD): δ 7.78 (s, 1H), 7.65 (d, J=7.6 Hz, 1H), 7.44 (d, J=8.0 Hz, 1H), 5.08 (s, 1H), 4.36~4.59 (m, 2H), 3.90~3.83 (m, 1H), 3.32~3.22 (m, 3H), 2.81 (d, J=17.2 Hz, 1H), 2.34~2.03 (m, 4H).

Example 1.9. Procedure I. Certain Provided Compounds were Made Following a Procedure Exemplified by Example 1.9.1

Example 1.9.1. (S)-3-((S)-isochroman-1-yl)morpholine (I-75) and (S)-3-((R)-isochroman-1-yl)morpholine (I-76)

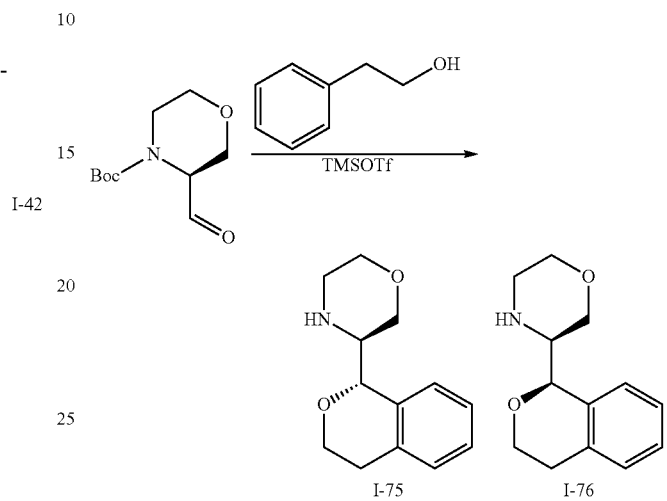

To a solution of (S)-tert-butyl 3-formylmorpholine-4-carboxylate (0.5 g, 2.32 mmol) in DCM (10 mL) was added TMSOTf (2.06 g, 9.28 mmol) and 2-phenylethanol (0.28 g, 2.32 mmol). The mixture was stirred at room temperature for 2 h, poured into ice-water, extracted with DCM (2×20 ml). The combined organic layers were dried, filtered, and solvent removed. The crude was purified by Prep-HPLC to provide (S)-3-((S)-isochroman-1-yl) morpholine (I-75) (70 mg) and (S)-3-((R)-isochroman-1-yl) morpholine (I-76) (50 mg) as orange oil.

(S)-3-((S)-isochroman-1-yl) morpholine (I-75): MS (ESI) m/z 220 (M+H)+. 1H NMR (HCl salt, 400 MHz, MeOD) δ 7.33 (m, 3H), 7.26 (m, 1H), 4.99 (s, 1H), 4.23 (m, 2H), 3.98 (m, 3H), 3.77 (m, 2H), 3.18 (m, 3H), 2.73 (m, 1H).

(S)-3-((R)-isochroman-1-yl) morpholine (I-76): MS (ESI) m/z 220 (M+H)+. 1H NMR (HCl salt, 400 MHz, MeOD) δ 7.22 (m, 3H), 7.15 (m, 1H), 4.82 (s, 1H), 4.18 (m, 1H), 3.72 (m, 2H), 3.38 (m, 4H), 2.98 (m, 3H), 2.63 (m, 1H).

Example 1.9.2. (S)-3-((S)-6-fluoroisochroman-1-yl) morpholine (I-77) and (S)-3-((R)-6-fluoroisochroman-1-yl)morpholine (I-78)

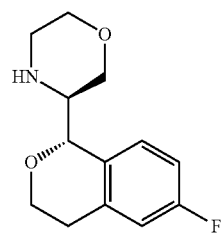

I-77

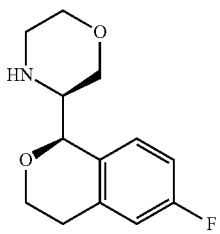

I-78

(S)-3-((S)-6-fluoroisochroman-1-yl)morpholine (I-77) and (S)-3-((R)-6-fluoroisochroman-1-yl)morpholine (I-78) were prepared using a procedure analogous to that described in Example 1.9.1, but using 2-(3-fluorophenyl)ethanol in place of 2-phenylethanol.

(S)-3-((S)-6-fluoroisochroman-1-yl)morpholine (I-77): MS (ESI) m/z 238 (M+H)+, 1H NMR (HCl salt, 400 MHz, MeOD) δ 7.23 (m, 1H), 6.97 (m, 1H), 6.90 (m, 1H), 4.79 (s, 1H), 4.17 (m, 1H), 3.76 (m, 1H), 3.64 (m, 1H), 3.39 (m, 4H), 3.00 (m, 3H), 2.65 (m, 1H).

(S)-3-((R)-6-fluoroisochroman-1-yl)morpholine (I-78): MS (ESI) m/z 238 (M+H)+, 1H NMR HCl salt, (400 MHz, MeOD) δ 7.23 (m, 1H), 6.97 (m, 1H), 6.90 (m, 1H), 4.69 (s, 1H), 4.17 (m, 1H), 3.91 (m, 1H), 3.70 (m, 3H), 3.47 (m, 1H), 3.29 (m, 1H), 3.03 (m, 1H), 2.82 (m, 2H), 2.67 (m, 1H).

Example 1.10. Procedure J

Example 1.10.1. (S)-1-((S)-pyrrolidin-2-yl)isochroman-8-carbonitrile (I-37) and (R)-1-((S)-pyrrolidin-2-yl)isochroman-8-carbonitrile (I-38)

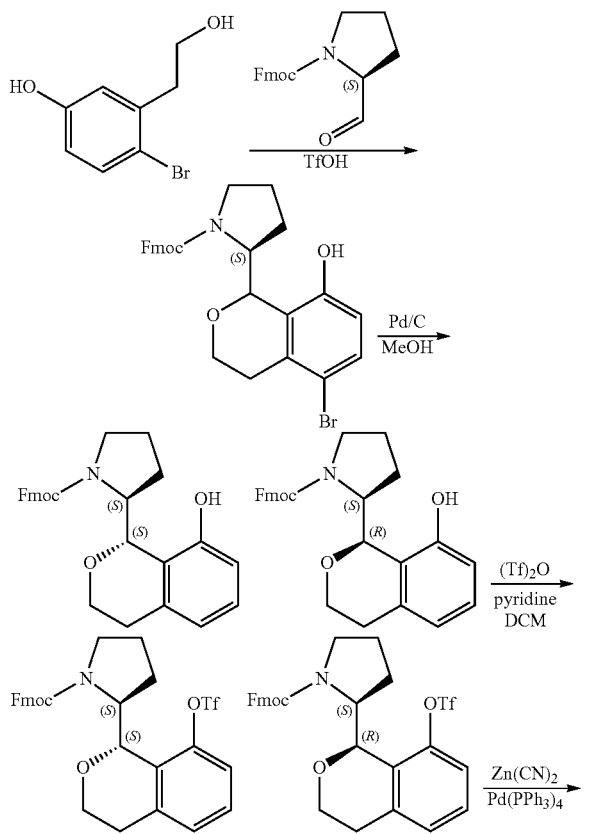

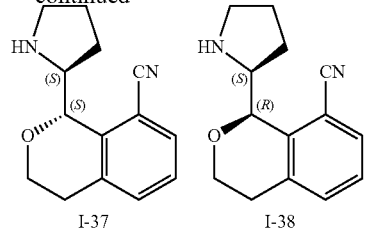

(a). (2S)-(9H-fluoren-9-yl)methyl 2-(5-bromo-8-hydroxyisochroman-1-yl)pyrrolidine-1-carboxylate

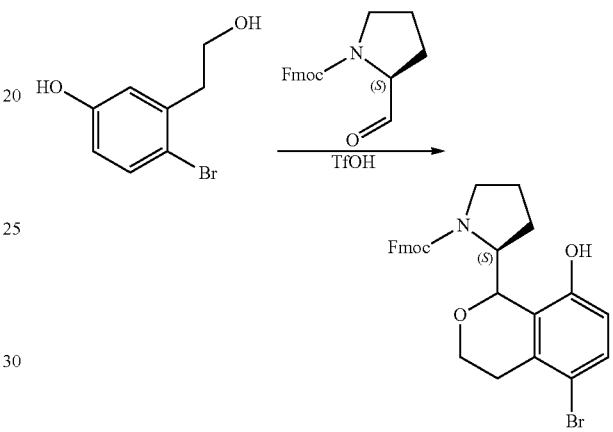

4-bromo-3-(2-hydroxyethyl)phenol (4.0 g, 18.43 mmol), (S)-(9H-fluoren-9-yl)methyl 2-formylpyrrolidine-1-carboxylate (8.88 g, 27.65 mmol) in toluene (40 mL) was stirred at 0° C. Trifluoromethanesulfonic acid (10 mL) was added dropwise to the solution at this temperature. The mixture was stirred at 0° C. for an additional 2-3 h and ice water (100 mL) was added. The mixture was filtered under reduced pressure, washed with methanol (100 mL). The filtrate was concentrated in vacuo and then extracted with ethyl acetate (3×100 mL). The combined organic layers were washed with brine (80 mL), dried over anhydrous sodium sulfate, filtered, and concentrated in vacuo to afford the crude product, which was purified by column chromatography (petroleum ether: ethyl acetate=20:1-10:1-5:1) to yield the desired product as a colorless solid. MS (ESI) m/z 520.1 (M+H)+

(b). (S)-(9H-fluoren-9-yl)methyl 2-((S)-8-hydroxyisochroman-1-yl)pyrrolidine-1-carboxylate and (S)-(9H-fluoren-9-yl)methyl 2-((R)-8-hydroxyisochroman-1-yl)pyrrolidine-1-carboxylate

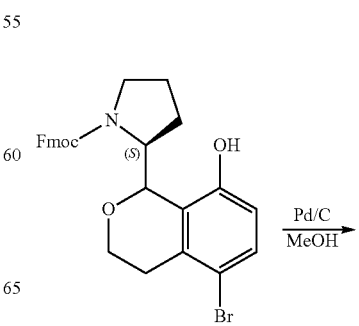

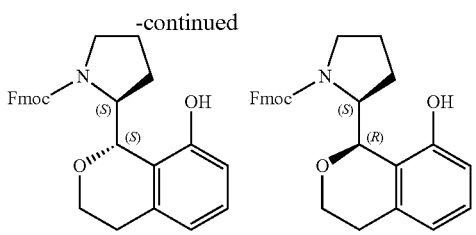

Palladium on activated carbon 10% Pd/C (3.2 g) was added to a solution of (2S)-(9H-fluoren-9-yl)methyl 2-(5-bromo-8-hydroxyisochroman-1-yl)pyrrolidine-1-carboxylate (10.3 g, 19.80 mmol) in methanol (150 mL). The mixture was stirred at room temperature under hydrogen overnight. The mixture was filtered through a celite pad under reduced pressure, washed with methanol (3×100 mL). The combined filtrate was concentrated in vacuum to afford the crude product, which was purified by column chromatography (petroleum ether: ethyl acetate=20:1-10:1-5:1) to afford the two stereoisomers, (S)-(9H-fluoren-9-yl)methyl 2-((S)-8-hydroxyisochroman-1-yl)pyrrolidine-1-carboxylate (1.1 g) and (S)-(9H-fluoren-9-yl)methyl 2-((R)-8-hydroxyisochroman-1-yl)pyrrolidine-1-carboxylate (2.1 g) as white solid. MS (ESI) m/z 442.1 (M+H)⁺

(c). (S)-(9H-fluoren-9-yl)methyl 2-((S)-8-(trifluoromethylsulfonyloxy) isochroman-1-yl)pyrrolidine-1-carboxylate

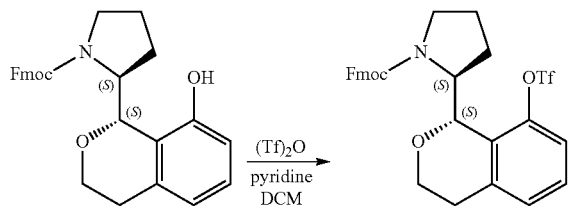

Trifluoromethanesulfonic anhydride (1.35 mL, 2.26 mmol) was added to a solution of (2S)-(9H-fluoren-9-yl)methyl 2-(8-hydroxyisochroman-1-yl)pyrrolidine-1-carboxylate (500 mg, 1.13 mmol), pyridine (890 mg, 11.3 mmol) in dichloromethane (60 mL) at 0° C. The mixture was stirred at 0° C. for about 2~3 h and ice water (80 mL) was added. The mixture was extracted with dichloromethane (3×100 mL). The organic layers were combined, washed, dried, filtered, and concentrated in vacuo to afford the crude product (850 mg) as a light yellow oil, which was used in the next step without further purification. MS (ESI) m/z 573.9 (M+H)⁺.

(d). (S)-1-((S)-pyrrolidin-2-yl)isochroman-8-carbonitrile (I-37)

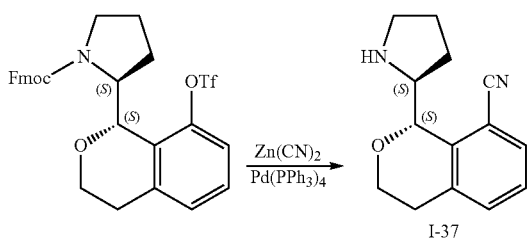

A mixture of (S)-(9H-fluoren-9-yl)methyl 2-((S)-8-(trifluoromethylsulfonyloxy) isochroman-1-yl)pyrrolidine-1-carboxylate (850 mg, 1.48 mmol), dicyanozinc (350 mg, 2.96 mmol), tetrakis(triphenylphosphine)platinum (350 mg, 0.30 mmol) in dimethyl sulfoxide (6 mL) was stirred at 120° C. under microwave reactor for 6.5 h. The mixture was filtered through a celite pad, washed with methanol (100 mL). The filtrate was concentrated and water (10 mL) was added. The mixture was extracted with dichloromethane: methanol=20:1 (3×80 mL). The organic layers were combined, washed with brine (80 mL), dried, filtered, and concentrated in vacuo to afford the crude product, which was purified by Pre-HPLC to afford 1-37 (158 mg) as a light yellow oil. MS (ESI) m/z 228.9 (M+H)⁺. ¹H NMR (HCl salt, 400 MHz, MeOD): δ 7.81 (d, J=7.6 Hz, 1H), 7.60~7.49 (m, 2H), 4.69 (d, J=11.6 Hz, 1H), 4.37~4.32 (q, J=6.4 Hz, 1H), 3.97~3.89 (m, 1H), 3.85~3.78 (m, 2H), 3.74~3.66 (m, 1H), 3.19~3.10 (m, 1H), 2.86~2.82 (dd, J¹=3.2 Hz, J²=13.6 Hz, 1H), 2.57~2.52 (m, 1H), 2.38~2.31 (m, 1H), 2.14~1.98 (m, 2H).

(e). (S)-(9H-fluoren-9-yl)methyl 2-((R)-8-(trifluoromethylsulfonyloxy) isochroman-1-yl)pyrrolidine-1-carboxylate

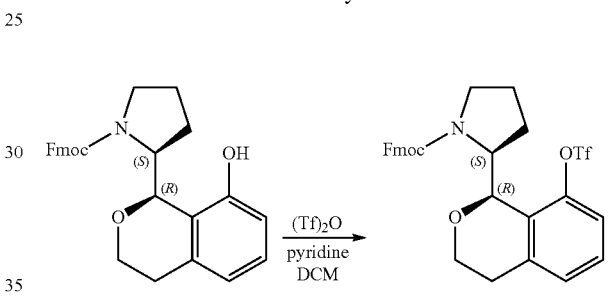

Trifluoromethanesulfonic anhydride (0.33 mL, 2 mmol) was added to a solution of (2S)-(9H-fluoren-9-yl)methyl 2-((R)-8-hydroxyisochroman-1-yl)pyrrolidine-1-carboxylate (441 mg, 1 mmol), pyridine (790 mg, 10.0 mmol) in dichloromethane (60 mL) at 0° C. The mixture was stirred at 0° C. for about 2~3 h and ice water (60 mL) was added. The mixture was extracted with dichloromethane (3×80 mL). The combined organic layers were washed with brine, dried, filtered, and concentrated in vacuo to afford the crude product (713 mg) as a light yellow oil, which was used in the next step without further purification. MS (ESI) m/z 573.9 (M+H)⁺.

(f). (S)-1-((R)-pyrrolidin-2-yl)isochroman-8-carbonitrile (I-38)

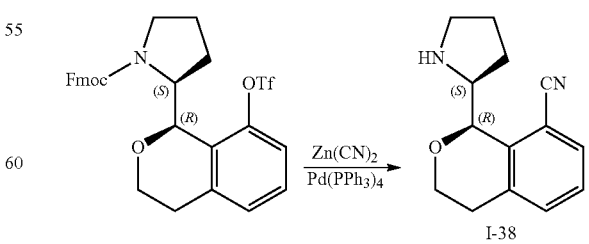

A mixture of (S)-(9H-fluoren-9-yl)methyl 2-((R)-8-(trifluoromethylsulfonyloxy) isochroman-1-yl)pyrrolidine-1-carboxylate (713 mg, 1.24 mmol), dicyanozinc (291 mg, 2.48 mmol), tetrakis(triphenylphosphine)platinum (1.43 g, 1.24 mmol) in dimethyl sulfoxide (6 mL) was stirred at 120° C. under microwave reactor for 6.5 h. The mixture was filtered through a celite pad, washed with methanol (100 mL). The filtrate was concentrated and water (10 mL) was added. The mixture was extracted with dichloromethane: methanol=20:1 (3×80 mL). The combined organic layers were washed with brine (80 mL), dried, filtered, and concentrated in vacuo to afford the crude product, which was purified by Pre-HPLC, followed by chiral HPLC purification using column: OZ-H 250*4.6 mm 5 μm; solvent: MeOH (0.1% DEA) to afford (S)-1-((R)-pyrrolidin-2-yl)isochroman-8-carbonitrile (I-38) as a light yellow oil (86 mg). MS (ESI) m/z 228.9 (M+H)⁺. ¹H NMR (HCl, 400 MHz, MeOD): δ 8.03 (d, J=8.4 Hz, 1H), 7.71~7.60 (m, 2H), 4.93 (d, J=8.4 Hz, 1H), 4.32~4.24 (m, 2H), 3.88~3.83 (m, 1H), 3.72~3.67 (m, 1H), 3.62~3.56 (m, 1H), 3.28~3.20 (m, 1H), 3.09~3.03 (m, 1H), 2.30~2.12 (m, 4H).

Example 1.11. Procedure K

Example 1.11.1. (S)-4,4-difluoro-2-((S)-isochroman-1-yl)pyrrolidine (I-63) and (S)-4,4-difluoro-2-((R)-isochroman-1-yl)pyrrolidine (I-64)

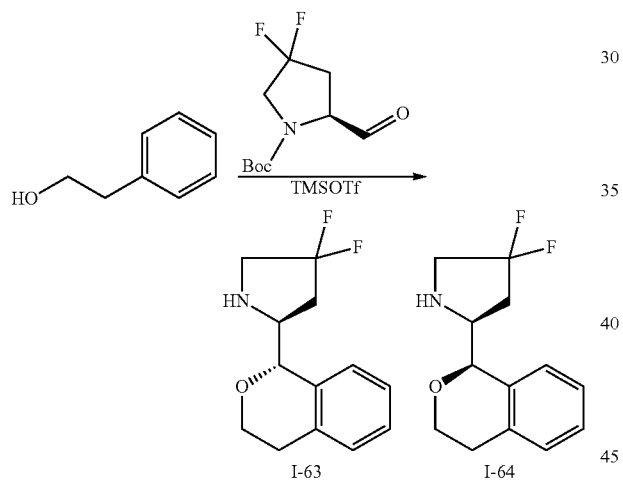

To a solution of (S)-tert-butyl 4,4-difluoro-2-formylpyrrolidine-1-carboxylate (800 mg, 3.4 mmol)) was added 2-phenylethanol (0.42 g, 3.4 mmol) and trimethylsilyl trifluoromethanesulfonate (2.27 g, 10.2 mmol). The reaction mixture was stirred at room temperature for 12 h. Water (100 mL) was added to the reaction vessel, and the resulting biphasic mixture was transferred to a reparatory funnel. The layers were separated, and the aqueous phase was extracted with DCM (2×100 mL). The combined organics were dried over anhydrous Na₂SO₄, filtered, and concentrated in vacuo to afford the crude product, which was purified by PREP-HPLC to afford (S)-4,4-difluoro-2-((S)-isochroman-1-yl) pyrrolidine (I-63, 200 mg) and (S)-4,4-difluoro-2-((R)-isochroman-1-yl)pyrrolidine (I-64, 180 mg).

(S)-4,4-difluoro-2-((S)-isochroman-1-yl)pyrrolidine (I-63): ESI: m/z=240 (M+H⁺). ¹HNMR (400 MHz, CDCl₃): δ 7.25-7.18 (m, 2H), 7.17-7.10 (m, 2H), 5.01 (s, 1H), 4.25 (ddd, J=11.1, 5.8, 1.3 Hz, 1H), 3.97-3.86 (m, 1H), 3.81-3.74 (m, 1H), 3.46-3.38 (m, 1H), 3.22-3.00 (m, 2H), 2.64 (d, J=16.2 Hz, 1H), 2.21-2.01 (m, 2H), 1.96-1.84 (m, 1H).

(S)-4,4-difluoro-2-((R)-isochroman-1-yl)pyrrolidine (I-64): ESI: m/z=240 (M+H⁺). ¹HNMR (400 MHz, CDCl₃): δ 7.25-7.18 (m, 2H), 7.17-7.10 (m, 2H), 5.01 (s, 1H), 4.25 (ddd, J=11.1, 5.8, 1.3 Hz, 1H), 3.97-3.86 (m, 1H), 3.81-3.74 (m, 1H), 3.46-3.38 (m, 1H), 3.22-3.00 (m, 2H), 2.64 (d, J=16.2 Hz, 1H), 2.21-2.01 (m, 2H), 1.96-1.84 (m, 1H).

Example 1.12. Procedure L. Certain Provided Compounds were Made Following a Procedure Exemplified by Example 1.12.1

Example 1.12.1. (S)-2-((R)-6-fluoroisochroman-1-yl)-1-methylpyrrolidine (I-69)

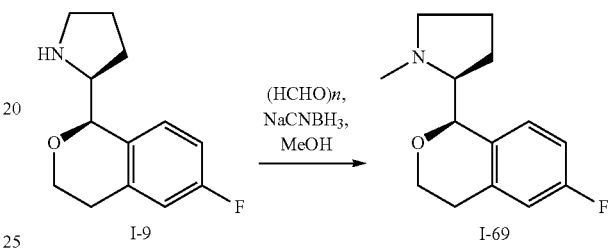

To a solution of (S)-2-((R)-6-fluoroisochroman-1-yl)pyrrolidine (I-9, 0.13 g, 0.6 mmol) in methanol (10 mL) was added (HCHO)n (0.09 g, 3 mmol) and NaCNBH₃ (0.15 g, 2.4 mmol) at room temperature. The mixture was stirred at this temperature overnight. The mixture was concentrated in vacuo to give the residue, which was purified by prep-HPLC, followed by neutralization with NaHCO₃ (aq. sat.). The solution was extraction with DCM (50 mL×2). The organic layers were dried, filtered, and solvent evaporated in vacuo to give the desired product as yellow oil (80 mg). (ESI) m/z: 236[M+H]⁺. ¹H NMR (HCl salt, 400 MHz, MeOD) δ 7.27~7.23 (dd, J¹=5.6 Hz, J²=8.8 Hz, 1H), 7.04~6.98 (m, 2H), 5.33 (s, 1H), 4.34~4.30 (m, 1H), 4.18~4.13 (m, 1H), 3.87~3.80 (m, 1H), 3.73~3.67 (m, 1H), 3.28~3.21 (q, J=8.8 Hz, 1H), 3.16~3.10 (m, 4H), 2.75~2.71 (d, J=16.4 Hz), 2.11~1.67 (m, 4H).

Example 1.12.2. (S)-1-ethyl-2-((R)-6-fluoroisochroman-1-yl)pyrrolidine (I-70)

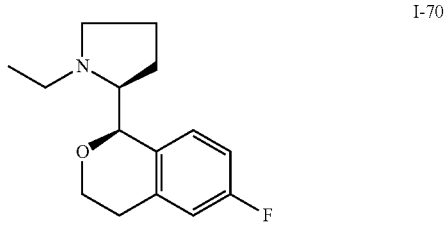 [SMILES: CCN1CCC[C@H]1[C@@H]1OCCc2cc(F)ccc21]

(S)-1-ethyl-2-((R)-6-fluoroisochroman-1-yl)pyrrolidine (I-70) was prepared using a procedure analogous to that described in Example 1.12.1, but using acetaldehyde in place of (HCHO)n. ESI: m/z: 250[M+H]⁺. ¹H NMR (HCl salt, 400 MHz, MeOD) δ 7.27~7.24 (dd, J¹=5.6 Hz, J²=8.4 Hz, 1H), 7.05~6.98 (m, 2H), 5.31 (s, 1H), 4.37~4.30 (m, 1H), 4.23~4.18 (m, 1H), 3.86~3.59 (m, 3H), 3.30~3.08 (m, 3H), 2.75~2.71 (d, J=16.4 Hz, 1H), 2.08~1.94 (m, 2H), 1.87~1.75 (m, 2H), 1.49~1.43 (t, 3H).

Example 1.13. Procedure M. Certain Provided Compounds were Made Following a Procedure Exemplified by Example 1.13.1

Example 1.13.1. (S)-2-((S)-5-fluoro-1,3-dihydroisobenzofuran-1-yl)pyrrolidine (I-118) and (S)-2-((R)-5-fluoro-1,3-dihydroisobenzofuran-1-yl)pyrrolidine (I-119)

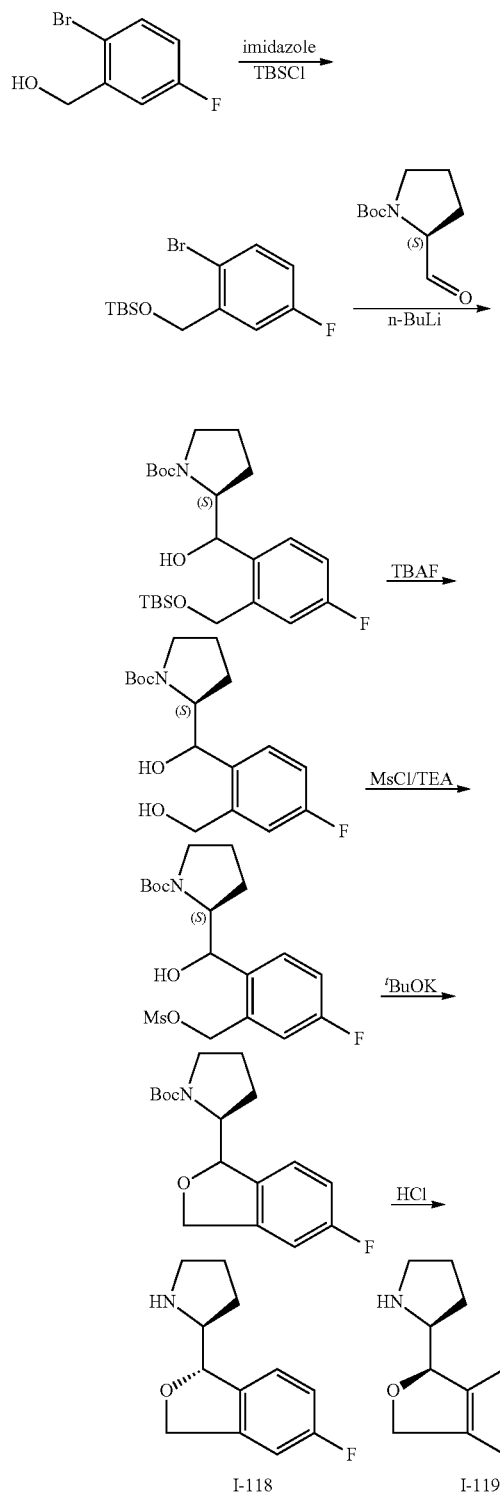

I-118    I-119

(a). (2-bromo-5-fluorobenzyloxy)(tert-butyl)dimethylsilane

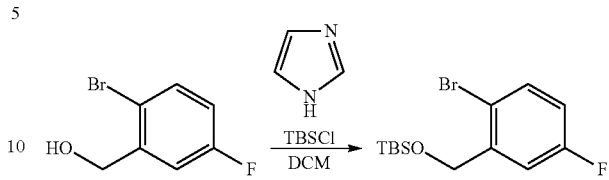

To a solution of (2-bromo-5-fluorophenyl)methanol (25.6 g, 124.86 mmol) in dichloromethane (750 mL) was added 1H-imidazole (17 g, 249.72 mmol) and tert-butylchlorodimethylsilane (37.64 g, 249.72 mmol). The reaction mixture was stirred at room temperature for 16 h and was then washed with brine (3×200 mL), dried over sodium sulfate, filtered, and concentrated in vacuo. The crude product was purified by silica gel column chromatography (eluted with petroleum ether) to give the product as a colorless oil (36.2 g).

(b). (2S)-tert-butyl2-((2-(((tert-butyldimethylsilyl)oxy)methyl)-4-fluorophenyl)(hydroxy) methyl)pyrrolidine-1-carboxylase

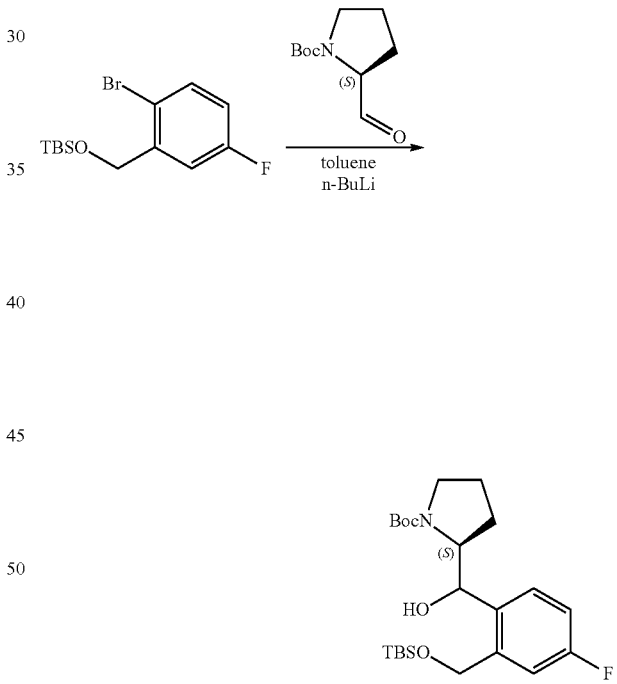

To a solution of ((2-bromo-5-fluorobenzyl)oxy)(tert-butyl)dimethylsilane (3.19 g, 10 mmol) in toluene (25 mL) was added dropwise tert-butyllithium (0.96 g, 15 mmol) at −78° C. The reaction was stirred at 0° C. for 1 h. (S)-tert-Butyl 2-formylpyrrolidine-1-carboxylate (2.99 g, 15 mmol)) in toluene (10 mL) was added dropwise. The reaction mixture was stirred at −78° C. for 3 h and poured into iced-water. The organic phase was separated and washed with brine (3×70 mL), dried over sodium sulfate and evaporated in vacuo to give the crude, which was purified by column chromatography (PE:EtOAc=15:1) to give the tittle compound (4 g) as colorless oil.

(c). (S)-tert-butyl2-((4-fluoro-2-(hydroxymethyl)phenyl)(hydroxy)methyl)pyrrolidine-1-carboxylate

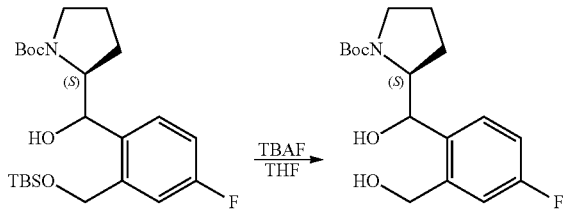

To a solution of (2S)-tert-butyl 2-((2-(((tert-butyldimethylsilyl)oxy)methyl)-4-fluorophenyl)(hydroxy)methyl)pyrrolidine-1-carboxylate (5.5 g, 11.4 mmol) in tetrahydrofuran (100 mL) was added tetrabutylammonium fluoride (2.98 g, 11.4 mmol). The reaction mixture was stirred at ambient temperature for 16 h and then concentrated to give a residue, which was diluted with ethyl acetate (200 mL), neutralized with saturated sodium bicarbonate solution, washed with brine (4×50 mL), dried over sodium sulfate and concentrated in vacuo. The crude product was purified by silica gel column chromatography (eluted with petroleum ether: ethyl acetate=5:1) to give the title compound as a colorless oil (3.3 g), MS (ESI): m/z 326 [M+H]⁺.

(d). (S)-tert-butyl 2-((4-fluoro-2-((methylsulfonyloxy)methyl)phenyl)(hydroxy) methyl)pyrrolidine-1-carboxylate

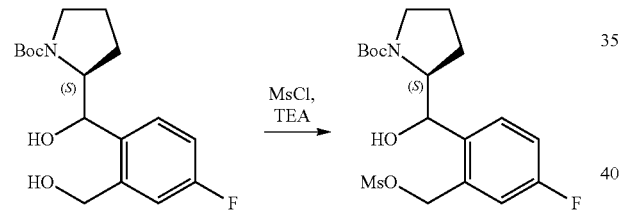

To a solution of (2S)-tert-butyl 2-((4-fluoro-2-(hydroxymethyl)phenyl)(hydroxy) methyl)pyrrolidine-1-carboxylate (3 g, 7.38 mmol) in ethyl acetate (150 mL) was added methanesulfonyl chloride (0.8 g, 7.01 mmol). The reaction mixture was stirred at room temperature for 30 min and then washed with water (3×100 mL). The organic layer was dried over sodium sulfate, filtered and concentrated to give the crude product (3.4 g), which was used in the next step without further purification.

(e). (S)-tert-butyl2-(5-fluoro-1,3-dihydroisobenzofuran-1-yl) pyrrolidine-1-carboxylate

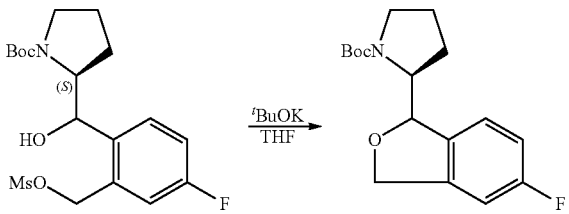

To a solution of (2S)-tert-butyl 2-((4-fluoro-2-(((methylsulfonyl)oxy)methyl)phenyl) (hydroxy)methyl)pyrrolidine-1-carboxylate (3 g, 7.44 mmol) in tetrahydrofuran (150 mL) was added potassium 2-methylpropan-2-olate (2.5 g, 22.32 mmol). The reaction mixture was stirred at room temperature for 1 h. Upon completion, water (100 mL) and ethyl acetate (100 mL) were added to the mixture. The organic layer was separated, washed with water (3×80 mL), dried over sodium sulfate, filtered and then concentrated to give the residue. The residue was purified by silica gel column chromatography (eluted with petroleum ether: ethyl acetate=20:1) to give the title compound (1.9 g) as colorless oil.

(f). (S)-2-((S)-5-fluoro-1,3-dihydroisobenzofuran-1-yl)pyrrolidine (I-118) and (S)-2-((R)-5-fluoro-1,3-dihydroisobenzofuran-1-yl)pyrrolidine (I-119)

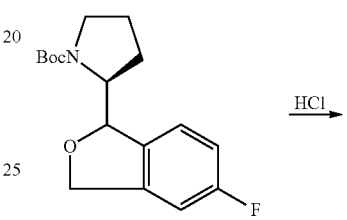

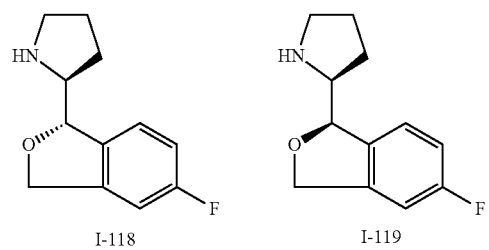

I-118   I-119

To a solution of (2S)-tert-butyl 2-(5-fluoro-1,3-dihydroisobenzofuran-1-yl) pyrrolidine-1-carboxylate (100 mg, 0.33 mmol) in methanol (10 mL) was added HCl/1,4-dioxane (0.58 g, 16 mmol). The reaction mixture was stirred at room temperature for 1 h to yield the a mixture of two diastereoisomers, which was separated by HPLC to give (S)-2-((S)-5-fluoro-1,3-dihydroisobenzofuran-1-yl)pyrrolidine (I-118) and (S)-2-((R)-5-fluoro-1,3-dihydroisobenzofuran-1-yl)pyrrolidine (I-119).

(S)-2-((S)-5-fluoro-1,3-dihydroisobenzofuran-1-yl)pyrrolidine (I-118): ESI: m/z=208 (M+H)⁺. ¹HNMR (HCl salt, 400 MHz, MeOD): δ 7.39-7.43 (m, 1H), 7.11-7.14 (m, 2H), 5.38 (s, 1H), 5.08-5.26 (m, 2H), 3.90-3.95 (m, 1H), 3.29-3.33 (m, 1H), 2.01-2.33 (m, 6H).

(S)-2-((R)-5-fluoro-1,3-dihydroisobenzofuran-1-yl)pyrrolidine (I-119): ESI: m/z=208 (M+H)⁺. ¹HNMR (HCl salt, 400 MHz, MeOD): δ 7.35-7.38 (m, 1H), 7.10-7.14 (m, 2H), 5.63 (s, 1H), 5.15-5.26 (m, 2H), 4.12-4.16 (m, 1H), 3.34-3.38 (m, 1H), 1.95-2.12 (m, 2H), 1.62-1.79 (m, 4H).

Example 1.13.2. (R)-2-((S)-5-fluoro-1,3-dihydroisobenzofuran-1-yl)pyrrolidine (I-120) and (R)-2-((R)-5-fluoro-1,3-dihydroisobenzofuran-1-yl)pyrrolidine (121)

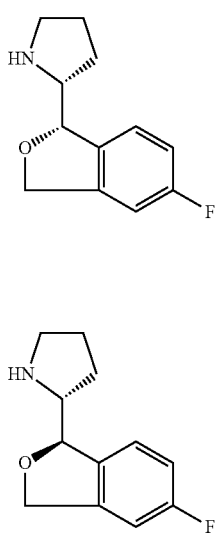

I-120

I-121

(R)-2-((S)-5-fluoro-1,3-dihydroisobenzofuran-1-yl)pyrrolidine (I-120) and (R)-2-((R)-5-fluoro-1,3-dihydroisobenzofuran-1-yl)pyrrolidine (I-121) were prepared using a procedure analogous to that described in Example 1.13.1, but using (R)-tert-butyl 2-formylpyrrolidine-1-carboxylate in place of (S)-tert-butyl 2-formylpyrrolidine-1-carboxylate.

(R)-2-((S)-5-fluoro-1,3-dihydroisobenzofuran-1-yl)pyrrolidine (I-120): ESI: m/z=208 (M+H)$^+$. $^1$HNMR (400 MHz, MeOD): δ 7.36-7.40 (m, 1H), 7.11-7.13 (m, 2H), 5.63 (s, 1H), 5.15-5.25 (m, 2H), 4.14-4.18 (m, 1H), 3.33-3.38 (m, 1H), 1.95-2.10 (m, 2H), 1.62-1.81 (m, 4H).

(R)-2-((R)-5-fluoro-1,3-dihydroisobenzofuran-1-yl)pyrrolidine (I-121): ESI: m/z=208 (M+H)$^+$. $^1$HNMR (400 MHz, MeOD): δ 7.40-7.43 (m, 1H), 7.10-7.14 (m, 2H), 5.39 (s, 1H), 5.08-5.37 (m, 2H), 3.90-3.96 (m, 1H), 3.28-3.33 (m, 1H), 2.08-2.35 (m, 6H).

Example 1.14. Procedure N. Certain Provided Compounds were Made Following a Procedure Exemplified by Example 1.14.1

Example 1.14.1. (S)-2-((S)-5-fluoro-1,3-dihydroisobenzofuran-1-yl)pyrrolidine (I-126) and (S)-2-((R)-5-fluoro-1,3-dihydroisobenzofuran-1-yl)pyrrolidine (I-133)

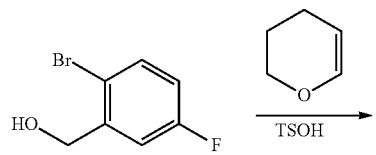

-continued

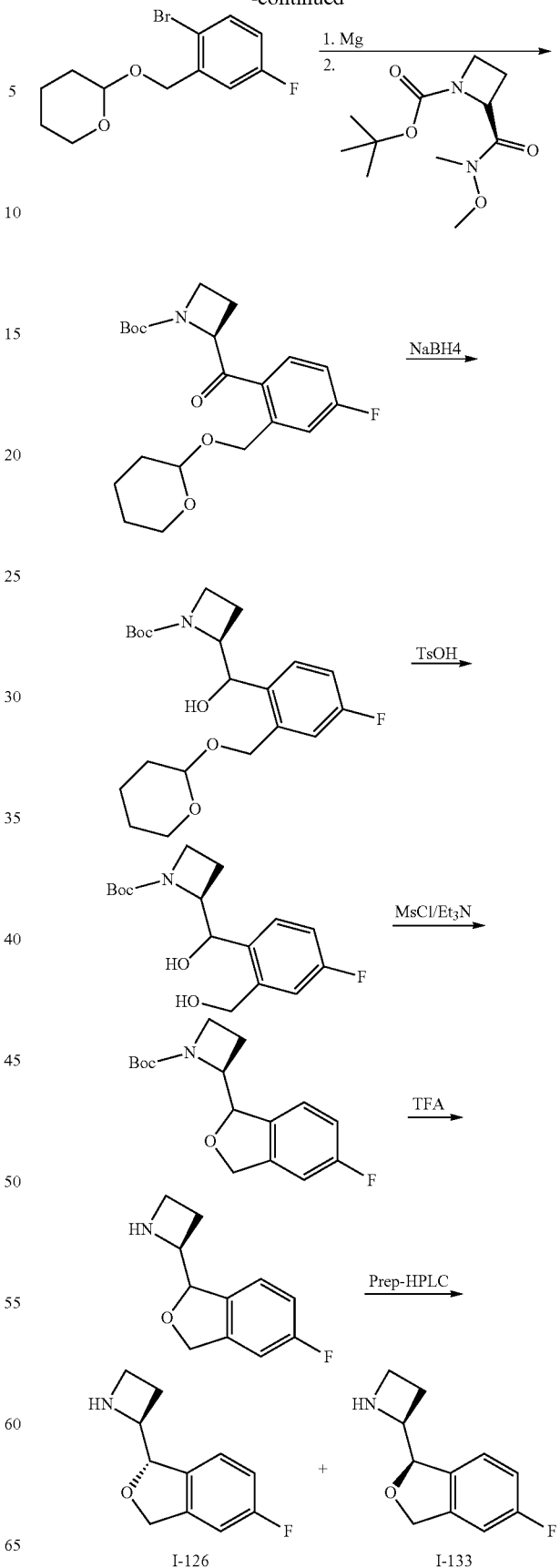

(a). 2-((2-bromo-5-fluorobenzyl)oxy)tetrahydro-2H-pyran

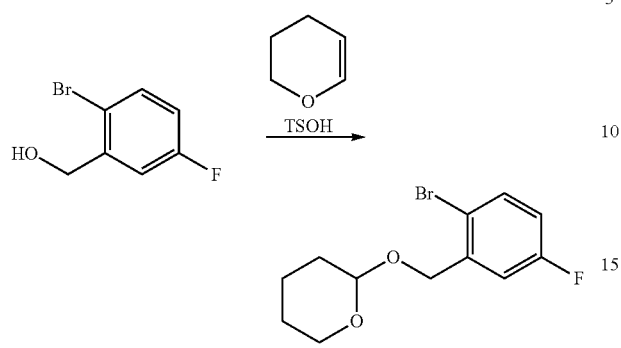

To a solution of (2-bromo-5-fluorophenyl)methanol (40 g, 195 mmol) in dichloromethane (200 ml) at 0° C. was added 4-methylbenzenesulfonic acid (1 g, 5.85 mmol) and 3,4-dihydro-2H-pyran (24.5 g, 292 mmol). The mixture was stirred at room temperature for 6 h. Saturated aqueous NaHCO$_3$ (300 mL) was added to the reaction vessel, and the resulting biphasic mixture was transferred to a reparatory funnel. The layers were separated, and the organic phase was washed with saturated aqueous NaCl (2×100 mL). The combined organics were dried over anhydrous sodium sulfate, filtered and concentrated in vacuo. The resulting oil was purified by flash column chromatography with an isocratic elution of EtOAc (5%) and petroleum ether (95%) to provide 2-((2-bromo-5-fluorobenzyl)oxy)tetrahydro-2H-pyran (41.9 g, 145 mmol) as a colorless oil.

(b). (2S)-tert-butyl-2-(4-fluoro-2-((tetrahydro-2H-pyran-2-yloxy)methyl) benzoyl)azetidine-1-carboxylase

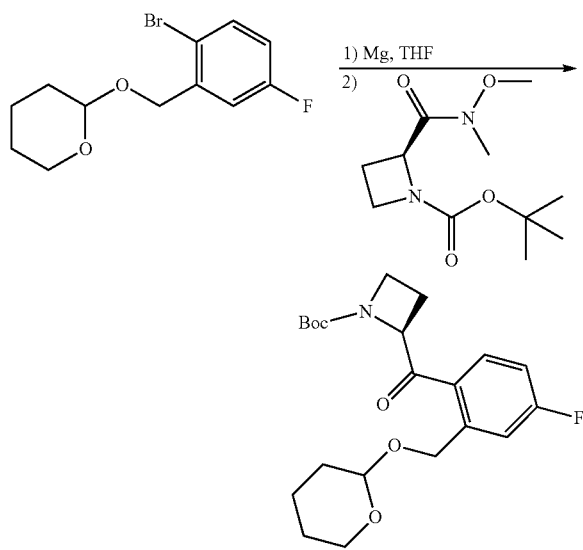

To a solution of 2-((2-bromo-5-fluorobenzyl)oxy)tetrahydro-2H-pyran (11.5 g, 40 mmol) in THF (40 ml) was added magnesium (1.94 g, 80 mmol) and a grain of iodine. The mixture was stirred at reflux for 2 h. Upon completion, (S)-tert-butyl-2-(methoxy-(methyl)carbamoyl)azetidine-1-carboxylate (4.88 g, 20 mmol) was added at 0° C. The reaction mixture was stirred at this temperature for 3 h. Water (100 mL) was added to the reaction vessel, and the resulting biphasic mixture was transferred to a reparatory funnel. The organic layer was separated and the aqueous layer was extraction with EtOAc (2×100 mL). The combined organics were dried over anhydrous sodium sulfate, filtered and concentrated in vacuo to afford the crude product, which was purified by flash column chromatography with an isocratic elution of EtOAc (20%) and petroleum ether (80%) to afford the title compound (6 g) as a colorless oil.

(c). (2S)-tert-butyl-2-((4-fluoro-2-((tetrahydro-2H-pyran-2-yloxy)methyl) phenyl)-(hydroxy)methyl) azetidine-1-carboxylate

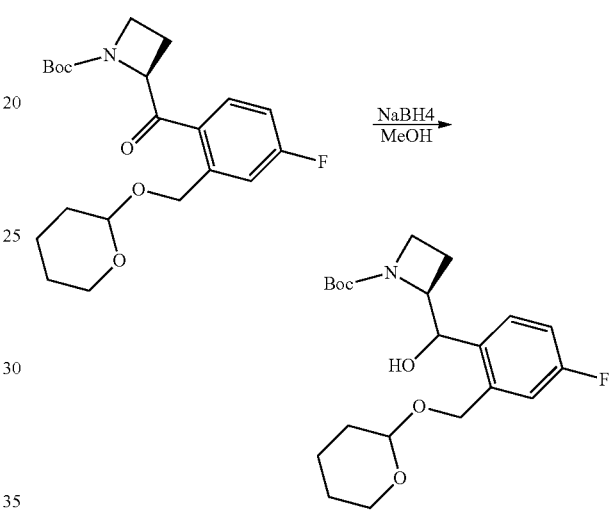

To a solution of (2S)-tert-butyl 2-(4-fluoro-2-(((tetrahydro-2H-pyran-2-yl) oxy)methyl) benzoyl)azetidine-1-carboxylate (6 g, 15.2 mmol) in MeOH (30 ml) was added NaBH$_4$ (0.575 g, 15.2 mmol). The mixture was stirred at room temperature for 3 h. Water (100 mL) was added to the reaction vessel, and the resulting biphasic mixture was transferred to a separatory funnel and extracted with EtOAc (2×200 mL). The combined organics were dried over anhydrous sodium sulfate, filtered and concentrated in vacuo. The resulting oil was purified by reverse phase HPLC to provide the title compound (5.2 g) as a white solid.

(d). (2S)-tert-butyl 2-((4-fluoro-2-(hydroxymethyl)phenyl) (hydroxy) methyl)azetidine-1-carboxylate

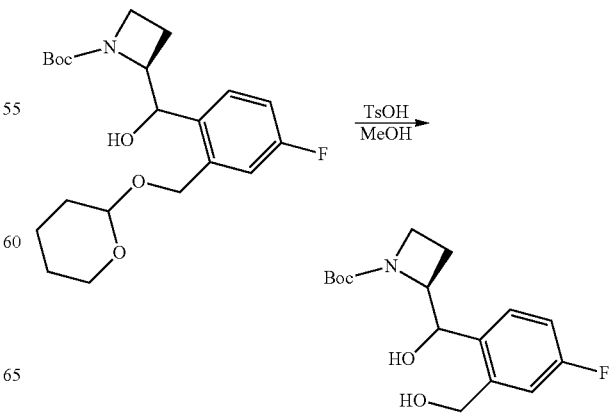

To a solution of (2S)-tert-butyl 2-((4-fluoro-2-(((tetrahydro-2H-pyran-2-yl)oxy)methyl) phenyl)(hydroxy)methyl)azetidine-1-carboxylate (3 g, 7.58 mmol) in MeOH (50 ml) was added 4-methylbenzenesulfonic acid (130 mg, 0.758 mmol). The mixture was stirred at room temperature for 3 h. Saturated aqueous NaHCO₃ (60 mL) was added to the reaction vessel, and the resulting biphasic mixture was transferred to a separatory funnel and extracted with DCM (2×50 mL). The combined organics were dried over anhydrous sodium sulfate, filtered and concentrated in vacuo. Crude product was used in next step without further purification.

(e). (4-tea-butyl 2-(5-fluoro-1,3-dihydroisobenzofuran-1-yl)azetidine-1-carboxylate

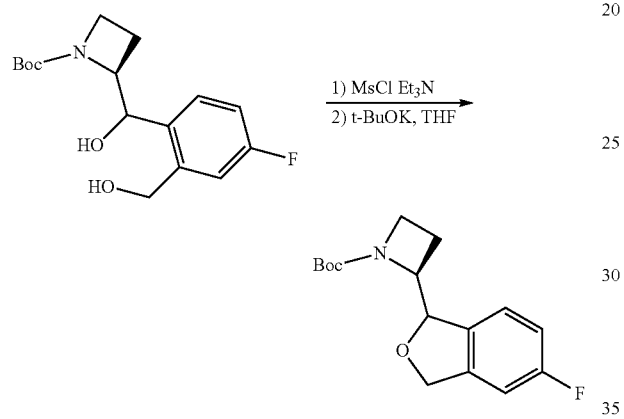

To a solution of ((2S)-tert-butyl 2-((4-fluoro-2-(hydroxymethyl)phenyl)(hydroxy) methyl)azetidine-1-carboxylate (8 g, 25.7 mmol) in DCM (30 ml) was added MsCl (5 g, 30.1 mmol), Et₃N (0.35 g, 2.57 mmol). The mixture was stirred at room temperature for 3 h. Solvent was removed and to the residue t-BuOK (3.37 g, 30.1 mmol) in THF (30 mL) was added. The mixture was stirred at room temperature for 5 h and then transferred to a separatory funnel and extracted with DCM (2×200 mL). The combined organics were dried over anhydrous sodium sulfate, filtered and concentrated in vacuo. The resulting oil was purified by flash column chromatography with an isocratic elution of EtOAc (10%) and petroleum ether (90%) to provide the title compound (5.6 g) as a white solid. ESI: m/z=605 (M+1)

(f). ((S)-2-((S)-5-fluoro-1,3-dihydroisobenzofuran-1-yl)azetidine (I-126) and (S)-2-((R)-5-fluoro-1,3-dihydroisobenzofuran-1-yl)azetidine (I-133)

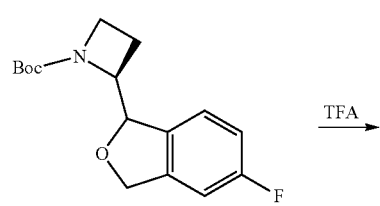

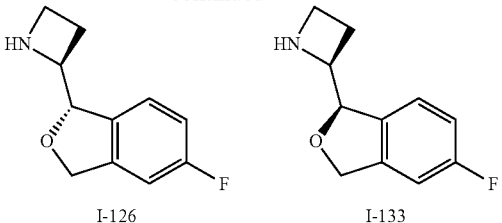

To a solution of (2S)-tert-butyl 2-(5-fluoro-1,3-dihydroisobenzofuran-1-yl)azetidine-1-carboxylate (5.6 g, 19.3 mmol) in DCM (30 ml) was added TFA (2.1 g, 21.2 mmol). The mixture was stirred at 0° C. for 3 h. Water (50 mL) was added to the reaction vessel, and the mixture was adjusted to pH=9 with solid NaHCO₃. The resulting biphasic mixture was transferred to a separatory funnel and extracted with DCM (3×100 mL). The combined organics were dried over anhydrous sodium sulfate, filtered and concentrated in vacuo to give crude, which was purified by PREP-HPLC to give ((S)-2-((S)-5-fluoro-1,3-dihydroisobenzofuran-1-yl)azetidine (I-126) (200 mg) and (S)-2-((R)-5-fluoro-1,3-dihydroisobenzofuran-1-yl)azetidine (I-133) as oil. ESI: m/z=194 (M+H⁺).

((S)-2-((S)-5-fluoro-1,3-dihydroisobenzofuran-1-yl)azetidine (I-126): ¹H NMR (400 MHz, MeOD) δ 7.21 (dd, J=8.3, 4.8 Hz, 1H), 7.07-6.89 (m, 2H), 5.29 (s, 1H), 5.16 (dd, J=12.7, 2.1 Hz, 1H), 5.01 (d, J=12.8 Hz, 1H), 4.75-4.72 (m, 1H), 3.94-3.91 (m, 1H), 3.75-3.68 (m, 1H), 2.51-2.43 (m, 1H), 2.58-2.40 (m, 1H).

Example 1.14.2. (R)-2-((S)-5-fluoro-1,3-dihydroisobenzofuran-1-yl)azetidine (I-127) and (R)-2-((R)-5-fluoro-1,3-dihydroisobenzofuran-1-yl)azetidine (I-128)

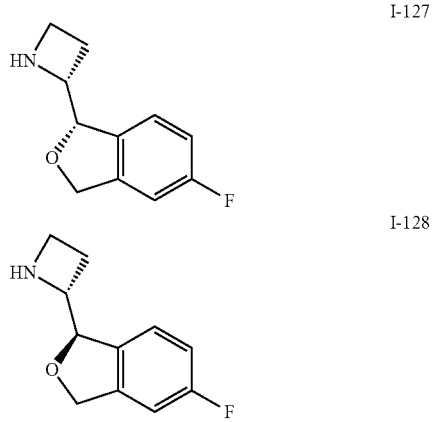

(R)-2-((S)-5-fluoro-1,3-dihydroisobenzofuran-1-yl)azetidine (I-127) and (R)-2-((R)-5-fluoro-1,3-dihydroisobenzofuran-1-yl)azetidine (I-128) were prepared using a procedure analogous to that described in Example 1.14.1, but using (R)-tert-butyl 2-(methoxy(methyl)carbamoyl)azetidine-1-carboxylate in place of (S)-tert-butyl 2-(methoxy(methyl)carbamoyl)azetidine-1-carboxylate.

(R)-2-((S)-5-fluoro-1,3-dihydroisobenzofuran-1-yl)azetidine (I-127): ESI: m/z=194 (M+H⁺). ¹H NMR (400 MHz, MeOD) δ 7.25 (dd, J=8.3, 4.8 Hz, 1H), 7.09-6.96 (m, 2H), 5.33 (s, 1H), 5.20 (dd, J=12.7, 1.9 Hz, 1H), 5.03 (dd, J=12.7, 1.1 Hz, 1H), 4.90-4.81 (m, 1H), 4.01 (dd, J=18.9, 9.3 Hz, 1H), 3.78 (td, J=10.1, 5.5 Hz, 1H), 3.23 (dt, J=3.3, 1.6 Hz, 1H), 2.77 (ddt, J=11.9, 9.9, 8.6 Hz, 1H), 2.59-2.47 (m, 1H), 1.92-1.91 (m, 1H).

(R)-2-((R)-5-fluoro-1,3-dihydroisobenzofuran-1-yl)azetidine (I-128): ESI: m/z=194 (M+H$^+$). $^1$H NMR (400 MHz, MeOD) δ 7.25 (dd, J=8.3, 4.8 Hz, 1H), 7.09-6.96 (m, 2H), 5.33 (s, 1H), 5.20 (dd, J=12.7, 1.9 Hz, 1H), 5.03 (dd, J=12.7, 1.1 Hz, 1H), 6.84-4.36 (m, 8H), 4.90-4.81 (m, 1H), 4.01 (dd, J=18.9, 9.3 Hz, 1H), 5.34-2.59 (m, 1H), 3.78 (td, J=10.1, 5.5 Hz, 1H), 3.23 (dt, J=3.3, 1.6 Hz, 1H), 2.77 (ddt, J=11.9, 9.9, 8.6 Hz, 1H), 2.59-2.47 (m, 1H), 1.92-1.91 (m, 1H), 1.08-0.90 (m, 1H).

Example 1.15. Procedure O. Certain Provided Compounds were Made Following a Procedure Exemplified by Example 1.15.1

Example 1.15.1. (R)-2-((S)-5-fluoro-1-methyl-1,3-dihydroisobenzofuran-1-yl)pyrrolidine (I-125)

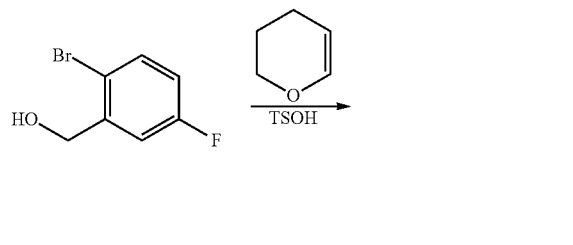

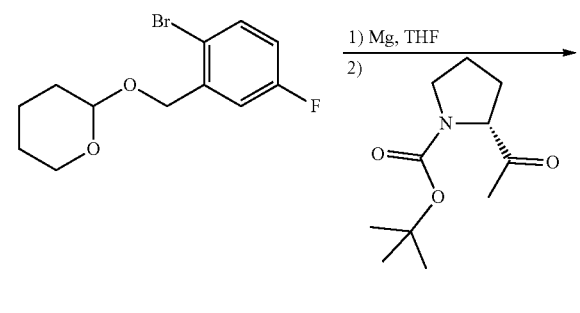

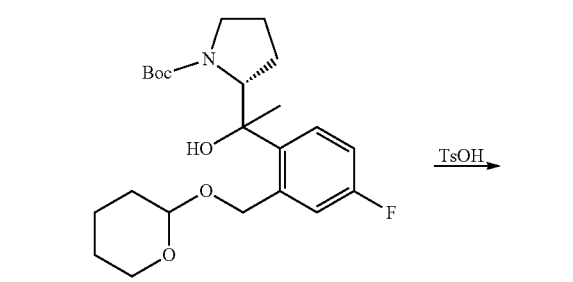

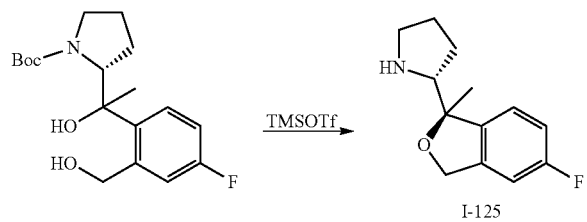

(a). 2-(2-bromo-5-fluorobenzyloxy)tetrahydro-2H-pyran

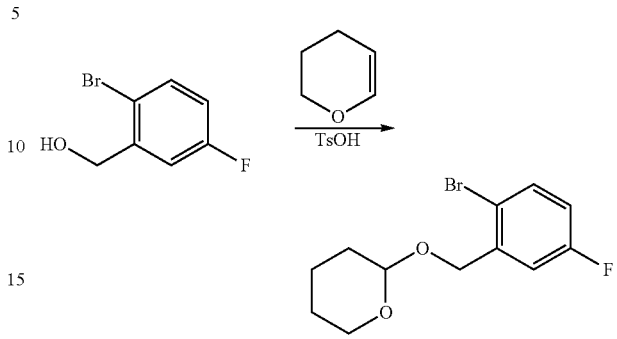

To a solution of (2-bromo-5-fluorophenyl)methanol (20 g, 97.5 mmol) in CH$_2$Cl$_2$ (100 ml) was added 4-methylbenzenesulfonic acid (0.502 g, 2.92 mmol) and 3,4-dihydro-2H-pyran (12.2 g, 146 mmol) at 0° C. The reaction was stirred at ambient temperature for 2 h. Upon completion, saturated aqueous NaHCO$_3$ (100 mL) was added to the reaction vessel, and the resulting biphasic mixture was transferred to a reparatory funnel. The layers were separated, and the organic phase was dried over anhydrous Na$_2$SO$_4$, filtered and concentrated in vacuo. The resulting oil was purified by flash column chromatography with an isocratic elution of petroleum ether (100%) and EtOAc (5%) to provide the title compound (22.9 g) as a colorless oil.

(b). (2R)-tert-butyl 2-(1-(4-fluoro-2-((tetrahydro-2H-pyran-2-yloxy)methyl) phenyl)-1-hydroxyethyl) pyrrolidine-1-carboxylate

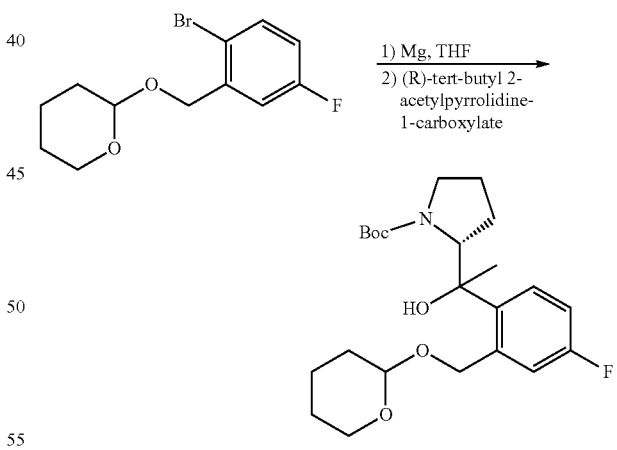

To a solution of 2-((2-bromo-5-fluorobenzyl)oxy)tetrahydro-2H-pyran (8.67 g, 30 mmol) in THF (40 ml) was added magnesium (1.45 g, 60 mmol) and one grain of iodine. The reaction was stirred at reflux for 2 h. Upon completion, (R)-tert-butyl 2-acetylpyrrolidine-1-carboxylate (6.12 g, 28.7 mmol) was added at 0° C. The mixture was stirred at this temperature for 3 h. Upon completion, water (50 mL) was added to the reaction vessel, and the resulting biphasic mixture was transferred to a reparatory funnel and extracted with EtOAc (2×50 mL). The combined organics were dried over anhydrous Na$_2$SO$_4$, filtered and concentrated in vacuo to afford an oil, which was purified by flash column chromatography with an isocratic elution of EtOAc (10%) and petroleum ether (90%) to provide the title compound (3.49 g) as a colorless oil.

(c). (2R)-tert-butyl 2-(1-(4-fluoro-2-(hydroxymethyl)phenyl)-1-hydroxyethyl)pyrrolidine-1-carboxylate

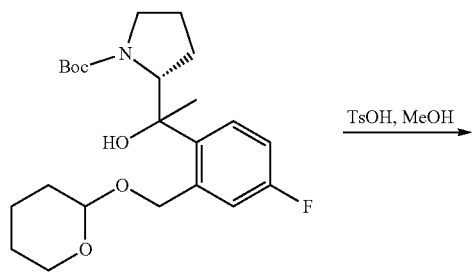

To a solution of (2R)-tert-butyl 2-(1-(4-fluoro-2-(((tetrahydro-2H-pyran-2-yl)oxy) methyl)phenyl)-1-hydroxyethyl) pyrrolidine-1-carboxylate (4 g, 9.44 mmol) in MeOH (100 mL) was added 4-methylbenzenesulfonic acid (323 mg, 1.88 mmol). The mixture was stirred at ambient temperature for 6 h. Upon completion, the solvent was evaporated in vacuo to afford an oil. Water (100 mL) was added to the reaction vessel, and the resulting biphasic mixture was transferred to a separatory funnel and extracted with DCM (2×100 mL). The combined organics were dried over anhydrous $Na_2SO_4$, filtered and concentrated in vacuo to afford a white solid, which was used in the next step without further purification. ESI: m/z=340 (M+H+).

(d). (R)-2-((S)-5-fluoro-1-methyl-1,3-dihydroisobenzofuran-1-yl) pyrrolidine (I-125)

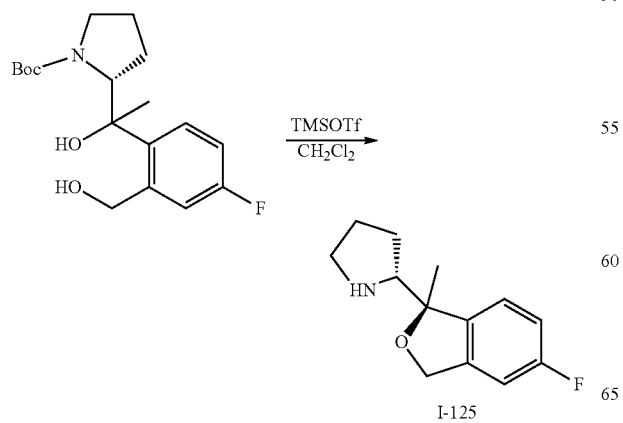

To a solution of (2R)-tert-butyl 2-(1-(4-fluoro-2-(hydroxymethyl)phenyl)-1-hydroxyethyl)pyrrolidine-1-carboxylate (1.2 g, 3.53 mmol) in $CH_2Cl_2$ (10 ml) was added trimethylsilyl trifluoromethanesulfonate (2.33 g, 10.5 mmol). The mixture was stirred at ambient temperature for 3 h. Water (60 mL) was added to the reaction vessel, and the resulting biphasic mixture was transferred to a separatory funnel and extracted with DCM (2×60 mL). The combined organics were dried over anhydrous $Na_2SO_4$, filtered and concentrated in vacuo. The resulting oil was purified by reverse phase HPLC to provide I-125 (497 mg). ESI: m/z=222 (M+H+). $^1$H NMR (400 MHz, MeOD) δ 7.46-7.37 (m, 1H), 7.20-7.07 (m, 2H), 5.22 (d, J=13.0 Hz, 1H), 5.11 (d, J=13.0 Hz, 1H), 4.14 (dd, J=12.1, 4.7 Hz, 1H), 3.28 (t, J=6.9 Hz, 2H), 2.43-2.27 (m, 1H), 2.24-2.01 (m, 3H), 1.51 (s, 3H).

Example 1.15.2. (S)-2-((R)-5-fluoro-1-methyl-1,3-dihydroisobenzofuran-1-yl)pyrrolidine (I-122)

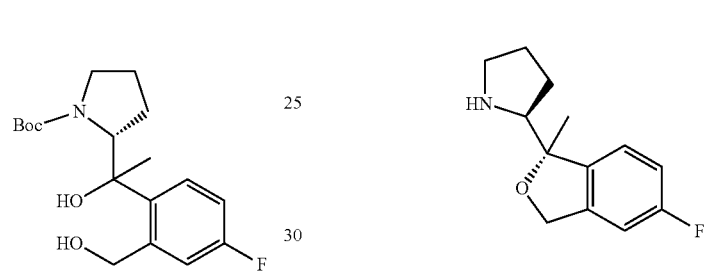

(S)-2-((R)-5-fluoro-1-methyl-1,3-dihydroisobenzofuran-1-yl)pyrrolidine (I-122) was prepared using a procedure analogous to that described in Example 1.15.1, but using (S)-tert-butyl 2-acetylpyrrolidine-1-carboxylate in place of (R)-tert-butyl 2-acetylpyrrolidine-1-carboxylate. ESI: m/z=222 (M+H+). $^1$H NMR (400 MHz, MeOD) δ 7.32 (dd, J=8.3, 4.8 Hz, 1H), 7.18-7.02 (m, 2H), 5.26-5.07 (m, 2H), 4.09-3.96 (m, 1H), 3.40-3.33 (m, 2H), 2.09-1.91 (m, 2H), 1.71-1.67 m, 1H), 1.65-1.52 (m, 4H).

Example 1.16. Procedure P. Certain Provided Compounds were Made Following a Procedure Exemplified by Example 1.16.1

Example 1.16.1. ((R)-2-((R)-5-fluoro-1-methyl-1,3-dihydroisobenzofuran-1-yl)pyrrolidine (I-124)

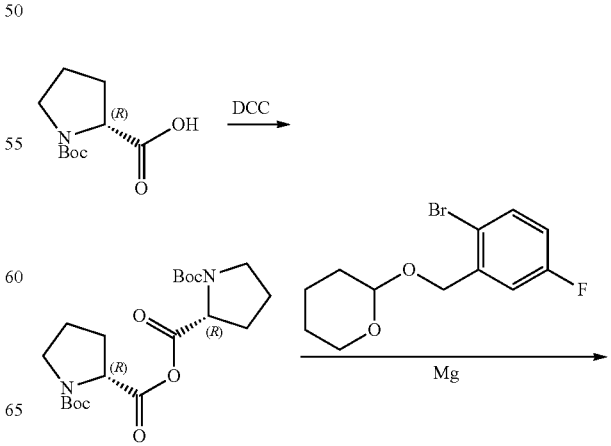

143

-continued

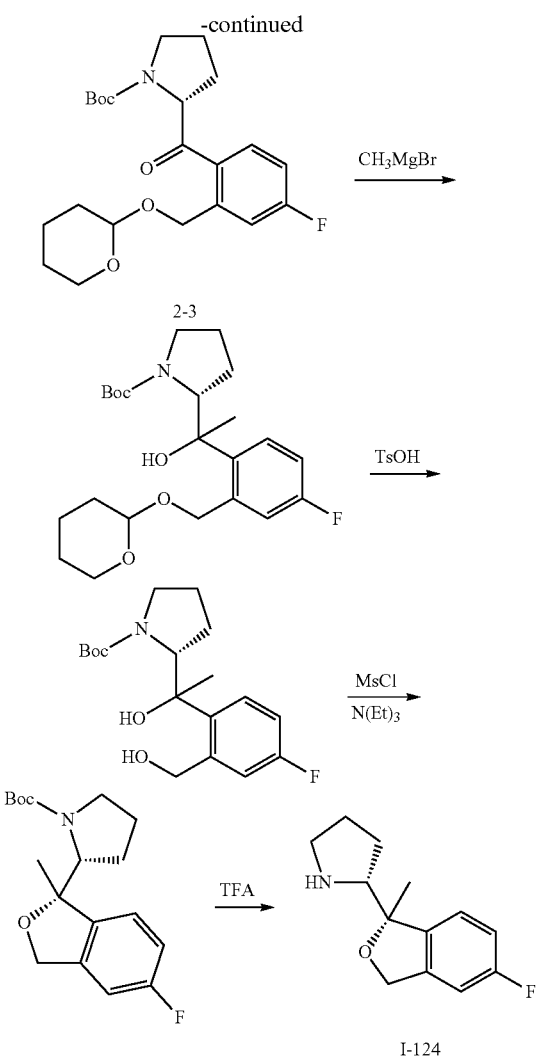

(a). (R)-1-(tert-butoxycarbonyl)pyrrolidine-2-carboxylic anhydride

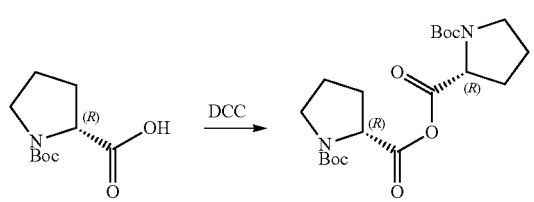

To a solution of (R)-1-(tert-butoxycarbonyl)pyrrolidine-2-carboxylic acid (20 g, 92.9 mmol) in $CH_2Cl_2$ (100 ml) was added N,N'-methanediylidenedicyclohexanamine (9.57 g, 46.4 mmol). The reaction was stirred at room temperature for 24 h. Upon completion, the white solid was filtered off. The filtrate was evaporated in vacuo to give an oil. After addition of ether (100 mL), the solid precipitation was filtered off. The filtrate was evaporated in vacuo to give the crude product, which was used in next step without further purification.

144

(b). (2R)-tert-butyl 2-(4-fluoro-2-((tetrahydro-2H-pyran-2-yloxy)methyl) benzoyl)-pyrrolidine-1-carboxylase

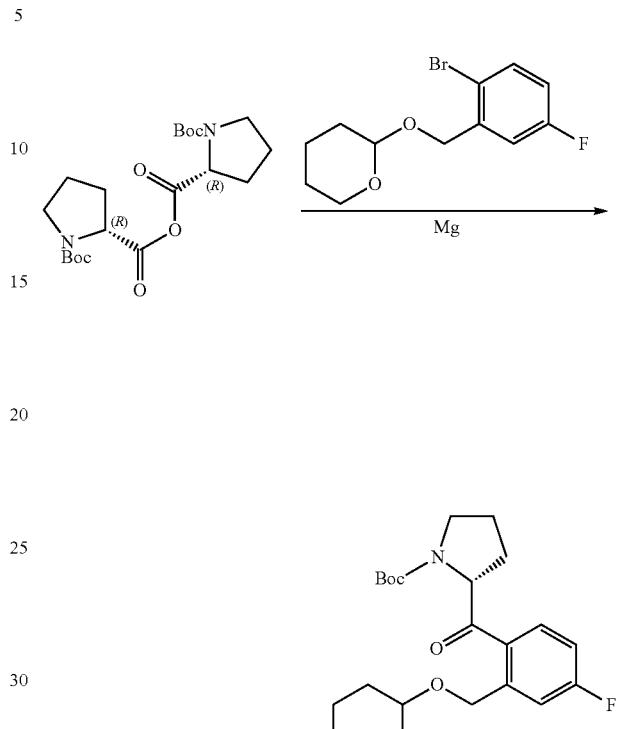

To a solution of 2-((2-bromo-5-fluorobenzyl)oxy)tetrahydro-2H-pyran (7 g, 24.2 mmol) in THF (20 ml) was added magnesium (1.17 g, 48.4 mmol). The mixture was stirred at reflux for 2 h. Upon completion, (4-fluoro-2-(((tetrahydro-2H-pyran-2-yl)oxy)methyl)phenyl)magnesium bromide (7.58 g, 24.2 mmol) was added. The reaction was stirred at this temperature for 3 h. Upon completion, water (50 mL) was added to the reaction vessel, and the resulting biphasic mixture was transferred to a reparatory funnel and extracted with EtOAc (2×50 mL). The combined organics were dried over anhydrous $Na_2SO_4$, filtered and concentrated in vacuo. The resulting oil was purified by flash column chromatography with an isocratic elution of EtOAc (10%) and petroleum ether (90%) to provide the title compound (5 g) as a colorless oil.

(c). (2R)-tert-butyl 2-(1-(4-fluoro-2-((tetrahydro-2H-pyran-2-yloxy)methyl) phenyl)-1-hydroxyethyl) pyrrolidine-1-carboxylate

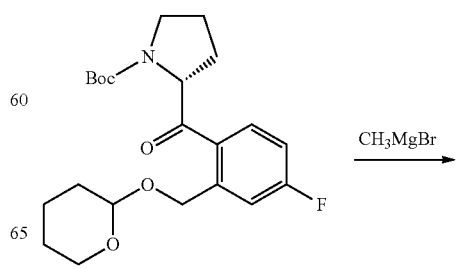

-continued

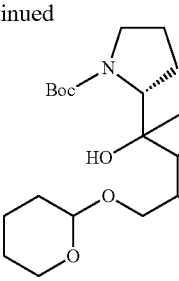

To a solution of (2R)-tert-butyl 2-(4-fluoro-2-(((tetrahydro-2H-pyran-2-yl)oxy)methyl) benzoyl)pyrrolidine-1-carboxylate (2.0 g, 4.90 mmol) in THF (20 ml) was added methylmagnesium bromide (4.89 mL, 14.7 mmol). The mixture was stirred at ambient temperature for 3 h. Saturated aqueous NH₄Cl (100 mL) was added to the reaction vessel, and the resulting biphasic mixture was transferred to a separatory funnel, and extracted with EtOAc (2×100 mL). The combined organics were dried over anhydrous Na₂SO₄, filtered and concentrated in vacuo to give the crude product, which was used in next step without further purification. ESI: m/z=446 (M+Na⁺).

(d). Preparation of (2R)-tert-butyl 2-(1-(4-fluoro-2-(hydroxymethyl)phenyl)-1-hydroxyl-ethyl)pyrrolidine-1-carboxylate

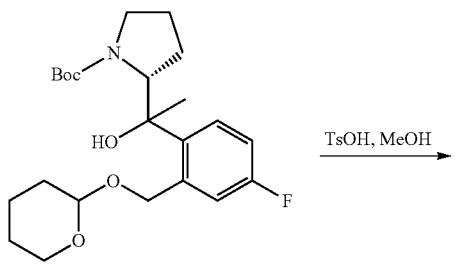

To a solution of (2R)-tert-butyl 2-(1-(4-fluoro-2-(((tetrahydro-2H-pyran-2-yl)oxy) methyl)phenyl)-1-hydroxyethyl) pyrrolidine-1-carboxylate (2.1 g, 4.95 mmol) in MeOH (80 ml) was added 4-methylbenzenesulfonic acid (85.2 mg, 495 μmol). The mixture was stirred at room temperature for 3 h, and then solvent evaporated in vacuo to give an oil. Saturated aqueous NaHCO₃ (10 mL) was then added to the reaction vessel, and the resulting biphasic mixture was transferred to a separatory funnel and extracted with EtOAc (2×100 mL). The combined organics were dried over anhydrous Na₂SO₄, filtered and concentrated in vacuo. The resulting oil was purified by flash column chromatography with an isocratic elution of EtOAc (20%) and petroleum ether (80%) to provide the title compound (1.49 g) as a colorless oil. ESI: m/z=340 (M+H⁺).

(e). (R)-tert-butyl 2-((S)-5-fluoro-1-methyl-1,3-dihydroiso benzofuran-1-yl)pyrrolidine-1-carboxylate

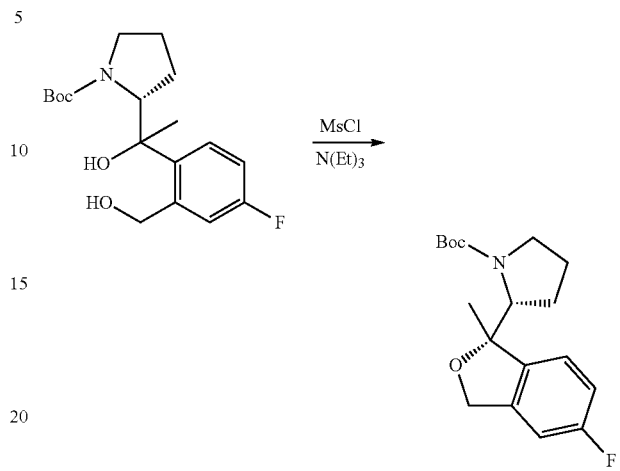

To a solution of (2R)-tert-butyl 2-(1-(4-fluoro-2-(hydroxymethyl)phenyl)-1-hydroxy ethyl)pyrrolidine-1-carboxylate (1.6 g, 4.71 mmol) in CH₂Cl₂ (30 ml) at 0° C. was added triethylamine (2.37 g, 23.5 mmol) and then followed by methanesulfonyl chloride (1.61 g, 14.1 mmol). The mixture was stirred at ambient temperature for 3 h. Water (100 mL) was added to the reaction vessel, and the resulting biphasic mixture was transferred to a reparatory funnel. The layers were separated, and the organic phase was washed with saturated aqueous NaCl (2×50 mL). The combined organics were dried over anhydrous Na₂SO₄, filtered and concentrated in vacuo. The resulting oil was purified by flash column chromatography with an isocratic elution of EtOAc (10%) and petroleum ether (90%) to provide the title compound (1.09 g) as a white solid.

(f). (R)-2-((R)-5-fluoro-1-methyl-1,3-dihydroisobenzofuran-1-yl) pyrrolidine (I-124)

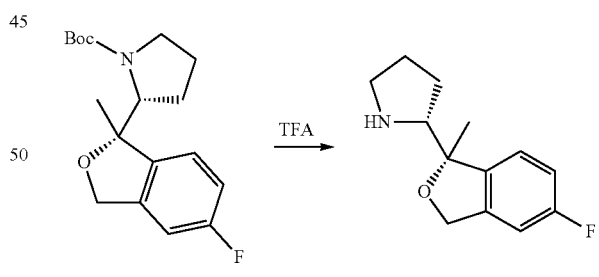

To a solution of (2R)-tert-butyl 2-(5-fluoro-1-methyl-1,3-dihydroisobenzofuran-1-yl)pyrrolidine-1-carboxylate (500 mg, 1.55 mmol) in CH₂Cl₂ (10 ml) was added 2,2,2-trifluoroacetic acid (1.76 g, 15.5 mmol). The reaction was stirred at room temperature for 2 h. Upon completion, the reaction mixture was evaporated in vacuo to afford the crude product. The resulting oil was purified by reverse phase HPLC to provide I-124 (200 mg) as a colorless oil. ESI: m/z=222 (M+1). ¹H NMR (500 MHz, MeOD): δ 7.25 (dd, J=8.3, 4.8 Hz, 1H), 7.05 (dd, J=15.0, 8.6 Hz, 2H), 5.18-5.03

(m, 2H), 3.58-3.41 (m, 1H), 3.14-3.09 (m, 1H), 2.96-2.91 (m, 1H), 1.83-1.74 (m, 2H), 1.62-1.49 (m, 4H), 1.45-1.37 (1H).

Example 1.16.2. (S)-2-((S)-5-fluoro-1-methyl-1,3-dihydroisobenzofuran-1-yl)pyrrolidine (I-123)

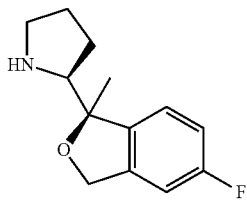

I-123

(S)-2-((S)-5-fluoro-1-methyl-1,3-dihydroisobenzofuran-1-yl)pyrrolidine (I-123) was prepared using a procedure analogous to that described in Example 1.16.1, but using (S)-1-(tert-butoxycarbonyl)pyrrolidine-2-carboxylic acid in place of (R)-1-(tert-butoxycarbonyl)pyrrolidine-2-carboxylic acid. ESI: m/z=222 (M+H+). $^1$H NMR (400 MHz, MeOD) δ 7.22 (dd, J=8.2, 4.9 Hz, 1H), 7.11-6.90 (m, 2H), 5.19-5.00 (m, 2H), 3.13-2.94 (m, 1H), 2.81-2.77 (m, 1H), 1.83-1.64 (m, 2H), 1.53 (s, 3H), 1.49-1.41 (m, 1H), 1.39-1.29 (m, 1H).

Example 1.17. Procedure Q

Example 1.17.1. 2-((S)-1-((S)-pyrrolidin-2-yl)isochroman-6-yl)pyridine (I-57) and 2-((R)-1-((S)-pyrrolidin-2-yl)isochroman-6-yl)pyridine (I-58)

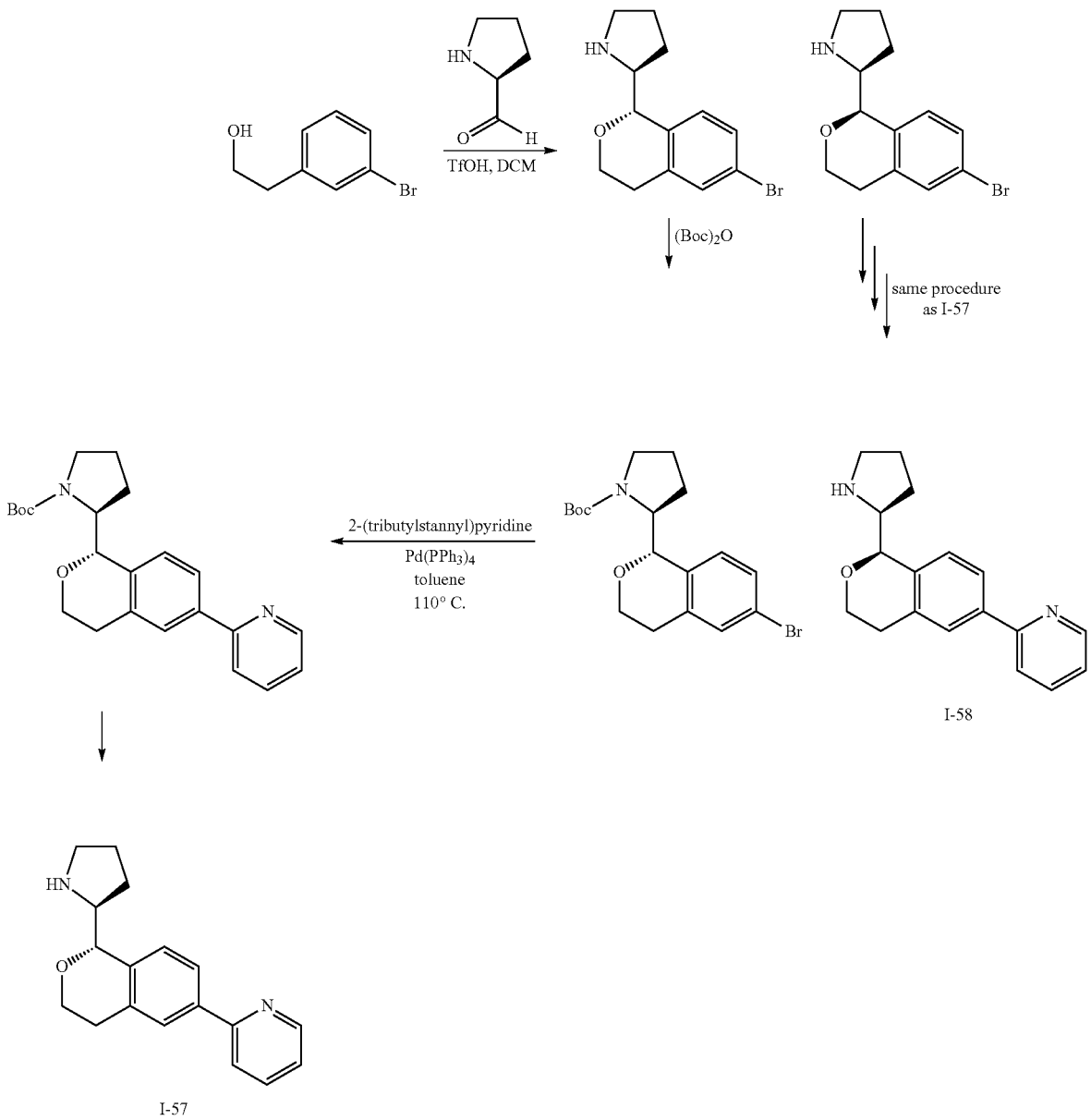

(a). (S)-2-((S)-6-bromoisochroman-1-yl)pyrrolidine and (S)-2-((R)-6-bromoisochroman-1-yl)pyrrolidine

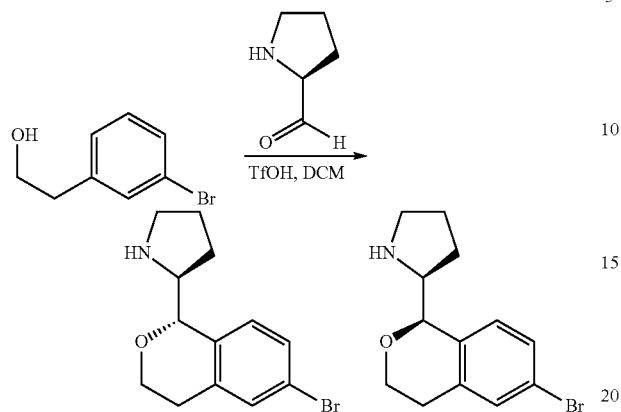

To a solution of 2-(3-bromophenyl)-ethanol (10 g, 49.7 mmol) in DCM (100 mL) was added (S)-pyrrolidine-2-carbaldehyde (5.9 g, 59.6 mmol) at 0° C. Trifluoromethanesulfonic acid (37.2 g, 248 mmol) was added dropwise. After addition, the mixture was stirred at this temperature for 8 h. Upon completion, water (5 mL) was added to the reaction vessel and the resulting biphasic mixture was transferred to a reparatory funnel. The layers were separated and the aqueous phase was extracted with EtOAc (2×50 mL). The combined organics were dried over anhydrous $Na_2SO_4$, filtered and concentrated in vacuo to give a mixture of two diastereoisomers, which was separated by Chiral-HPLC (Column: OZ-H 250*4.6 mm 5 µm, Mobile Phase: MeOH (0.1% DEA) to yield (S)-2-((S)-6-bromoisochroman-1-yl)pyrrolidine (6.12 g) and (5)-2-((R)-6-bromoisochroman-1-yl)pyrrolidine (6.13 g). MS (ESI) m/z 284 $[M+H]^+$.

(b). (S)-tert-butyl 2-((S)-6-bromoisochroman-1-yl)pyrrolidine-1-carboxylase

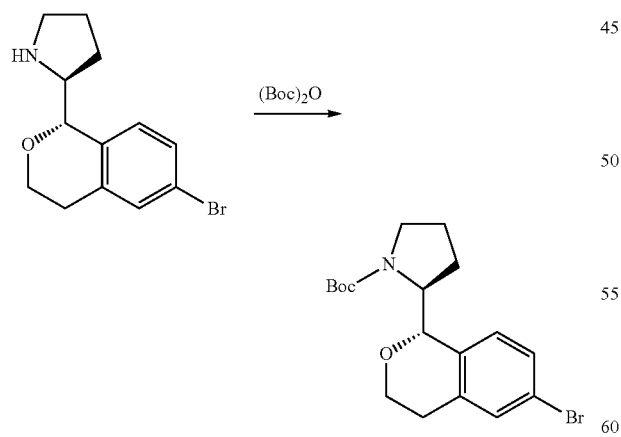

To a solution of (S)-2-((S)-6-bromoisochroman-1-yl)pyrrolidine (6 g, 21.2 mmol) in NaOH/Water (30 ml) at room temperature was added ditertbutyl dicarbonate (5.54 g, 25.4 mmol). The reaction was stirred at this temperature for 2 h. Upon completion, the resulting biphasic mixture was transferred to a separatory funnel. The layers were separated and the aqueous phase was washed with DCM (2×50 mL). The combined organics were dried over anhydrous $Na_2SO_4$, filtered and concentrated in vacuo. MS (ESI) m/z: 384 $[M+H]^+$.

(c). (S)-tert-butyl 2-((S)-6-(pyridin-2-yl)isochroman-1-yl) pyrrolidine-1-carboxylase

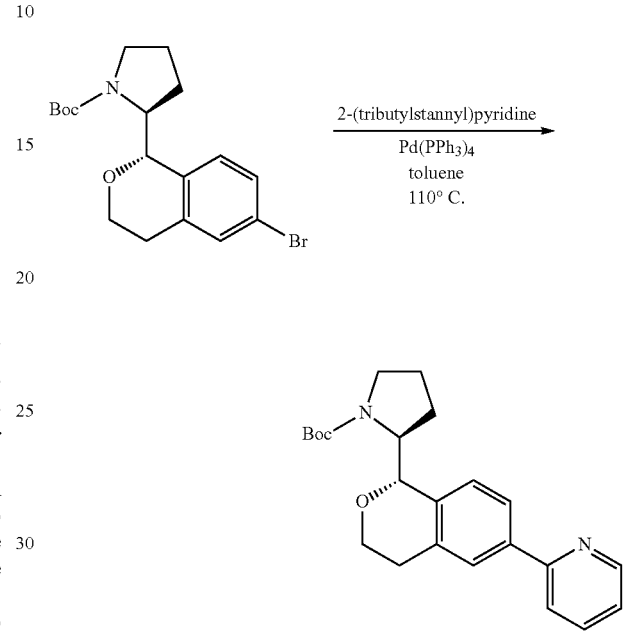

To a solution of (S)-tert-butyl 2-((S)-6-bromoisochroman-1-yl)pyrrolidine-1-carboxylate (2 g, 5.23 mmol) in toluene (50 ml) was added 2-(tributylstannyl)pyridine (2.3 g, 6.27 mmol) and palladium-triphenylphosphane (1:4) (6.04 mg, 0.523 mmol). The mixture was stirred at 110° C. for 6 h. Upon completion, water (5 mL) was added to the reaction vessel and the resulting biphasic mixture was transferred to a separatory funnel. The layers were separated and the aqueous phase was washed with EtOAc (2×50 mL). The combined organics were dried over anhydrous $Na_2SO_4$, filtered and concentrated in vacuo. The resulting oil was purified by flash column chromatography (petroleum ether/EtOAc from 20:1 to 5:1) to provide the title product (1.36 g) as a colorless oil. MS (ESI) m/z: 381 $[M+H]^+$.

(d). 2-((S)-1-((S)-pyrrolidin-2-yl)isochroman-6-yl)pyridine (I-57)

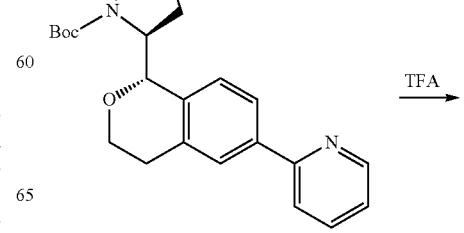

-continued

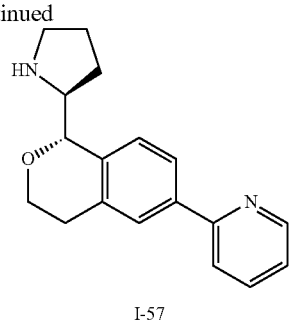

I-57

To a solution of (5)-tert-butyl 2-((S)-6-(pyridin-2-yl)isochroman-1-yl)pyrrolidine-1-carboxylate (500 mg, 1.31 mmol) in dichloromethane (50 mL), trifluoroacetic acid (224 mg, 1.97 mmol) was added dropwise at 0° C. After addition, the mixture was stirred at this temperature for about 3 h. After workup, 2-((S)-1-((S)-pyrrolidin-2-yl)isochroman-6-yl)pyridine (I-57) was obtained. MS (ESI) m/z: 281 [M+H]⁺. ¹H NMR (HCl salt, 400 MHz, MeOD): δ 8.89 (d, J=5.8 Hz, 1H), 8.78-8.68 (m, 1H), 8.46 (d, J=8.2 Hz, 1H), 8.10 (t, J=6.8 Hz, 1H), 7.97-7.86 (m, 2H), 7.70 (d, J=8.2 Hz, 1H), 5.17 (d, J=2.2 Hz, 1H), 4.91 (s, 11H), 4.45-4.33 (m, 2H), 3.92 (td, J=11.3, 3.3 Hz, 1H), 3.66-3.14 (m, 6H), 2.92 (d, J=16.6 Hz, 1H), 2.35 (dt, J=16.8, 6.9 Hz, 2H), 2.15 (ddd, J=21.1, 13.0, 6.0 Hz, 2H).

(e). 2-((R)-1-((S)-pyrrolidin-2-yl)isochroman-6-yl)pyridine (I-58)

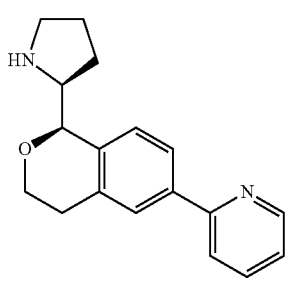

I-58

I-58 was synthesized using the same method as Compound I-57 as described above. (ESI) m/z: 281 [M+H]⁺. ¹H NMR (400 MHz, CDCl₃) δ 8.72-8.65 (m, 1H), 7.82-7.68 (m, 3H), 7.31-7.19 (m, 3H), 5.04 (d, J=2.4 Hz, 1H), 4.23 (ddd, J=11.1, 5.7, 1.6 Hz, 1H), 3.77 (td, J=11.3, 3.0 Hz, 1H), 3.69-3.60 (m, 1H), 3.48 (s, 1H), 3.20-2.95 (m, 2H), 2.85 (dt, J=11.1, 7.6 Hz, 1H), 2.73 (d, J=16.2 Hz, 1H), 2.01 (s, 4H), 1.70 (dd, J=14.3, 7.0 Hz, 2H), 1.49 (ddd, J=15.0, 7.7, 2.7 Hz, 2H).

Example 1.18. Procedure R. Certain Provided Compounds were Made Following a Procedure Exemplified by Example 1.18.1

Example 1.18.1. 5-((S)-1-((S)-pyrrolidin-2-yl)isochroman-6-yl)isoxazole (I-55)

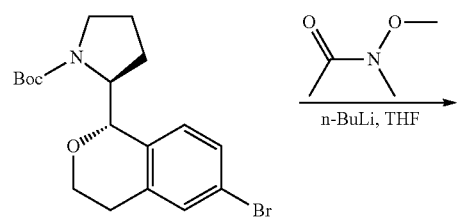

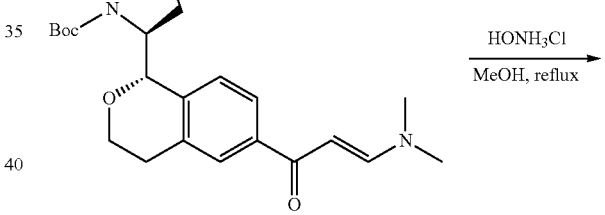

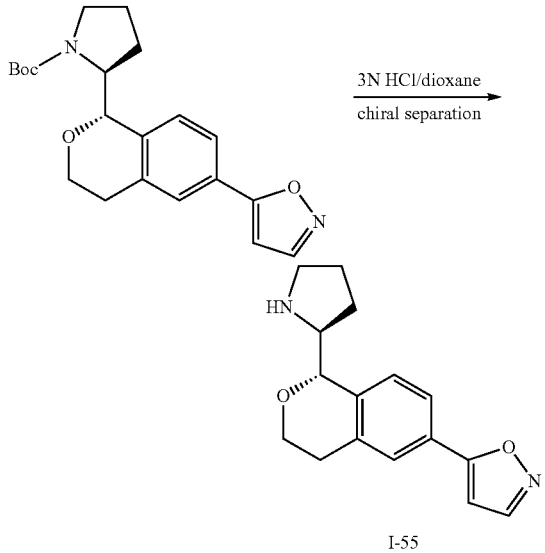

I-55

(a). (S)-tert-butyl 2-((S)-6-acetylisochroman-1-yl) pyrrolidine-1-carboxylate

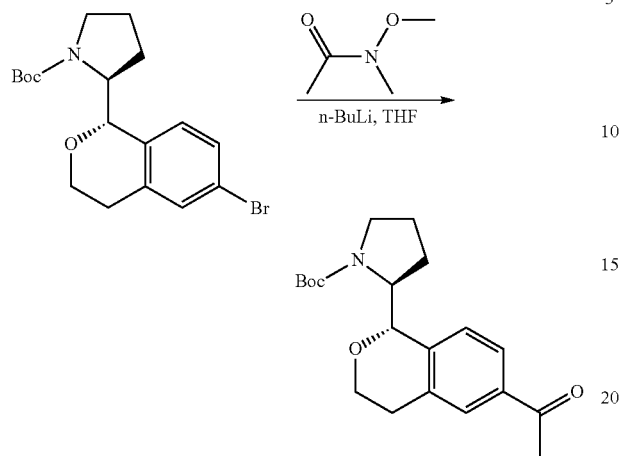

To a solution of (S)-tert-butyl 2-((S)-6-bromoisochroman-1-yl)pyrrolidine-1-carboxylate (1.5 g, 3.32 mmol) in THF (25 mL) was added n-BuLi (1.6 N in hexane) (3.1 mL) at −78° C. under nitrogen. After the mixture was stirred at this temperature for 1 h, a solution of N-methoxy-N-methylacetamide (444 mg, 4.31 mmol) in THF (2 mL) was added. The mixture was allowed to warm to room temperature and stirred for another 1 h. The mixture was quenched with water (100 mL), extracted with EtOAc (70 mL×2), dried and concentrated in vacuo to give the crude, which was purified by prep-TLC, eluted with PE:EtOAc=5:1 to yield the title compound.

(b). (S)-tert-butyl 2-((S)-6-((E)-3-(dimethylamino) acryloyl) isochroman-1-yl)pyrrolidine-1-carboxylate

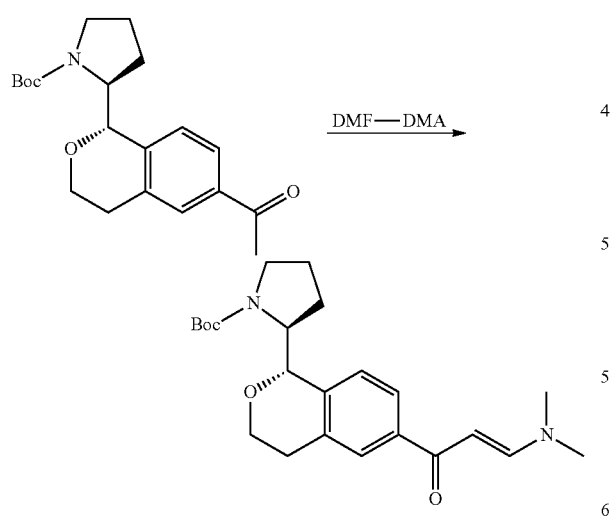

A solution of (S)-tert-butyl 2-((S)-6-acetylisochroman-1-yl)pyrrolidine-1-carboxylate (520 mg, 1.50 mmol) and DMF-DMA (0.535 g, 4.5 mmol) was heated to 100° C. with stirring overnight. The mixture was concentrated in vacuo to give the crude, which was used directly in the next step. (ESI) m/z: 401[M+H]$^+$.

(c). (S)-tert-butyl 2-((S)-6-(isoxazol-5-yl)isochroman-1-yl) pyrrolidine-1-carboxylate

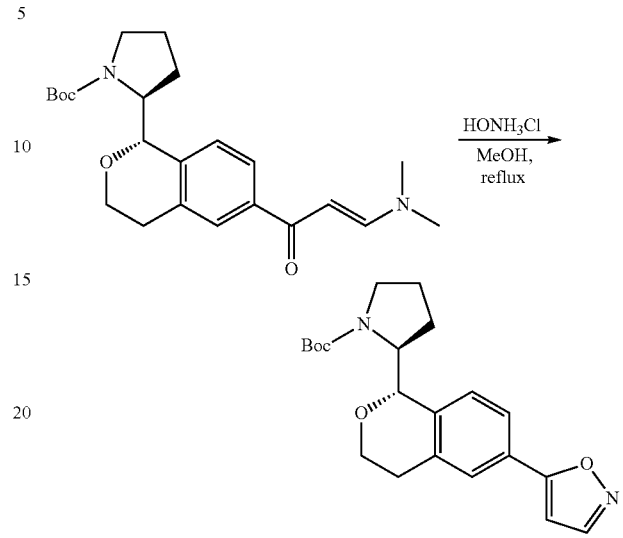

To a solution of (S)-tert-butyl 2-((S)-6-((E)-3-(dimethylamino)acryloyl) isochroman-1-yl)pyrrolidine-1-carboxylate (720 mg, 0.876 mmol) in MeOH (30 mL) was added hydroxylamine hydrochloride (182 mg, 2.62 mmol). The mixture was heated to 70° C. with stirring for 3 h. The mixture was concentrated in vacuo to give the crude, which was diluted with water (100 mL), extracted with DCM (70 mL×2). The organic phase was dried, filtered and concentrated in vacuo to give the crude product. (ESI) m/z: 315[M-56+H]$^+$.

(d). 5-((S)-1-((S)-pyrrolidin-2-yl)isochroman-6-yl) isoxazole (I-55)

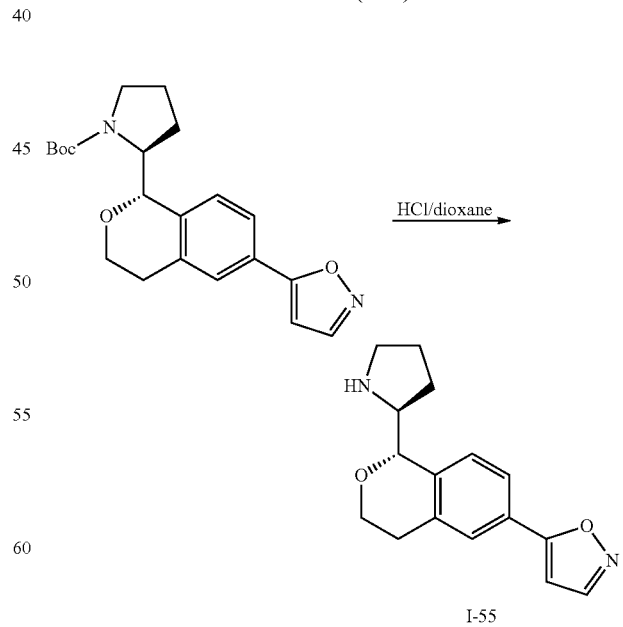

To a solution of (S)-tert-butyl 2-((S)-6-(isoxazol-5-yl) isochroman-1-yl) pyrrolidine-1-carboxylate (420 mg, 0.812 mmol) in DCM (5 mL) was added 3N HCl/dioxane (6 mL)

at room temperature. The mixture was stirred at room temperature for 3 h and then concentrated in vacuo to give the crude, which was purified by prep. HPLC to give a residue. The residue was freeze-dried to give the TFA salt, which was basified with sat. NaHCO₃, extracted with DCM/MeOH=20:1 (50 mL×2), dried and concentrated in vacuo to yield I-55. (ESI) m/z: 271[M+H]⁺. ¹HNMR(HCl salt, 400 MHz, MeOD): δ 8.46 (s, 1H), 7.81-7.79 (d, J=8.0 Hz, 1H), 7.75 (s, 1H), 7.51-7.49 (d, J=8.0 Hz, 1H), 6.85 (s, 1H), 5.09 (s, 1H), 4.37-4.28 (m, 2H), 3.91-3.85 (m, 1H), 3.30-3.23 (m, 3H), 2.84-2.80 (d, J=16.4 Hz, 1H), 2.34-2.25 (m, 2H), 2.20-2.04 (m, 2H).

Example 1.18.2. 5-((R)-1-((S)-pyrrolidin-2-yl)isochroman-6-yl)isoxazole (I-56)

I-56

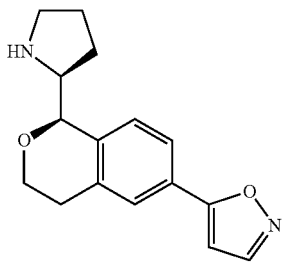

5-((R)-1-((S)-pyrrolidin-2-yl)isochroman-6-yl)isoxazole (I-56) was prepared using a procedure analogous to that described in Example 1.18.1, but using (S)-tert-butyl 2-((R)-6-bromoisochroman-1-yl)pyrrolidine-1-carboxylate in place of (S)-tert-butyl 2-((S)-6-bromoisochroman-1-yl)pyrrolidine-1-carboxylate. (ESI) m/z: 271[M+H]⁺. ¹HNMR (400 MHz, MeOD): δ 8.46-8.45 (d, J=2.0 Hz, 1H), 7.76-7.74 (d, J=8.0 Hz, 1H), 7.73 (s, 1H), 7.41-7.39 (d, J=7.6 Hz, 1H), 6.84-6.83 (d, J=1.6 Hz, 1H), 5.28 (s, 1H), 4.46-4.41 (m, 1H), 4.37-4.33 (m, 1H), 3.88-3.81 (m, 1H), 3.40-3.37 (m, 2H), 3.21-3.13 (m, 1H), 2.83-2.79 (d, J=16.4 Hz, 1H), 2.09-1.95 (m, 2H), 1.83-1.77 (m, 2H).

Example 1.19. Procedure S

Example 1.19.1. 3-(6-fluoroisochroman-1-yl)pyrrolidine (I-129, I-130, I-131, I-132)

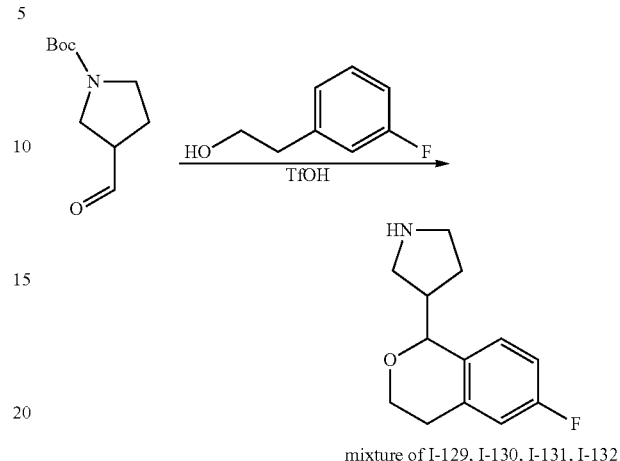

mixture of I-129, I-130, I-131, I-132

To a mixture of tert-butyl 3-formylpyrrolidine-1-carboxylate (550 mg, 2.76 mmol) and 2-(3-fluorophenyl)ethanol (386 mg, 2.76 mmol) was added trifluoromethanesulfonic acid (1.24 g, 8.28 mmol) at 0° C. The mixture was stirred at room temperature for another 2 h. Upon completion, the mixture was quenched with sat. NaHCO₃ (100 mL) till pH>7, extracted with DCM (80 mL×2). The organic layers were dried and concentrated to give the crude, which was purified by prep-HPLC to give the desired product as TFA salt, which was basified with sat. NaHCO₃ (30 mL) again, extracted with DCM (2×20 mL), dried and concentrated in vacuo to yield the mixture of 4 stereoisomers. (ESI) m/z: 222[M+H]⁺. ¹HNMR (400 MHz, CDCl₃): δ 7.11-7.06 (m, 1H), 6.92-6.87 (m, 1H), 6.84-6.82 (m, 1H), 4.80-4.78 (d, J=6.8 Hz, 1H), 4.21-4.16 (m, 1H), 3.87 (s, 1H), 3.72-3.64 (m, 1H), 3.25-2.76 (m, 6H), 2.63-2.58 (d, J=16.8 Hz, 1H), 2.07-1.99 (m, 1H), 1.66-1.46 (m, 1H).

Example 1.20. Procedure T

Example 1.20.1. (S)-2-((R)-6,8-dihydro-[1,3]dioxolo[4,5-e]isobenzofuran-8-yl)-pyrrolidine (I-141) and (S)-2-((S)-6,8-dihydro-[1,3]dioxolo[4,5-e]isobenzofuran-8-yl)-pyrrolidine (I-142)

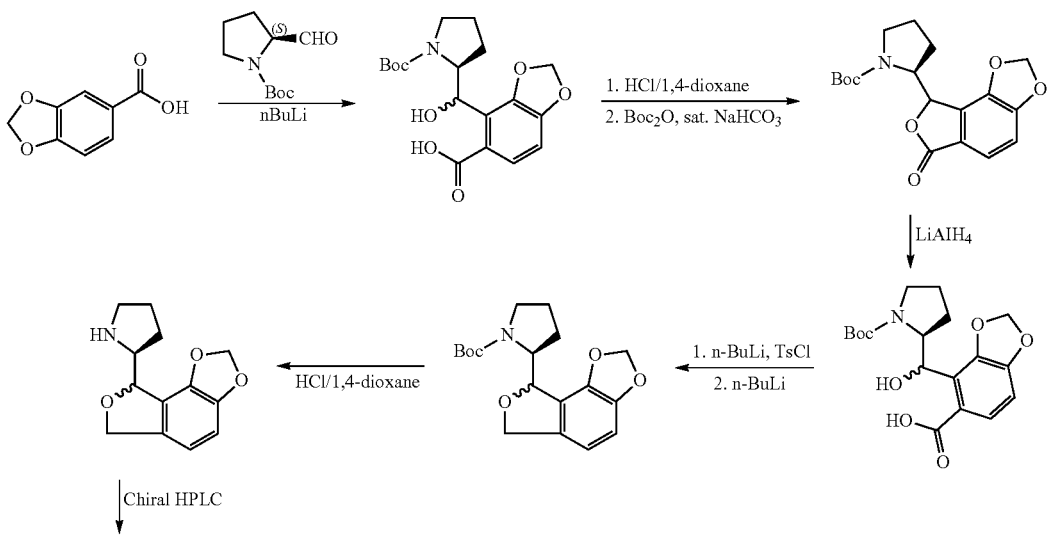

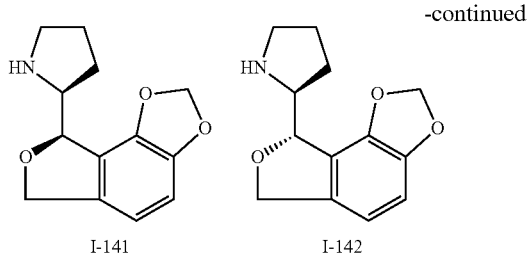

I-141          I-142

(a). 4-(((S)-1-(tert-butoxycarbonyl)pyrrolidin-2-yl)(hydroxy)methyl)benzo[d][1,3]dioxole-5-carboxylic acid (b). (2S)-tert-butyl 2-(6-oxo-6,8-dihydro-[1,3]dioxolo[4,5-e]isobenzofuran-8-yl)pyrroledine-1-carboxylate

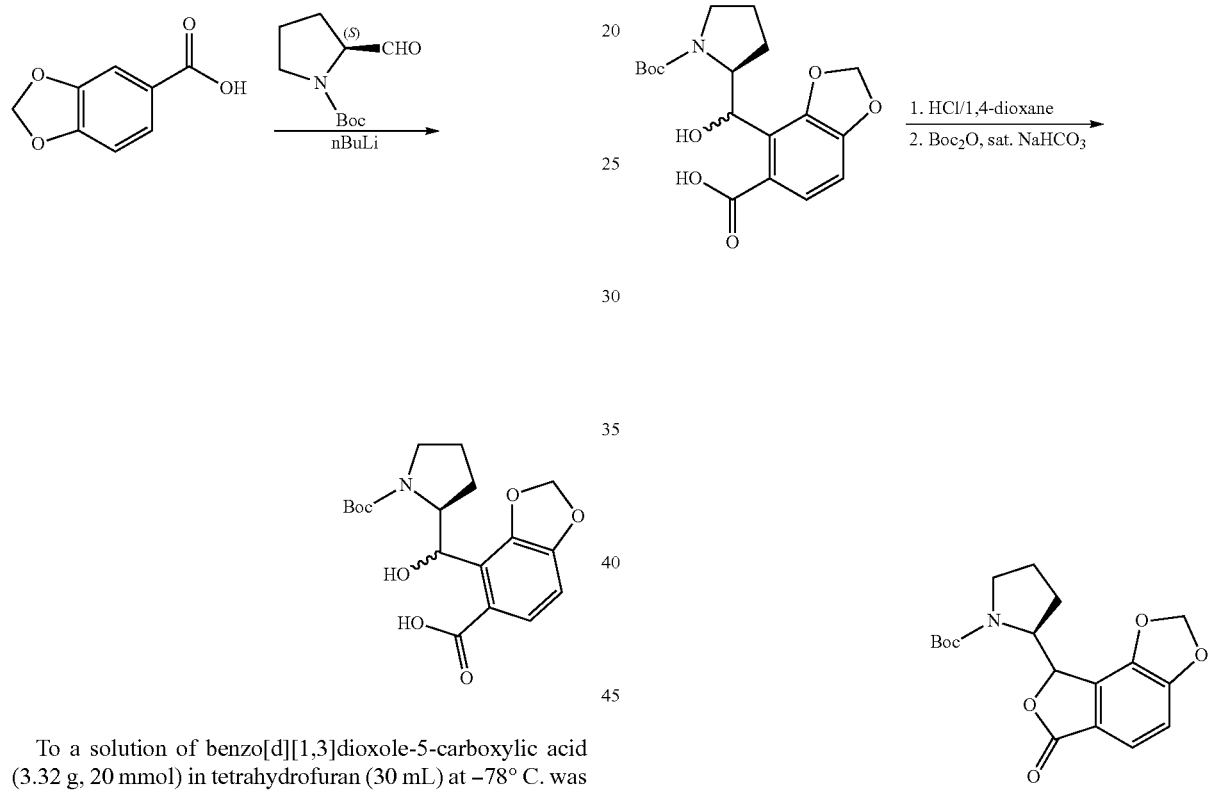

To a solution of benzo[d][1,3]dioxole-5-carboxylic acid (3.32 g, 20 mmol) in tetrahydrofuran (30 mL) at −78° C. was added n-butyllithium in n-hexane (2.5 M, 17.5 mL, 44.0 mmol) dropwise over a period of 15 min. The reaction temperature was allowed to rise to −20° C. slowly. The mixture was stirred at this temperature for 1 h and cooled to −78° C. again. To the mixture was added a solution of (S)-tert-butyl 2-formylpyrrolidine-1-carboxylate (5.97 g, 15 mmol) in tetrahydrofuran (5 mL) dropwise over a period of 5 min. The reaction mixture was stirred for 6 h and then quenched with water (100 mL) at −78° C. The mixture was washed with ethyl acetate (3×50 mL) and the combined organic phase was extracted with water (50 mL). The combined aqueous layers were adjusted to pH=5 carefully with 0.5 M HCl solution at 0° C., extracted with dichloromethane (3×50 mL), dried over sodium sulfate and concentrated in vacuo to give crude 4-(((S)-1-(tert-butoxycarbonyl)pyrrolidin-2-yl) (hydroxy)methyl)benzo[d][1,3]dioxole-5-carboxylic acid as a yellow oil (5.5 g, purity ca. 50%); MS (ESI): m/z=366 [M+H]⁺.

To a solution of 4-(((S)-1-(tert-butoxycarbonyl)pyrrolidin-2-yl)(hydroxy)methyl) benzo[d][1,3]dioxole-5-carboxylic acid (5.5 g, Purity: 50%, 7.52 mmol) in methanol (100 mL) was added 4 M HCl/1,4-dioxane (2.74 g, 75.2 mmol). The reaction mixture was stirred at room temperature for 16 h and concentrated to give a residue. To the residue was added water (30 mL), tetrahydrofuran (30 mL), sodium bicarbonate (2.48 g, 29.6 mmol), and di-tert-butyl dicarbonate (3.23 g, 14.8 mmol). The reaction mixture was stirred at room temperature for 3 h and then extracted with ethyl acetate (3×60 mL). The combined organic layers were dried over sodium sulfate and concentrated in vacuo. The crude product was purified by silica gel column chromatography (eluted with petroleum ether: ethyl acetate=3:1) to give (2S)-tert-butyl 2-(6-oxo-6,8-dihydro-[1,3]dioxolo[4,5-e] isobenzofuran-8-yl) pyrrolidine-1-carboxylate as a white solid (2.4 g). MS (ESI): m/z=292 [M-55]⁺.

(c) (2S)-tert-butyl 2-(hydroxy(5-(hydroxymethyl)benzo[d][1,3]dioxol-4-yl)methyl)pyrrolidine-1-carboxylate

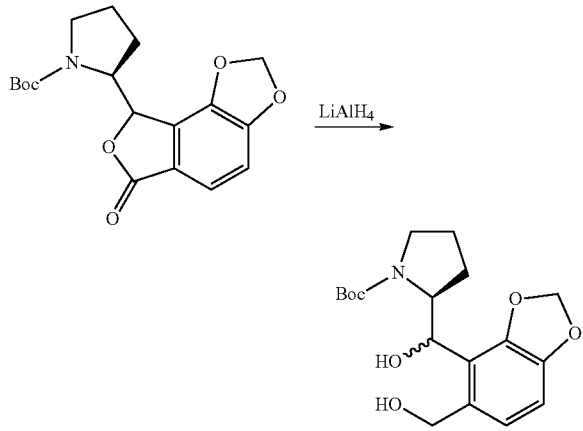

To a solution of (2S)-tert-butyl 2-(6-oxo-6,8-dihydro-[1,3]dioxolo[4,5-e] isobenzofuran-8-yl)pyrrolidine-1-carboxylate (2.1 g, 6.04 mmol) in tetrahydrofuran (100 mL) at 0° C. was added lithium aluminium hydride (229 mg, 6.04 mmol) in portions. The reaction was stirred at 0° C. for 1 h and then quenched with water (0.5 mL in 10 mL tetrahydrofuran, dropwise at 0° C. over 5 mins) and then 15% sodium hydroxide solution (0.5 mL). The mixture was stirred at 0° C. for 30 min and filtered through celite. The filtered cake was washed with dichloromethane (200 mL). The combined filtrate was concentrated to give a residue which was diluted with brine (50 mL), extracted with ethyl acetate (3×100 mL). The organic layers were dried over sodium sulfate and concentrated in vacuo. The crude product was purified by silica gel column chromatography (eluted with petroleum ether: ethyl acetate=1:1) to give (2S)-tert-butyl 2-(hydroxy (5-(hydroxymethyl)benzo[d][1,3]dioxol-4-yl)methyl) pyrrolidine-1-carboxylate as a white solid (2.0 g). MS (ESI): m/z=352 [M+H]$^+$.

(d). (2S)-tert-butyl 2-(6,8-dihydro-[1,3]dioxolo[4,5-e]isobenzofuran-8-yl)pyrrolidine-1-carboxylate

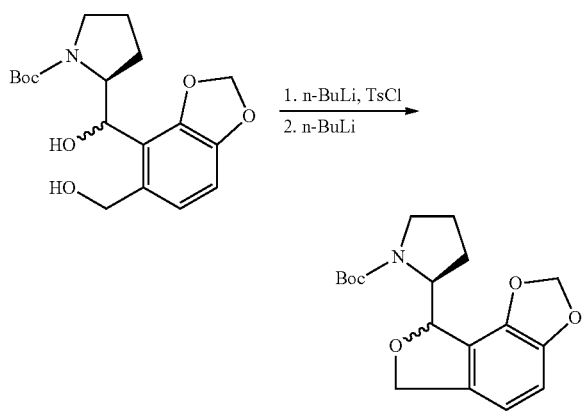

To a solution of (2S)-tert-butyl 2-(hydroxy(5-(hydroxymethyl)benzo[d][1,3] dioxol-4-yl)methyl)pyrrolidine-1-carboxylate (1.9 g, 5.40 mmol) in tetrahydrofuran (120 mL) at −78° C. was added n-butyllithium in n-hexane (2.5 M, 2.37 mL, 5.94 mmol). The reaction was stirred at this temperature for 30 min. Then a solution of 4-methylbenzene-1-sulfonyl chloride (1.13 g, 5.94 mmol) in tetrahydrofuran (12 mL) was added. After the reaction mixture was stirred at this temperature for 1 h, a solution of n-butyllithium in n-hexane (2.5 M, 2.37 mL, 5.94 mmol) was added. The mixture was allowed to warm to room temperature slowly, stirred at room temperature for an additional 16 h and then quenched with water (150 mL) at 0° C. It was extracted with ethyl acetate (3×100 mL) and the organic layers were dried over sodium sulfate and concentrated in vacuo. The crude product was purified by Prep-TLC (eluted with petroleum ether: ethyl acetate=4:1) to give (2S)-tert-butyl 2-(6,8-dihydro-[1,3]dioxolo[4,5-e]isobenzofuran-8-yl)pyrrolidine-1-carboxylate as a yellow oil (680 mg). MS (ESI): m/z=334 [M+H]$^+$.

(e). (S)-2-((R)-6,8-dihydro-[1,3]dioxolo[4,5-e]isobenzofuran-8-yl)pyrrolidine (I-141) and (S)-2-((S)-6,8-dihydro-[1,3]dioxolo[4,5-e]isobenzofuran-8-yl)pyrrolidine (I-142)

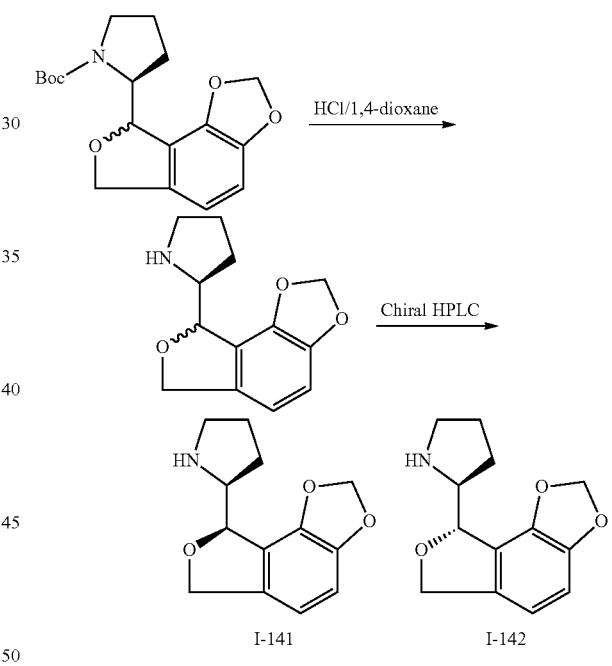

To a solution of (2S)-tert-butyl 2-(6,8-dihydro-[1,3]dioxolo[4,5-e] isobenzofuran-8-yl)pyrrolidine-1-carboxylate (1.1 g, 3.3 mmol) in dichloromethane (10 mL) was added 4 M hydrochloric acid/1,4-dioxane solution (4 M, 2 mL, 8 mmol). The mixture was stirred at room temperature for 6 h and concentrated in vacuo to give a residue, which was washed with petroleum ether (50 mL), followed by ethyl acetate (5 mL) to give the hydrochloride salt of (2S)-2-(6,8-dihydro-[1,3]dioxolo[4,5-e]isobenzofuran-8-yl)pyrrolidine as a yellow solid (0.7 g). This mixture of two diastereoisomers was separated by Chiral HPLC (Co-Solvent: MeOH (0.5% NH4OH), Column: AS-H 4.6×250 mm 5 μm) to give (S)-2-((R)-6,8-dihydroisobenzofuro[4,5-d][1,3]dioxol-8-yl)pyrrolidine (I-141, 282 mg colorless oil) and (S)-2-((S)-6,8-dihydroisobenzofuro[4,5-d][1,3]dioxol-8-yl)pyrrolidine (I-142, 124 mg colorless oil).

(S)-2-((R)-6,8-dihydroisobenzofuro[4,5-d][1,3]dioxol-8-yl)pyrrolidine (I-141): MS (ESI): m/z 233 [M+H]$^+$; $^1$HNMR (HCl salt, 400 MHz, MeOD): δ 6.87-6.89 (d, J=8 Hz, 1H), 6.78-6.80 (d, J=8 Hz, 1H), 6.01-6.04 (dd, J=11.6 Hz, 2H), 5.61-5.61 (d, J=2 Hz, 1H), 4.90-5.18 (m, 2H), 4.04-4.09 (m, 1H), 3.31-3.34 (m, 1H), 1.74-2.07 (m, 4H).

(S)-2-((S)-6,8-dihydroisobenzofuro[4,5-d][1,3]dioxol-8-yl)pyrrolidine (I-142): MS (ESI): m/z 233 [M+H]$^+$, $^1$HNMR (HCl salt, 400 MHz, MeOD): δ 6.88-6.90 (d, J=8 Hz, 1H), 6.80-6.82 (d, J=8 Hz, 1H), 6.02-6.06 (dd, J=15.2 Hz, 2H), 5.40-5.41 (d, J=4 Hz, 1H), 5.16-5.19 (d, J=12 Hz, 1H), 5.02-5.04 (d, J=8 Hz, 1H), 3.87-3.91 (m, 1H), 3.25-3.36 (m, 2H), 2.28-2.31 (m, 1H), 2.06-2.17 (m, 3H).

Example 1.21. Procedure U. Certain Provided Compounds were Made Following a Procedure Exemplified by Example 1.21.1

Example 1.21.1. (S)-2-((1R,4S)-4,6-difluoroisochroman-1-yl)pyrrolidine (I-137) and (S)-2-((1R,4R)-4,6-difluoroisochroman-1-yl)pyrrolidine (I-138)

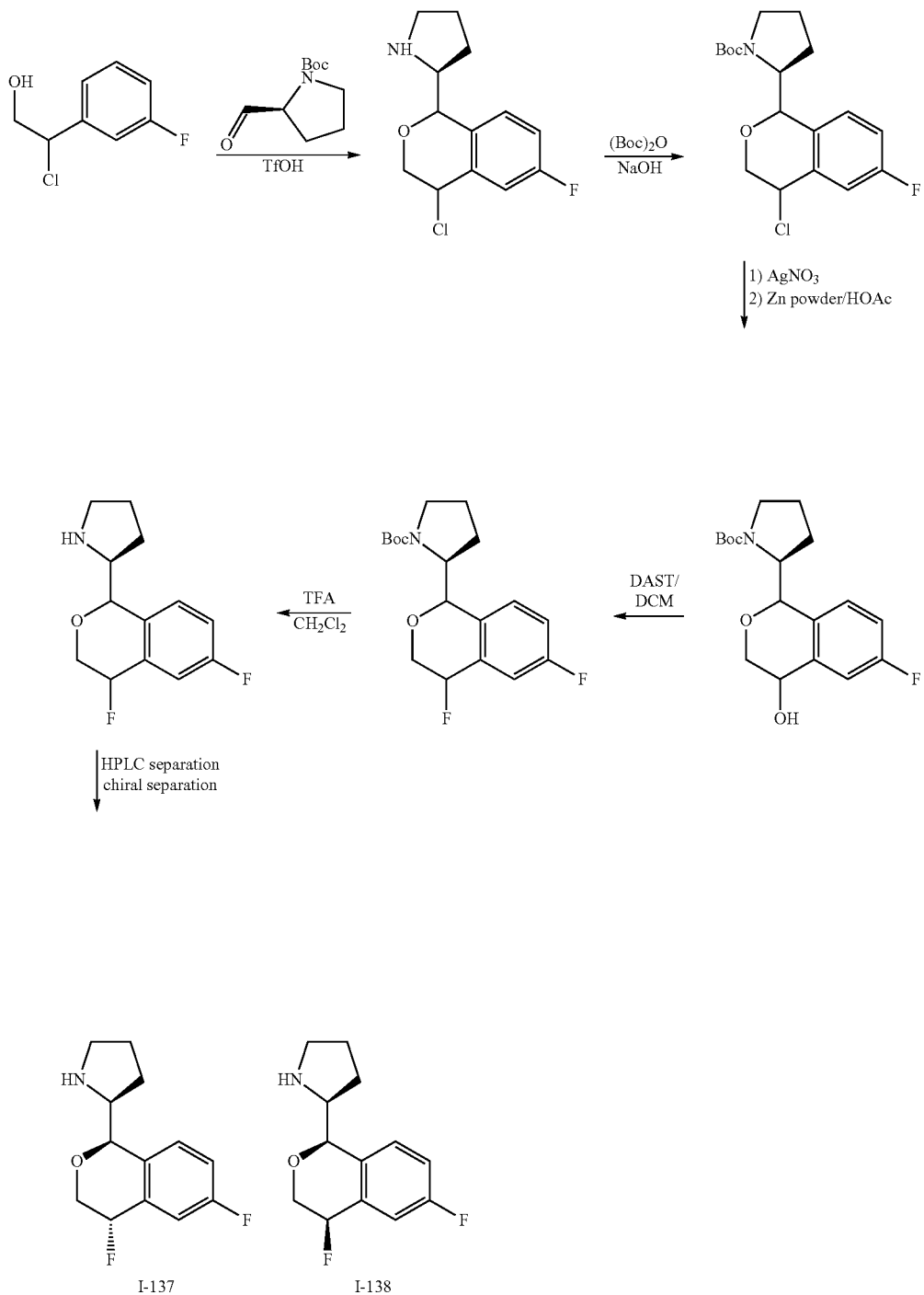

(a). (2S)-tert-butyl 2-(4-chloro-6-fluoroisochroman-1-yl)pyrrolidine-1-carboxylate

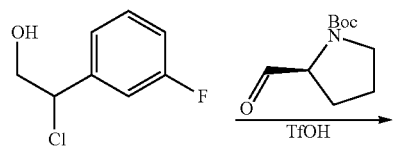

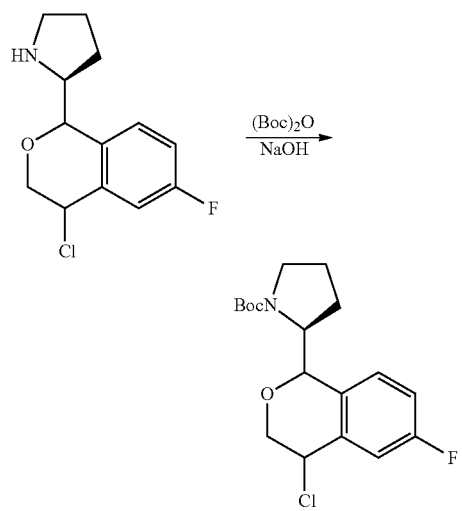

To a solution of 2-chloro-2-(3-fluorophenyl)ethanol (50 g, 287 mmol) in dichloromethane (300 ml) in ice salt bath was added trifluoromethanesulfonic acid (129 g, 861 mmol) and (S)-tert-butyl 2-formylpyrrolidine-1-carboxylate (114 g, 574 mmol) dropwise (inner temperature was kept <−5° C.). After the addition, the mixture was stirred at room temperature for 3 h and was then basified with sodium hydroxide (20% aq.) to pH=10. Di-tert-butyl dicarbonate (188 g, 861 mmol) was added. The mixture was stirred at room temperature for 3 h, quenched with water (300 mL), and extracted with dichloromethane (200 mL×2). The combined organic layers were dried and concentrated in vacuo to give a residue, which was purified by silica gel chromatography eluted with petroleum ether:ethyl acetate=10:1 to give the desired product (65 g) as a yellow oil.

(b). (2S)-tert-butyl 2-(6-fluoro-4-hydroxyisochroman-1-yl)pyrrolidine-1-carboxylate

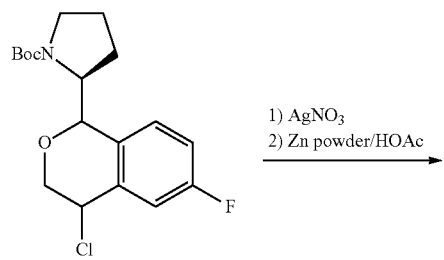

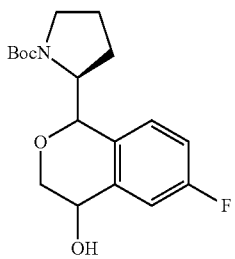

To a solution of (2S)-tert-butyl 2-(4-chloro-6-fluoroisochroman-1-yl)pyrrolidine-1-carboxylate (50 g, 140.8 mmol) in tetrahydrofuran/water (200 mL, 1:1) was added silver nitrate (119.7 g, 704 mmol). The mixture was heated to reflux for 4 h. Upon cooling to room temperature, the mixture was extracted with ethyl acetate (200 mL×3) and the organic layers were dried and concentrated in vacuo to give a residue. To the residue was added acetic acid (200 mL) and zinc powder (45.8 g, 704 mmol) at room temperature. The mixture was stirred at room temperature for 2 h and then filtered over celit. The filtrate was evaporated in vacuo to give an oil, which was dissolved in water (500 mL) and extracted with ethyl acetate (200 mL). The organic layers were washed with sodium bicarbonate (aq. Sat.), dried and concentrated in vacuo to give the crude product which was purified by flash column chromatography with petroleum ether:ethyl acetate=2:1 to provide (2S)-tert-butyl 2-(6-fluoro-4-hydroxyisochroman-1-yl)pyrrolidine-1-carboxylate (35.0 g) as a yellow oil.

(c). (2S)-tert-butyl 2-(4,6-difluoroisochroman-1-yl)pyrrolidine-1-carboxylate

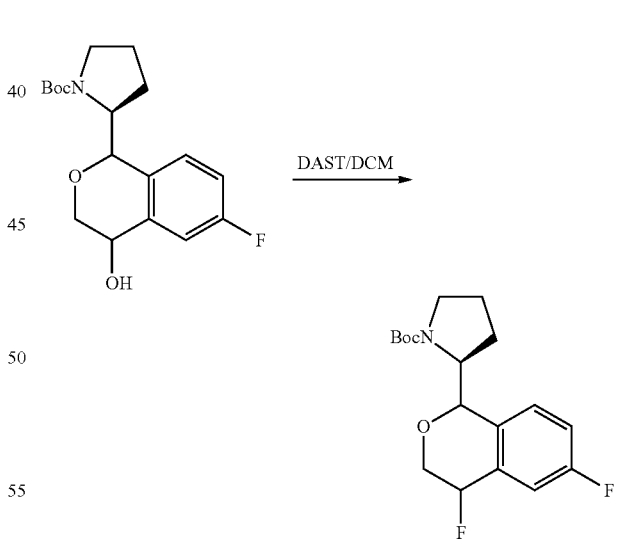

To a solution of (2S)-tert-butyl 2-(6-fluoro-4-hydroxyisochroman-1-yl) pyrrolidine-1-carboxylate (30 g, 88.9 mmol) in dichloromethane (60 mL) in ice salt bath was added diethylaminosulfurtrifluoride (21.5 g, 133 mmol) dropwise. The mixture was stirred at this temperature for 1 h and then poured into saturated aqueous sodium bicarbonate (300 mL). The resulting biphasic mixture was transferred to a reparatory funnel. The layers were separated and the water phase was extracted with dichloromethane (2×200 mL). The combined organic layers were dried over anhydrous sodium sulfate, filtered and concentrated in vacuo. The resulting oil was purified by flash column chromatography with a gradient elution of petroleum ether:ethyl acetate=10:1 to provide (2S)-tert-butyl 2-(4,6-difluoroisochroman-1-yl)pyrrolidine-1-carboxylate (16 g) as a yellow oil.

(d). (S)-2-((1R,4S)-4,6-difluoroisochroman-1-yl)pyrrolidine (I-137) and (S)-2-((1R,4R)-4,6-difluoroisochroman-1-yl)pyrrolidine (I-138)

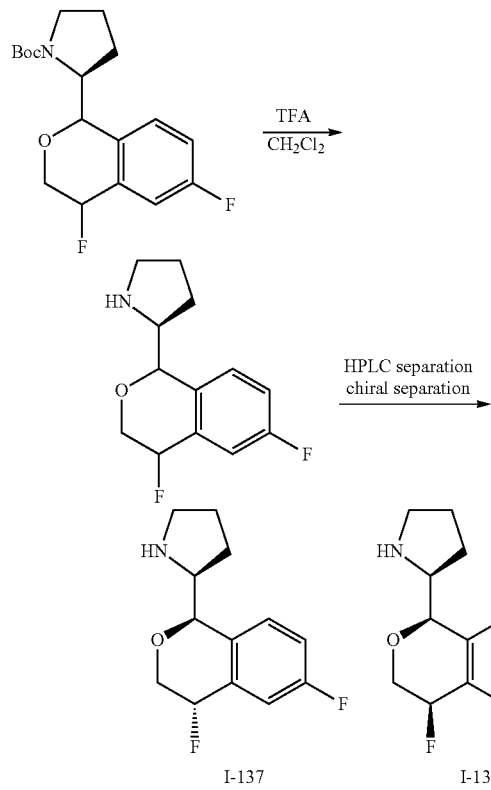

To a solution of (2S)-tert-butyl 2-(4,6-difluoroisochroman-1-yl)pyrrolidine-1-carboxylate (5.8 g, 17.1 mmol) in dichloromethane (L) was added trifluoroacetic acid (30 mL). The mixture was stirred at room temperature for 3 h and then evaporated in vacuo to give the crude product, which was purified by Prep-HPLC, followed by chiral separation: Column: AY-H (250×4.6 mm 5 μm); Mobile Phase: n-Hexane (0.1% DEA): EtOH (0.1% DEA)=90:10 to give (S)-2-((1R, 4S)-4,6-difluoroisochroman-1-yl)pyrrolidine (I-137, 900 mg) and (S)-2-((1R,4R)-4,6-difluoroisochroman-1-yl)pyrrolidine (I-138, 860 mg).

(S)-2-((1R,4S)-4,6-difluoroisochroman-1-yl)pyrrolidine (I-137): MS (ESI): m/z=240[M+H]$^+$; $^1$H NMR (HCl salt, 400 MHz, MeOD): δ 7.35~7.30 (m, 1H), 7.20~7.16 (m, 1H), 5.81~5.65 (m, 1H), 5.24 (s, 1H), 4.51~4.48 (m, 1H), 4.41~4.36 (m, 1H) 3.75~3.69 (m, 1H), 3.37~3.31 (m, 2H), 2.06~2.1.91 (m, 2H), 1.83~1.68 (m, 2H).

(S)-2-((1R,4R)-4,6-difluoroisochroman-1-yl)pyrrolidine (I-138): MS (ESI): m/z=240[M+H]$^+$; 1H NMR (HCl salt, 400 MHz, MeOD): δ 7.38-7.42 (m, 1H), 7.23-7.32 (m, 2H), 5.33-5.45 (m, 1H), 5.16-5.18 (m, 1H), 4.44-4.51 (m, 2H), 3.90-4.03 (m, 1H), 3.34-3.42 (m, 2H), 1.78-2.07 (m, 4H).

Example 1.21.2. (2S)-2-((1R)-4,6-difluoroisochroman-1-yl)azetidine (I-135) and (2S)-2-((1S)-4,6-difluoroisochroman-1-yl)azetidine (I-136)

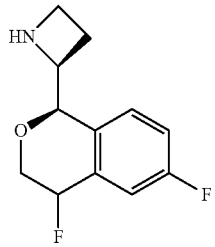

I-135

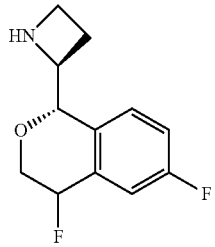

I-136

(2S)-2-((1R)-4,6-difluoroisochroman-1-yl)azetidine (I-135) and (2S)-2-((1S)-4,6-difluoroisochroman-1-yl)azetidine (136) were prepared using a procedure analogous to that described in Example 1.21.1, but using (5)-tert-butyl 2-formylazetidine-1-carboxylate in place of (S)-tert-butyl 2-formylpyrrolidine-1-carboxylate.

(2S)-2-((1R)-4,6-difluoroisochroman-1-yl)azetidine (I-135): MS (ESI): m/z=224 [M+H]$^+$; $^1$H NMR (HCl salt, 400 MHz, MeOD): δ 7.35~7.32 (m, 1H), 7.25~7.22 (m, 1H), 7.18~7.13 (m, 1H) 5.89~5.72 (m, 1H), 5.17~5.12 (m, 2H), 4.62~4.57 (m, 1H), 4.03~3.77 (m, 3H) 2.32~2.26 (m, 2H).

(2S)-2-((1S)-4,6-difluoroisochroman-1-yl)azetidine (136): MS (ESI): m/z=224 [M+H]$^+$; $^1$H NMR (HCl slat, 400 MHz, MeOD): δ 7.35~7.30 (m, 2H), 7.22~7.17 (m, 1H), 5.72~5.61 (m, 1H), 5.11~5.08 (m, 2H), 4.49~4.43 (m, 1H), 4.11~4.04 (m, 1H), 3.93~3.81 (m, 2H), 2.98~2.94 (m, 1H), 2.60~2.56 (m, 1H).

Example 1.22. Procedure V

Example 1.22.1. (1R)-6-fluoro-1-((S)-pyrrolidin-2-yl)isochroman-4-ol (I-134)

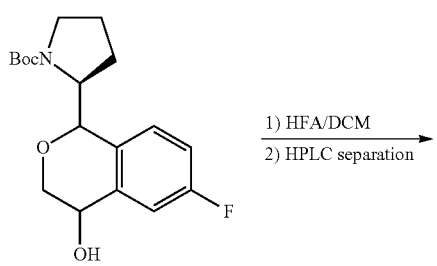

1) HFA/DCM
2) HPLC separation

-continued

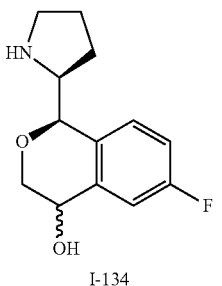

I-134

To a solution of (S)-tert-butyl 2-((R)-6-fluoro-4-hydroxyisochroman-1-yl) pyrrolidine-1-carboxylate (2.2 g, 6.5 mmol, prepared in Example 21.1) in dichloromethane (20 mL) was added trifluoroacetic acid (6 mL). The mixture was stirred at room temperature for 3 h and then evaporated in vacuo to get a residue, which was purified by Prep-HPLC to give (1R)-6-fluoro-1-((S)-pyrrolidin-2-yl)isochroman-4-ol (650 mg). m/z=238[M+H]$^+$. $^1$H NMR (HCl salt, 400 MHz, MeOD): δ 7.36~7.33 (m, 1H), 7.28~7.25 (m, 1H), 7.08~7.03 (m, 1H) 5.22 (s, 1H), 4.82~4.78 (m, 1H), 4.39~4.35 (m, 1H) 4.30~4.26 (m, 1H), 3.46 (t, J=10.4 Hz, 1H), 3.38~3.28 (m, 2H), 2.05~1.91 (m, 2H), 1.77~1.68 (m, 2H).

Example 2. Biological Assays

Example 2.1. In Vitro Assay

Certain compounds were tested by in vitro binding assays using standard procedures. Table 2 shows the membrane source, radioligand, ligand used to define non-specific binding and incubation conditions for each receptor. These receptors and assays are well known to those skilled in the art, as exemplified by the following: Abramovitz, M. et al. (2000), *Biochem. Biophys. Acta.*, 1483: 285-293 (EP4, IP (PGI$_2$)); Aharony, D. et al. (1993), *Mol. Pharmacol.*, 44: 356-363 (NK2); Ardati, A. et al. (1997), *Mol. Pharmacol.*, 51: 816-824 (NOP (ORL1)); Bignon, E. et al. (1999), *J. Pharmacol. Exp. Ther.* 289: 742-751 (CCK$_1$ (CCK$_A$)); Bloomquist, B. T. et al. (1998), *Biochem. Biophys. Res. Commun.*, 243: 474-479 (GAL$_2$); Brockhaus, M. et al. (1990), *Proc. Natl. Acad. Sci. U.S.A.*, 87: 3127-3131 (TNF-α); Brown, G. B. (1986), *J. Neurosci.*, 6: 2064-2070 (Na+ channel (site 2)); Buchan, K. W. et al. (1994), *Brit. J. Pharmacol.*, 112: 1251-1257 (ETA); Cesura, A. M. et al. (1990), *Mol. Pharmacol.*, 37: 358-366 (MAO-A); Choi, D. S. et al. (1994), *FEBS Lett.*, 352: 393-399 (5-HT2B); Clark, A. F. et al. (1996), *Invest. Ophtalmol. Vis. Sci.*, 37: 805-813 (GR); Couvineau, A. et al. (1985), *Biochem. J.*, 231: 139-143 (VPAC$_1$ (VIP$_1$)); Dorje, F. et al. (1991), *J. Pharmacol. Exp. Ther.*, 256: 727-733 (M1, M2, M3, M4); Ferry, G. et al. (2001), *Eur. J. Pharmacol.*, 417: 77-89 (PPARγ); Fuchs, S. et al. (2001), *Mol. Med.*, 7: 115-124 (ETB); Fuhlendorff, J. et al. (1990), *Proc. Natl. Acad. Sci. U.S.A.*, 87: 182-186 (Y2); Ganapathy M E. et al. (1999), *J. Pharmacol. Exp. Ther.*, 289: 251-260 (sigma (non-selective)); Gopalakrishnan, M. et al. (1996), *J. Pharmacol. Exp. Ther.*, 276: 289-297 (N neuronal α4β2); Greengrass, P. and Bremner, R. (1979), *Eur. J. Pharmacol.*, 55: 323-326 (α$_1$ (non-selective)); Grandy, D. K. et al. (1989), *Proc. Natl. Acad. Sci. U.S.A.*, 86: 9762-9766 (D25); Guard, S. et al. (1993), *Eur. J. Pharmacol.*, 240: 177-184 (BB (non-selective)); Heuillet, E. et al. (1993), *J. Neurochem.*, 60: 868-876 (NK1, P2X); Hope, A. G. et al. (1996), *Brit. J. Pharmacol.*, 118: 1237-1245 (5-HT3); Hoyer, D. et al. (1985), *Eur. J. Pharmacol.*, 118: 1-12 (5-HT1B); Hugues, M. et al. (1982), *J. Biol. Chem.*, 257: 2762-2769 (5-HT2A, SKCa channel); Joseph, S. S. et al. (2004), *Naun.-Sch. Arch. Pharm.*, 369: 525-532 (β2); Le, M. T. et al. (2005), *Eur. J. Pharmacol.*, 513: 35-45 (AT1); Le Fur, G. et al. (1983), *Life Sci.*, 33: 449-457) (BZD (peripheral); Lee, Y. M. et al. (1993), *J. Biol. Chem.*, 268: 8164-8169 (CCK$_2$ (CCK$_B$)); Leurs, R. et al. (1994), *Brit. J. Pharmacol.*, 112: 847-854 (H2); Levin, M. C. et al. (2002), *J. Biol. Chem.*, 277: 30429-30435 (β1); Lewin, A. H. et al. (1989), *Mol. Pharmacol.*, 35: 189-194 (Cl— channel (GABA-gated)); Lukas, R. J. (1986), *J. Neurochem.*, 46: 1936-1941 (N muscle-type); Luthin, D. R. et al. (1995), *Mol. Pharmacol.*, 47: 307-313; (A2A); Mackenzie, R. G. et al. (1994), *Eur. J. Pharmacol.*, 266: 79-85 (D3); Mulheron, J. G. et al. (1994), *J. Biol. Chem.*, 269: 12954-12962 (5-HT1A); Meng, F. et al. (1993), *Proc. Natl. Acad. Sci. U.S.A.*, 90: 9954-9958 (K (KOP)); Monsma, F. J. et al. (1993), *Mol. Pharmacol.*, 43: 320-327 (5-HT6); Neote, K. et al. (1993), *Cell*, 72: 415-425 (CCR1); Pacholczyk, T. et al. (1991), *Nature*, 350: 350-354 (sst (non-selective, norepinephrine transporter)); Peralta, E. G. et al. (1987), *Embo. J.*, 6: 3923-3929 (M3); Pristupa, Z. B. et al. (1994), *Mol. Pharmacol.*, 45: 125-135 (dopamine transporter); Pruneau, D. et al. (1998), *Brit. J. Pharmacol.*, 125: 365-372 (B2); Rees, S. et al. (1994), *FEBS Lett.*, 355: 242-246 (5-HT5a); Reynolds, I. J. et al. (1986), *J. Pharmacol. Exp. Ther.*, 237: 731-738 (Ca2+ channel (L, verapamil site)); Rinaldi-Carmona, M. et al. (1996), *J. Pharmacol. Exp. Ther.*, 278: 871-878 (CB1); Salvatore, C. A. et al. (1993), *Proc. Natl. Acad. Sci. U.S.A.*, 90: 10365-10369 (A3); Sarau, H. M. et al. (1997), *J. Pharmacol. Exp. Ther.*, 281: 1303-1311 (NK3); Schioth, H. B. et al. (1997), *Neuropeptides*, 31: 565-571 (MC4); Sharples, C. G. V. et al. (2000), *J. Neurosci.*, 20: 2783-2791 (N neuronal α7); Shen, Y. et al. (1993), *J. Biol. Chem.*, 268: 18200-18204 (5-HT7); Sills, M. A. et al. (1991), *Eur. J. Pharmacol.*, 192: 19-24 (NMDA); Simon, J. et al. (1995), *Pharmacol. Toxicol.*, 76: 302-307 (P2Y); Simonin, F. et al. (1994), *Mol. Pharmacol.*, 46: 1015-1021 (δ$_2$ (DOP)); Smit, M. J. et al. (1996), *Brit. J. Pharmacol.*, 117: 1071-1080 (H1); Sorensen, R. G. and Blaustein, M. P. (1989), *Mol. Pharmacol.*, 36: 689-698 (KV channel); Speth, R. C. et al. (1979), *Life Sci.*, 24: 351-358 (BZD (central)); Stam, N.J. et al. (1994), *Eur. J. Pharmacol.*, 269: 339-348 (5-HT2C); Sullivan, K. A. et al. (1997), *Biochem. Biophys. Res. Commun.*, 233: 823-828 (GAL$_1$); Tahara, A. et al. (1998), *Brit. J. Pharmacol.*, 125: 1463-1470 (V1a); Tatsumi, M. et al. (1999), *Eur. J. Pharmacol.*, 368: 277-283 (5-HT transporter); Townsend-Nicholson, A. and Schofield, P. R. (1994), *J. Biol. Chem.*, 269: 2373-2376 (A1); Tsuji, A. et al. (1988), *Antimicrob. Agents Chemother.*, 32: 190-194 (GABA (non-selective)); Tsuzuki, S. et al. (1994), *Biochem. Biophys. Res. Commun.*, 200: 1449-1454 (AT2); Uhlen, S. and Wikberg, J. E. (1991), *Pharmacol. Toxicol.*, 69: 341-350 (α$_2$ (non-selective)); Van Tol, H. H. M. et al. (1992), *Nature*, 358: 149-152 (D$_{4,4}$); Vignon, J. et al. (1986), *Brain Res.*, 378: 133-141 (PCP); Vita, N. et al. (1993), *FEBS Lett.*, 317: 139-142 (NTS$_1$ (NT$_1$)); White, J. R. et al. (1998), *J. Biol. Chem.*, 273: 10095-10098 (CXCR2 (IL-8B), μ (MOP)); Wieland, H. A. et al. (1995), *J. Pharmacol. Exp. Ther.*, 275: 143-149 (Y1); Witt-Enderby, P. A. and Dubocovich, M. L. (1996), *Mol. Pharmacol.*, 50: 166-174 (MT$_1$ (ML$_{1A}$)); Zhou, Q. Y. et al. (1990), *Nature*, 347: 76-80 (D1).

Briefly, a membrane was incubated with a radioligand in the presence and absence of a test compound under the relevant condition, prior to filtration and washing. The amount of the radioligand bound to a membrane was determined using liquid scintillation counting. Total binding (the binding of a radioligand to both receptor and non-receptor sites) was determined by incubating a membrane with a radioligand alone. Non-specific binding (binding to non-receptor sites) of a radioligand was determined by incubating a membrane in the presence of a saturating concentration of an unlabeled ligand (the ligand used to define non-specific binding). Specific binding (binding to receptor sites only) was calculated by subtracting non-specific binding from total binding.

TABLE 2

| Assay | Source | Ligand | Conc. (nM) | Non Specific | Incubation |
|---|---|---|---|---|---|
| A1 | human recombinant (CHO cells) | [3H]DPCPX | 1 | DPCPX (1 μM) | 60 min RT |
| A2A | human recombinant (HEK-293 cells) | [3H]CGS 21680 | 6 | NECA (10 μM) | 120 min RT |
| A3 | human recombinant (HEK-293 cells) | [125I]AB-MECA | 0.15 | IB-MECA (1 μM) | 120 min RT |
| $\alpha_1$ (non-selective) | rat cerebral cortex | [3H]prazosin | 0.25 | prazosin (0.5 μM) | 60 min RT |
| $\alpha_2$ (non-selective) | rat cerebral cortex | [3H]RX 821002 | 0.5 | (−)epinephrine (100 μM) | 60 min RT |
| $\beta_1$ | human recombinant (HEK-293 cells) | [3H](−)CGP 12177 | 0.3 | alprenolol (50 μM) | 60 min RT |
| $\beta_2$ | human recombinant (CHO cells) | [3H](−)CGP 12177 | 0.3 | alprenolol (50 μM) | 120 min RT |
| AT1 | human recombinant (HEK-293 cells) | [125I][Sar1, Ile8]-AT-II | 0.05 | angiotensin-II (10 μM) | 120 min 37° C. |
| AT2 | human recombinant (HEK-293 cells) | [125I]CGP 42112A | 0.01 | angiotensin-II (1 μM) | 4 hr 37° C. |
| BZD (peripheral) | rat heart | [3H]PK 11195 | 0.2 | PK 11195 (10 μM) | 15 min RT |
| BB (non-selective) | rat cerebral cortex | [125I][Tyr4]bombesin | 0.01 | bombesin (1 μM) | 60 min RT |
| B2 | human recombinant (CHO cells) | [3H]bradykinin | 0.3 | bradykinin (1 μM) | 60 min RT |
| CB1 | human recombinant (CHO cells) | [3H]CP 55940 | 0.5 | WIN 55212-2 (10 μM) | 120 min 37° C. |
| CCK$_1$ (CCK$_A$) | human recombinant (CHO cells) | [125I]CCK-8s | 0.08 | CCK-8s (1 μM) | 60 min RT |
| CCK$_2$ (CCK$_B$) | human recombinant (CHO cells) | [125I]CCK-8s | 0.08 | CCK-8s (1 μM) | 60 min RT |
| D1 | human recombinant (CHO cells) | [3H]SCH 23390 | 0.3 | SCH 23390 (1 μM) | 60 min RT |
| D2S | human recombinant (HEK-293 cells) | [3H]methyl-spiperone | 0.3 | (+)butaclamol (10 μM) | 60 min RT |
| D3 | human recombinant (CHO cells) | [3H]methyl-spiperone | 0.3 | (+)butaclamol (10 μM) | 60 min RT |
| D$_{4.4}$ | human recombinant (CHO cells) | [3H]methyl-spiperone | 0.3 | (+)butaclamol (10 μM) | 60 min RT |
| ETA | human recombinant (CHO cells) | [125I]endothelin-1 | 0.03 | endothelin-1 (100 nM) | 120 min 37° C. |
| ETB | human recombinant (CHO cells) | [125I]endothelin-1 | 0.03 | endothelin-1 (0.1 μM) | 120 min 37° C. |
| GABA (non-selective) | rat cerebral cortex | [3H]GABA | 10 | GABA (100 μM) | 60 min RT |
| GAL$_1$ | human recombinant (HEK-293 cells) | [125I]galanin | 0.1 | galanin (1 μM) | 80 min RT |

TABLE 2-continued

| Assay | Source | Ligand | Conc. (nM) | Non Specific | Incubation |
|---|---|---|---|---|---|
| $GAL_2$ | human recombinant (CHO cells) | [125I]galanin | 0.05 | galanin (1 μM) | 120 min RT |
| CXCR2 (IL-8B) | human recombinant (HEK-293 cells) | [125I]IL-8 | 0.025 | IL-8 (30 nM) | 60 min RT |
| CCR1 | human recombinant (HEK-293 cells) | [125I]MIP-1α | 0.01 | MIP-1α (100 nM) | 120 min RT |
| TNF-α | U-937 cells | [125I]TNF-α | 0.1 | TNF-α (10 nM) | 120 min 4° C. |
| H1 | human recombinant (HEK-293 cells) | [3H]pyrilamine | 1 | pyrilamine (1 μM) | 60 min RT |
| H2 | human recombinant (CHO cells) | [125I]APT | 0.075 | tiotidine (100 μM) | 120 min RT |
| MC4 | human recombinant (CHO cells) | [125I]NDP-α-MSH | 0.05 | NDP-α-MSH (1 μM) | 120 min 37° C. |
| $MT_1$ ($ML_{1A}$) | human recombinant (CHO cells) | [125I]2-iodomelatonin | 0.01 | melatonin (1 μM) | 60 min RT |
| M1 | human recombinant (CHO cells) | [3H]pirenzepine | 2 | atropine (1 μM) | 60 min RT |
| M2 | human recombinant (CHO cells) | [3H]AF-DX 384 | 2 | atropine (1 μM) | 60 min RT |
| M3 | human recombinant (CHO cells) | [3H]4-DAMP | 0.2 | atropine (1 μM) | 60 min RT |
| M4 | human recombinant (CHO cells) | [3H]4-DAMP | 0.2 | atropine (1 μM) | 60 min RT |
| M5 | human recombinant (CHO cells) | [3H]4-DAMP | 0.3 | atropine (1 μM) | 60 min RT |
| NK1 | U-373MG cells (endogenous) | [125I]BH-SP | 0.15 | [Sar9, Met(O2)11]-SP (1 μM) | 60 min RT |
| NK2 | human recombinant (CHO cells) | [125I]NKA | 0.1 | [Nleu10]-NKA (4-10) (300 nM) | 60 min RT |
| NK3 | human recombinant (CHO cells) | [3H]SR 142801 | 0.4 | SB 222200 (10 μM) | 120 min RT |
| Y1 | SK-N-MC cells (endogenous) | [125I]peptide YY | 0.025 | NPY (1 μM) | 120 min 37° C. |
| Y2 | KAN-TS cells | [125I]peptide YY | 0.015 | NPY (1 μM) | 60 min 37° C. |
| $NTS_1$ ($NT_1$) | human recombinant (CHO cells) | [125I]Tyr3-neurotensin | 0.05 | neurotensin (1 μM) | 60 min 4° C. |
| N neuronal α4β2 | SH-SY5Y cells (human recombinant) | [3H]cytisine | 0.6 | nicotine (10 μM) | 120 min 4° C. |
| N neuronal α7 | SH-SY5Y cells (human recombinant) | [125I]α-bungarotoxin | 0.05 | α-bungarotoxin (1 μM) | 120 min 37° C. |
| N muscle-type | TE671 cells (endogenous) | [125I]α-bungarotoxin | 0.5 | α-bungarotoxin (5 μM) | 120 min RT |
| $δ_2$ (DOP) | human recombinant (CHO cells) | [3H]DADLE | 0.5 | naltrexone (10 μM) | 120 min RT |
| κ (KOP) | rat recombinant (CHO cells) | [3H]U 69593 | 1 | naloxone (10 μM) | 60 min RT |
| μ (MOP) | human recombinant (HEK-293 cells) | [3H]DAMGO | 0.5 | naloxone (10 μM) | 120 min RT |

TABLE 2-continued

| Assay | Source | Ligand | Conc. (nM) | Non Specific | Incubation |
|---|---|---|---|---|---|
| NOP (ORL1) | human recombinant (HEK-293 cells) | [3H]nociceptin | 0.2 | nociceptin (1 µM) | 60 min RT |
| PPARγ | human recombinant (E. coli) | [3H]rosiglitazone | 5 | rosiglitazone (10 µM) | 120 min 4° C. |
| EP4 | human recombinant (HEK-293 cells) | [3H]PGE2 | 0.5 | PGE2 (10 µM) | 120 min RT |
| IP (PGI$_2$) | human recombinant (HEK-293 cells) | [3H]iloprost | 6 | iloprost (10 µM) | 60 min RT |
| P2Y | rat cerebral cortex | [35S]dATPαS | 10 | dATPαS | 60 min RT |
| 5-HT1A | human recombinant (HEK-293 cells) | [3H]8-OH-DPAT | 0.3 | 8-OH-DPAT (10 µM) | 60 min RT |
| 5-HT1B | rat cerebral cortex | [125I]CYP (+30 µM isoproterenol) | 0.1 | serotonin (10 µM) | 120 min 37° C. |
| 5-HT2A | human recombinant (HEK-293 cells) | [3H]ketanserin | 0.5 | ketanserin (1 µM) | 60 min RT |
| 5-HT2B | human recombinant (CHO cells) | [125I](±)DOI | 0.2 | (±)DOI (1 µM) | 60 min RT |
| 5-HT2C | human recombinant (HEK-293 cells) | [3H]mesulergine | 1 | RS 102221 (10 µM) | 120 min 37° C. |
| 5-HT5a | human recombinant (HEK-293 cells) | [3H]LSD | 1.5 | serotonin (100 µM) | 120 min 37° C. |
| 5-HT6 | human recombinant (CHO cells) | [3H]LSD | 2 | serotonin (100 µM) | 120 min 37° C. |
| 5-HT7 | human recombinant (CHO cells) | [3H]LSD | 4 | serotonin (10 µM) | 120 min RT |
| sigma (non-selective) | Jurkat cells (endogenous) | [3H]DTG | 10 | Haloperidol (10 µM) | 120 min RT |
| sst (non-selective) | AtT-20 cells | [125I]Tyr11-somatostatin-14 | 0.05 | somatostatin-14 (300 nM) | 60 min 37° C. |
| GR | IM-9 cells (cytosol) | [3H]dexamethasone | 1.5 | triamcinolone (10 µM) | 6 hr 4° C. |
| VPAC$_1$ (VIP$_1$) | human recombinant (CHO cells) | [125I]VIP | 0.04 | VIP (1 µM) | 60 min RT |
| V1a | human recombinant (CHO cells) | [3H]AVP | 0.3 | AVP (1 µM) | 60 min RT |
| BZD (central) | rat cerebral cortex | [3H]flunitrazepam | 0.4 | diazepam (3 µM) | 60 min 4° C. |
| NMDA | rat cerebral cortex | [3H]CGP 39653 | 5 | L-glutamate (100 µM) | 60 min 4° C. |
| PCP | rat cerebral cortex | [3H]TCP | 10 | MK 801 (10 µM) | 120 min 37° C. |
| P2X | rat urinary bladder | [3H]α,β-MeATP | 3 | α,β-MeATP (10 µM) | 120 min 4° C. |
| 5-HT3 | human recombinant (CHO cells) | [3H]BRL 43694 | 0.5 | MDL 72222 (10 µM) | 120 min RT |
| Ca2+ channel (L, verapamil site) | rat cerebral cortex | [3H]D888 | 3 | D 600 (10 µM) | 120 min RT |
| KV channel | rat cerebral cortex | [125I]α-dendrotoxin | 0.01 | α-dendrotoxin (50 nM) | 80 min RT |
| SKCa channel | rat cerebral cortex | [125I]apamin | 0.007 | apamin (100 nM) | 60 min 4° C. |
| Na+ channel (site 2) | rat cerebral cortex | [3H]batrachotoxinin | 10 | veratridine (300 µM) | 60 min 37° C. |

TABLE 2-continued

| Assay | Source | Ligand | Conc. (nM) | Non Specific | Incubation |
|---|---|---|---|---|---|
| Cl- channel (GABA-gated) | rat cerebral cortex | [35S]TBPS | 3 | picrotoxinin (20 µM) | 120 min RT |
| norepinephrine transporter | human recombinant (CHO cells) | [3H]nisoxetine | 1 | desipramine (1 µM) | 120 min 4° C. |
| dopamine transporter | human recombinant (CHO cells) | [3H]BTCP | 4 | BTCP (10 µM) | 120 min 4° C. |
| 5-HT transporter | human recombinant (CHO cells) | [3H]imipramine | 2 | imipramine (10 µM) | 60 min RT |
| MAO-A | rat cerebral cortex | [3H]Ro 41-1049 | 10 | clorgyline (1 µM) | 60 min 37° C. |

Table 3 shows certain compounds and receptors for which the test compound's specific binding (measured by percentage inhibition) was greater than 50%.

TABLE 3

| Compound | Receptor (percent inhibition) |
|---|---|
| I-1 | α1 (55%); α2 (95%); 5HT1a (79%); 5HT2b (79%); 5HT2c (63%); 5HT7 (88%) |
| I-5 | α1 (59%); α2 (96%); GABA (57%); KOP (71%); 5HT1a (52%); 5HT2b (72%); 5HT7 (60%) |
| I-9 | 5HT7 (80%); α1 (73%); α2 (91%); 5HT1a (77%); 5HT2b (76%); 5HT2c (61%) |
| I-29 | α1 (69%); α2 (97%); k (89%); 5HT1a (71%); 5HT2b (80%); 5HT2c (67%); 5HT7 (52%) |
| I-83 | α2 (77%); 5HT1a (87%); 5HT2b (83%); 5HT2c (64%); 5HT5a (58%); 5HT7 (99%) |
| I-90 | α1 (64%); α2 (71%); 5HT1a (64%); 5HT2b (77%); 5HT2c (59%); 5HT7 (96%); Sert (80%); sigma (63%) |
| I-94 | α1 (72%); κ (67%); 5HT2b (76%); 5HT7 (74%); sigma (85%) |
| I-96 | α1 (81%); α2 (81%); 5HT2b (58%); 5HT7 (69%); M4 (53%) |

Example 2.2. Neuropharmacological Assay (SmartCube™)

In order to further demonstrate the utility of the provided compounds to treat neurological and psychiatric diseases and disorders, exemplary compounds were evaluated using the neuropharmacological screen described in S. L. Roberds et al., Front. Neurosci. 2011 Sep. 9; 5:103 (doi: 10.3389/fnins.2011.00103) ("Roberds"). As reported in Roberds, because psychiatric diseases generally result from disorders of cell-cell communication or circuitry, intact systems are useful in detecting improvement in disease-relevant endpoints. These endpoints are typically behavioral in nature, often requiring human observation and interpretation. To facilitate testing of multiple compounds for behavioral effects relevant to psychiatric disease, PsychoGenics, Inc. (Tarrytown, N.Y., "PGI") developed SmartCube™, an automated system in which behaviors of compound-treated mice are captured by digital video and analyzed with computer algorithms. (D. Brunner et al., Drug Discov. Today 2002, 7:S107-S112). PGI Analytical Systems uses data from SmartCube™ to compare the behavioral signature of a test compound to a database of behavioral signatures obtained using a large set of diverse reference compounds. (The composition of the database as well as validation of the method is further described in Roberds). In this way, the neuropharmacological effects of a test compound can be predicted by similarity to major classes of compounds, such as antipsychotics, anxiolytics and antidepressants.

The SmartCube™ system produces an activity signature indicating the probability that the activity of the test compound at the administered dose matches a given class of neuropharmacological agents. (See, e.g., Roberds, FIGS. 2 and 3). The test compound is simultaneously compared against multiple classes of agents; thus, a separate probability is generated for each behavioral effect measured (e.g., anxiolytic activity, analgesic activity, etc.). In Table 4, these probabilities are reported for each behavioral effect measured as follows:

| LOQ≤ | + | <5% |
| 5%≤ | ++ | <25% |
| 25%≤ | +++ | <50% |
| 50%≤ | ++++ | | where LOQ is the limit of quantification.

Provided compounds were dissolved in a mixture of Pharmasolve™ (N-methyl-2-pyrrolidone), polyethylene glycol and propylene glycol, and were injected i.p. 15 min. before the behavioral test. For each compound, injections were administered at 3 different doses. For each behavioral effect measured, results for the most efficacious dose(s) are presented.

TABLE 4

| Compound | DP | AX | SD | PS | MS | AD | CE | AG | XG | HA | UN |
|---|---|---|---|---|---|---|---|---|---|---|---|
| I-1 | ++ | ++ | ++ | +++ | ++ | + | ++ | ++ | + | + | ++ |
| I-2 | + | ++ | ++ | ++ | ++ | + | + | + | + | + | + |
| I-3 | +++ | ++ | ++ | ++ | ++ | + | ++ | ++ | + | + | +++ |
| I-4 | ++ | +++ | + | ++ | + | + | ++ | ++ | + | + | + |
| I-5 | ++ | ++ | + | +++ | ++ | + | ++ | ++ | + | + | +++ |
| I-6 | ++ | ++ | + | ++ | + | + | + | + | + | + | +++ |
| I-7 | ++ | ++ | + | ++ | + | + | ++ | ++ | + | + | +++ |
| I-8 | +++ | ++ | ++ | +++ | + | + | ++ | + | + | + | ++ |
| I-9 | ++ | ++ | ++ | +++ | ++ | + | ++ | ++ | + | + | +++ |

TABLE 4-continued

| Compound | DP | AX | SD | PS | MS | AD | CE | AG | XG | HA | UN |
|---|---|---|---|---|---|---|---|---|---|---|---|
| I-10 | ++ | ++ | + | ++ | + | + | ++ | ++ | + | + | + |
| I-11 | ++ | ++ | + | +++ | + | + | ++ | ++ | + | + | ++ |
| I-12 | ++ | ++ | + | ++ | + | + | + | ++ | + | + | ++++ |
| I-13 | +++ | ++ | + | ++++ | ++ | + | ++ | ++ | + | + | ++ |
| I-14 | +++ | ++ | + | +++ | ++ | + | ++ | ++ | + | + | + |
| I-15 | ++ | +++ | + | ++ | + | + | ++ | ++ | + | + | + |
| I-16 | ++ | ++ | + | +++ | ++ | + | ++ | + | + | + | +++ |
| I-17 | +++ | ++ | + | ++ | + | + | ++ | + | + | + | + |
| I-18 | ++ | +++ | ++ | +++ | ++ | + | ++ | ++ | + | + | ++ |
| I-19 | + | ++ | + | ++++ | + | + | ++ | + | + | + | ++++ |
| I-20 | ++ | ++ | ++ | ++++ | ++ | + | ++ | ++ | + | + | +++ |
| I-21 | ++ | ++ | + | ++ | + | + | + | ++ | + | + | +++ |
| I-22 | +++ | ++ | + | +++ | + | + | ++ | ++ | + | + | + |
| I-23 | ++ | ++ | ++ | +++ | ++ | + | ++ | +++ | + | + | + |
| I-24 | +++ | ++ | ++ | ++ | ++ | + | ++ | ++ | + | + | + |
| I-25 | ++ | ++ | + | ++ | + | + | ++ | +++ | + | + | ++ |
| I-26 | + | ++ | + | + | + | + | + | + | + | + | + |
| I-27 | ++ | +++ | + | ++ | ++ | + | ++ | ++ | + | + | + |
| I-28 | ++ | +++ | + | ++ | + | + | + | ++ | + | + | ++ |
| I-29 | ++ | +++ | + | ++ | ++ | + | +++ | ++ | + | + | ++ |
| I-30 | ++ | +++ | ++ | +++ | + | + | ++ | ++ | + | + | + |
| I-31 | ++ | +++ | ++ | +++ | ++ | + | ++ | ++ | + | + | + |
| I-32 | ++ | ++ | ++ | +++ | + | + | ++ | +++ | + | + | + |
| I-33 | ++ | ++ | ++ | +++ | + | + | ++ | + | + | + | + |
| I-34 | ++ | ++ | ++ | ++ | + | + | ++ | ++ | + | + | +++ |
| I-35 | ++ | ++ | ++ | +++ | + | + | ++ | + | + | + | ++ |
| I-36 | ++ | ++ | + | +++ | ++ | + | ++ | ++ | + | + | ++ |
| I-37 | ++ | ++ | + | ++ | + | + | + | + | + | + | +++ |
| I-38 | ++ | ++ | + | + | + | + | + | ++ | + | + | + |
| I-39 | + | ++ | + | + | + | + | ++ | ++ | + | + | ++ |
| I-40 | ++ | ++ | + | +++ | + | + | ++ | ++ | + | + | + |
| I-41 | +++ | ++ | ++ | ++ | ++ | + | ++ | ++ | + | + | + |
| I-42 | +++ | ++ | ++ | ++ | + | + | ++ | ++ | + | + | + |
| I-43 | ++ | +++ | + | ++ | + | + | ++ | ++ | + | + | + |
| I-44 | ++ | +++ | + | +++ | ++ | + | ++ | ++ | + | + | + |
| I-45 | ++ | +++ | + | ++ | + | + | + | ++ | + | + | + |
| I-46 | ++ | ++ | ++ | ++++ | + | + | ++ | ++ | + | + | + |
| I-47 | + | ++ | + | + | + | + | + | + | + | + | + |
| I-48 | ++ | ++ | + | ++ | + | + | ++ | +++ | + | + | + |
| I-49 | ++ | ++ | ++ | ++ | ++ | + | ++ | ++ | + | + | ++ |
| I-50 | ++ | +++ | + | ++ | + | + | ++ | ++ | + | + | +++ |
| I-51 | + | ++ | + | + | + | + | + | ++ | + | + | ++ |
| I-52 | ++ | ++++ | + | ++ | + | + | ++ | ++ | + | + | +++ |
| I-53 | + | + | + | + | + | + | + | + | + | + | + |
| I-54 | +++ | +++ | + | ++ | ++ | + | ++ | ++ | + | + | + |
| I-55 | + | + | + | + | + | + | + | + | + | + | + |
| I-56 | +++ | ++ | + | ++ | ++ | ++ | ++ | +++ | + | + | + |
| I-57 | + | + | + | + | + | + | + | + | + | + | + |
| I-58 | +++ | ++ | + | ++ | ++ | + | + | ++ | + | + | + |
| I-59 | ++ | ++ | + | ++ | ++ | + | ++ | + | + | + | + |
| I-60 | ++ | ++ | ++ | +++ | + | + | ++ | ++ | + | + | ++ |
| I-61 | ++ | ++ | + | ++ | ++ | + | + | +++ | ++ | + | + |
| I-62 | ++ | ++ | + | ++ | + | + | +++ | ++ | + | + | + |
| I-63 | + | + | + | + | + | + | + | + | + | + | + |
| I-64 | + | ++ | + | + | + | + | + | + | + | + | + |
| I-65 | ++ | ++ | ++ | ++ | + | + | ++ | +++ | + | + | + |
| I-66 | ++ | ++ | + | +++ | + | + | ++ | ++ | + | + | ++ |
| I-67 | + | + | + | + | + | + | + | + | + | + | + |
| I-68 | + | + | + | + | + | + | + | + | + | + | + |
| I-69 | ++ | ++ | + | ++ | + | + | ++ | +++ | + | + | + |
| I-70 | ++ | ++ | + | + | + | + | + | ++ | + | + | + |
| I-71 | ++ | +++ | + | ++ | ++ | + | ++ | + | + | + | + |
| I-72 | + | ++ | + | + | + | + | + | ++ | ++ | + | +++ |
| I-73 | ++ | ++ | + | + | ++ | + | ++ | ++ | + | + | +++ |
| I-74 | ++ | ++ | ++ | +++ | + | + | ++ | ++ | + | + | + |
| I-75 | +++ | ++ | ++ | ++ | ++ | + | ++ | + | + | + | + |
| I-76 | ++ | ++ | + | ++ | + | + | + | ++ | + | + | + |
| I-77 | + | ++ | + | + | + | + | + | + | + | + | + |
| I-78 | ++ | +++ | + | ++ | + | + | ++ | ++ | + | + | + |
| I-79 | ++ | +++ | + | +++ | ++ | ++ | ++ | ++ | + | + | + |
| I-80 | +++ | ++ | + | ++ | ++ | + | ++ | ++ | + | + | +++ |
| I-81 | ++ | +++ | +++ | ++ | + | + | ++ | ++ | + | + | + |
| I-82 | +++ | ++ | ++ | ++ | ++ | + | ++ | ++ | + | + | ++ |
| I-83 | ++ | ++ | + | +++ | ++ | ++ | +++ | ++ | + | + | + |
| I-84 | ++ | ++ | ++ | ++++ | ++ | + | + | + | + | + | + |
| I-85 | ++ | ++ | ++ | +++ | + | + | ++ | + | + | + | ++ |
| I-86 | ++ | +++ | ++ | +++ | + | + | ++ | +++ | + | + | ++ |
| I-87 | ++ | ++ | + | +++ | + | + | + | ++ | + | + | ++ |

TABLE 4-continued

| Compound | DP | AX | SD | PS | MS | AD | CE | AG | XG | HA | UN |
|---|---|---|---|---|---|---|---|---|---|---|---|
| I-88 | ++ | +++ | + | ++ | + | + | ++ | ++ | + | + | +++ |
| I-89 | +++ | ++ | + | +++ | ++ | ++ | ++ | ++ | + | + | + |
| I-90 | +++ | +++ | ++ | ++ | + | + | ++ | ++ | + | + | ++ |
| I-91 | ++ | ++ | ++ | +++ | + | + | ++ | ++ | + | + | ++ |
| I-92 | ++ | ++ | + | +++ | ++ | + | +++ | ++ | + | + | + |
| I-93 | +++ | ++ | ++ | ++ | + | ++ | ++ | +++ | + | + | ++ |
| I-94 | +++ | ++ | + | +++ | + | + | ++ | ++ | + | + | ++ |
| I-95 | ++ | ++ | + | ++ | + | + | ++ | +++ | + | + | + |
| I-96 | +++ | ++ | + | +++ | ++ | + | ++ | +++ | + | + | + |
| I-97 | ++ | ++ | ++ | +++ | ++ | + | ++ | +++ | + | + | + |
| I-98 | +++ | ++ | ++ | +++ | ++ | + | + | + | + | + | + |
| I-99 | +++ | ++ | ++ | ++ | + | + | ++ | ++ | + | + | + |
| I-100 | ++ | ++ | ++ | +++ | ++ | + | +++ | ++ | + | + | + |
| I-101 | ++ | ++ | + | + | + | + | + | + | + | + | + |
| I-102 | ++ | +++ | + | ++ | ++ | + | ++ | ++ | + | + | + |
| I-103 | ++ | ++ | ++ | + | + | + | + | ++ | + | + | +++ |
| I-104 | ++ | ++ | ++ | + | + | + | + | +++ | + | + | ++ |
| I-105 | ++ | +++ | ++ | ++ | + | + | ++ | ++ | + | + | ++++ |
| I-106 | + | ++ | + | ++ | + | + | +++ | ++ | + | + | + |
| I-107 | ++ | +++ | ++ | +++ | ++ | + | ++ | ++ | + | + | ++ |
| I-108 | ++ | ++ | ++ | +++ | + | + | ++ | ++ | + | + | ++ |
| I-109 | +++ | ++ | ++ | ++ | ++ | + | + | ++ | + | + | ++ |
| I-110 | ++ | ++ | ++ | ++++ | + | + | ++ | ++ | + | + | +++ |
| I-111 | ++ | ++ | ++ | ++++ | + | + | ++ | ++ | + | + | +++ |
| I-112 | ++ | ++ | + | +++ | + | + | ++ | + | + | + | + |
| I-113 | +++ | ++ | ++ | ++ | + | + | ++ | ++ | + | + | + |
| I-114 | +++ | ++ | ++ | ++ | + | + | ++ | ++ | + | + | + |
| I-115 | ++ | ++ | ++ | ++ | + | + | ++ | ++ | + | + | +++ |
| I-116 | ++ | ++ | ++ | +++ | + | + | + | + | + | + | + |
| I-117 | ++ | ++ | + | +++ | + | + | ++ | + | + | + | + |
| I-118 | ++ | +++ | ++ | +++ | ++ | + | ++ | ++ | + | + | + |
| I-119 | ++ | ++ | + | +++ | + | + | ++ | +++ | + | + | + |
| I-120 | ++ | ++ | ++ | ++ | ++ | + | +++ | ++ | + | + | ++ |
| I-121 | ++ | +++ | ++ | ++ | + | + | ++ | +++ | + | + | ++ |
| I-122 | ++ | ++ | + | + | + | + | + | + | + | + | + |
| I-123 | + | + | + | + | + | + | + | + | + | + | + |
| I-124 | + | + | + | + | + | + | + | + | + | + | + |
| I-125 | ++++ | ++ | ++ | + | + | + | ++ | ++ | + | + | + |
| I-126 | +++ | ++ | ++ | +++ | + | + | ++ | ++ | + | + | ++ |
| I-127 | ++ | ++ | + | ++ | + | + | ++ | ++ | + | + | ++ |
| I-128 | ++ | ++ | + | ++++ | + | + | + | ++ | + | + | + |
| I-134 | + | ++ | + | + | + | + | + | + | + | + | + |
| I-135 | ++ | ++ | ++ | +++ | ++ | + | ++ | ++ | + | + | ++ |
| I-137 | ++ | ++ | ++ | ++++ | ++ | + | ++ | ++ | + | + | ++ |
| I-138 | ++ | ++ | + | +++ | + | + | + | + | + | + | ++ |
| I-139 | ++ | ++ | + | +++ | + | + | ++ | + | + | + | + |
| I-140 | ++ | ++ | +++ | ++ | ++ | + | +++ | ++ | + | + | ++ |
| I-141 | ++ | ++ | + | ++ | + | ++ | +++ | ++ | + | ++ | ++++ |
| I-142 | ++ | +++ | + | ++ | + | + | ++ | ++ | + | + | ++ |
| I-143 | ++ | ++ | + | ++ | + | + | + | ++ | + | + | +++ |
| I-144 | +++ | ++ | + | +++ | ++ | ++ | ++ | ++ | + | + | +++ |

DP: anti-depressant;

AX: anxiolytic;

SD: sedative hypnotic;

PS: anti-psychotic;

MS: mood stabilizer;

AD: ADHD;

CE: cognitive enhancer;

AG: analgesic;

XG: anxiogenic;

HA: hallucinogen;

UN: uncharacterized CNS activity.

Some embodiments of the present invention are enumerated below. In such presentations, an embodiment reciting a "compound" with reference to another enumerated embodiment either that itself explicitly recites "or a pharmaceutically acceptable salt thereof" or that refers ultimately to an enumerated embodiment that does, is intended to encompass both free compounds and pharmaceutically acceptable salts thereof. As a convention, the phrase "or a pharmaceutically acceptable salt thereof" is explicitly recited when the structural formula of the compound is explicitly recited, but no difference in inclusion or exclusion of pharmaceutically acceptable salts is thereby intended. For example, both embodiments 1 and 6 are intended to encompass both the free compounds and pharmaceutically acceptable salts thereof.

1. A compound of formula I:

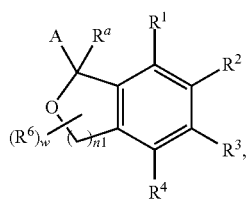

(I)

or a pharmaceutically acceptable salt thereof, wherein:

A is

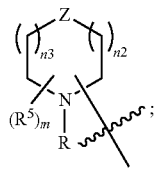

m is 0, 1, or 2;
n1 is 1, 2, or 3;
n2 is 0 or 1;
n3 is 0 or 1;
R is —H or $C_1$-$C_3$ alkyl;
$R^a$ is —H or $C_1$-$C_3$ alkyl;
$R^1$, $R^2$, $R^3$, and $R^4$ are independently —H, halo, —OH, —NH$_2$, $C_1$-$C_3$ alkyl, —OR$^7$, —NHR$^7$, —N(R$^7$)R$^7$, —CN, phenyl, or 5- or 6-membered heteroaryl, wherein:
  each instance of $R^2$ independently is unsubstituted $C_1$-$C_2$ alkyl or $C_1$-$C_2$ alkyl substituted with 1-3 halo,
  each instance of $C_1$-$C_3$ alkyl independently is unsubstituted or substituted with 1-3 halo, and
  the phenyl or heteroaryl is unsubstituted or substituted with 1 or 2 groups independently selected from halo, —OH, —OCH$_3$, —OCF$_3$, —NH$_2$, —NH(CH$_3$), —N(CH$_3$)$_2$, —CH$_3$, ethyl, —CF$_3$, and —CN,
  optionally wherein
  two adjacent instances of $R^1$, $R^2$, $R^3$, and $R^4$ together form —O—CH$_2$—O—, —O—CH(CH$_3$)—O—, —O—C(CH$_3$)$_2$—O—, —O—CH$_2$—CH$_2$—O—, or —O—C(CH$_3$)$_2$—C(CH$_3$)$_2$—O—;

each instance of $R^5$ independently is halo, —CH$_3$, or ethyl;
each instance of $R^6$ independently is halo, —CH$_3$, ethyl or —OH;
w is 0, 1, or 2; and
Z is C or O;
provided that the compound is not:

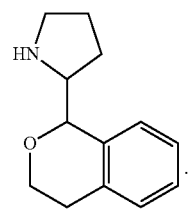

2. The compound of embodiment 1 of formula (Ia):

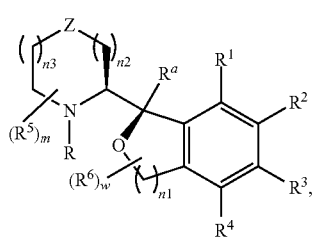

(Ia)

or a pharmaceutically acceptable salt thereof.

3. The compound of embodiment 1 of formula (Ib):

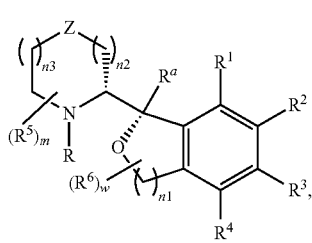

(Ib)

or a pharmaceutically acceptable salt thereof.

4. The compound of embodiment 1 of formula (Ic):

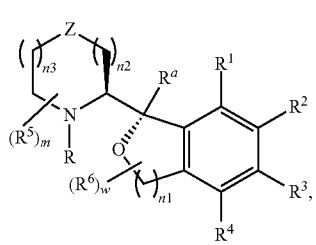

(Ic)

or a pharmaceutically acceptable salt thereof.

5. The compound of embodiment 1 of formula (Id):

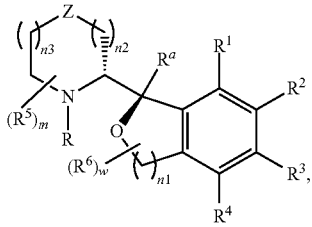

(Id)

or a pharmaceutically acceptable salt thereof.
6. The compound of any of embodiments 1-5, wherein Z is C.
7. The compound of embodiment 6, wherein n2 is 0 and n3 is 0.
8. The compound of embodiment 6, wherein one of n2 and n3 is 0 and the other is 1.
9. The compound of embodiment 6, wherein n2 is 1 and n3 is 1.
10. The compound of any of embodiments 1-5, wherein n2 is 1 and Z is O.
11. The compound of embodiment 10, wherein n3 is 1.
12. The compound of embodiment 1 of formula (I-C):

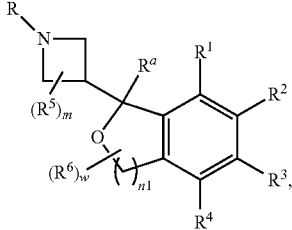

(I-C)

or a pharmaceutically acceptable salt thereof.
13. The compound of any of embodiments 1-12, wherein n1 is 1.
14. The compound of any of embodiments 1-12, wherein n1 is 2.
15. The compound of any of embodiments 1-12, wherein n1 is 3.
16. The compound of any of embodiments 1-15, wherein at least two of $R^1$, $R^2$, $R^3$, and $R^4$ are —H.
17. The compound of any of embodiments 1-15, wherein at least three of $R^1$, $R^2$, $R^3$, and $R^4$ are —H.
18. The compound of any of embodiments 1-17, wherein the 5- or 6-membered heteroaryl has at least 1 nitrogen ring atom and is unsubstituted or substituted with 1 group selected from halo, —OH, —OCH$_3$, —OCF$_3$, —NH$_2$, —NH(CH$_3$), —N(CH$_3$)$_2$, —CH$_3$, ethyl, —CF$_3$, and —CN.
19. The compound of embodiment 18, wherein the heteroaryl is unsubstituted pyridyl, pyrimidinyl, pyrrolyl, pyrazolyl, isoxazolyl, imidazolyl, or oxazolyl.
20. The compound of embodiment 18, wherein the heteroaryl is unsubstituted pyridyl or isoxazolyl.
21. The compound of any of embodiments 1-16 or 18-20, wherein two adjacent instances of $R^1$, $R^2$, $R^3$, and $R^4$ together form —O—CH$_2$—O—, —O—CH(CH$_3$)—O—, or —O—C(CH$_3$)$_2$—O—.
22. The compound of embodiment 21, wherein two adjacent instances of $R^1$, $R^2$, $R^3$, and $R^4$ together form —O—CH$_2$—O—.
23. The compound of any of embodiments 1-22, wherein $R^a$ is —H.
24. The compound of any of embodiments 1-23, wherein R is —H.
25. The compound of any of embodiments 1-24, wherein each instance of $R^5$ is —F or —CH$_3$.
26. The compound of any of embodiments 1-25, wherein each instance of $R^6$ is —F or —CH$_3$.
27. The compound of any of embodiments 1-25, wherein each instance of $R^6$ is —CH$_3$.
28. The compound of any of embodiments 1-24, 26, or 27, wherein m is 0.
29. The compound of any of embodiments 1-25, wherein w is 0.
30. The compound of any of embodiments 1-24, wherein m is 0 and w is 0.
31. The compound of any of embodiments 1-30, wherein $R^1$, $R^2$, $R^3$, and $R^4$ are independently —H, halo, C$_1$-C$_3$ alkyl, —OR$^7$ or —CN.
32. The compound of any of embodiments 1-30, wherein $R^1$, $R^2$, $R^3$, and $R^4$ are independently —H, —F, —CH$_3$, —OCH$_3$, or —CN.
33. A composition comprising a compound according to any one of embodiments 1 to 32 and a pharmaceutically acceptable carrier, adjuvant, or vehicle.
34. A method for treating a neurological or psychiatric disorder in a patient, comprising administering to said patient an effective amount of the compound according to any of embodiments 1-32.
35. The method according to embodiment 34, wherein the neurological or psychiatric disorder is major depression, schizophrenia, bipolar disorder, obsessive compulsive disorder (OCD), panic disorder, or posttraumatic stress disorder (PTSD).
36. The method according to embodiment 34, wherein the neurological or psychiatric disorder is bipolar disorder, mania, psychosis, or schizophrenia.

What is claimed is:
1. A compound of formula:

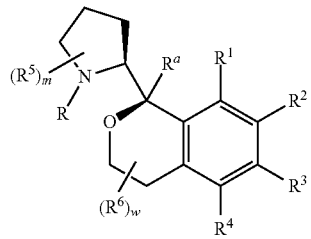

or a pharmaceutically acceptable salt thereof, wherein:
m is 0, 1, or 2;
R is —H or C$_1$-C$_3$ alkyl;
$R^a$ is —H or C$_1$-C$_3$ alkyl;
$R^1$, $R^2$, $R^3$, and $R^4$ are independently —H, halo, —OH, —NH$_2$, C$_1$-C$_3$ alkyl, —OR$^7$, —NHR$^7$, —N(R$^7$)R$^7$, —CN, phenyl, or 5- or 6-membered heteroaryl, wherein:
each instance of $R^7$ independently is unsubstituted C$_1$-C$_2$ alkyl or C$_1$-C$_2$ alkyl substituted with 1-3 halo,
each instance of C$_1$-C$_3$ alkyl independently is unsubstituted or substituted with 1-3 halo, and the phenyl or heteroaryl is unsubstituted or substituted with 1 or 2 groups independently selected from halo, —OH, —OCH₃, —OCF₃, —NH₂, —NH(CH₃), —N(CH₃)₂, —CH₃, ethyl, —CF₃, and —CN, optionally wherein two adjacent instances of R¹, R², R³, and R⁴ together form —O—CH₂—O—, —O—CH(CH₃)—O—, —O—C(CH₃)₂—O—, —O—CH₂—CH₂—O—, or —O—C(CH₃)₂—C(CH₃)₂—O—;

each instance of R⁵ independently is halo, —CH₃, or ethyl;

each instance of R⁶ independently is halo, —CH₃, ethyl or —OH;

w is 0, 1, or 2; and provided that the compound is not:

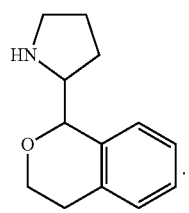

2. The compound of claim 1, or a pharmaceutically acceptable salt thereof, wherein at least two of R¹, R², R³, and R⁴ are —H.

3. The compound of claim 1, or a pharmaceutically acceptable salt thereof, wherein at least three of R¹, R², R³, and R⁴ are —H.

4. The compound of claim 1, or a pharmaceutically acceptable salt thereof, wherein the 5- or 6-membered heteroaryl has at least 1 nitrogen ring atom and is unsubstituted or substituted with 1 group selected from halo, —OH, —OCH₃, —OCF₃, —NH₂, —NH(CH₃), —N(CH₃)₂, —CH₃, ethyl, —CF₃, and —CN.

5. The compound of claim 4, or a pharmaceutically acceptable salt thereof, wherein the heteroaryl is unsubstituted pyridyl, pyrimidinyl, pyrrolyl, pyrazolyl, isoxazolyl, imidazolyl, or oxazolyl.

6. The compound of claim 4, or a pharmaceutically acceptable salt thereof, wherein the heteroaryl is unsubstituted pyridyl or isoxazolyl.

7. The compound of claim 1, or a pharmaceutically acceptable salt thereof, wherein two adjacent instances of R¹, R², R³, and R⁴ together form —O—CH₂—O—, —O—CH(CH₃)—O—, or —O—C(CH₃)₂—O—.

8. The compound of claim 7, or a pharmaceutically acceptable salt thereof, wherein two adjacent instances of R¹, R², R³, and R⁴ together form —O—CH₂—O—.

9. The compound of claim 1, or a pharmaceutically acceptable salt thereof, wherein $R^a$ is —H.

10. The compound of claim 1, or a pharmaceutically acceptable salt thereof, wherein R is —H.

11. The compound of claim 1, or a pharmaceutically acceptable salt thereof, wherein each instance of R⁵ is —F or —CH₃.

12. The compound of claim 1, or a pharmaceutically acceptable salt thereof, wherein each instance of R⁶ is —F or —CH₃.

13. The compound of claim 1, or a pharmaceutically acceptable salt thereof, wherein each instance of R⁶ is —CH₃.

14. The compound of claim 1, or a pharmaceutically acceptable salt thereof, wherein m is 0.

15. The compound of claim 1, or a pharmaceutically acceptable salt thereof, wherein w is 0.

16. The compound of claim 1, or a pharmaceutically acceptable salt thereof, wherein m is 0 and w is 0.

17. The compound of claim 1, or a pharmaceutically acceptable salt thereof, wherein R¹, R², R³, and R⁴ are independently —H, halo, C₁-C₃ alkyl, —OR⁷ or —CN.

18. The compound of claim 1, or a pharmaceutically acceptable salt thereof, wherein R¹, R², R³, and R⁴ are independently —H, —F, —CH₃, —OCH₃, or —CN.

19. The compound of claim 1, or a pharmaceutically acceptable salt thereof, wherein R³ is —F or —CH₃.

20. A composition comprising a compound according to claim 1, or a pharmaceutically acceptable salt thereof, and a pharmaceutically acceptable carrier, adjuvant, or vehicle.

21. The composition according to claim 20, wherein said composition is a pharmaceutically acceptable composition.

22. A compound selected from:

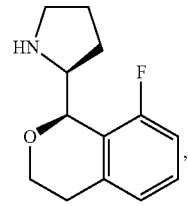

I-1

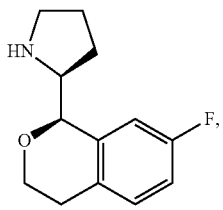

I-5

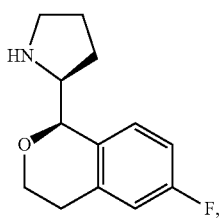

I-9

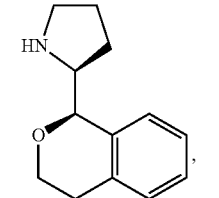

I-13

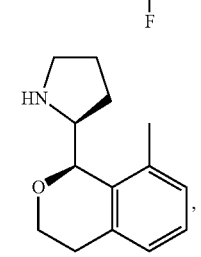

I-22

I-25
I-29
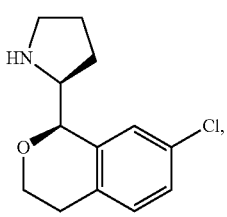
I-34
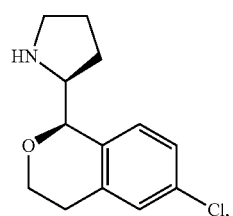
I-38
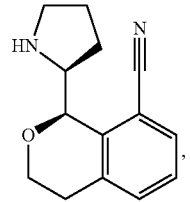
I-40
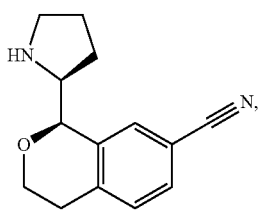
I-44
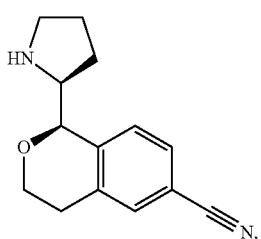
I-47
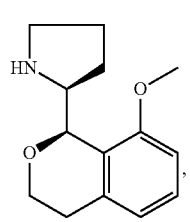
I-52
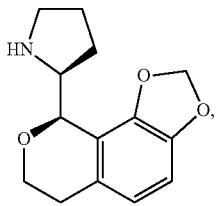
I-54
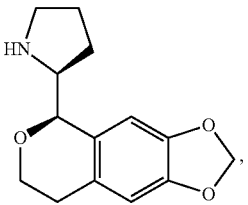
I-56
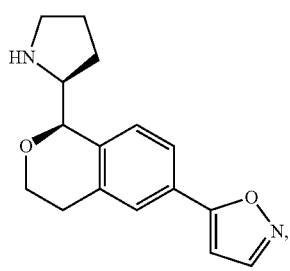
I-58
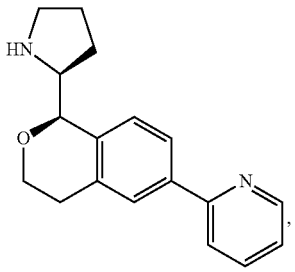
I-59
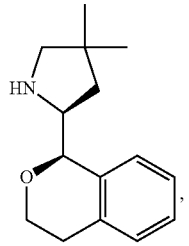
I-64
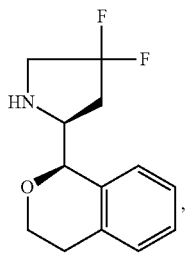

I-66 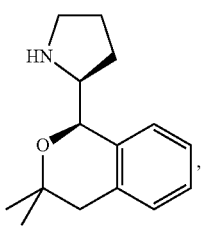

I-69 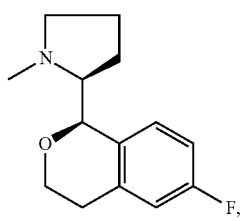

I-70 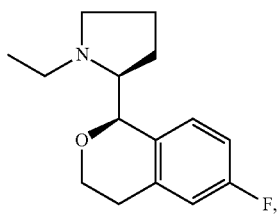

I-134 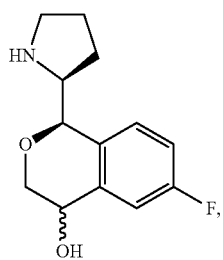

I-137 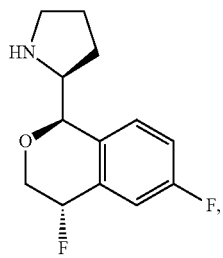

I-138 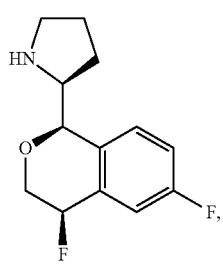

I-140 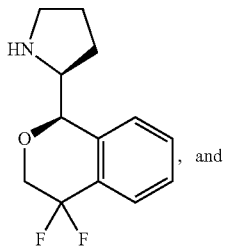, and

I-145 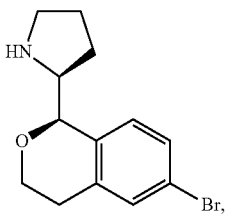

or a pharmaceutically acceptable salt thereof.

23. A composition comprising a compound according to claim 22, or a pharmaceutically acceptable salt thereof, and a pharmaceutically acceptable carrier, adjuvant, or vehicle.

24. The composition according to claim 23, wherein said composition is a pharmaceutically acceptable composition.

25. A compound of formula:

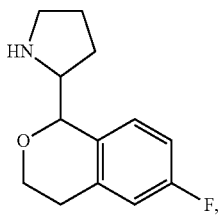

or a pharmaceutically acceptable salt thereof.

26. A compound of claim 25, or a pharmaceutically acceptable salt thereof, selected from:

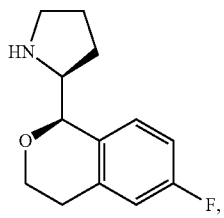 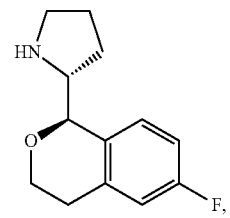

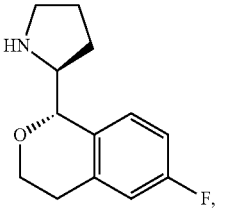, or 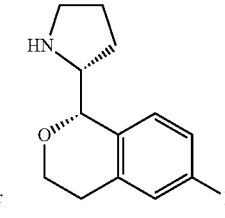

or a mixture of two or more thereof.

27. A composition comprising a compound according to claim 25, or a pharmaceutically acceptable salt thereof, and a pharmaceutically acceptable carrier, adjuvant, or vehicle.

28. The composition according to claim 27, wherein said composition is a pharmaceutically acceptable composition.

29. A composition comprising a compound according to claim 26, or a pharmaceutically acceptable salt thereof, or a mixture of two or more thereof, and a pharmaceutically acceptable carrier, adjuvant, or vehicle.

30. The composition according to claim 29, wherein said composition is a pharmaceutically acceptable composition.

31. A compound of formula:

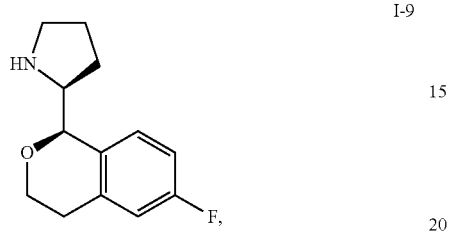

I-9 or a pharmaceutically acceptable salt thereof.

32. A composition comprising a compound according to claim 31, or a pharmaceutically acceptable salt thereof, and a pharmaceutically acceptable carrier, adjuvant, or vehicle.

33. The composition according to claim 32, wherein said composition is a pharmaceutically acceptable composition.

* * * * *